(12) United States Patent
Shen-Orr et al.

(10) Patent No.: US 10,119,959 B2
(45) Date of Patent: Nov. 6, 2018

(54) METHOD OF ASSAYING AN INDIVIDUAL FOR IMMUNE IMPAIRMENT

(75) Inventors: Shai S. Shen-Orr, Menlo Park, CA (US); Atul J. Butte, Menlo Park, CA (US); Mark M. Davis, Atherton, CA (US); David Furman, San Francisco, CA (US); Brian A. Kidd, Palo Alto, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 199 days.

(21) Appl. No.: 13/168,974

(22) Filed: Jun. 25, 2011

(65) Prior Publication Data

US 2012/0021414 A1 Jan. 26, 2012

Related U.S. Application Data

(60) Provisional application No. 61/358,884, filed on Jun. 25, 2010.

(51) Int. Cl.
*G01N 31/00* (2006.01)
*G01N 33/50* (2006.01)

(52) U.S. Cl.
CPC ..... *G01N 33/5091* (2013.01); *G01N 2333/52* (2013.01); *G01N 2333/70514* (2013.01); *G01N 2333/70517* (2013.01); *G01N 2333/70521* (2013.01); *G01N 2800/60* (2013.01)

(58) Field of Classification Search
None
See application file for complete search history.

(56) References Cited

U.S. PATENT DOCUMENTS

2001/0041362 A1* 11/2001 Taniguchi .............. C07K 14/55
435/325

FOREIGN PATENT DOCUMENTS

| WO | 2006012507 A2 | 2/2006 |
| WO | 2009134944 A2 | 11/2009 |
| WO | 2010006291 A1 | 1/2010 |

OTHER PUBLICATIONS

Hann et al. (Cellular Signalling, 2005, 17: 1542-1550).*
Wikby et al. (Biogerontology, 2008, 9:299-308).*
Krutzik et al. (Nature Methods, May 2006; vol. 3, Nol. 5, pp. 361-368).*
Ademokun et al., "The ageing B cell population: Composition and function", Biogerontology, 2010, vol. 11, pp. 125-137.
Barrett et al., "NCBI GEO: mining tens of millions of expression profiles—database and tools update", Nucleic Acids Research, 2007, vol. 35, Database issue, pp. 760-765.
Choi et al., "Combining multiple microarray studies and modeling interstudy variation", Bioinformatics, 2003, vol. 19, Suppl. 1, pp. i84-i90.
Cobb et al., Application of genome-wide expression analysis to human health and disease, PNAS, Mar. 29, 2005, vol. 102, No. 13, pp. 4801-4806.
Coudeville et al., "Relationship between haemagglutination-inhibiting antibody titres and clinical protection against influenza: development and application of a bayesian random-effects model", Medical Research Methodology, 2010, vol. 10, 11 pgs.
Davis, "A Prescription for Human Immunology", Immunity, Dec. 19, 2008, vol. 29, No. 6, pp. 835-838.
De Magalhaes et al., "The Human Ageing Genomic Resources: online databases and tools for biogerontologists", Aging Cell, Feb. 2009, vol. 8, No. 1, pp. 65-72.
De Visser et al., "Paradoxical roles of the immune system during cancer development", Nature Reviews, Jan. 2006, vol. 6, pp. 24-37.
Effros et al, "The role of $CD8^+$ T-cell replicative senescence in human aging", Immunological Reviews, 2005, vol. 205, pp. 147-157.
Evans et al., "The DAF-2 Insulin-like Signaling Pathway Independently Regulates Aging and Immunity in C. Elegans", Aging Cell, Dec. 2008, vol. 7, No. 6, pp. 879-893.
Fagnoni et al., "Expansion of cytotoxic $CD8^+$ $CD28^-$ T cells in healthy ageing people, including centenarians", Immunology 1996, vol. 88, pp. 501-507.
Fagnoni et al., "Shortage of circulating naive $CD8^+$ T cells provides new insights of immunodeficiency in aging", Blood, May 1, 2000, vol. 95, No. 9, pp. 2860-2868.
Franceschi et al., "Inflamm-aging, An evolutionary Perspective on Immunosenescence", Annals New York Academy of Sciences, vol. 908, pp. 244-254.
Frew, "Allergen immunotherapy", J. Allergy Clin. Immunol, 2010, vol. 125, pp. S306-S313.
Gernez et al., "Altered phosphorylated signal transducer and activator of transcription profile of CD4+CD161+ T cells in asthma: Modulation by allergic status and oral corticosteroids", J. Allergy Clin. Immunol., Dec. 2007, vol. 120, No. 6, pp. 1441-1448.
Goodwin et al., "Antibody response to influenza vaccination in the elderly: a quantitative review", Vaccine, 2006, vol. 24, 1159-1167.
Hansson, "Inflammation, Atherosclerosis, and Coronary Artery Disease", The New England Journal of Medicine, Apr. 21, 2005, vol. 352, No. 16, pp. 1685-1695.

(Continued)

*Primary Examiner* — Pablo S Whaley
(74) *Attorney, Agent, or Firm* — KPPB LLP

(57) ABSTRACT

Embodiments of the present invention provide diagnostic markers of immunosenescence and methods of identifying individuals with impaired immune function based on a combination of such markers obtained from various analyzes, primarily from blood, testing immune function including the analysis of immune cell subset frequencies, gene expression, cytokine and chemokine levels, and signaling responses to stimulation with cytokines ('cytokine response'). Particular combinations of markers can predict with high accuracy whether an individual will respond to active vaccination and become protected against recurring diseases.

10 Claims, 36 Drawing Sheets

(56) References Cited

OTHER PUBLICATIONS

Figure 1:
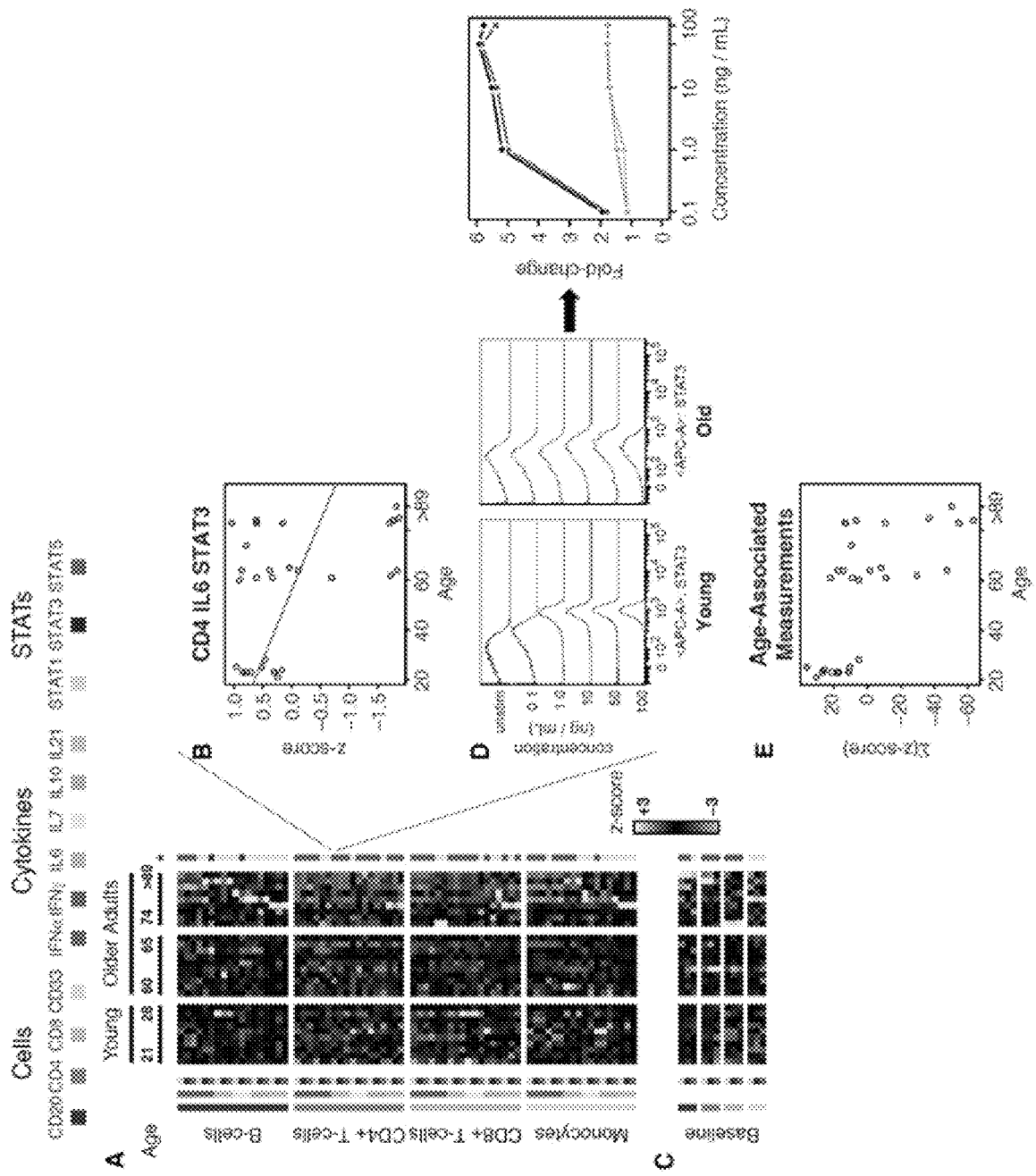

Hobson et al., "The role of serum haemagglutination-inhibiting antibody in protection against challenge infection with influenza A2 and B viruses", J. Hyg., Cambridge, 1972, vol. 70, pp. 767-777.
Irish et al., "B-cell signaling networks reveal a negative prognostic human lymphoma cell subset that emerges during tumor progression", PNAS, Jul. 20, 2010, vol. 107, No. 29, pp. 12747-12754.
Jones et al., "Revving the Engine: Signal Transduction Fuels T Cell Activation", Immunity, Aug. 2007, vol. 27, pp. 173-178.
Kirkwood, "Evolution of ageing", Mechanisms of Ageing and Development, 200, vol. 123, pp. 737-745.
Krutzik et al., "Fluorescent cell barcoding in flow cytometry allows high-throughput drub screening and signaling profiling", Nature Methods, May 2006, vol. 3, No. 5, pp. 361-368.
Langfelder et al., "WGCNA: an R package for weighted correlation network analysis", BMC Bioinformatics, 2008, vol. 9, 13 pgs.
Lifson et al., "Variables Affecting T-Lymphocyte Subsets in a Volunteer Blood Donor Population", Clinical Immunology and Immunopathology, 1985, vol. 36, pp. 151-160.
Perez et al., "Phospho-proteomic immune analysis by flow cytometry: from mechanism to translational medicine at the single-cell level", Immunological Reviews, 2006, vol. 210, pp. 208-228.
Potter et al., "Determinants of Immunity to Influenza Infection in Man", British Medical Bulletin, 1979, vol. 35, No. 1, pp. 69-75.
Rodwell et al., "A Transcriptional Profile of Aging in the Human Kidney", PLoS Biology, Dec. 2004, vol. 2, Issue 12, 2191-2201.
Rojo et al., "Neuroinflammation: Implications for the Pathogenesis and Molecular Diagnosis of Alzheimer's Disease", Archives of Medical Research, 2008, vol. 39, pp. 1-16.
Sansoni et al., "The immune system in extreme longevity", Experimental Gerontology, 2008, vol. 43, pp. 61-65.
Sarup et al., "Flies selected for longevity retain a young gene expression profile", Age, 2011, vol. 33, pp. 69-80.
Shaw et al., "Aging of the innate immune system", Current Opinion in Immunology, 2010, vol. 22, pp. 507-513.
Shaw et al., The *E. elegans* TGF-β Dauer Pathway Regulates Longevity via Insulin Signaling, Current Biology, Oct. 9, 2007, vol. 17, pp. 1635-1645.
Shen-Orr et al., "Cell type-specific gene expression differences in complex tissues", Nat Methods, Apr. 2010, vol. 7, No. 4, pp. 287-289.
Shurin et al., "Dynamic alteration of soluble serum biomarkers in healthy aging", Cytokine, 2007, vol. 39, pp. 123-129.
Southworth et al., "Aging Mice Show a Decreasing Correlation of Gene Expression within Genetic Modules", PLoS Genetics, Dec. 2009, vol. 5, Issue 12, 13 pgs.
Storey et al., "Statistical significance for genomewide studies", PNAS, Aug. 5, 2003, vol. 100, No. 16, pp. 9440-9445.
Strindhall et al., "No Immune Risk Profile Among Individuals Who Reach 100 years of Age: Findings from the Swedish NONA Immune Longitudinal Study", Experimental Gerontology, 2007, vol. 42, No. 8 pp. 753-760.
Tusher et al., "Significance analysis of microarrays applied to the ionizing radiation response", PNAS, Apr. 24, 2001, vol. 98, No. 9, pp. 5116-5121.
Wassel et al., "Association of Circulating C-Reactive Prtein and Interleukin-6 with Longevity into the 80s and 90s: The Rancho Bernardo Study", J. Clin. Endocrinol. Metab., Oct. 2010, vol. 95, No. 10, pp. 4748-4755.
Weiskopf et al., "The aging of the immune system", European Society for Organ Transplantation, 2009, vol. 22, pp. 1041-1050.
Weng et al., "$CD28^-$ T cells: their role in the age-associated decline of immune function", Trends Immunol., Jul. 2009, vol. 30, No. 1, pp. 306-312.
Whitney et al., "Individuality and variation in gene expression patterns in human blood", PNAS, Feb. 18, 2003, vol. 100, No. 4, pp. 1896-1901.
Wikby et al., "The immune risk phenotype is associated with IL-6 in the terminal decline stage: Findings from the Swedish NONA immune longitudinal study of very late life functioning", Mechanisms of Ageing and Development, 2006, vol. 127, pp. 695-704.
Witten et al., "A penalized matrix decomposition, with applications to sparse principal components and canonical correlation analysis", Biostatistics, 2009, vol. 10, No. 3, pp. 515-534.

\* cited by examiner

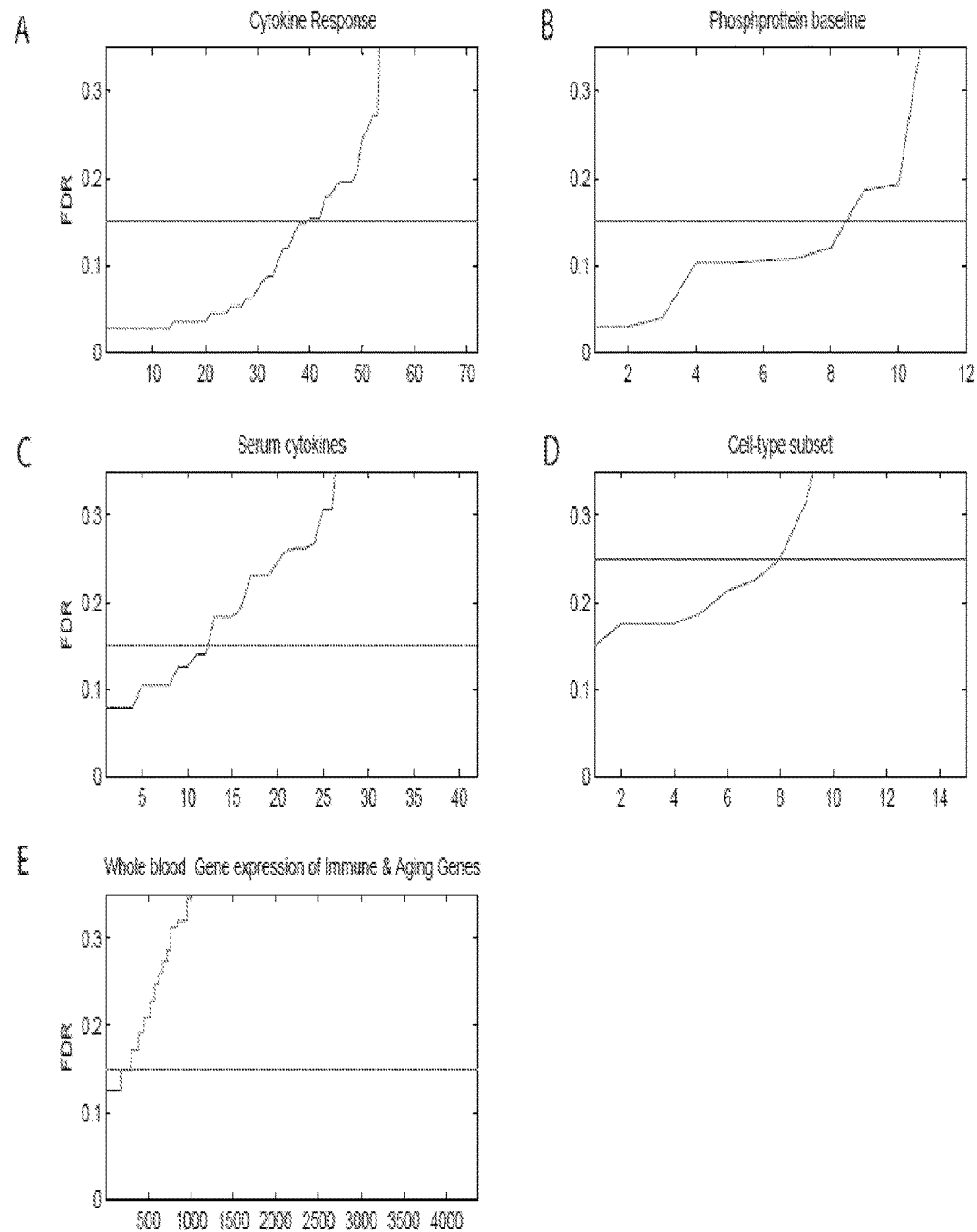

METHOD OF ASSAYING AN INDIVIDUAL FOR IMMUNE IMPAIRMENT

RELATED APPLICATION

This application claims priority and other benefits from U.S. Provisional Patent Application Ser. No. 61/358,884, filed Jun. 25, 2010, entitled "Methods of identifying individuals with impaired immune function". Its entire content is specifically incorporated herein by reference.

STATEMENT OF GOVERNMENT SUPPORT

This invention was made with government support under U19 AI057229 awarded by the National Institutes of Health. The government has certain rights in the invention.

BACKGROUND

Deterioration of immune function is a prominent hallmark of aging and is only partially explainable by a loss of naïve and central memory CD4 T cells due to thymic involution. Defects in both the innate and adaptive immune system of the elderly have been described and include changes in immune cell-subsets abundance and relative frequencies, altered hematopoiesis, impairments in antigen presentation, decreased B cell as well as T cell proliferation, a reduced TCR repertoire and defect in antibody production (Weiskopf et al., 2009). Ultimately these alterations result in a sharp decline in the response to new and persisting antigens (immunosenescence). Thus it is not surprising that infectious diseases are one of the major causes of mortality in those over the age of 65 and that protective vaccination of the elderly is more difficult to establish than in younger individuals (Goodwin, 2006).

Active immunization and activation of T cell-mediated as well as humoral immune response can be achieved through the administration of immunogenic material or vaccines. Vaccination seeks to prevent, ameliorate or even treat against the harmful effects of pathogens and carcinogens, and regular vaccination has become an integral part of preventive medicine.

Due to the complexity of the immune system, studies of immunosenescence often only investigate one or a few variables of an individual's immune system. This has made it difficult to draw general conclusions about the phenomena being described or how they might relate to each other. Individuals who suffer from an impaired immune function generally face the risk of increased morbidity and mortality. This is particularly relevant for older individuals who show a reduced response to vaccination or have persistent cytomegalovirus infection (Strindhall et al., 2007). The immune system of those individuals can be phenotypically characterized as having an inverted CD4+ to CD8+ T-cell ratio (below one), and a high frequency of CD8+CD28– T-cells (Wikby et al., 2008). There is also evidence that other major causes of mortality in older individuals, such as cardiovascular diseases, cancer and Alzheimer's disease, might involve defects in normal immune function (Hansson, 2005; de Visser et al., 2006; Rojo et al., 2008). This raises the possibility that a functional immune response is a key factor in the maintenance of good health and longevity.

One of the most challenging topics facing the maintenance of good health and longevity is the identification of immunocompromised individuals who might appear healthy, but who have an underlying, undetected impairment of immune function and, so, face the risk of increased morbidity and mortality. The present invention addresses this issue.

SUMMARY

Embodiments of the present invention provide diagnostic markers of immunosenescence and methods of identifying individuals with impaired immune function based on a combination of such markers obtained from various analyses, primarily from blood, testing immune function including the analysis of immune cell subset frequencies, gene expression, cytokine and chemokine levels, and signaling responses to stimulation with cytokines ('cytokine response'). Particular combinations of markers can predict with high accuracy whether an individual will respond to active vaccination and become protected against recurring diseases.

The above summary is not intended to include all features and aspects of the present invention nor does it imply that the invention must include all features and aspects discussed in this summary.

INCORPORATION BY REFERENCE

All publications mentioned in this specification are herein incorporated by reference to the same extent as if each individual publication or patent application was specifically and individually indicated to be incorporated by reference.

DRAWINGS

The accompanying drawings illustrate embodiments of the invention and, together with the description, serve to explain the invention. These drawings are offered by way of illustration and not by way of limitation; it is emphasized that the various features of the drawings may not be to-scale.

FIGS. 1A-1E: Phosphorylation of STATs in response to cytokine stimulation drops with age. (A) Heat map of 72 cytokine stimulation assays measured across 29 individuals of different ages. Each assay measures the fold-change phosphor-STAT-1, -3 or -5 in one of four immune cell subsets (B-cell, CD4 T-helper cells, CD8 cytotoxic T cells and monocytes) stimulated by one of six cytokines (IFN-α, IFN-γ, IL6, IL7, IL10 and IL21) and measured by flow cytometry. Each assay appears in a single row and is color coded (left of heatmap) by the condition (cell subset, cytokine, pSTAT combination) (see legend on top). Coloring of the heat map cells reflects the normalized fold-change z-scores, that is, the number of standard deviations from the population mean of the assay. Age-associated differences at a ($q<0.15$) are marked on right (red decrease with age, purple, increase; grey, no significant difference). (B) Example scatter plot illustrating the reduced fold-change response of some older individual in CD4$^+$ T cells stimulated by IL6 and assayed for STAT-3 phosphoprylation. (C) Baseline phosphoSTAT levels increase with age. Shown are normalized z-scores. (D) Reduced cellular response in old individuals is independent of stimulus concentration. The entire 72-condition cytokine response assay was repeated at five different doses per stimuli for two young and two older individuals, whose average fold-change response to cytokine stimulation was respectively high or low. Shown is an example histogram (left) and line plot visualization (right) of the fold-change cytokine response as a function of cytokine stimuli concentration for each of the two young (black) and two old (cyan) individuals. A fold change of 1 signifies no change from baseline. The young individuals show a significantly higher fold-change response than that observed in old individuals, at all concentrations (See FIG. 10 for all other assays). (E) A general reduction in cytokine responses is observed with age with some individuals showing systemic impairments in multiple assays. The y-axis plots the sum of z-scores all 39 age-associated responses.

Figure 2A:
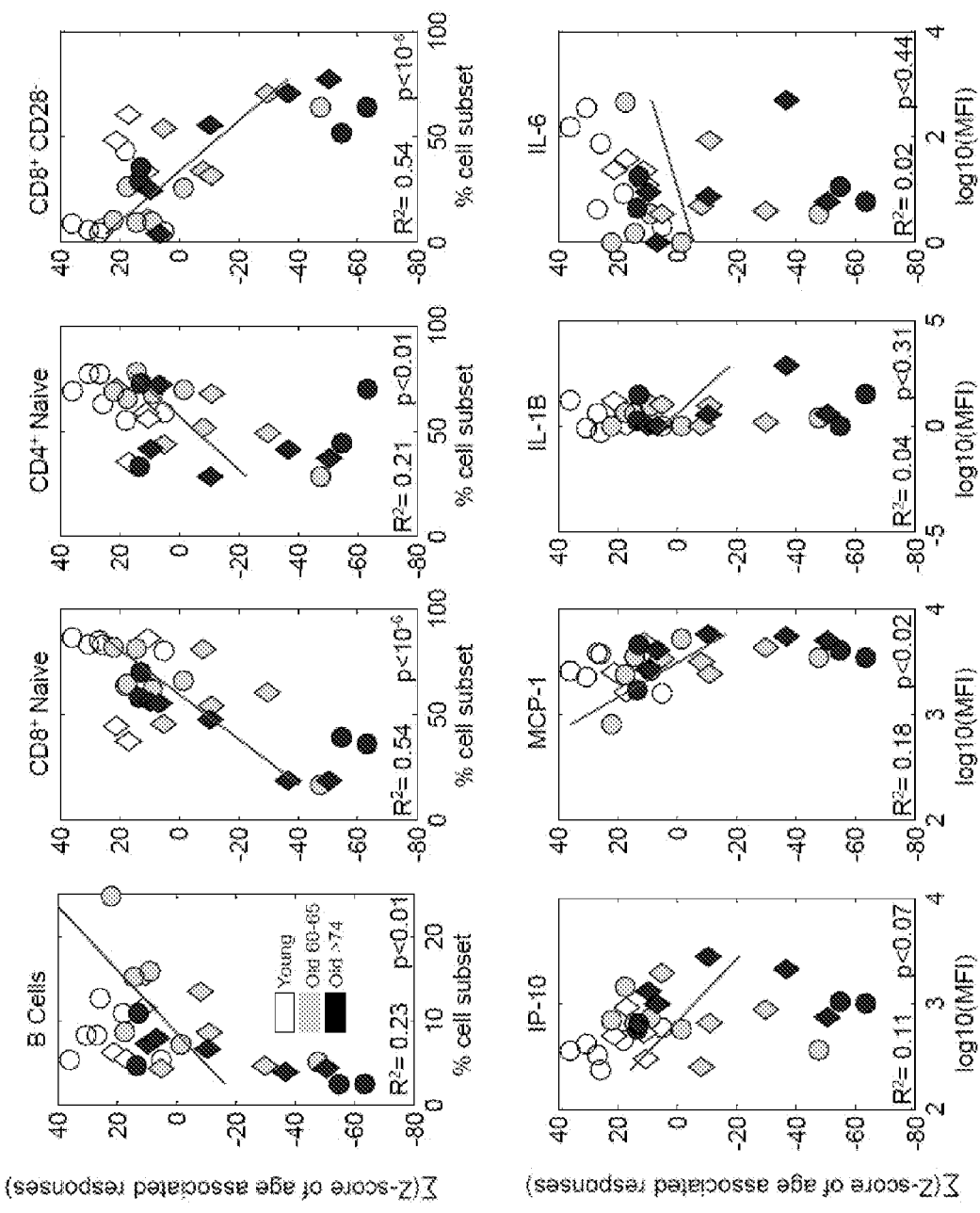
Figure 2B:
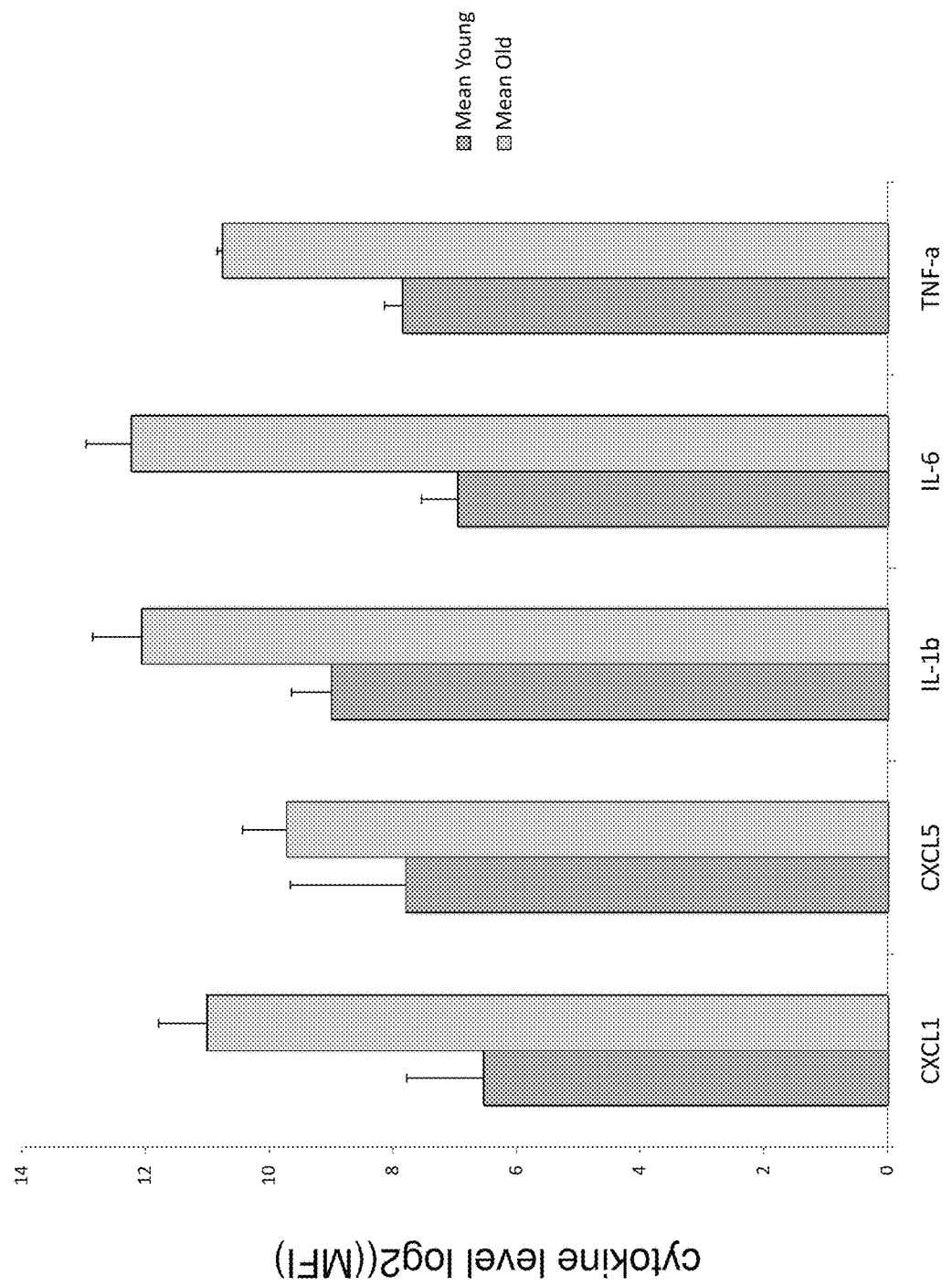
Figure 2C:
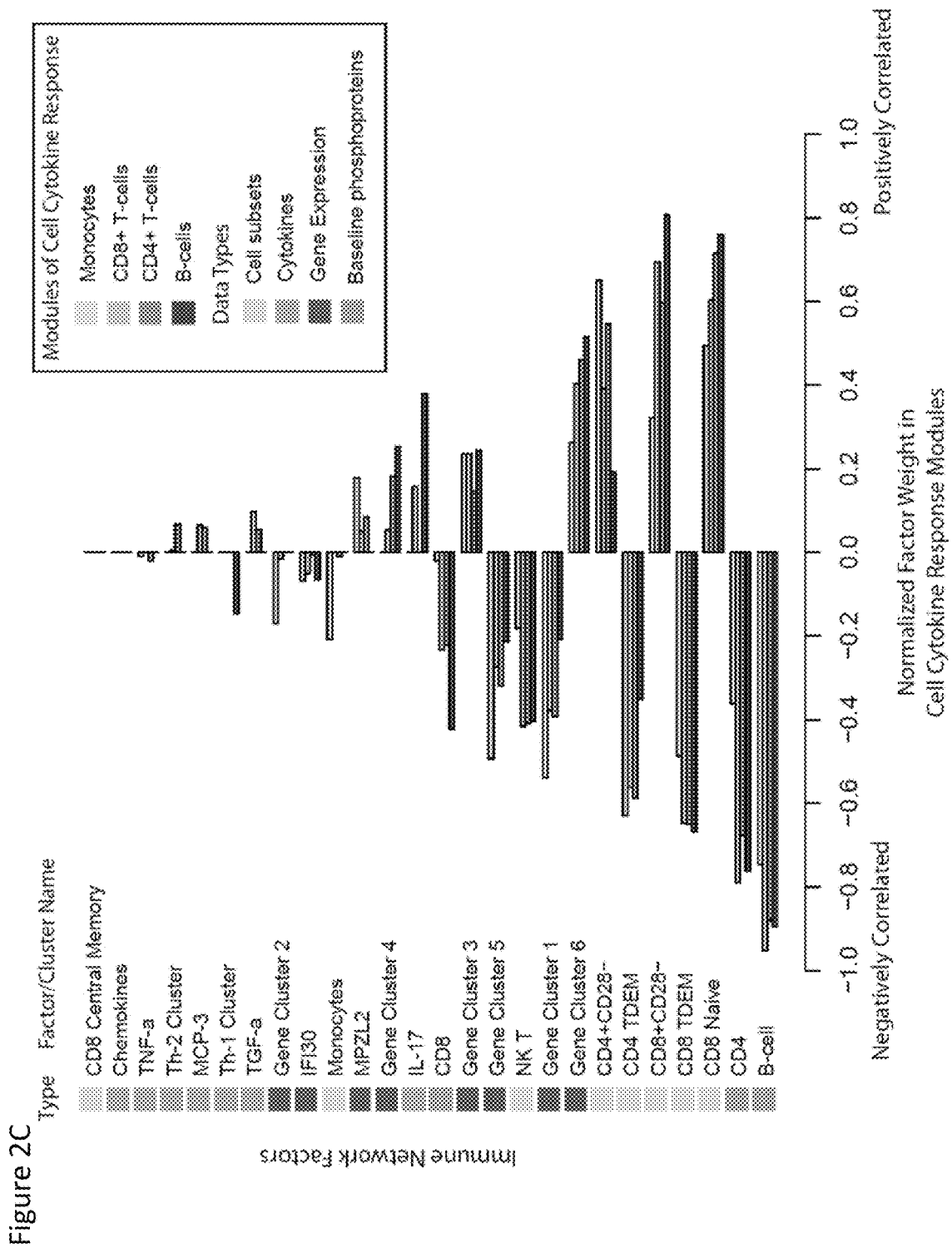

FIGS. 2A-2C: Systemic impairments in cytokine responses with age co-occur in a single individual with dysfunctional immune cell subsets and increased inflammation. (A) Age associated cytokine response deficiencies correlate with known cell subset immunosenescence markers such as the drop CD4+ and CDS+ naive cell frequency, and known serum chemokine changes with age, but as measured in serum, not with cytokines such as IL-6 and IL-1 that are proinflammatory and known to rise with age. (B) Biological validation of increased proinflammatory cytokine environment at baseline in sorted monocytes of two cytokine stimulation non-responsive older individuals (cyan) compared to two young individuals (orange). (C) Sparse canonical correlation analysis identifies a module of network nodes whose weighted linear combination is maximally correlated with the cytokine response deficiency of a given cell type. The normalized weights of each cell's maximally correlated module are shown in a bar plot format (grayscale), sorted by the weights of the module maximally correlated with B-cell cytokine response.

Figure 3A:
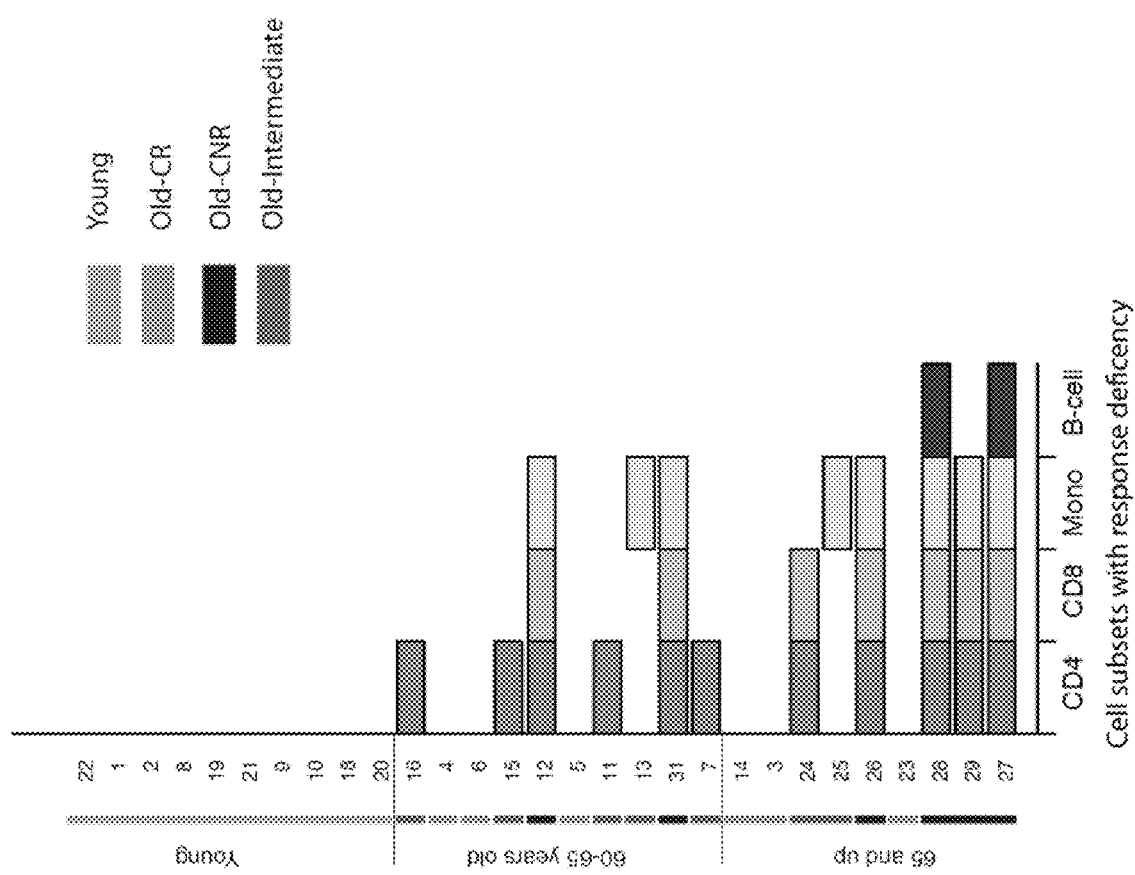
Figure 3B:
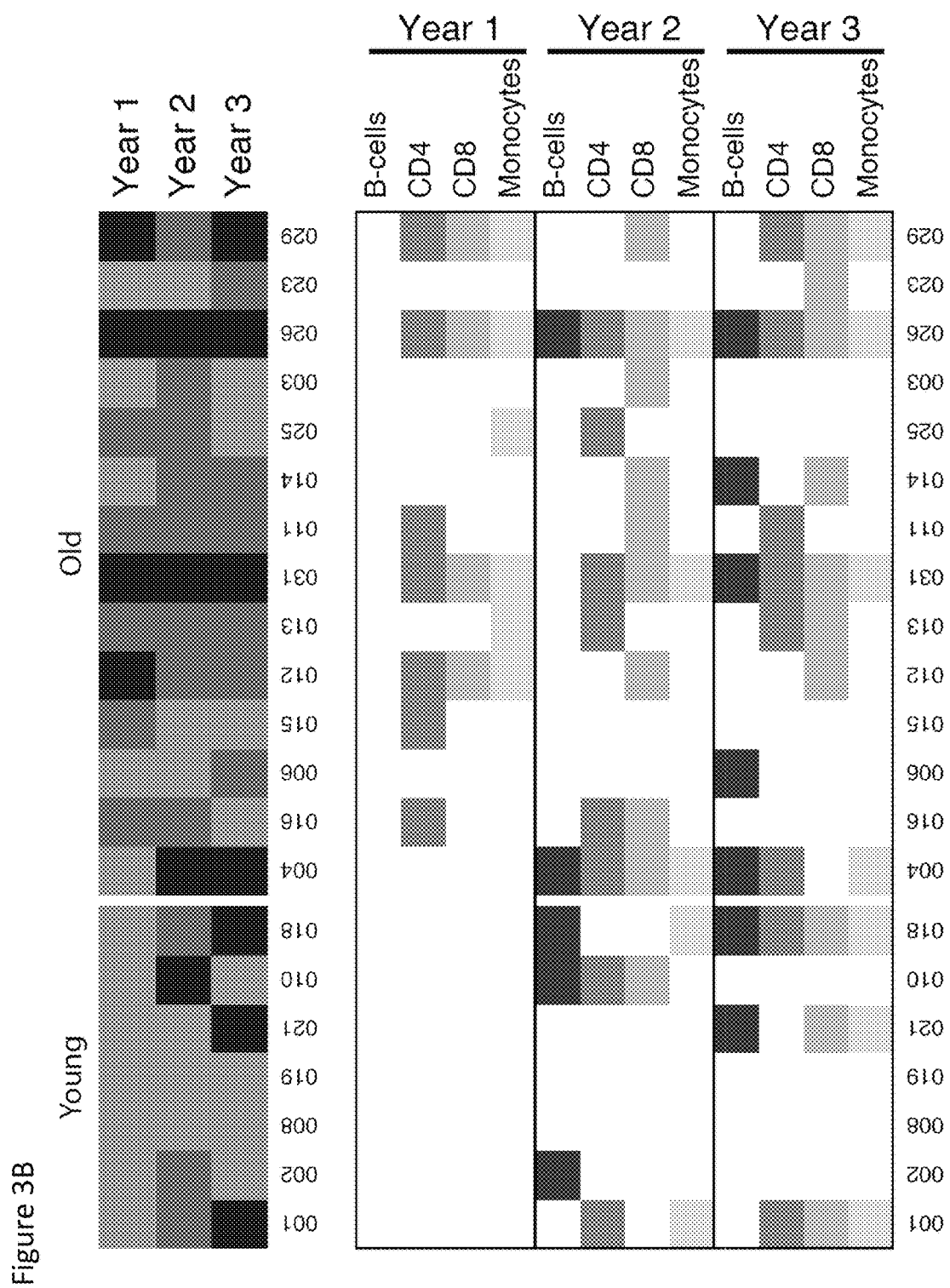

FIGS. 3A-B: Cytokine responses define distinct age-related subgroups that are longitudinally stable. (A) Individuals are stratified as CR (green), CNR (blue) or an intermediate phenotype (purple) by scoring the number of cell-types for that individual in which significant impairment was observed compared with the mean of the young. (B) A longitudinal study of cytokine non-response (cytokine deficiency) in 21 returning individuals. Cytokine response state is stable or worsen with time ($p<0.02$). Shown are cytokine response class (top) or cell state (bottom) for baseline (year 1) and two subsequent years.

Figure 4A:
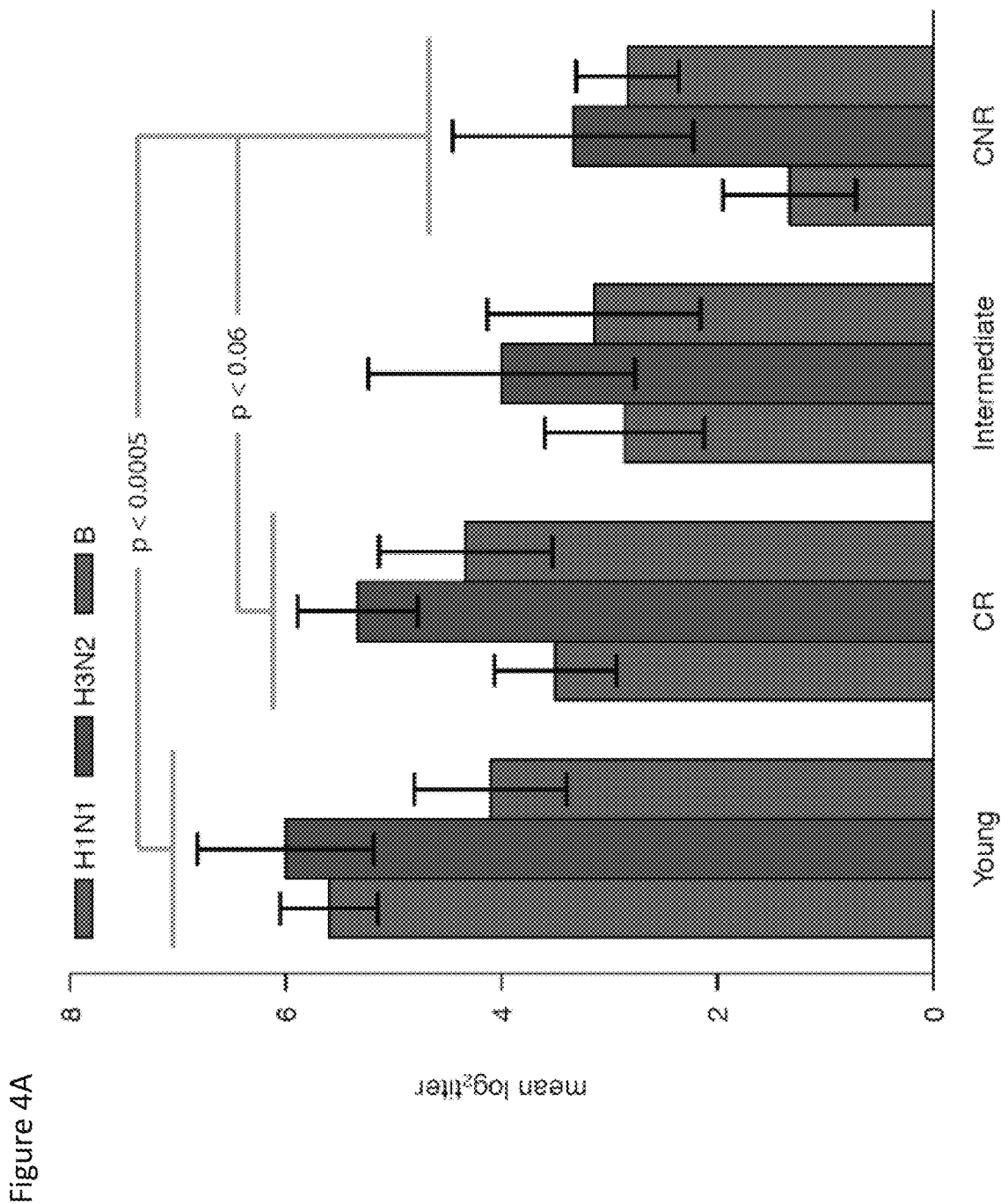
Figure 4B:
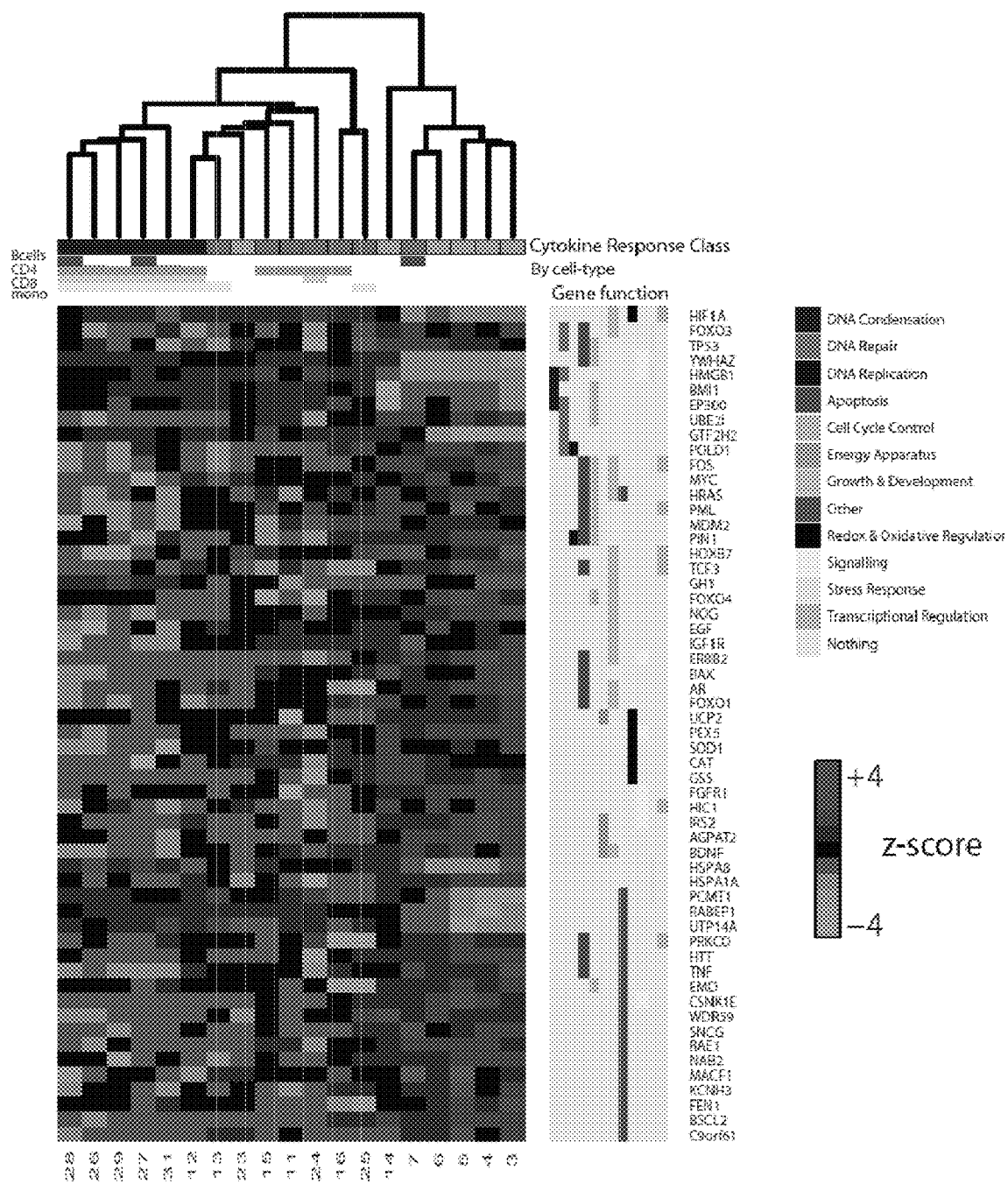

FIGS. 4A-B: Cytokine responder and non-responder older individuals have distinctly different immune system profiles. (A) The young and the CR group show more robust pre-vaccination antibody titer levels, compared with the CNR when considered simultaneously across all strains. At the population level, an antibody titer of 1:30-1:40 (above 5 on log 2 scale) represents probability of 50% protection against Influenza infection. Standard errors are shown. (B) Heatmap showing the association between immune system state and longevity. The z-score normalized expression of the top 60 longevity-associated genes from GenAge that are differentially expressed between CR and CNR (out of 159). Shown are all older individuals. Colored boxes on top reflect their cytokine response classification and the specific cells in which their response was reduced. Two distinct clusters of CR and CNR are observed with additional individuals clustering in CR. Genes are clustered by pathway membership (matrix on right).

Figure 5A:
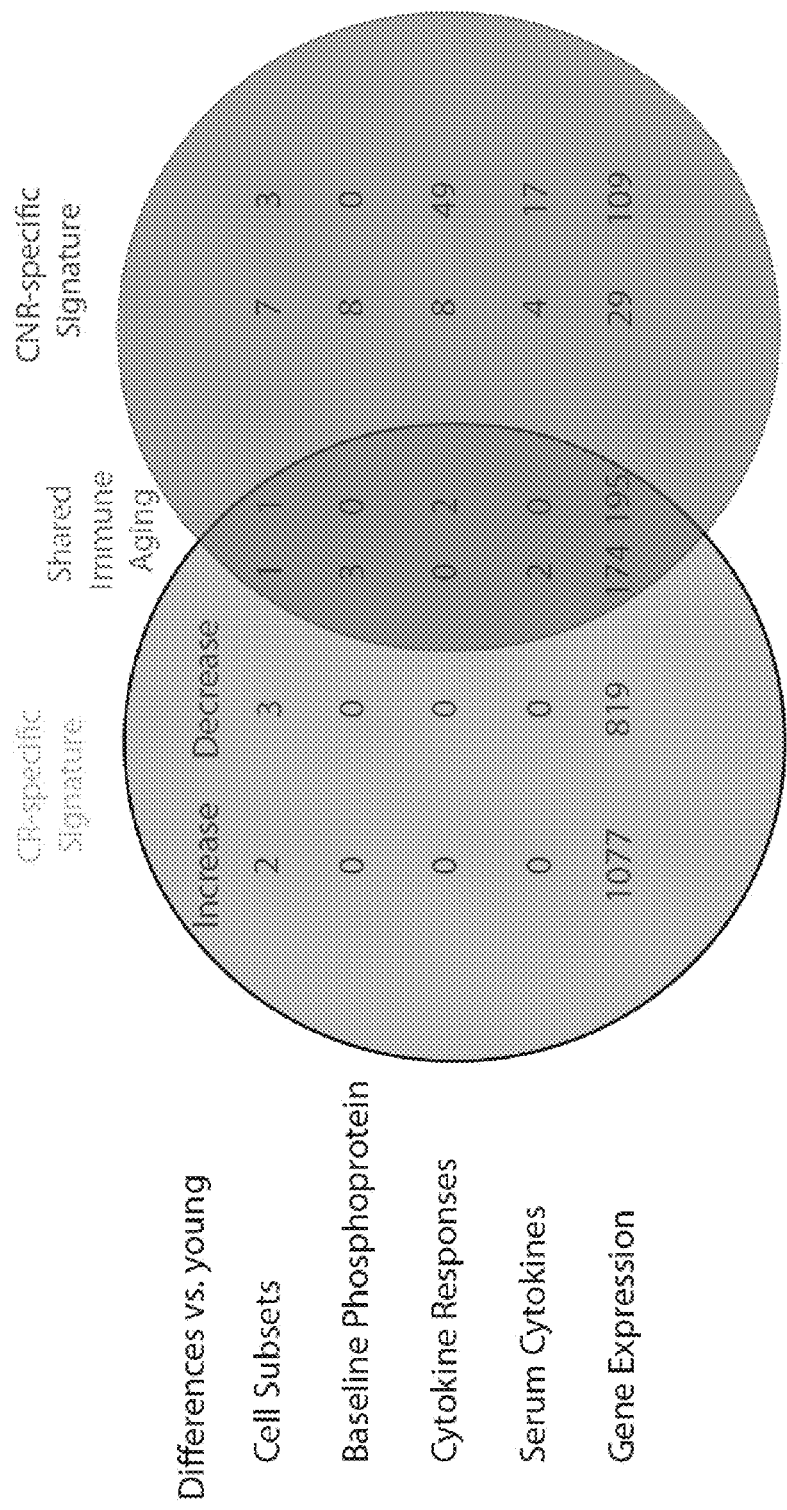
Figure 5B:
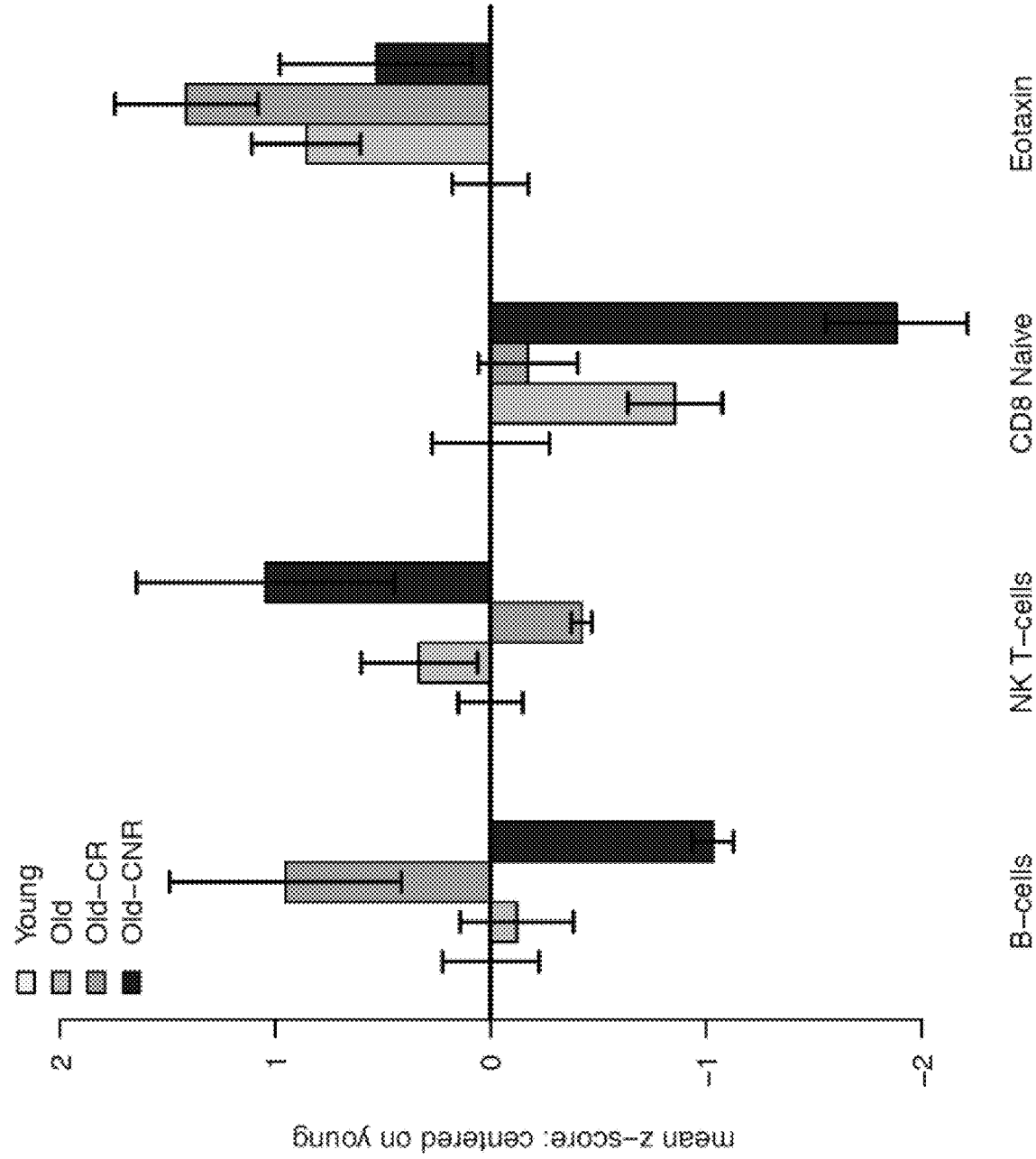

FIGS. 5A-B. Stratification of older individuals by cytokine response yields increased resolution to age dependent changes. (A) Venn diagram summarizing the number of identified markers for each of the CR and CNR-specific signatures, as well as those changes that occur, independent of cytokine responses, with age. (B) Differing proportions of CR and CNR older individuals in aging studies may explain many of the controversies in the immunosenescence literature. Examples highlight changes in age which either exclusive for both CR and CNR or common to both. Distinct: changes in the frequency of Eotaxin, NKT cells and B cells that are masked by the heterogeneity of older individuals. Common: The reduction in CDS+ nai:ve cells is common to all older individuals, though much more dramatic in CNR. Standard errors are shown.

Figure 6A:
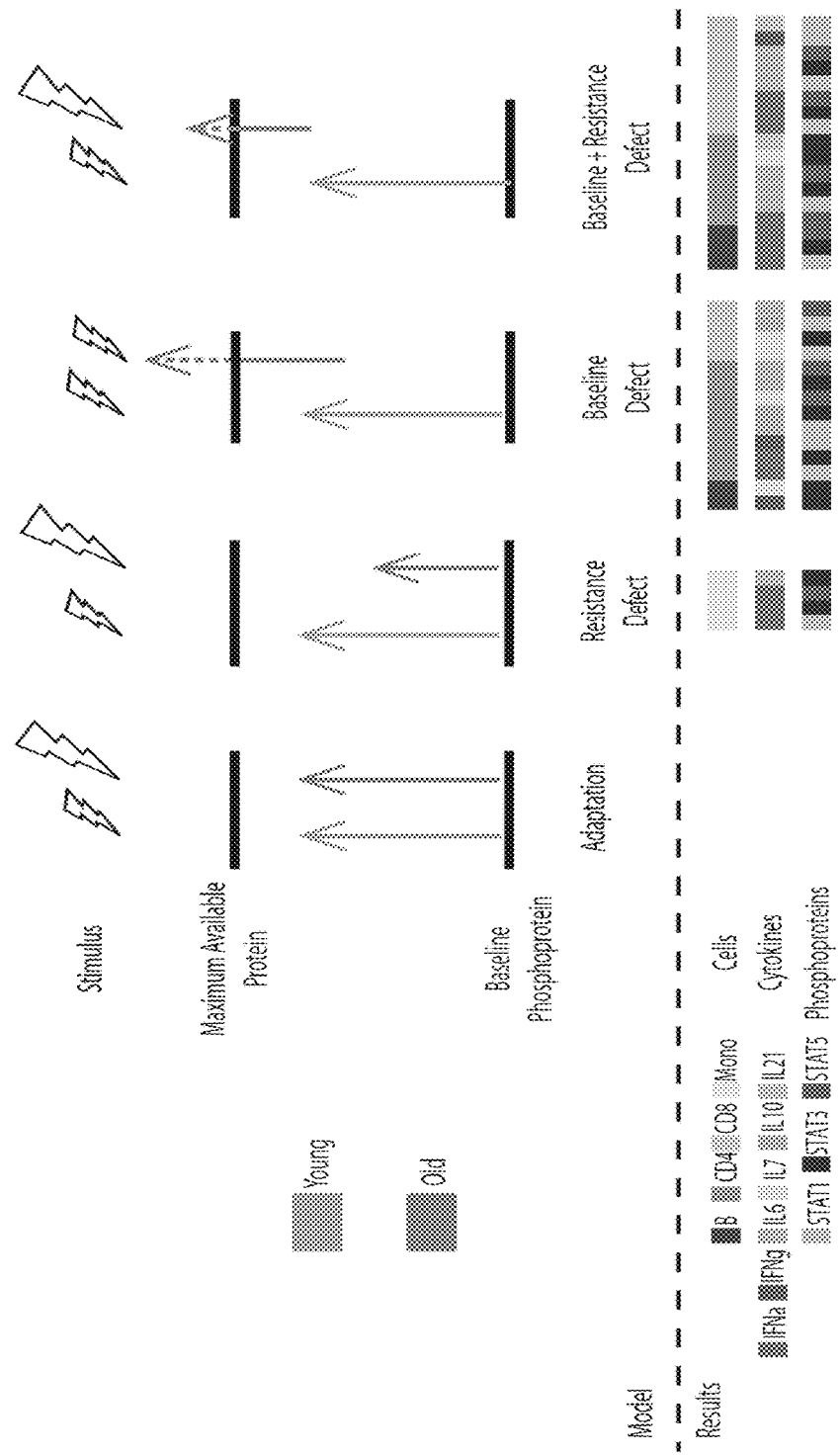
Figure 6B:
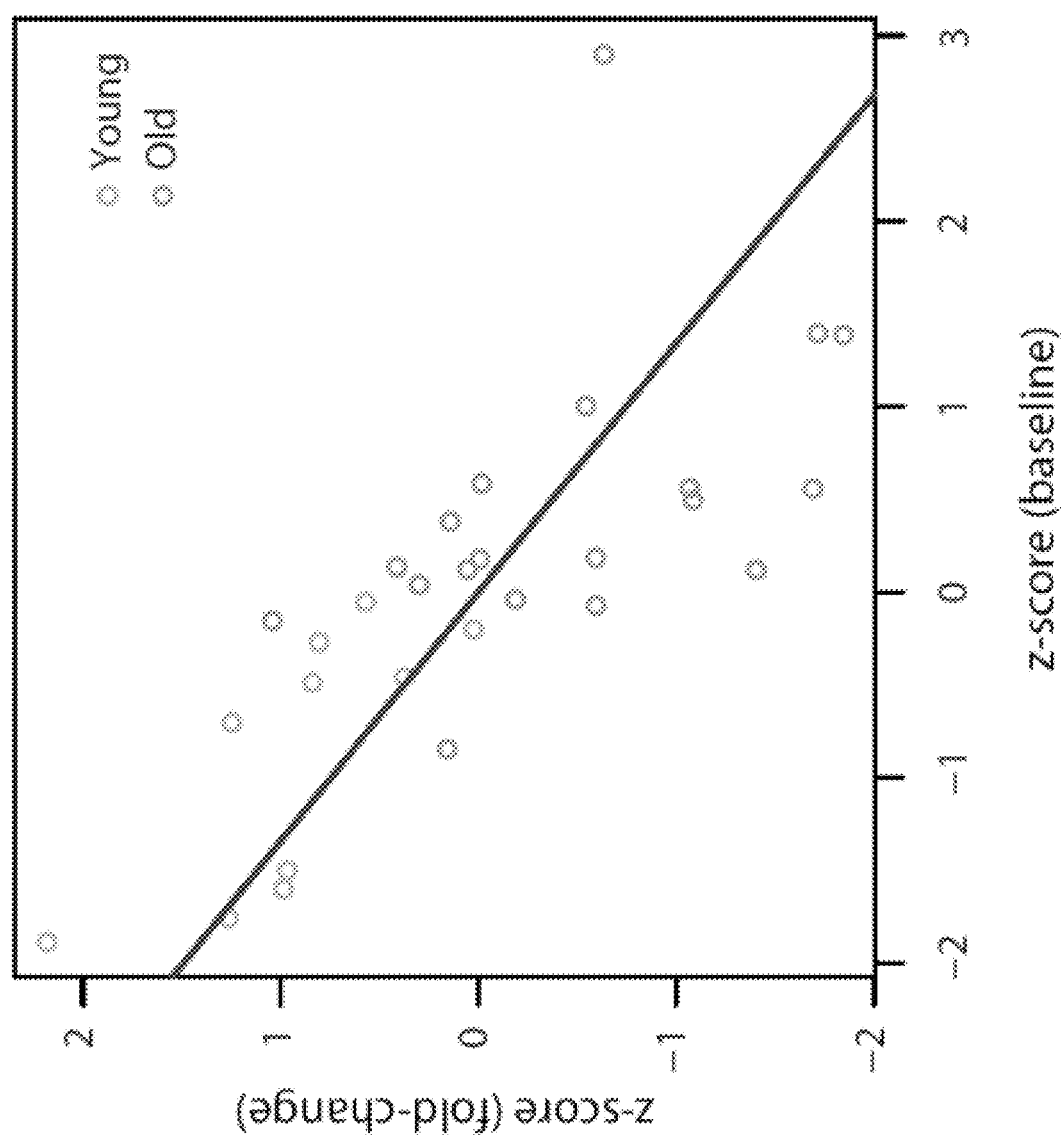
Figure 6C:
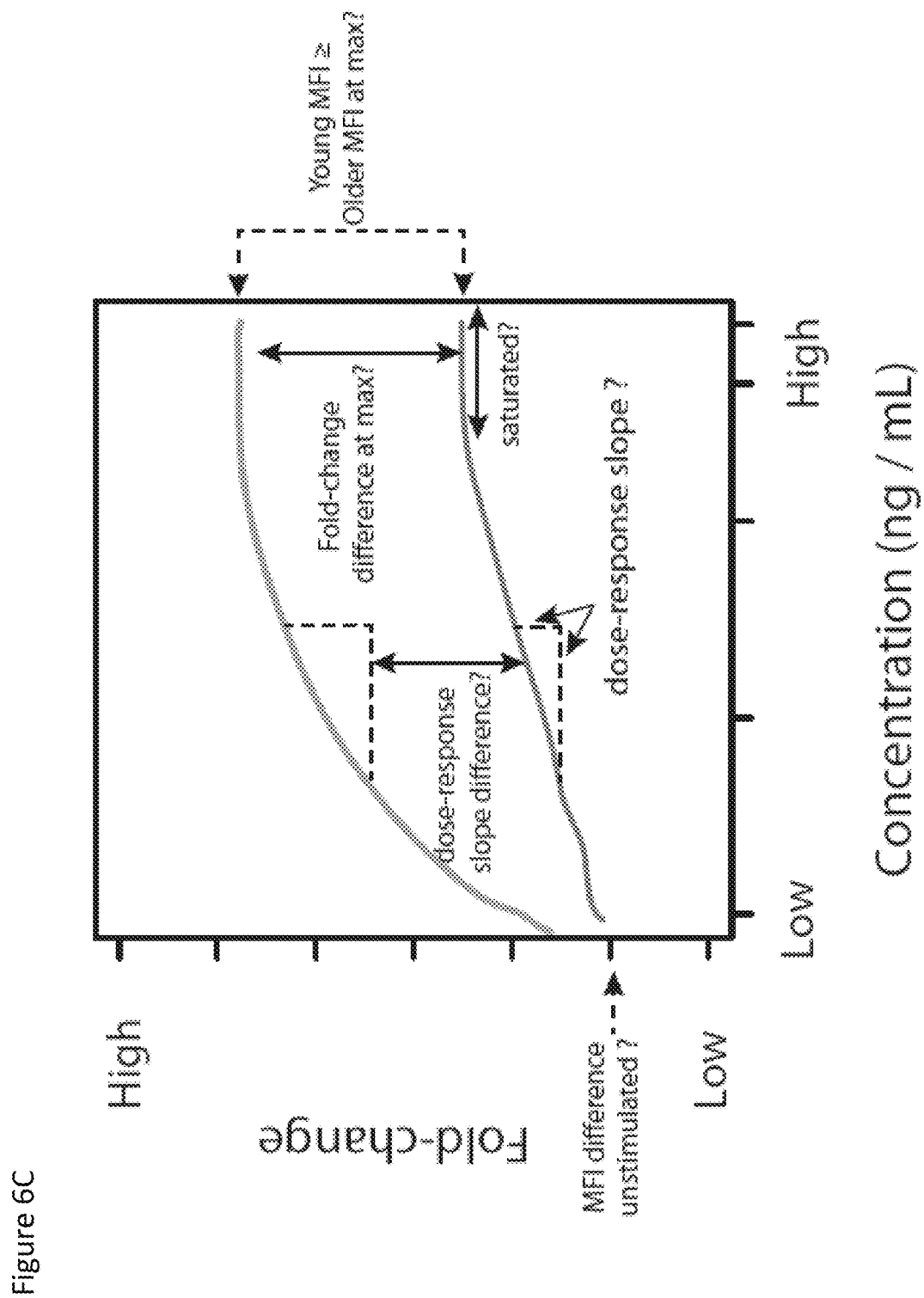

FIGS. 6A-C: Reduced responses to cytokine stimulation are primarily due to increased basal levels of phosphorylated STAT proteins and to alterations in response potential of IL6 and IFNa pathways. (A) Top: Four model classes which may yield the observed unresponsive cells phenotype: (1) successful adaptation to increased background abundance of cytokines, (2) a resistance defect in the signaling machinery of cells from older individuals, (3) an increase in baseline pSTAT levels, which may yield a reduced fold-change response to stimulation by exhausting finite quantities of protein to phosphorylate (4) a combination of both baseline and resistance defect factors. Bottom: Each age-associated cytokine responses deficiencies is classified into one of the four models using a decision tree. No adaptation is observed. Only the monocyte stimulations could be classified solely as a resistance defect. The rest all showed a significant elevation in the older individuals' baseline pSTAT levels, with IL6 and IFNa also showing defects in resistance pathways. (B) Inverse relationship between normalized baseline phosphoprotein abundance of pSTAT1 in CDS cells (X-axis) and normalized fold-change response to stimulation by IFNa (Y-axis). Older individuals show a higher baseline level of pSTAT1 with a decreased response. (C) A cartoon model illustrating the queries used to discriminate between the different models of immune cells unresponsiveness.

Figure 7:
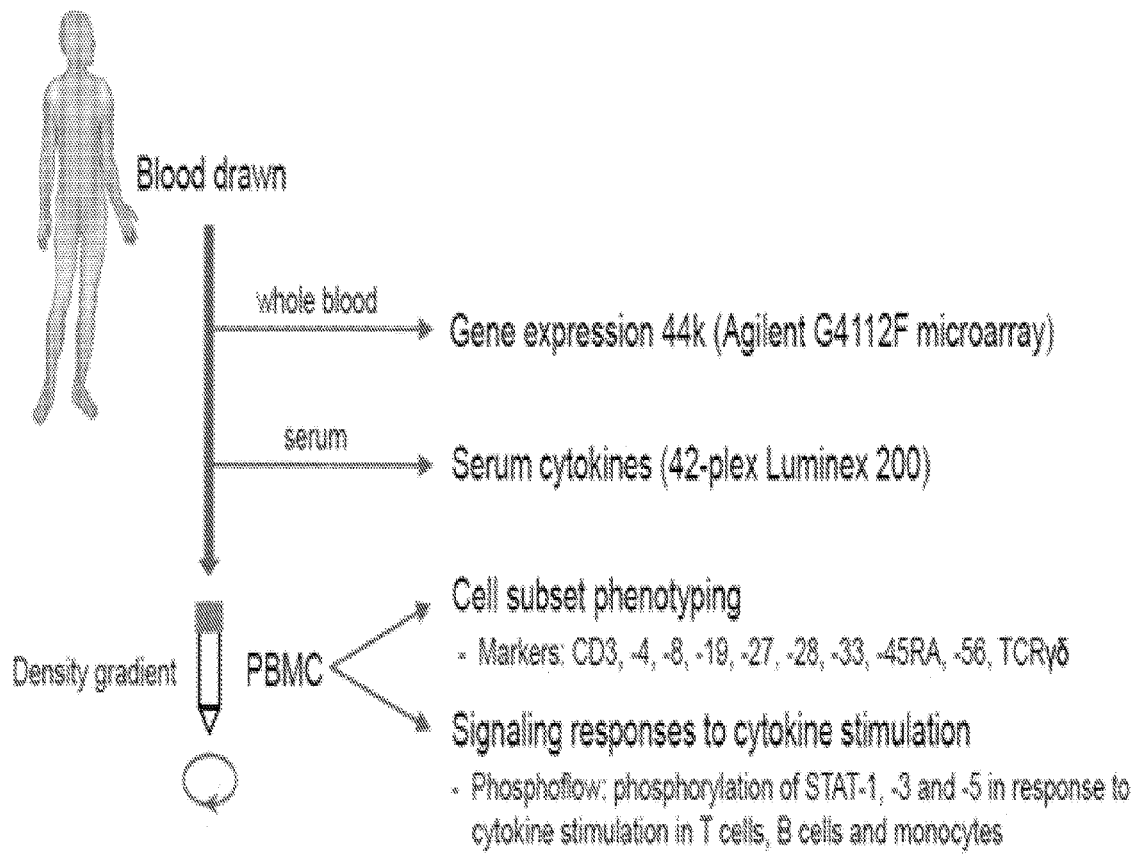
Figure 8A:
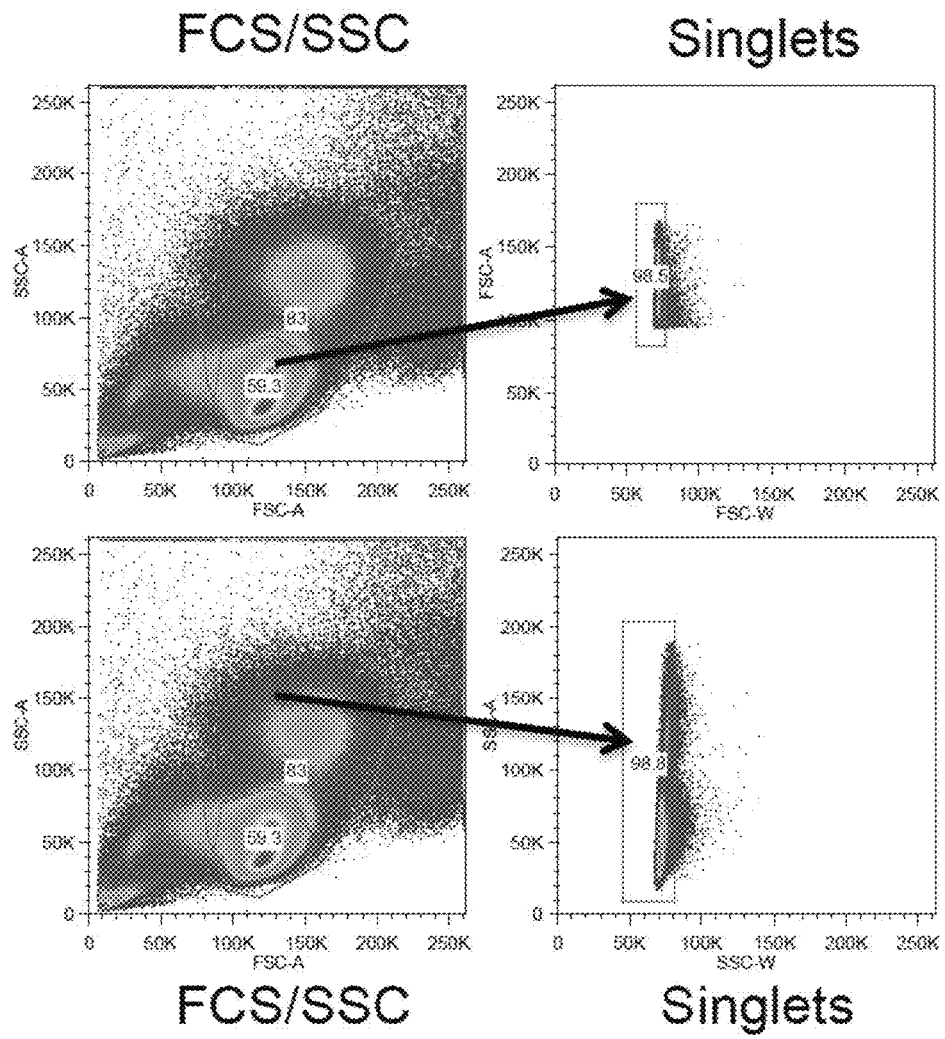
Figure 8B:
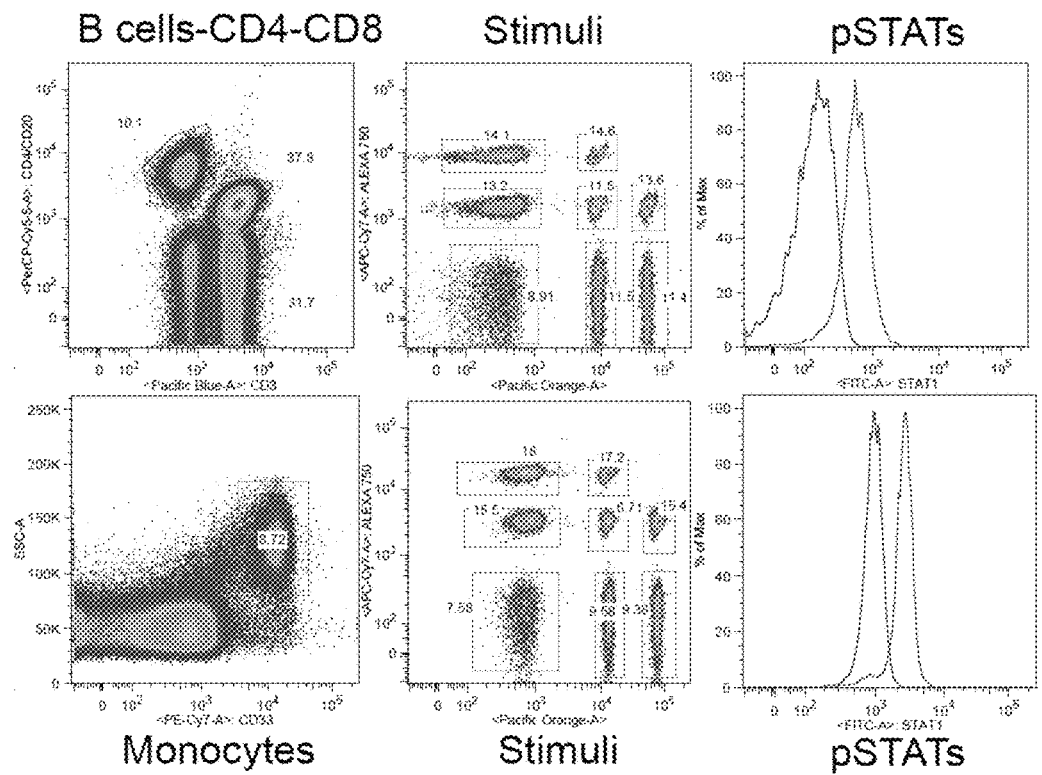
Figure 10A:
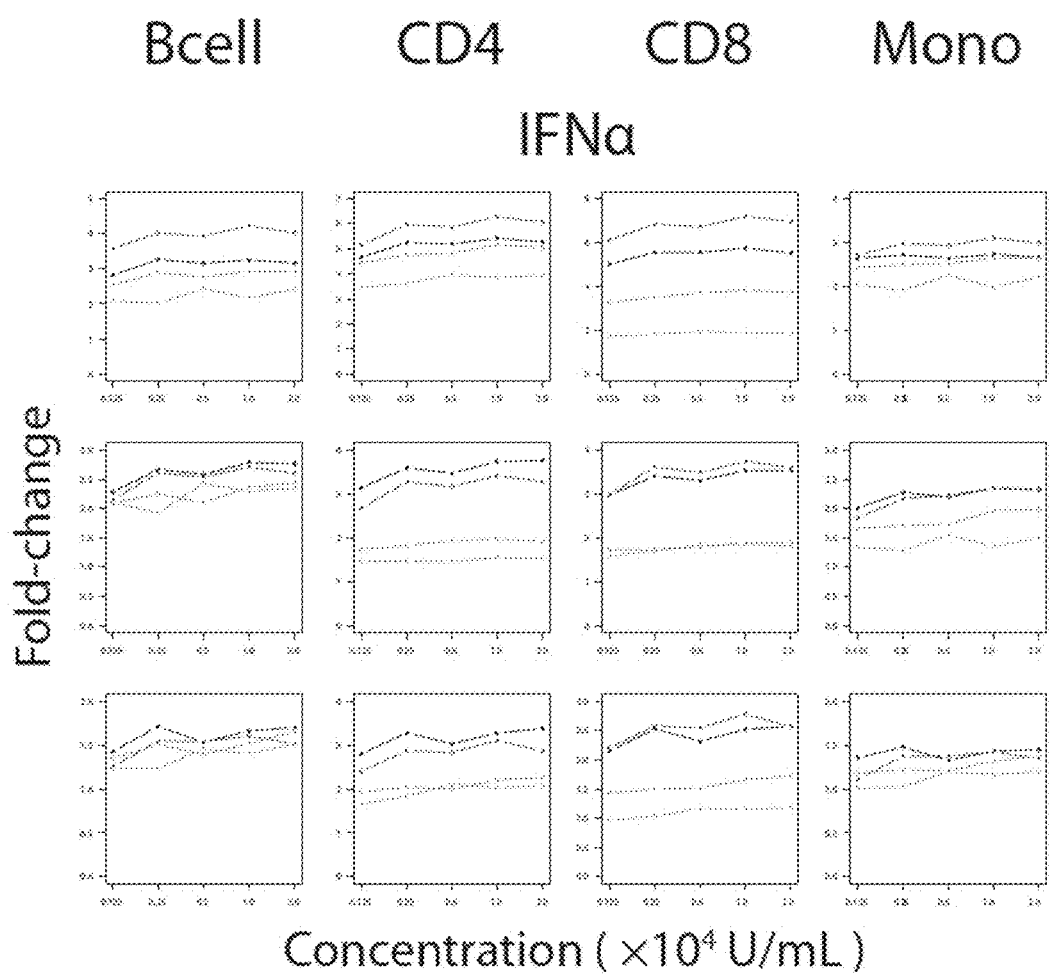
Figure 10B:
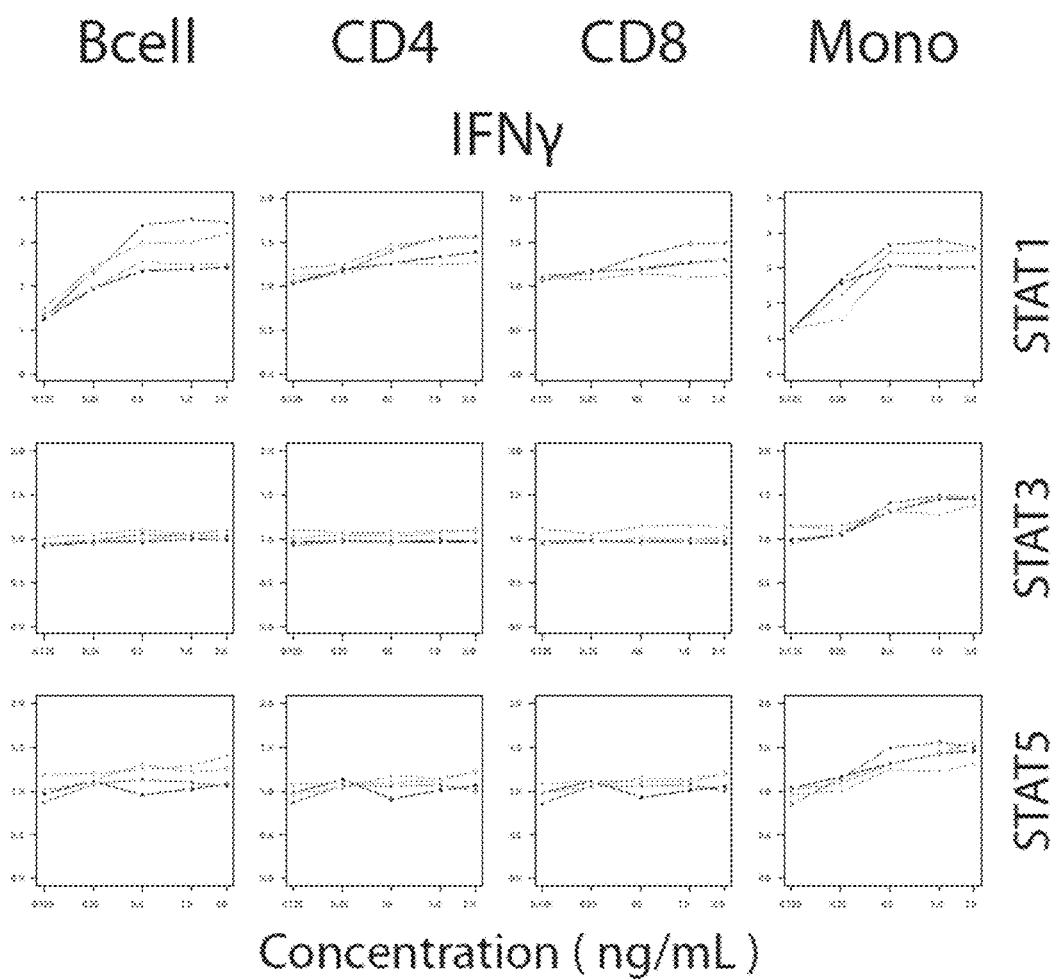
Figure 10C:
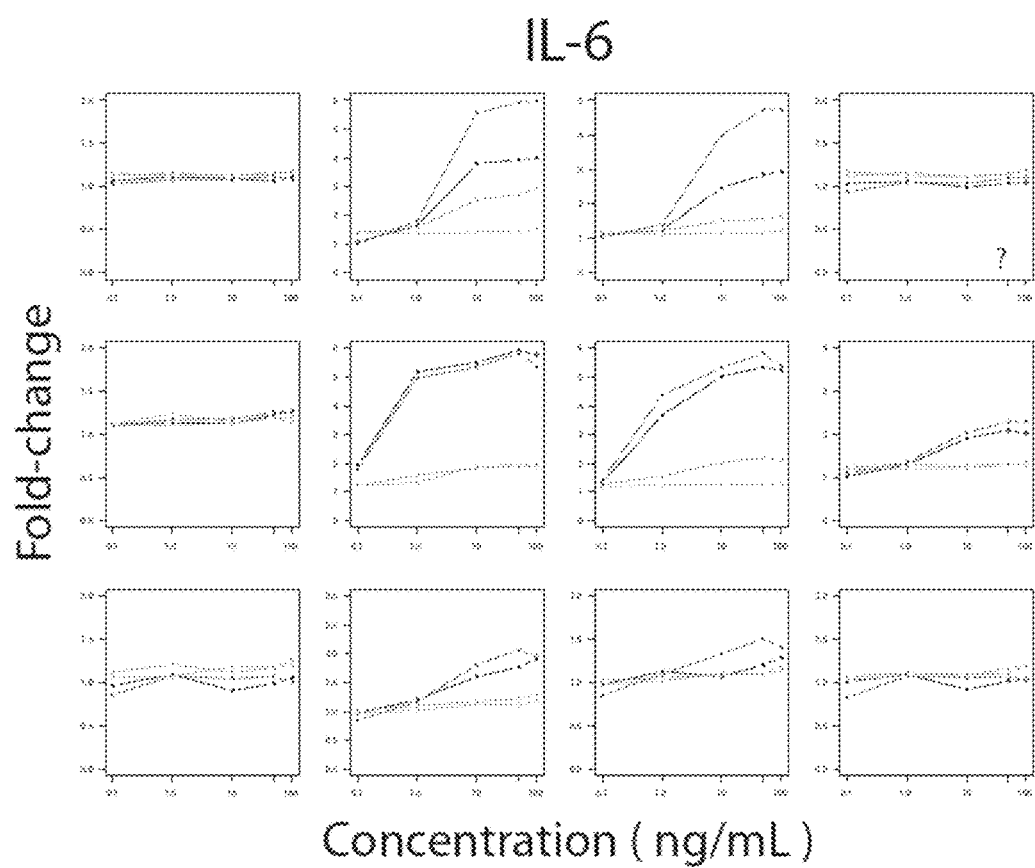
Figure 10D:
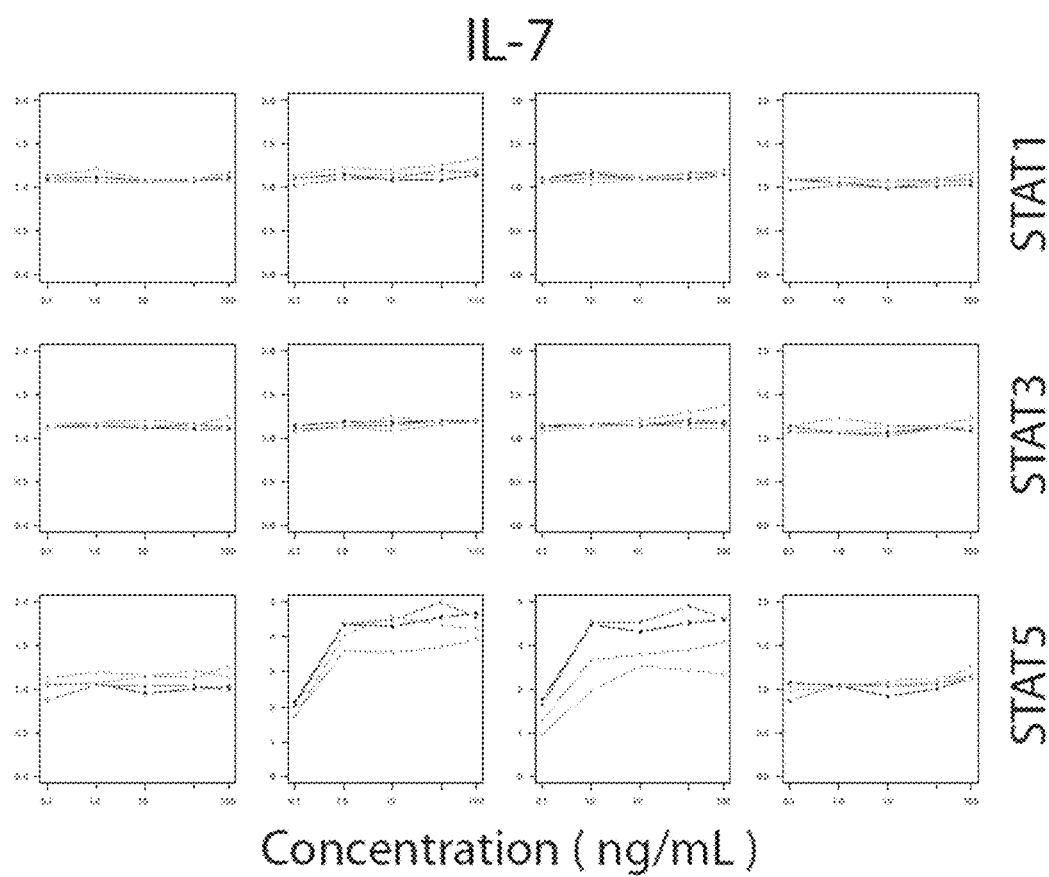
Figure 10E:
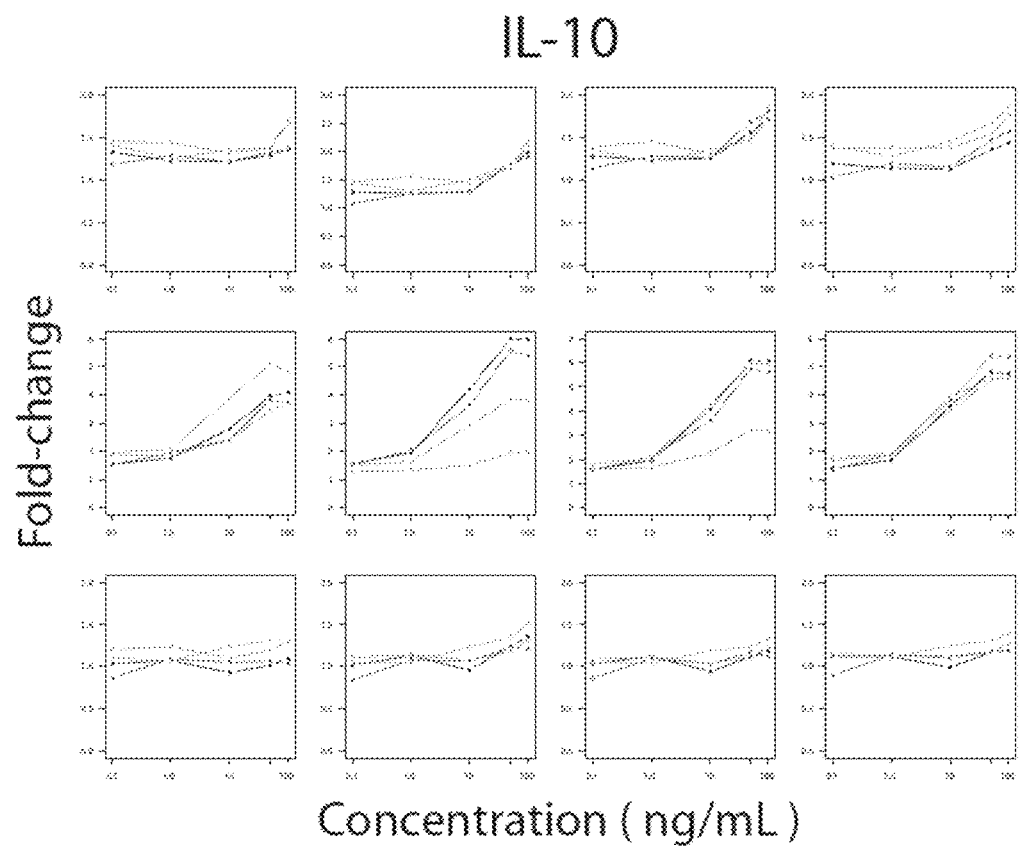
Figure 10F:
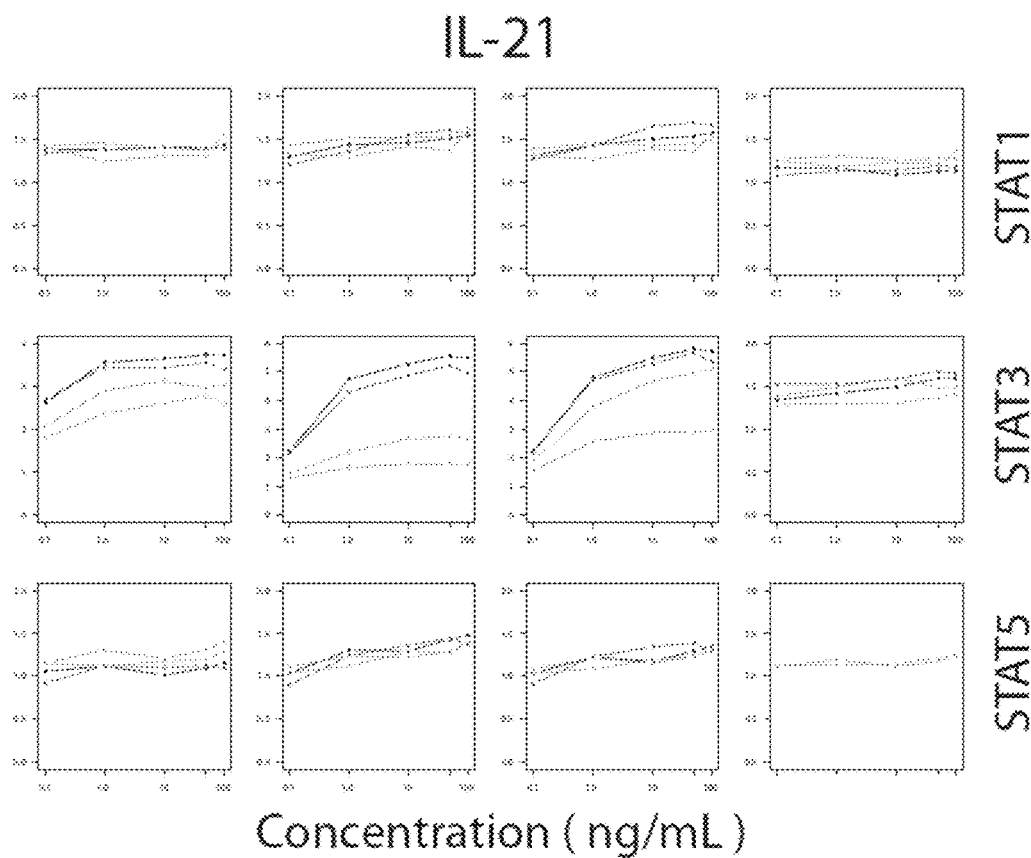

FIG. 7: Study schematic design—'One stop shop' multi-level biological analysis of blood from subjects of different age groups & gender FIGS. 8A-8B: Immune cell subset gating scheme.

FIGS. 9A-9E: Number of measurements called significantly associated with age as a function of false discovery rate. Gene expression studies focused primarily on the immune and aging associated 2863 genes on the array which are measured by 4364 probes.

FIGS. 10A-10F: Reduced cellular response in the elderly is not concentration dependent. Shown are all dose-response curves for the 72 assays performed between young (grey) and old (cyan).

Figure 11:
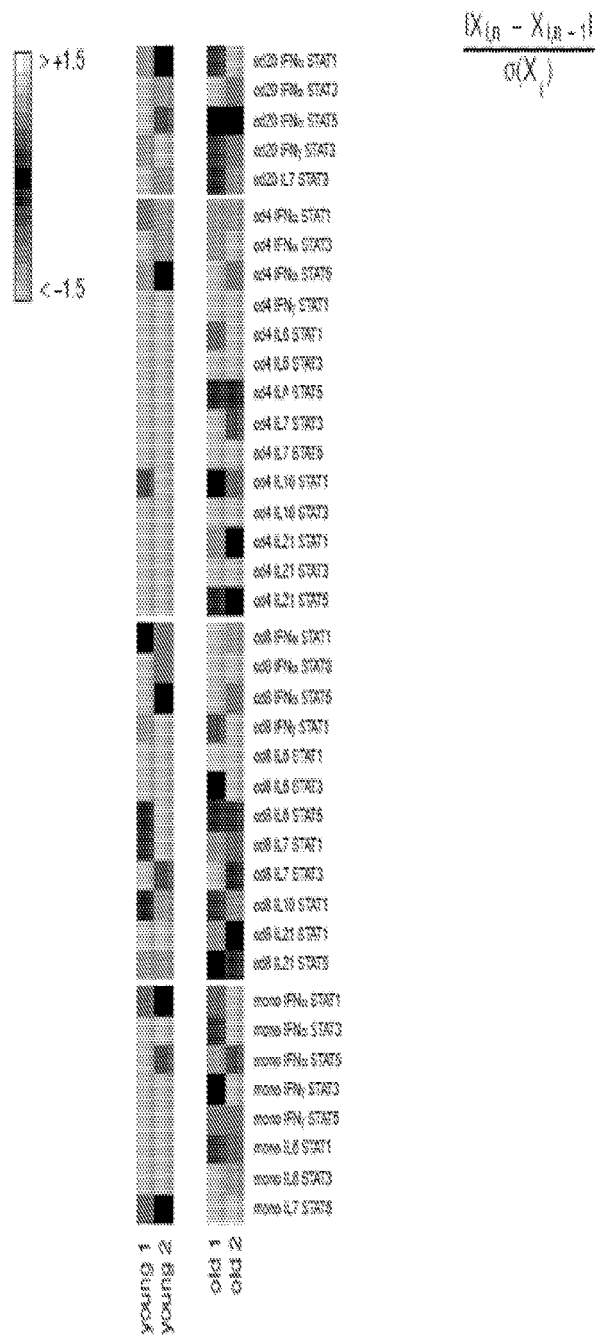

FIG. 11: The majority of age-associated cytokine responses reach saturation in both young and older subjects at the highest concentration level. The standard deviation of the two last points in the dose response curve was calculated and visualized in a heatmap format. Very few of the assays are still changing significantly. Shown are all assays in which a foldchange response 2:2 is observed in at least one concentration in one or more subjects.

Figure 12:
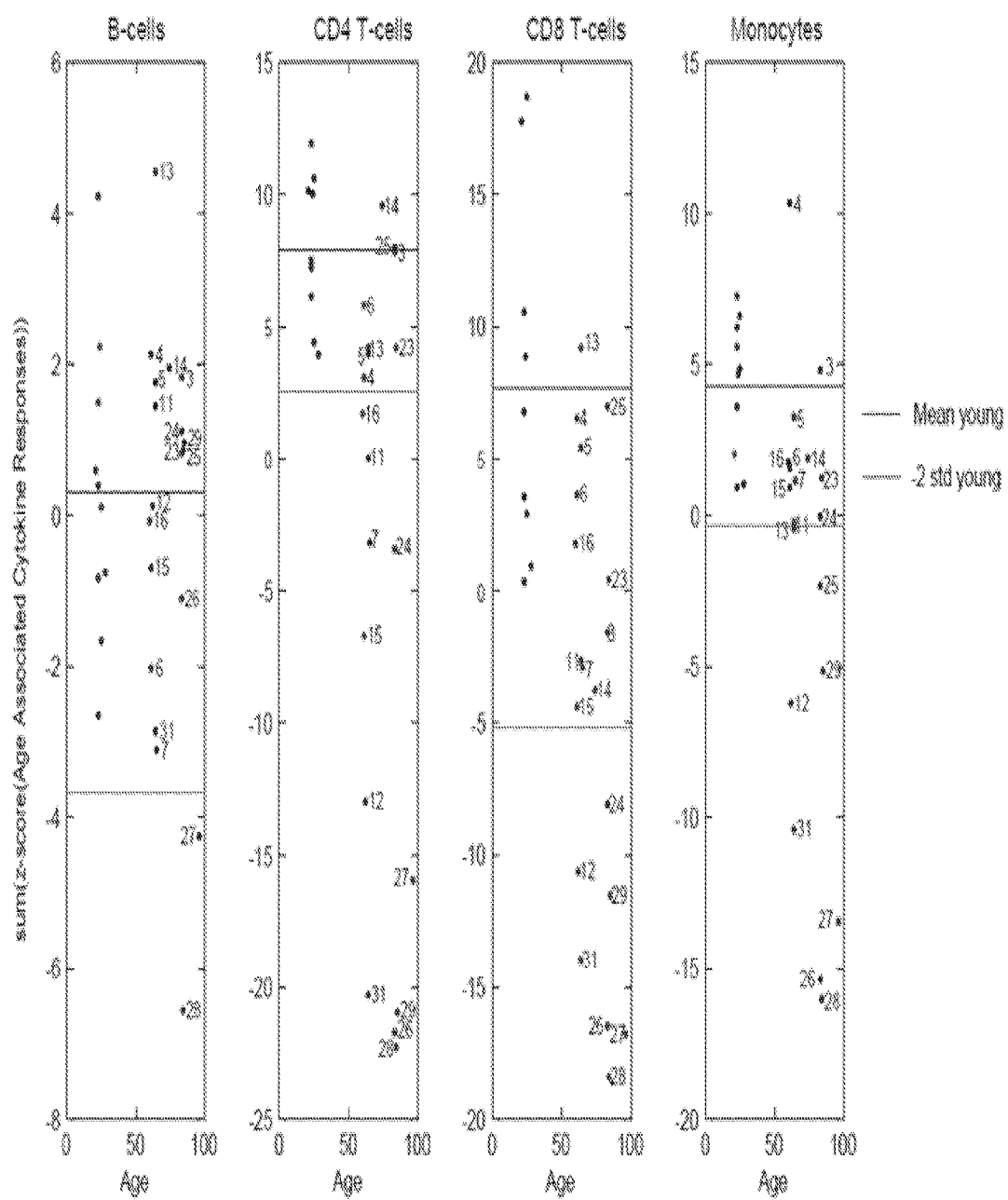

FIG. 12: Cytokine stimulation responses by cell-type used to define CR and CNR. Sum of z-score normalized age-associated cytokine stimulation responses by cell-type. Dashed black line is the average of the young subjects. Dashed red line is 2 standard deviations from the young average. The IDs of older subject subjects are listed for each cell-type.

Figure 13:
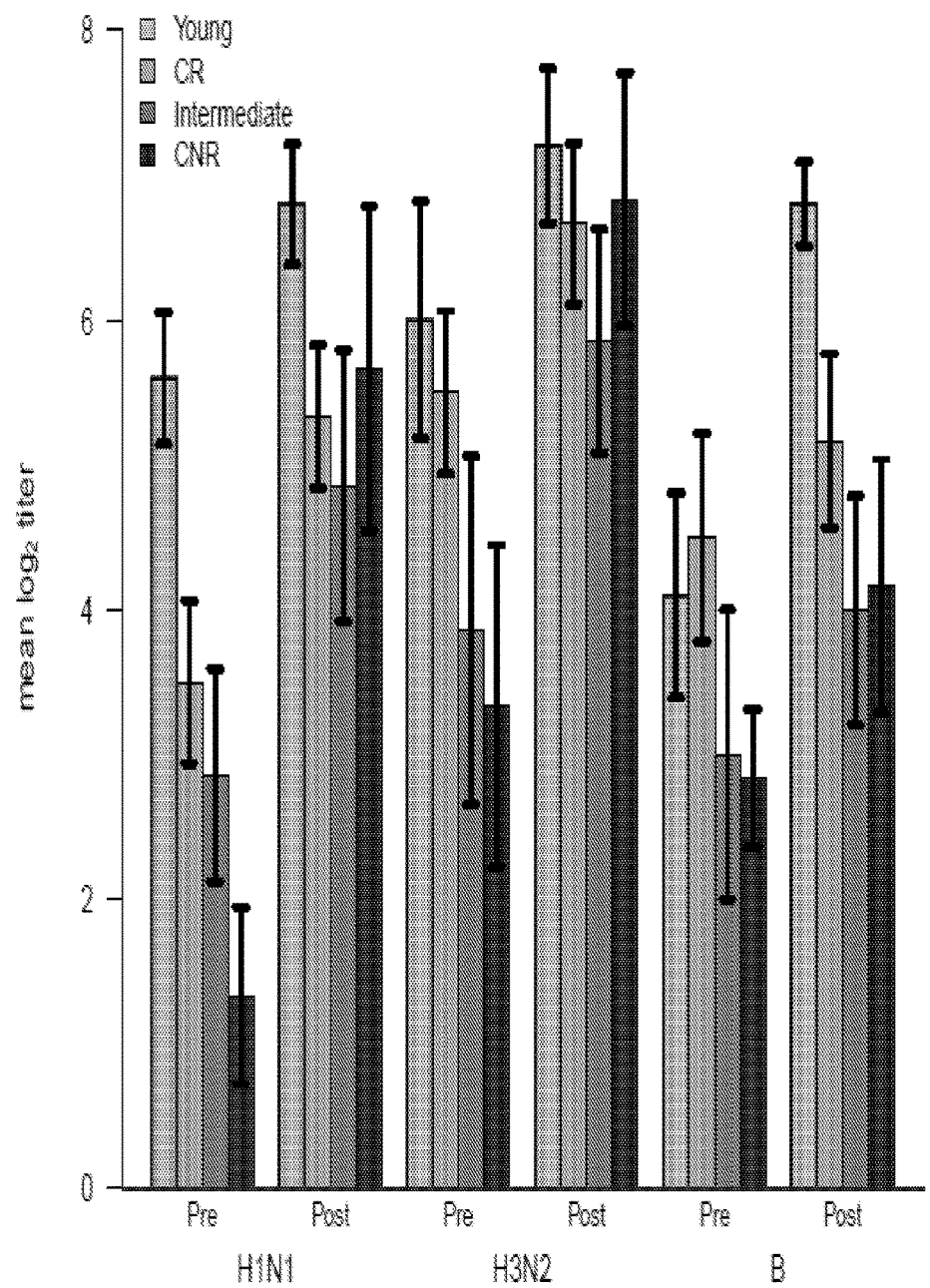

FIG. 13: HAI titers grouped by cytokine responses. Titer levels pre and post vaccine grouped by response category and strain in vaccine. Seroprotection is clinically defined as a value of −5 on this scale and seroconversion as a four-fold of higher change.

Figure 14:
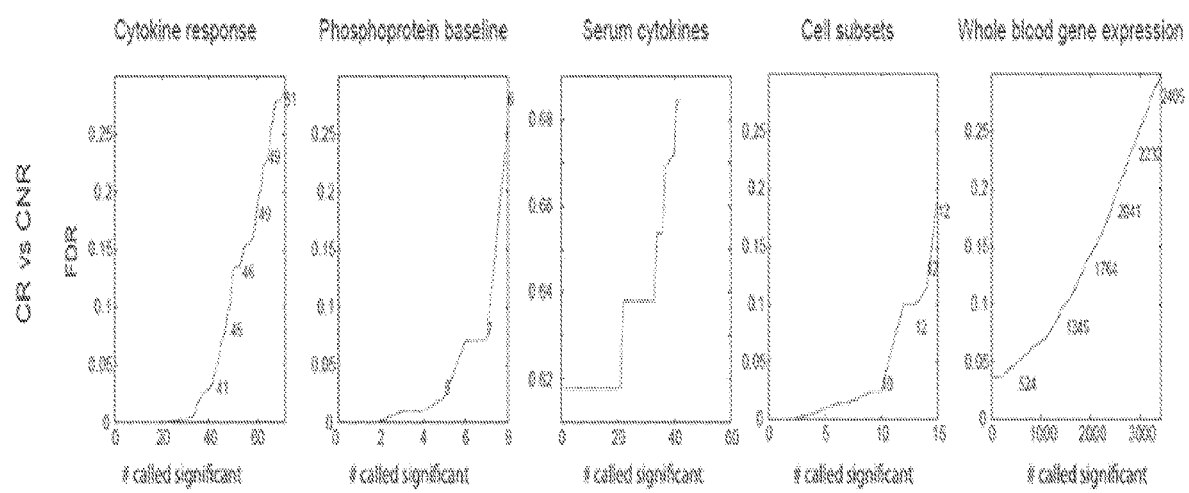

FIG. 14: Number of measurements called significantly different between CR and CNR as a function of false discovery rate.

Figure 15:
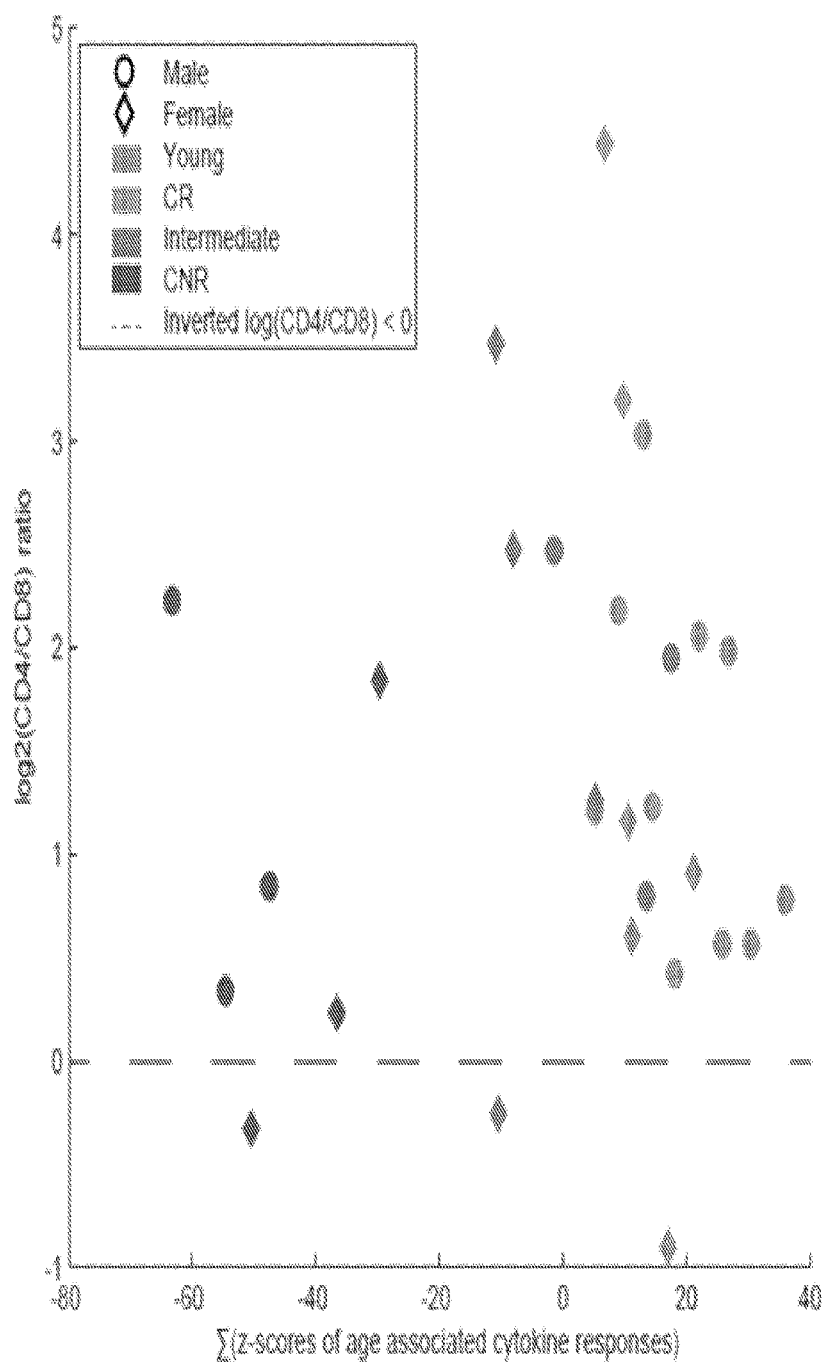

FIG. 15: The "Immune Risk Profile" of inverted CD4/CD8 ($<1$) ratio is not age specific and is highly variable.

Though correlated, an inverted CD4/CD8 ratio is not specific or required for systemic impairments in cytokine responses. Shown is the ratio of CD4 to CDS frequency as a function of the sum of all age-associated cytokine response assays. Young, CR, CNR and Intermediates are colored by their cytokine response class in year 1 in orange, green, purple or blue respectively.

Figure 16:
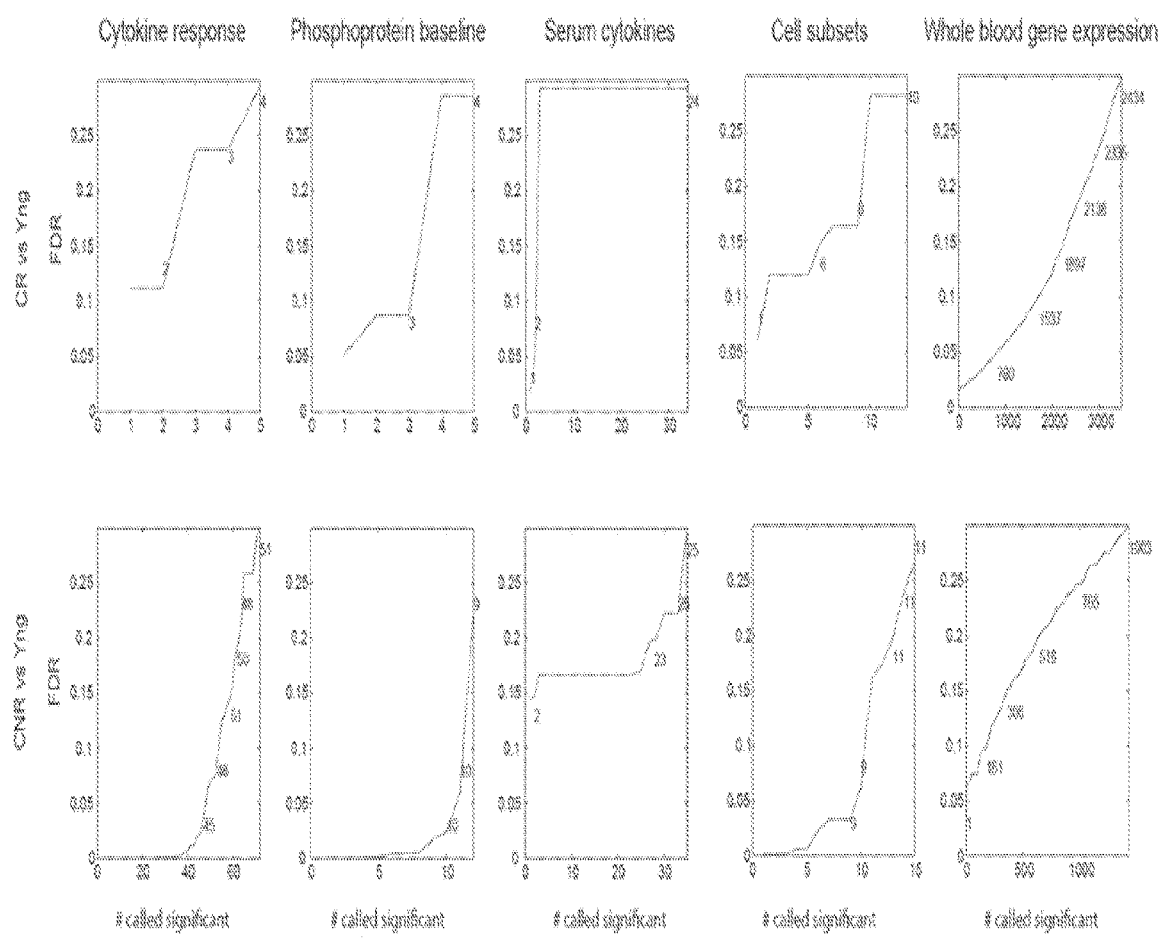

FIG. 16: Number of measurements called significantly different between CR and the young and CNR and the young as a function of false discovery rate.

Figure 17:
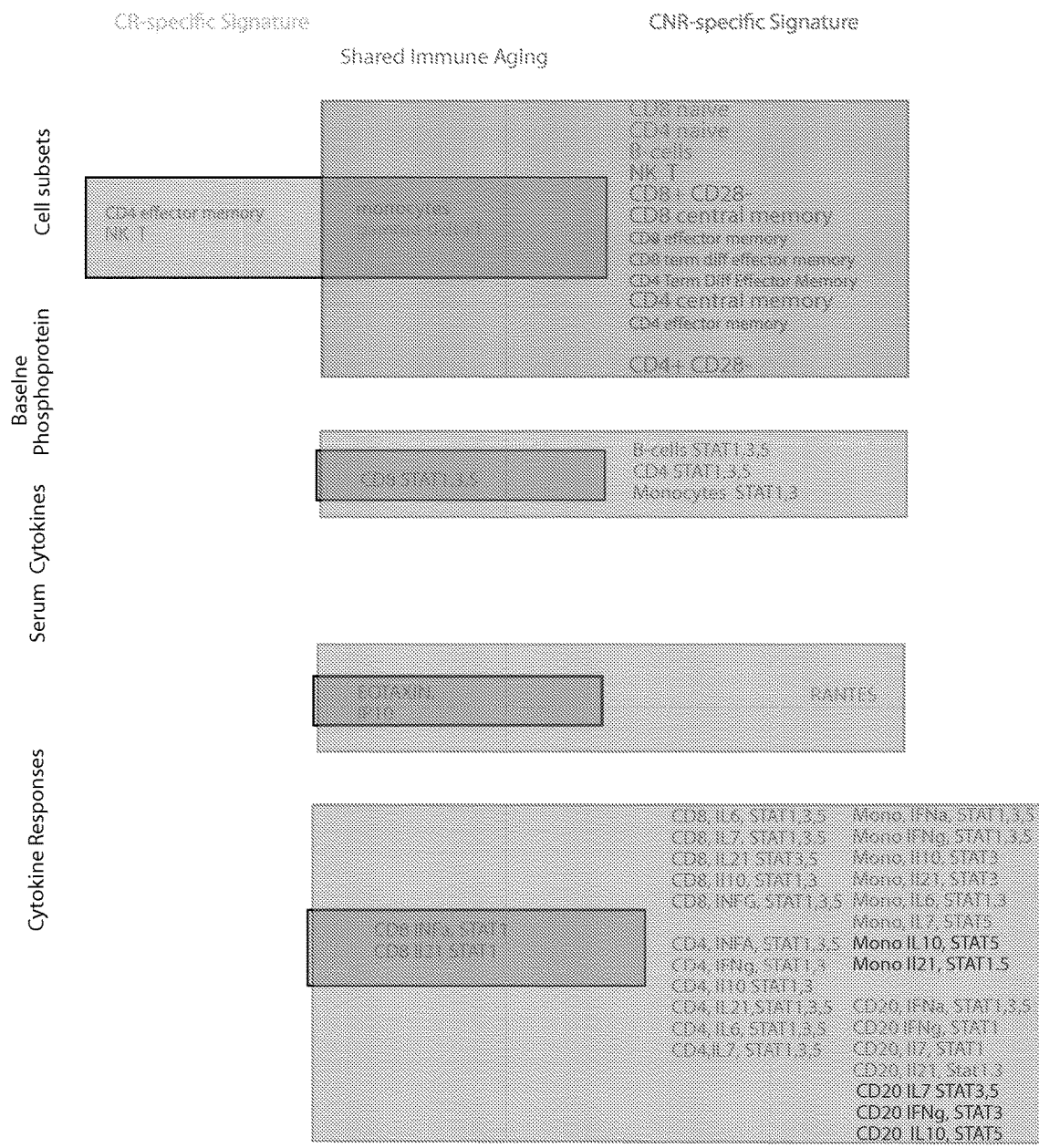
Figure 18A:
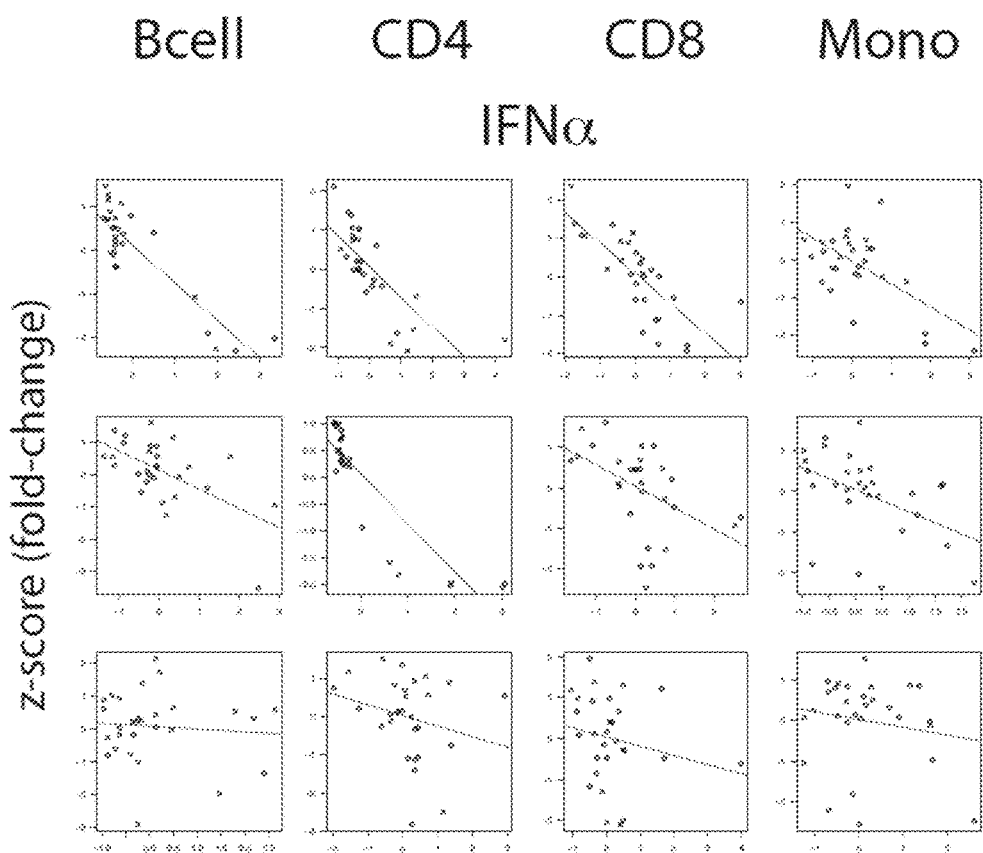
Figure 18B:
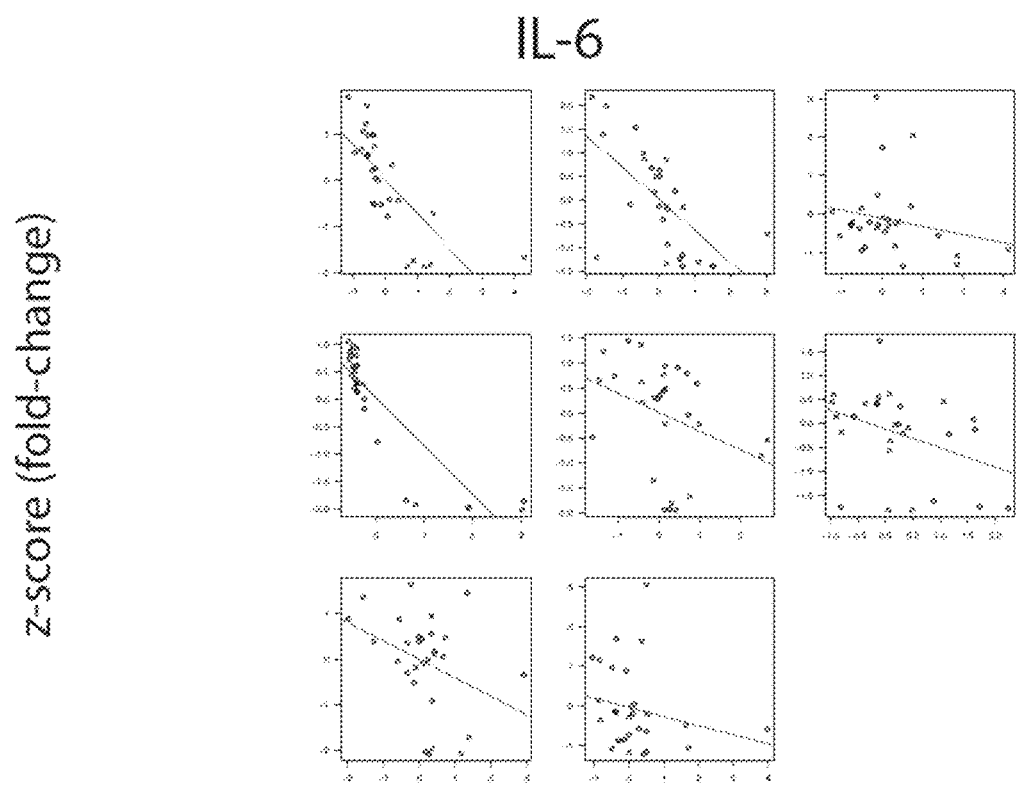
Figure 18C:
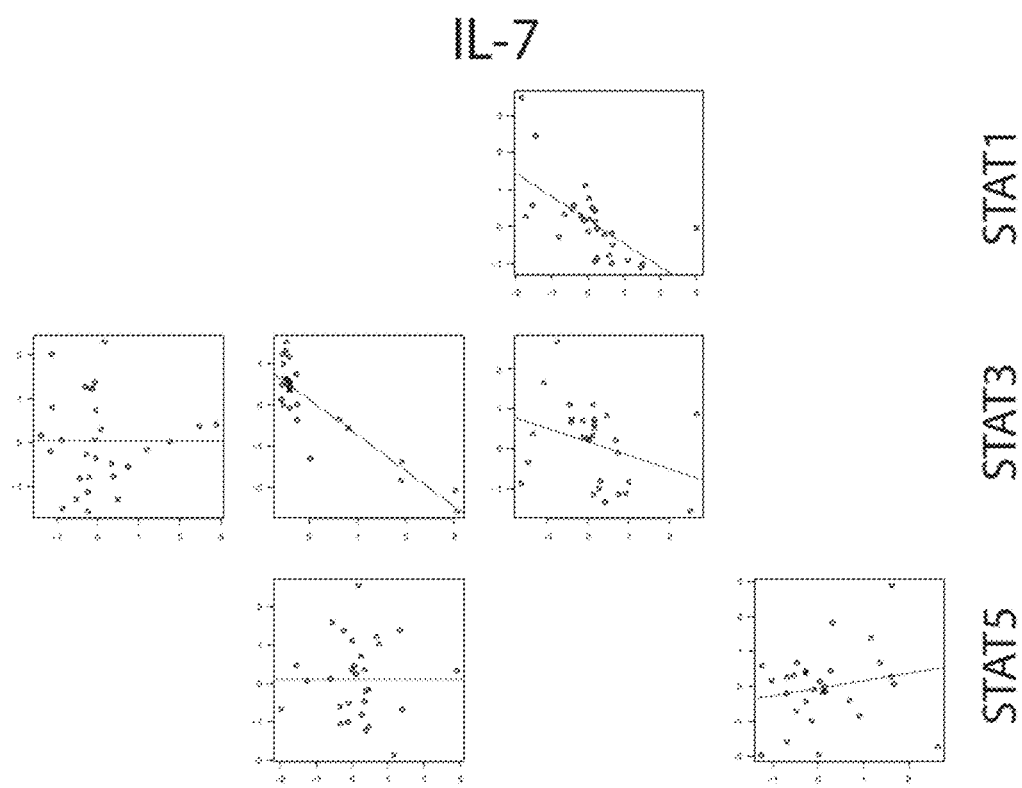
Figure 18D:
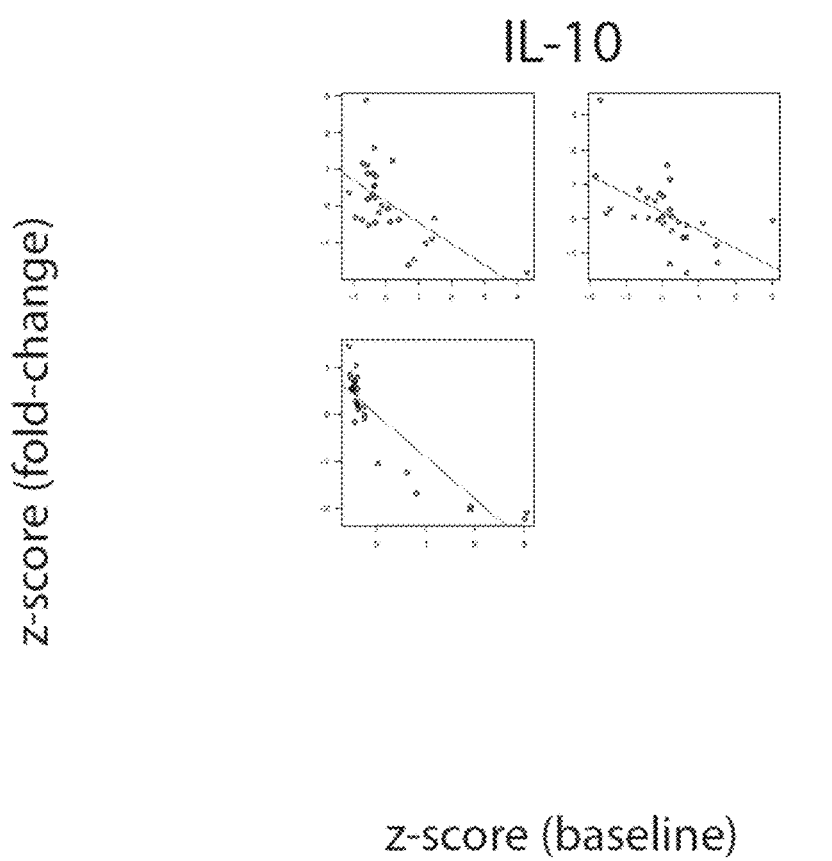
Figure 18E:
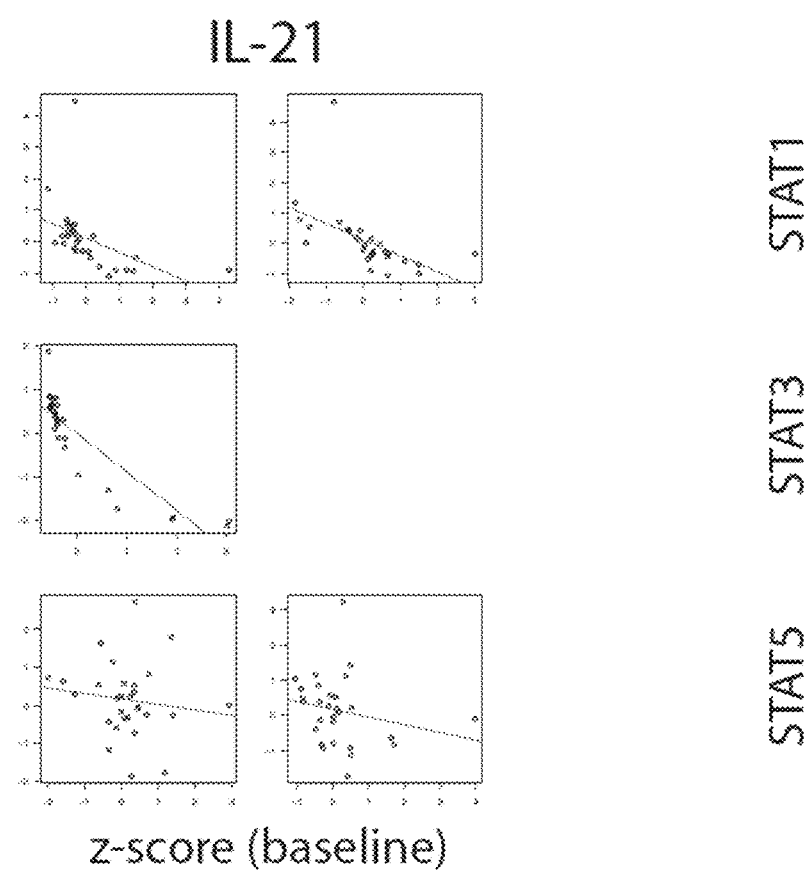

FIG. 17: Detailed classification of age-associated changes by cytokine response. Venn diagram illustrating the identified markers for each of the CR and CNR specific signatures, as well as those changes that occur, independent of cytokine responses, with age. For gene expression and statistics, see Table S7-S9.

FIGS. 18A-18E: An Inverse relationship between normalized baseline phosphoprotein abundance and fold-change. Shown are only those 39 assays for which an age-associated difference was detected in the data. Normalized Fold-change response on the Y axis, normalized baseline on the X.

Figure 19:
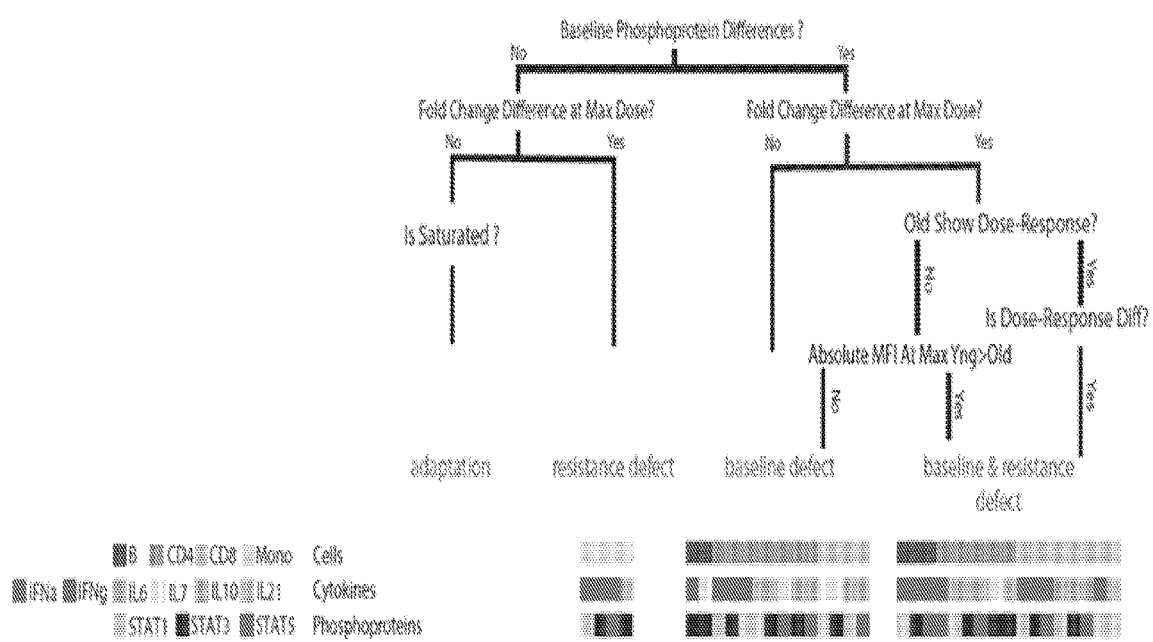

FIG. 19: Classification of cytokine response deficiency by cause. A decision tree over the cytokine response fixed dose and dose-response assays can discriminate between the different models of immune cells unresponsiveness. Shown are the decision tree classification for all age-associated cytokine responses as identified from the entire study population. No adaptation is observed. Only the monocyte stimulations could be classified solely as a resistance defect. The rest all showed a significant elevation in the older subjects' baseline pSTAT levels, with IL6 and IFNa also showing defects in resistance pathways.

Table S1: Study design demographics

Table S2: Significant age-associated measurement from regression analysis of all subjects.

Table S3: GEO Datasets used in meta-analysis of aging gene expression data. Table lists all GSM data ids used for comparisons.

Table S4: Genes found to be significantly associated with age in the meta-analysis.

Table S5: Network cluster membership.

Table S6: Cytokine response modules feature weights

Table S7: Significant differences between CR and CNR.

Table S8: Medication category listing for CR and CNR.

Table S9: Age-associated differences common to both CR and CNR,

Table S10: CR-specific measurements.

Table S11: CNR-specific measurements.

Table S12: Dose-response classification results.

Definitions

The practice of the present invention may employ conventional techniques of chemistry, molecular biology, recombinant DNA, microbiology, cell biology, immunology and biochemistry, which are within the capabilities of a person of ordinary skill in the art. Such techniques are fully explained in the literature. For definitions, terms of art and standard methods known in the art, see, for example, Sambrook and Russell 'Molecular Cloning: A Laboratory Manual', Cold Spring Harbor Laboratory Press (2001); 'Current Protocols in Molecular Biology', John Wiley & Sons (2007); William Paul 'Fundamental Immunology', Lippincott Williams & Wilkins (1999); M. J. Gait 'Oligonucleotide Synthesis: A Practical Approach', Oxford University Press (1984); R. Ian Freshney "Culture of Animal Cells: A Manual of Basic Technique', Wiley-Liss (2000); 'Current Protocols in Microbiology', John Wiley & Sons (2007); 'Current Protocols in Cell Biology', John Wiley & Sons (2007); Wilson & Walker 'Principles and Techniques of Practical Biochemistry', Cambridge University Press (2000); Roe, Crabtree, & Kahn 'DNA Isolation and Sequencing: Essential Techniques', John Wiley & Sons (1996); D. Lilley & Dahlberg 'Methods of Enzymology: DNA Structure Part A: Synthesis and Physical Analysis of DNA Methods in Enzymology', Academic Press (1992); Harlow & Lane 'Using Antibodies: A Laboratory Manual: Portable Protocol No. I', Cold Spring Harbor Laboratory Press (1999); Harlow & Lane 'Antibodies: A Laboratory Manual', Cold Spring Harbor Laboratory Press (1988); Roskams & Rodgers 'Lab Ref: A Handbook of Recipes, Reagents, and Other Reference Tools for Use at the Bench', Cold Spring Harbor Laboratory Press (2002); Alon U (2007). An introduction to systems biology: design principles of biological circuits (Boca Raton, Fla.: Chapman & Hall/CRC). Each of these general texts is herein incorporated by reference.

Unless defined otherwise, all technical and scientific terms used herein have the same meaning as commonly understood by a person of ordinary skill in the art to which this invention belongs. The following definitions are intended to also include their various grammatical forms, where applicable.

The term "impaired immune function", as used herein, refers to any reduction in immune function in an individual, as compared to a fully healthy individual. Individuals with an impaired immune function are readily identifiable by substantially increased abundance of CD8+ CD28– cells or more broadly by reduced cytokine responses, increased baseline phosphoprotein levels and other co-occurring measures.

The term "older individual", "elderly individual" or "elderly", as used herein, defines a human being who is about 60 years of age or older.

The term"young individual", as used herein, defines a human being between 18 and 30 years of age.

The term "activation", as used herein, refers to a physiological condition upon exposure to a substance, allergen, drug, protein, chemical, or other stimulus, or upon removal of a substance, allergen, drug, protein, chemical or other stimulus.

The terms "active immunization", "immunization", and "vaccination", as used herein, refer to the acquisition of immunologic memory and long-term protection against recurring diseases through antibody production in response to administration of an immunogenic antigen.

The term "cytometry", as used herein, refers to a process in which physical and/or chemical characteristics of single cells, or by extension, of other biological or nonbiological particles in roughly the same size or stage, are measured. In "flow cytometry", the measurements are made as the cells or particles pass through the measuring apparatus (flow cytometer) in a fluid stream. A cell sorter, or flow sorter, is a flow cytometer that uses electrical and/or mechanical means to divert and collect cells (or other small particles) with measured characteristis that fall within a user-selected range of values.

Immune system profiling and data output. In order to identify impairment of immune function in an individual, an immune system profile is established from measurements of immune cell subset frequencies, gene expression, cytokine and chemokine levels, and signaling responses to stimulation with cytokines. Following data analysis, the identified immune system profile is transformed into information for graphical display or output to a computer-readable medium, computer or computer network.

DETAILED DESCRIPTION

Embodiments of the present invention provide diagnostic markers of immunosenescence and methods of identifying individuals with impaired immune function based on a combination of such markers obtained from various analyses, primarily from blood, testing immune function including the analysis of immune cell subset frequencies, gene expression, cytokine and chemokine levels, and signaling responses to stimulation with cytokines ('cytokine response'). Particular combinations of markers can predict with high accuracy whether an individual will respond to active vaccination and become protected against recurring diseases.

Cells of the Immune System

White blood cells or leukocytes are cells of the immune system that defend the human body against infectious disease and foreign materials and are often characterized as granulocytes or agranulocytes, depending on the presence or absence of granules. There are various types of leukocytes, which are all produced in the bone marrow and derived from (multipotent) hematopoietic stem cells. Leukocytes are found throughout the body, including the blood and lymphatic system. Granulocytes encompass neutrophils, basophils, and eosinophils, while agranulocytes include lymphocytes, monocytes and macrophages.

B lymphocytes ("B cells") and T (thymus) lymphocytes ("T cells") constitute the two major classes of lymphocytes and play crucial roles in the immune response; hereby provide B cells a 'humoral' immune response through secreted antibodies, while T cells provide a cell-mediated immune response through the activation of various cells of the immune systems such as macrophages, natural killer cells, cytotoxic T cells, cytokines etc.

B cells are precursors of antibody-secreting cells and, upon activation, differentiate either into antibody-secreting cells for a primary response via secreted antibodies upon a first exposure to an antigen or into memory B cells which provide a strong antibody response upon a second exposure to that same antigen.

T cells can function as (i) effector cells in cell-mediated responses, as (ii) helper cells in both humoral and cell-mediated immune responses or as (iii) regulatory cells. Typical functions of effector T cells are, for example, the lysis of pathogen-infected cells or the lysis of neoplastic cells, while typical functions of helper T cells are aiding in the production of specific antibodies by B cells; (immune) regulatory T cells, in contrast, are able to suppress immune responses.

The Innate Immune System and Immune Response

Pathogens such as viruses cause an inflammatory reaction in the body through chemokine-mediated recruitment of leukocytes to the site of infection. Neutrophils are attracted first, followed by monocytes, macrophages, natural killer cells, cytokines as well as other innate immune cells. Those innate immune cells then provide critical signals for dendritic cells that help to initiate a T cell-mediated, antigen-dependent or adaptive immune.

Cytokines are peptides, proteins and glycoproteins that are secreted by cells of the immune system and, as signaling molecules, carry signals between cells. Based on their function, cytokines can be classified as lymphokines, interleukins and chemokines. They are often categorized into a) the IL-2 subfamily, b) the interferon (IFN) subfamily and c) the IL-10 subfamily.

T Cell-Mediated, Antigen-Dependent or Adaptive Immune Response

Secondary lymphoid tissues are the focal point of an adaptive immune response, because there naïve T cells are presented with and activated through physical contact with mature dendritic cells that present specific foreign antigen peptide/MHC complexes.

The transition from innate to adaptive phases of the immune response involves antigen uptake by antigen-presenting cells, particularly by dendritic cells. Dendritic cells support clonal expansion and differentiation of activated, antigen-specific T cells by providing proliferative information through foreign antigen peptide/MHC complexes and possibly through costimulatory ligands such as CD80 and CD86, which are ligands for CD28, an important cell-surface receptor on T cells that helps to initiate mitogenic signaling in naïve T cells.

After naïve helper T cells (CD4 T cells) have become activated and begin to divide and differentiate according to signals from dendritic cells and other co-stimulatory ligands, at least three subsets of effector CD4 T cells ($T_{H1}$, $T_{H2}$ and $T_{H17}$) emerge with specialized homing properties and functions in the adaptive immune response.

Immunosenescence

Defects in both the innate and adaptive immune system have been described and include changes in immune cell subsets abundance and relative frequencies, altered hematopoiesis, impairments in antigen presentation, decreased B cell as well as T cell proliferation, a reduced TCR repertoire and defects in antibody production (Weiskopf et al., 2009). Ultimately these alterations result in a sharp decline in the response to new and persisting antigens and are referred to in the aggregate as immunosenescence. Thus it is not surprising that infectious diseases are one of the major causes of mortality in those over the age of 65 and that protective vaccination of the elderly is more difficult to establish than in younger individuals (Goodwin et al., 2006).

Signal Transducers and Activator of Transcription (STAT) Proteins

The STAT proteins regulate many aspects of cell growth, survival and differentiation. The transcription factors of this family are activated by the Janus Kinase JAK and dysregulation of this pathway is frequently observed in primary tumors and leads to increased angiogenesis, enhanced survival of tumors and immunosuppression.

There are seven STAT proteins, namely STAT1, STAT2, STAT3, STAT4, STAT5A, STAT5B and STAT6. STAT proteins were originally described as latent cytoplasmic transcription factors that require phosphorylation for nuclear retention. The unphosphorylated STAT protein shuttles between cytosol and the nucleus waiting for its activation signal. Once the activated transcription factors reaches the nucleus it binds to a consensus DNA-recognition motif called gamma activated sites (GAS) in the promotor region of cytokine inducible genes and activates transcription of these genes.

Utility of the Invention

While it is well known that the immune response in older individuals decreases with increasing age, no clear causal link has been established. Due to the complexity of the immune system, only a small fraction of the immune system is conventionally investigated which has made it difficult to draw general conclusions about the phenomena observed to date.

Embodiments of the present invention provide methods to identify individuals, particularly older individuals, who look on the outside healthy, but might already be at an increased risk for infection due to an impairment of their immune system, by comprehensively evaluating, primarily from blood specimen, a multitude of biomarkers obtained from various analyses testing immune function including the analysis of immune cell subset frequencies, gene expression, cytokine and chemokine levels, and signaling responses to stimulation with cytokines ('cytokine response'). This provides a full picture readout with wide diagnostic applications to individuals of any age who might be at risk of developing an impaired immune function or already experiencing signs of an impaired immune function. Diagnostic application of these biomarkers to individuals of any age and health status followed by an appropriate treatment, if necessary, may reduce the risk of infection as well as morbidity and increase lifespan.

Embodiments of the present invention provide diagnostic markers of immunosenescence and methods of identifying individuals with impaired immune function based on a combination of such markers obtained from various analyses, primarily from blood, testing immune function including the analysis of immune cell subset frequencies, gene expression, cytokine and chemokine levels, and signaling responses to stimulation with cytokines ('cytokine response'). Particular combinations of markers can predict with high accuracy whether an individual will respond to active vaccination and become protected against recurring diseases Following active vaccination, older individuals often don't develop a fully functioning adaptive immune response, as would be evidenced by a strong antibody production against an introduced immunogen, and, thus, do not obtain the benefits of long-lasting protection against recurring diseases. It is an advantage of the present invention that particular combinations of markers can predict with a very high accuracy whether an individual will respond appropriately to active vaccination and become protected against recurring diseases.

As illustrated in particular embodiments of the present invention, cell cytokine responses are reduced with age and independent from the stimuli dose (see FIGS. 2A-2C and 3A-3B), and correlate with increased cytokine baseline levels (see FIGS. 4A-4B). Poor cytokine response correlates with other immunosenescence phenotypes (see FIGS. 5A-5B). Stratification of older adults by cytokine response yields increased resolution to age dependent changes.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible. In the following, experimental procedures and examples will be described to illustrate parts of the invention.

Experimental Procedures

The following methods and materials were used in the examples that are described further below.

Sample Collection. Peripheral blood samples were obtained from 29 male and female volunteers aged 18-96 (see Table S8 for demographics) at the Stanford Clinical Trials Research Unit as part of an influenza vaccine study. All volunteers were considered to be currently healthy after an evaluation of their medical history and assessment of their vital signs. Females of childbearing potential were tested for pregnancy by a urine sample. Volunteers had no active systemic or serious concurrent illness, no history of immunodeficiency, nor any known or suspected impairment of immunologic function, including clinically significant liver disease, diabetes mellitus treated with insulin, moderate to severe renal disease, blood pressure >150/95 at screening, chronic hepatitis B or C, recent or current use of immunosuppressive medication. In addition, none of the volunteers were recipients or donors of blood or blood products within the past 6 months and 6 weeks respectively nor showed any signs of febrile illness on day of enrollment and baseline blood draw. Informed consent was obtained from all of the subjects enrolled in this study, and the study protocol was approved by the Stanford University Administrative Panels on Human Subjects in Medical Research (IRBs). In total, 120 ml whole blood (~40 mL/visit) whole blood was drawn per subject and processed by standard procedures to PBMC and serum, if needed (see below). All analyses described here were performed from samples drawn on the same visit (visit 1) with the exception of cell-subset phenotyping, which were analyzed from blood drawn 21 days after initial visit following verification that cell-subset frequencies do not alter significantly in that time frame.

Whole Blood Gene Expression. Total RNA was extracted from the PAXgene RNA blood (PreAanalytiX GmbH, VWR part#77776-026, USA) using the QIAcube automation RNA extraction procedure according to the manufacturer's protocol (Qiagene Inc., Valencia, Calif., USA). Amount of total RNA, and A260/A280 and A260/A230 nm ratios were assessed using the NanoDrop 1000 (Thermo Fisher Scientific Inc., Wilmington, Del.). RNA integrity was assessed using the Agilent 2100 Bioanalyzer (Agilent Technologies, Santa Clara, Calif.). In each sample the RNA integrity number (RIN) were measured. A two-color gene expression system was used to determine the expressed mRNAs in the given samples. For each sample, 500 ng of total RNA were labeled with Cyanine 3-CTP and 500 ng of Universal Human Reference RNA (Stratagene, Cat Nr: 740000) were labeled with Cyanine 5-CTP. The combined labeled sampled were hybridized onto the Agilent whole human genome microarrays (G4112F, Agilent Technologies, Santa Clara, USA). After hybridization, the mRNA slides were scanned on an Agilent DNA microarray scanner (Agilent Technologies, Santa Clara, USA). Agilent Feature Extraction Software (Version 10.5.1.1) was used to extract the microarray images data. After checking the quality of each subject array, the Feature Extraction files were imported into R Bioconductor and analyzed using the Agi4x44PreProcess package for probe filtering, quantile normalization and replicate probe summarization. We required that probes be detected, above background and the negative controls on the array, unsaturated, and not be detected as a population outlier, or nonuniform outlier with a lower limit of detection of 75. For all subsequent analyses, we included 29,849 array elements whose expression fulfills these criteria. The original microarray data files were entered into the Stanford Microarray Database, and they can be accessed by choosing "public login" and then selecting experimenter "HIMC" and experiments "Gergana".

Serum cytokine levels. Serum samples were obtained by centrifugation of clotted blood and stored at −80° C. before cytokine levels determination. 42-plex kits were purchased from Millipore and used according to manufacturer's recommendations with modifications as described below. Briefly, samples were mixed with antibody linked polystyrene beads on 96-well filter plates and incubated at room temperature for 2 hours followed by overnight incubation at 4° C. Plates were then vacuum filtered and washed twice prior to 2-hour incubation with biotinylated detection antibody. Samples were filtered as above, washed twice and resuspended in streptavidin-PE. After incubation for 40 minutes at room temperature, two additional vacuum washes were performed, and the samples resuspended in Reading Buffer. Each sample was measured in duplicate. Plates were read using a Luminex LabMap200 instrument with a lower bound of 100 beads per sample per cytokine. The Luminex LabMap200 outputs the fluorescence intensity of each bead measured for a given cytokine in a sample. For each well, we considered the median fluorescence intensity (MFI) of all beads measured for that cytokine in a well as its abundance and averaged the MFI of the two replicates to obtain the abundance of a cytokine in a sample.

HAI assays. Participants were immunized with one dose of the trivalent inactivated seasonal influenza vaccine (TIV) post baseline blood draw, as described above. Blood samples were collected on day 0 before vaccination, as well as day 7 and day 28 post vaccination. Sera were prepared with the day 0 and day 28 blood samples. The HAI assay was performed using a standard technique (Prevention, 1998); serially diluted 25-µl aliquots of serum samples in PBS were mixed with 25-µl aliquots of virus, corresponding to four HA units, in V-bottom 96-well plates (Nunc, Rochester, N.Y., USA) and incubated for 30 minutes at room temperature. At the end of the incubation, 50 µl of 0.5% chicken (for influenza A/H1N1 and B viruses) or turkey (for influenza A/H3N2 virus) red blood cells was added and incubated for a minimum of 45 minutes before reading for HAI activity. The HAI titer of a given sample was defined as the reciprocal of the last serum dilution with no HA activity. A titer of 2 was assigned to all samples in which the first dilution (1:4) was negative.

PBMC phenotyping. Whole blood samples were subjected to density gradient centrifugation and PBMC were collected for phenotyping and phosphoflow assay (see below). Cells were frozen in DMSO with 10% FBS at −80° C. overnight prior to transferring to liquid nitrogen. For cell subset analysis, cells were thawed, washed twice with warm culture media and stained with the following antibody cocktail: CD3 AmCyan, CD4 Pacific Blue, CD8 APCH7, CD28 APC, CD27 PE, CD45RA PE-Cy5, CD19 Alexa Fluor700, CD56 PE, CD33 PE-Cy7, TCRγδ APC, all reagents from BD Biosciences. Incubation with antibodies was performed for 30 min at 4° C. Cells were washed and resuspended in FACS buffer. Data were collected using DIVA software in an LRSII instrument (BD Biosciences). Data analysis was performed using FlowJo 8.8.6 by gating on live cells, then using double gating for singlet discrimination, followed by cell subset specific gating. The median fluorescent intensity was used in the calculation of percentage of positive cells for a given cell subset.

Phosphorylation of STAT Proteins in Response to Cytokine Stimulation.

Thawed PBMC were rested for 1 hour in warm RPMI media with 10% FBS (culture media) before stimulation. Cells were distributed in 96-deep well blocks and stimulated for 15 min at 37° C. with IFN-γ, IL6, IL7, IL10, IL21 at 50 ng/ml or with $10^4$ U/ml IFN-α. After stimulation, cells were fixed with 1.5% PFA at room temperature for 10 min and washed with an excess of plain PBS. Cells were then span down at 2000 rpm for 5 min at 4° C. and permeabilized with 100% cold methanol for 20 min on ice. Stimuli conditions were barcoded using a 3×3 matrix with Pacific Orange and Alexa Fluor 750 (Invitrogen Corp) at 0.03 and 0.04 ug/ml for low staining and 0.2 and 0.3 ug/ml for high staining, respectively (Krutzik and Nolan, 2006). Incubation with barcoding dyes was performed at 4° C. for 30 minutes. After several washes with FACS buffer (PBS 2% FBS, 0.1% Na Azide) stimulated and barcoded cells were pooled into single tubes and stained for 30 min at 4° C. with an antibody cocktail containing anti pSTAT1 Alexa Fluor 488, pSTAT3 Alexa Fluor 647, pSTAT5 PE, CD3 Pacific Blue, CD4 PerCP-Cy5.5, CD20 PerCP-Cy5.5 and CD33 PE-Cy7 (all from BD Phosflow). After washing, cells were resuspended in FACS buffer and acquisition was performed on an LSRII instrument (BD Biosciences). Data were collected using DIVA software in an LRSII instrument (BD Biosciences). Data analysis was performed using FlowJo 8.8.6. by gating on live cells, then using double gating for singlet discrimination, followed by cell subset specific gating (see FIG. 8A-8B for gating strategy). A drawback of this technology that limits the cell subset resolution is the availability of commercial antibodies that bind to epitopes resistant to methanol fixation. Therefore, we used antibodies to CD3 and CD4 to identify CD4 ($CD3^+CD4^+$) and non-CD4 T cells ($CD3^+CD4^-$); CD20 for B cells and CD33 to identify monocytes. One caveat of this strategy is the contribution of γδ- and NK-T cells to the CD8 signal, because all three subsets are $CD3^+CD4^-$. Gamma-delta and NKT cells constitute only a minority of lymphocytes while the frequency of CD8 T cells is often more than 30% of PBMC. We thus refer to the non-CD4 fraction as CD8+ T cells. Phosphorylation of STAT1, 3, and 5 proteins in B cells, CD4/CD8 T cells or monocytes was analyzed by debarcoding on stimuli-specific gating (see FIG. 8A-8B). Fold change between stimulated and unstimulated conditions was calculated using the 90th percentile of the Pstat1, 3, or 5 positive cells. Using the median fluorescent intensity instead of the 90th percentile did not alter the observation of significant age dependent decline in phosphoprotein levels in response to cytokine stimulation.

We analyzed 29 samples at a single cytokine stimuli concentration, performed over the course of 3 days by 2 different subjects. Baseline phosphoprotein abundance in a given cell was measured in 6 replicates, averaged and day normalized by dividing the average measurement on a given day. Fold-change difference due to stimulation was computed as the ratio of the cell, cytokine stimulation, phosphoprotein measure to the raw, un-normalized, cell-phosphoprotein matching baseline that was measured on the same plate. Fold-change values were normalized by the average fold-change difference of a given cell-cytokine stimulation-phosphoprotein measure on a given day. We tested each assay for day dependent differences. No significant differences between days were detected post-day normalization and cytokine responders and non-responders were present in all three days.

For the dose-response assay, we measured three pairs of old and young subjects that we paired on a single 96-deep well plate and stimulated for 15 min at 37° C. The protocol was identical to the one described above, with the exception of the cytokine stimulation doses: for IFN-γ, IL6, IL7, IL10, and IL21 we stimulated cells with 0.1, 1, 10, 50 and 100 ng/ml of cytokine whereas for IFN-α we stimulated with 0.12, 0.25, 0.5 1 and 2×10⁴ U/ml. Baseline phosphorylated STAT levels were measured for each subject per plate in 5 replicates. Sample normalization was performed in the same manner as is described above for all 29 samples. To determine if a fold-change difference exists for a given cell, cytokine, phosphoprotein assay between old and young we used a t-test at the highest dose stimuli concentration and corrected for multiple hypotheses testing (Storey and Tibshirani, 2003). Of the three pairs of old-young samples we tested, one pair was missing a single, but different, measurement for each stimulus. Though the results were fully consistent with those observed in the two other old-young pairs (i.e. the young subject showed increased fold-change for all doses for a large number of assays), we did not include results from this pair in any of the analysis discussed here.

Cytokine levels in cultured monocytes and T cells. PBMC from two young and two older subjects were thawed and washed once with warm RPMI media supplemented with 10% FBS. After 1 hour incubation at 37° C., cells were chilled on ice and washed with cold PBS with 0.5% BSA and 2 mM EDTA. Prior to enrichment cells were incubated for 10 min with FcR blocking reagent (Miltenyi). Monocytes, CD4⁺ and CD8⁺ T cells were negatively selected by magnetic sorting using the Monocyte Isolation Kit 11, CD4 T cell isolation Kit 11 and CD8 T cell Isolation kit (Miltenyi), respectively. More than 85% purity was achieved as evidenced by further staining with cognate antibodies and flow cytometry analysis (not shown). Enriched cell populations were resuspended in serum-free media (AIM V, Invitrogen), plated at $0.5 \times 10^6$/ml and stimulated with IL-6 or IFN-α at 50 ng/ml and $10^4$ U/ml, respectively or left alone. Incubation with cytokines was conducted at 37° C. for 18 hours. Supernatants were analyzed for cytokine expression using the Luminex LabMap200 platform.

Regression analysis for age-associated traits. We used a linear regression model to identify measurements that showed a statistically significant change in expression with age. Our linear regression model accounted for both age and gender differences. Mathematically, our model takes the form:

$$Y_{ij} = \beta_j^0 + \beta_j^{Age} * Age_i + \beta_j^{Gender} * Gender_i + e_{ij}$$

Where $Y_{ij}$ is the in subject i of measurement of j where j is either a gene expression, cell-subset phenotype, cytokine abundance or baseline phosphoflow measurement. In the case of gene expression and phosphoflow cases Y is in log 2 space. We applied the model to each data measurement. To compute p-values of the beta coefficient of age and gender, we permuted the data measurement with respect to age and gender, 200 times, and then recomputed the regression. For each permutation we tested were the absolute value of the permuted derived betas was greater or equal in size to the absolute value of the true beta coefficients. P-values for each beta were then calculated as the ratio of the number of times the betas from the permuted regressions exceeded the betas the true data regression over the total number of trials. To reduce the effects of outliers on our results, for both the serum cytokine and cytokine response were single subjects (29 and 25 respectively), were outliers, we used a robust regression model with a bi-square weight model. To correct for multiple hypothesis testing, we considered the regression p-values for all measurements of a single data type simultaneously and calculated a q-value (Storey and Tibshirani, 2003) for each. We applied a q-value threshold of 0.15 (unless stated otherwise) and report the p-value of the regression, the age coefficient and q-value. In the case of gene expression we first filtered the data in an independent manner (see below).

Gene subset selection. For gene expression, to restrict the number of multiple hypotheses corrections we were required to make, we considered a selected gene subset of immune and aging related genes for analysis, based on independent prior evidence from unrelated experiments (Table S2).

For immune genes we used ImmPort—the Immunology Database and Analysis Portal (2009) which contains manually curated immune related gene list (Mar. 3, 2009 version). All entries that did not map to a single ENSEMBL gene ID (mostly those mapping to a specific allele or exon) were discarded. The resultant list includes 3272 genes of which we mapped to the array using Entrez gene IDs. In total 2644 genes had one or more probes on the array for a total of 4708 probes.

We annotated genes as being related to aging and longevity by two different methods. First, we considered any gene that was annotated as aging related in the GenAge database (*Build* 15, 17 Mar. 2010) (de Magalhaes et al., 2009) as such. GenAge is a manually curated database of genes related to aging. This includes the few genes directly related to aging in humans and the best candidate genes obtained from model organisms. This yielded 243 longevity/aging genes. In addition, we performed a meta-analysis of aging related gene expression datasets to find a robust set of aging related genes. To do so, we identified 58 gene expression datasets (GDS) or gene expression series (GSE), comprising a total of 2152 microarray chips, in NCBI's Gene Expression Omnibus (GEO) (Barrett et al., 2007) which sampled gene expression in 'normal' aging across five species: human, rat, mouse, worm, and fly. As an subject dataset or series may combine samples drawn from different experimental conditions, tissue types or populations (such as different mouse strains or genders), these were further divided into a total of 114 comparisons between young and old samples. To create a profile of genes differentially expressed between young and old, we performed two types of meta-analysis. We looked at genes measured in at least ten comparisons, and used the modified t-test (Tusher et al., 2001) and Fisher's exact test, to identify genes significantly differentially expressed between young and old. We also computed a meta effect estimate, a meta fold-change, using a linear model, weighted by the inverse of the variance in expression (Choi et al., 2003). Performing this procedure yielded an additional 261 aging related genes (239 could be mapped on array with an EntrezID).

Network construction and spCCA. We identified as set of immune system modules from peripheral blood which best correlated with cell-subset specific cytokine responses in five steps: sample outlier filtering, supervised functional classification, within data type correlation and spCCA to identify co-regulated clusters.

First, for each of the 5 different data types (gene expression, cell subset, serum cytokines, cytokine stimulation response and baseline phosphoprotein levels), we filtered outlier samples that may have strong effects on correlation analysis by computing for each datatype, the overall sample correlation. Samples whose distance from all other samples was markedly different were removed from this analysis. This procedure identified two outlier samples, one sample (29) from the serum cytokine dataset and one sample (25) for cytokine response assays. Next, for specific data-types we classified nodes by function and/or co-expression. In particular cytokine responses were classified by type (baseline, response or baseline and response), cytokines by functionality. For phosphoprotein baseline measurements we clustered the data from the different STAT molecules within a cell together. Cell subsets were maintained as unique nodes at the cellular level. To cluster by co-expression we used the R library WGCNA (Langfelder and Horvath, 2008) which dynamically dissect clusters of strong correlations by exponentiation of the correlation matrix by a positive value determined empirically for each dataset by a fit of cluster connectivity to a scale free topology. We set the minimal cluster size for all datasets to 1, with the exception of gene expression for which minimal cluster size was set to 10. The outcome of applying this procedure for each dataset was to group highly correlated measurements in each data type together. This procedure yielded: (1) four cytokine response nodes, one for each cell subset, (2) three phosphoprotein nodes containing all age-associated baseline differences by cell type, (3) six nodes representing cell-subset frequencies, (4) five serum cytokine nodes, and (5) six gene expression nodes and two singletons containing all 279 age-associated genes (see Table S5 for which measurements were captured in each node).

For the purpose of identifying those measurements that are correlated with the cytokine response phenotype, we split the above described immune measurements into two matrices, the first consisting solely of subjects' cell-type average cytokine response and the second of all other factors/clusters and then applied spCCA (Witten et al., 2009). To set the penalty tuning parameters we performed sparse canonical correlation analysis on the real data set compared the magnitude of the first maximally correlated association to that observed in 1000 permutations of the data over a range of penalty parameters equally set for each data type. We observed similarly high z-scores (above 3) across the entire range of tested parameters. Penalties of 0.5 and 0.7 were chosen for the two matrices respectively as they showed a good z-score, strong correlations between measurements ($r=0.89$, $r_{permuted}=0.59$, p-value <0.001) and a reasonable number of non-zero weights for interpretation. Importantly, though a cytokine response may consist of a weighted average of each of the four cell types, setting the penalty to 0.5 yielded a single non-zero weight for cytokine response, corresponding to a single cell-type, for each recursive iteration of the algorithm. A more permissive penalty (0.7) yielded multiple non-zero cytokine response but for only a minor gain in increased correlation. Thus, the linear combination of immune measurement we report is based on a 0.5 penalty and to a first approximation is orthogonal and maximally correlated with a single cell-type in which the cytokine response deficiency is observed. To enable comparison of the four weighted modules, weights were normalized by the maximum weight within a given linear combination and multiplied by the correlation of that maximal correlation observed between that module and the single unit weight of the cytokine response. We note that despite normalization of all the data, the magnitude of baseline phosphoprotein and cell-type frequency association with cytokine responses may be inflated by their measurement on the same technological platform.

Classification and Comparison of Cytokine Response Profiles. We introduced two modifications to the cytokine response classification protocol for the longitudinal analysis the years subsequent to year 1: First, as the range of the data in the assay was reduced in the subsequent years (likely due to antibody batch effects), we used a standard deviation threshold of one (instead of two) from the responses of the young group returning that year, to determine an subject's cellular response state. Second, if a response of a young subject was in itself an outlier, the mean and standard deviation of the young group was recomputed leaving that result out, effectively maintaining the scoring system as relative to good health. This latter procedure was not required in the first year, as the cell-specific distribution of young subjects was very tight there were no outliers.

To evaluate how stable the cytokine response phenotype was over the course of the three years, we created a model for the likelihood of remaining in the same classification or moving toward the non-responder category and compared this to the null model where the classification for any given year is random (i.e. equal probability of being classified into one of the three categories each year).

In the direct comparison of CR to CNR, as the number of samples did not permit direct consideration of gender and age in the comparison, we estimated their effect by single variable comparisons of gender and old-age differences in the data.

Tests of significance for determining immune response deficiency type. We used the dose-response data to distinguish between baseline and response causes for the lower fold-change levels we observed in the older subjects. To do so we devised a decision tree consisting of 6 consecutive tests, the application of which on a given cell, cytokine stimulation, phosphoprotein assay should implicate the mechanism inhibiting the full fold-change response:

(1) Use a one-tailed t-test to test whether the baseline phosphoprotein levels in the older subjects are significantly higher than that of the young (uses the complete dataset).
(2) Use a one-tailed t-test to test whether a significant fold-change difference is observed between the two older subjects and the two younger at the highest dose level.
(3) Use an f-test on computed ratio of fold-change between the lowest and highest stimulation doses to test if dose-response curve of the older subjects show a significant incline.
(4) Use an f-test to test if the dose-response of the younger subjects (ratio of fold-change between the lowest and highest stimulation doses) is significantly greater than that of the elderly.
(5) Use a two-tailed t-test to ask if the MFI at the highest stimulation dose is equal between the elderly and young subjects.

Tests (1) and (2) are used to identify if baseline phosphoprotein level differences, fold-change or both exist. Test (3) is used to identify if a given assay is in saturation for all doses, whereas (4) identifies if saturation is only observed in the older subject group or alternatively if no saturation exists, whether the younger subjects are more sensitive in their response for an increased dose. In the case test (4) indicates saturation of response in the older subjects, test (5) asks whether both the older subjects and the young reached saturation and if so, was it at the same ceiling (total available protein for phosphorylation).

EXAMPLES

The following examples are put forth so as to provide those of ordinary skill in the art with a complete disclosure and description of how to make and use the present invention; they are not intended to limit the scope of what the inventors regard as their invention. Unless indicated otherwise, part are parts by weight, molecular weight is average molecular weight, temperature is in degrees Centigrade, and pressure is at or near atmospheric.

Example 1: Age-Dependent Differences are Detectable from the Cellular to the Molecular Level Age-dependent differences were detectable from the cellular to the molecular level. To identify age-associated differences, multiple regression analysis was performed a on all samples according to age and gender. For multiple hypotheses correction, a false discovery rate was chosen that maximized the number of true positives while still being amenable for follow-up analyses. The false discovery rate is denoted as q-value and was set to q≤0.15 unless otherwise noted; see FIG. 9 and Experimental Procedures.

In white blood cells a decrease in $CD8^+$ naïve cells was detected with age, but no other age-associated changes in cell subset frequency. A high variance in frequency was noted between individuals that was particularly prominent in the elderly group (>73 years old) and that affected the regression analysis. However, at a q≤0.25, 8 of the 15 cell subsets surveyed showed age-associated changes in frequency (see Table S2). These included an increase in the frequency of monocytes, and an increase in $CD8^+$ and $CD4^+$ cells lacking CD28 expression, which is a critical molecule for robust T cell activation in both $CD8^+$ and $CD4^+$ T cells. In addition, increases in the frequency of NKT cells were noted and in both $CD8^+$ and $CD4^+$ "memory" T cells, i.e., the cells that respond to previously encountered antigens.

Table S2 summarizes twelve serum proteins whose serum levels were changed as a function of age. These included the chemokines IP-10 and Eotaxin, both of which increased sharply with age as previously reported (Shurin et al., 2007), as did IL-12, which is known to regulate IP-10 production. The only pro-inflammatory cytokine that was found to increase with age was TNF-α. Both Th1 (IFN-γ and IFN-α2) and Th2 (IL-4, 5, 7) related cytokines decreased with age, as did the macrophage activation cytokines MRC-3 and TGF-α. With respect to the ability of white blood cells of these individuals to functionally respond to signaling cues from cytokines, of the 12 baseline and 72 response assays that were conducted (4 cell subsets, stimulated by 6 cytokines and measuring phosphorylation level of STAT-1, -3, and -5), an age-associated difference in 8 baseline and 39 response measurements was detected, 33 of which showed a 2-fold or greater response to stimulation in at least one person (see FIG. 1A-C, FIGS. 9A-B).

The gene expression analysis in these studies was limited to those genes which had previously been independently associated with either immunological or longevity phenotypes. Based on curated databases of immunology (2009) and aging (de Magalhaes et al., 2009) 2713 immune-related genes and 239 aging-related genes were measured on human genome microarrays (Agilent 4×44 whole human genome microarrays). A cross-species meta-analysis of 114 aging-related gene expression experiments identified an additional 40 genes (see Table S3 and S4). In total, these comprised 2863 genes that corresponded to 4364 unique probes on the array. Testing this set of probes for age-associated differences yielded 294 probes (q≤0.15, FIG. 9E), which corresponded to 279 unique immune and aging-related genes that were found up- or down-regulated with age (see Table S2).

Example 2: The Cytokine Responses of Older Adults are Systemically Reduced, Independent of Concentration Cytokine response assays that assess the phosphorylation state of intracellular signaling proteins have been shown to be predictive of disease outcome in several cases (22; 27). On average older individuals exhibited lower phosphorylation states in response to stimulation than the young (FIGS. 1A and 1B). To address the possibility that low responses to cytokines might be due to low sensitivity of cells from older individuals, dose-response experiments were carried out and increasing concentrations of all 6 cytokines were assayed in all 4 cell subsets in 2 young and 2 old poor cytokine responders. Differences between old and young were consistently observed in the majority of assays (FIG. 1D, FIGS. 10A-10F), even at the highest, saturating doses (FIG. 11). 30 age-associated differences were identified at the highest cytokine concentrations; of those, 20 showed a 2-fold or higher change and a significant reduction in the responses of older individuals versus the younger cohort (FIG. 1D, FIGS. 10A-10F). Thus, in comparison to young individuals, older individuals were not able to mount an equally strong response to cytokine stimulation, even at saturating levels. Furthermore, individuals who were deficient in one cytokine response were, for the most part, deficient in others as well. This correlation was also true across cell-types. For example, those individuals who were deficient in their $CD4^+$ T cell responses also tended to be deficient in their $CD8^+$ T cell responses and in many cases in either or both monocytes and B-cells, suggesting a systemic condition (see FIG. 1E). Taken together, multiple impairments to respond to cytokine signals occurred with age, independent of the stimuli concentration.

Example 3: Cytokine Response Deficiencies and Immunosenescence Markers Co-Occur in the Single Individuals In further studies, a potential relationship was investigated between the cytokine response phenotype and other immune measures such as cell subsets and cytokines. This revealed a high concordance of the cytokine response deficiency with hallmarks of immunosenescence alterations in cell subsets (see FIG. 2A, top), such as the drop in $CD8^+$ and $CD4^+$ naïve cell frequencies ($R^2=0.54$, $p<10^{-6}$ and $R^2=0.54$, $p<10^{-6}$ respectively) (Fagnoni et al., 2000), the increase in occurrence of $CD8^+CD28^-$ cells ($R^2=0.54$, $p<10^{-6}$) (Effros et al., 2005; Fagnoni et al., 1996) and the decline in B-cell frequency ($R^2=0.23$, $p<0.01$).

Cytokine responses in serum proteins showed significant association with log transformed intensity measurements of macrophage chemokine MCP-1 ($R^2=0.23$, $p<0.01$) and more mildly with the innate immunity chemokine IP-10 ($R^2=0.18$, $p<0.07$) (see FIG. 2A, bottom). However, pro-inflammatory cytokines showed no significant association with reduced cytokine responses. Aside from TNF-α, no increase in pro-inflammatory cytokines in serum was detected. In particular, no significant age or cytokine response association was observed for IL-6, whose increase has been associated with aging in many other studies (Franceschi et al., 2000; Shaw et al., 2010; Wikby et al., 2006), and has most recently been linked with mortality (Wassel et al., 2010). For a direct analysis of cytokine levels from sorted cells, monocytes, $CD4^+$ and $CD8^+$ T cells from PBMC of two young and two older individuals were isolated and cultured, and then the secreted cytokine levels of these cells were profiled across 50 different cytokines after 18 hours of incubation at 37° C. These assays showed a dramatically increased abundance of pro-inflammatory cytokines (IL-6, IL-1b, TNFα) and chemokines (CXCL1, CXCL5) in the monocytes of the older individuals (see FIG. 2B). No other significant differences in cytokine abundance were detected either in monocytes or in the CD4$^+$ or CD8$^+$ T-cells. Taken together, these associations suggested that a subset of older individuals exhibited immune system impairments that were concomitant at multiple levels, and to which the systemic reduction in cytokine response was closely linked.

Sparse canonical correlation analysis (spCCA) (Witten et al., 2009), an unsupervised statistical technique, was used to identify linear combinations of weighted factors, that showed maximal correlation with cytokine response. For simplification, highly co-varying factors internal to a single type of measurement were first clustered, including the cytokine responses themselves by cell subsets. spCCA identified four distinct and significant maximally correlated sets of factors, one for each of the four cell subsets in which cytokine response deficiencies had been observed (see FIG. 2C and Table S6). These multi-factor combinations ('modules') showed considerably higher correlation with cytokine responses than the correlation that were observed with single known immunosenescence markers. The specific combination of an increase in B-cell baseline phosphoproteins, a decline in CD8$^+$ naïve cell frequency and 14 other factors formed a module which correlated with B-cell cytokine response with an r=0.89 at a significance of p<0.0001. (r=0.87, 0.87, 0.74 for CD4+, CD8+ and monocytes respectively). The modules correlating with a cytokine response deficiency of a given cell subset often included molecular measurements from cell subsets other than their own and at higher weights, indicating inter-cellular dependencies of these deficiencies.

Example 4: Cytokine Responses Define Distinct Age-Related Subgroups that are Longitudinally Stable; Definition of Cytokine Responders Versus Cytokine Non-Responders For assessing the extent of variation in the various analyses, a scoring system for cytokine deficiency was defined by first calculating for every individual the sum of age-associated cytokine responses in each cell subset, and then comparing to see if it was markedly different from that observed in the young group for that cell subset (two standard deviations from the mean of the young).

The scoring system was defined as a relative scoring system with respect to those generally considered healthy, and reflected the extent of both intra- and inter-cellular effects of cytokine response deficiencies on an individual's immune system.

Under this scoring system, none of the young individuals showed any cytokine response impairments, whereas multiple impairments were observed in older individuals. Furthermore, among older individuals we observed a high amount of variation in the cytokine response score, suggesting the possibility of distinct phenotypes. Therefore, older individuals were defined as cytokine responders (CR), if the sum of their responses in each of the cell subsets was within two standard deviations of the average response in the young individuals in at least three of the four tested cell subsets. Accordingly, older individuals were defined as cytokine non-responders (CNR), if their sum of age-associated responses was below two standard deviations of the average response in the young individuals in at least three of the four tested cell subsets (see FIG. 12 and Experimental Procedures). Under these criteria, six older individuals were identified as CR and six as CNR. The remaining seven older individuals we designated as 'Intermediate', as they did not meet either of these extreme criteria, but rather showed generally milder reductions in response to cytokine stimulation than observed in CNR and in only one or two of the four tested cell subsets (see FIG. 3A).

To determine the stability of the cytokine response phenotype, a subset of patients (n=21) was examined who had returned to participate in a subsequent three year-long longitudinal study. A similar scoring system was used to classify the response, with minor modifications (see Experimental Procedures). The analysis of each of the three years of the study showed conservation of the cytokine response phenotype both at the cell-type level and the class (CR, CNR or Intermediate) (see FIG. 3B, p=0.019 by permutation). This was particularly notable amongst older individuals, with individuals generally maintaining either the same state or progressing towards the non-responder category.

Furthermore, most shifts in cytokine response state were gradual, meaning that CR did not shift to a CNR state in directly subsequent years or vice versa, but rather passed through the intermediate state. The results from the longitudinal data strongly suggested that fluctuations are not random, but rather a true biological phenomenon whose phenotype in individuals is likely to remain invariant or worsen over time.

Example 5: Cytokine Responders and Cytokine Non-Responders have Distinctly Different Immune System Profiles The CR and CNR profiles form two distinct and stable extremes of an important immune phenotype. Further studies were carried out to investigate whether stratification by cytokine response and direct comparison between groups would uncover further significant differences. The participating individuals in this study were vaccinated with a seasonal, inactivated influenza vaccine containing three different strains of influenza. Their antibody titers against all three strains were tested before and approximately 3 weeks after vaccination using a standard hemagglutinin inhibition assay (HAI). It is generally accepted that, at the population level, a pre-vaccination antibody titer of 1:30 to 1:40 represents a 50% probability of protection against Influenza infection (Hobson et al., 1972; Potter and Oxford, 1979; (Coudeville et al., 2010).

Here, the young and the CR group showed similar pre-vaccination antibody titer levels, which were significantly more robust than those of CNR when considered simultaneously across all strains (see FIG. 4A, p=0.0005 and p=0.06 respectively, by Fisher's exact test performed on p-values obtained from permuted data). Response to vaccination, as measured by antibody titers post-vaccination, were similar in CR and CNR (see FIG. 13), suggesting that the CNR group had remained responsive to the vaccination and would, therefore, particularly benefit from vaccination.

In addition, the individuals in this study were also tracked with respect to their medical history and concomitant medication. A third of CR individuals reported previous cardiovascular related surgery or hypertension versus two thirds of CNR. While there was a great variation in the medications that the individuals took, the CNR group took significantly more medications than the CR group (p<0.06), which was likely due to the higher incidence of cardiovascular issues in the CNR group. Yet no single mechanism-of-action drug class distinguished CNR from CR (see Table S8), suggesting that the differences between the two groups were not the result of a simple drug effect, but rather a surrogate of their medical condition.

In further analyses, all genomic, molecular, and cellular measurements that had been obtained in the course of the described studies were investigated for specific differences between the CR and CNR groups. A uniform threshold across all measurement modalities of $q\leq0.1$ (see FIG. 14) identified 1565 measurements that were different between CR and CNR (ANOVA, see Table S7, similar results were obtained by a permutation test). The CNR group showed a significant decrease in most (48/72) of the cytokine stimulation response assays. In agreement with our current knowledge of low phosphoprotein baseline levels being the cause for any cytokine response defects, elevated baseline phosphorylation was detected in CNR individuals for STAT1, 3 and 5 proteins in B- and CD4* T-cells, as well as for STAT1 in monocytes. 13 out of 15 measured cell-subsets had detectable differences in frequency between CR and CNR (see Table S7), including significantly lower levels of B-cells, $CD8^+$ and $CD4^+$ nave T-cells ($p\leq0.01$), and $CD8^+$ $CD28^-$ T-cells ($p<10^6$), all known markers of immunosenescence. No serum proteins were detected as differentially expressed between the two groups.

The increase in $CD8^+CD28^-$ T cells and the evidence of an inflammatory state was found to be consistent with the previously described "Immune Risk Profile" for immunosenescence (Wikby et al., 2006). This profile was previously estimated to be present in 16% of older individuals 60-94 years of age (Wikby et al., 2008). Furthermore, it had been reported that individuals with such a profile showed increased morbidity and mortality (Strindhall et al., 2007). An inverted CD4/CD8 cell subset ratio (below 1), is characteristic of such an immune risk profile (Strindhall et al., 2007; Wikby et al., 2008). Therefore, the relationship of the CD4/CD8 ratio to age and cytokine response was also analyzed in the present studies (see FIG. 15). Only three individuals (one young, one a CNR and the other an intermediate) had a CD4/CD8 ratio below 1. Furthermore, the CD4/CD8 ratio was highly variable, not only in the present studies, but also in much larger cohorts, investigated by other groups (Lifson et al., 1985), where the CD4/CD8 ratio has been reported to generally rise as opposed to decrease with age. In the present studies, most young individuals showed much lower CD4/CD8 ratios similar to that of CNR, whereas CR showed elevated CD4/CD8 ratio levels.

1493 mRNAs were detected as differentially expressed between CR and CNR (see Table S7). Further studies detected 151 longevity-associated genes that were differentially expressed between the CR and CNR individuals (Table S7). These included genes in multiple pathways associated with lifespan, such as redox (e.g. SOD1, $p<10^4$), DNA surveillance (e.g. SIRT6, $p<0.02$), nutrient sensing (insulin-like growth factor 1 receptor $p<10^{-5}$), apoptosis (e.g. the forkhead transcription factor FOXO/DAF-16 family members FOXO1, FOXO3 and FOXL2 $p<10^4$) and cellular proliferation (e.g. cMyc, MDM2, $p<0.04$).

Within the context of immune cell function, these genes may either be in conflict or parallel their role in lifespan extension (match directionality). Genes of the growth hormone signaling pathway were upregulated in CR individuals, while genes of the redox response pathway were downregulated in CRR individuals, according to their expected directionality in longevity. In contrast, genes in the insulin response pathway and cellular proliferation genes were up-regulated in CR over CNR, and appeared to be opposing longevity, but in tune with a functionally active immune system (Jones and Thompson, 2007), a possible necessity for long life in a non-sterile environment. The three cytokine response phenotypes (CR, intermediate or CNR), that had been identified in the older individuals, were almost entirely reflected at the gene expression level when clustering older individuals by the set of longevity associated genes, as shown in FIG. 4B. These results suggest that cytokine response stratification can identify older individuals with distinctly different immune system profiles and differing influenza protection phenotype.

Example 6: Classification of Age-Associated Differences by Cytokine Response

A major conundrum in the study of aging is to ascertain whether a detectable age-associated change describes a process of deterioration or one that is protective. In the present studies, genes and immune traits were investigated that were different between either the CNR and the young or the CR and the young ($q\leq0.15$, FIG. 16), but that were not different in the same direction in the reciprocal group comparison ($q\leq0.2$). A third comparison targeted age-associated differences that were shared between the CR and CNR (q:S0.2). In total, this procedure classified 215, 1,901 and 378 measurements as CNR specific, CR specific or shared between the CR and the CNR (see FIG. 5A for summary statistics, FIG. 17 and Tables S9-S11).

The majority of immunosenescence markers identified in the present studies were specific to CNR, whereas the profile of CR was closer to that of the young (see FIG. 5B). For example, the frequency of B-cells in the blood had previously been reported to decline with age (Ademokun et al., 2010), but comparing the two subgroups each directly to the young revealed that B-cell frequency decline was indeed correlated with aging, but only in the CNR group ($p<0.004$). Similarly, a NKT cell increase had been reported in aging (Shaw et al., 2010) but this was again only observed in CNR.

For both B-cell and NKT cell frequencies, CR showed the reciprocal phenotype (high B-cell, low NKT cell frequency) when compared to the young. For other previously identified age associated changes, such as CD8 naïve cell frequency or serum Eotaxin abundance, both groups showed consistent differences compared to the young, though the change in magnitude was not significant in CR.

CNR specific changes included large shifts in cell subset proportions, additional cytokine responses that were impaired and increased baseline elevations for all cells but CD8+ T-cells (see FIG. 17). Only few (138) genes were detected as differentially expressed with age and specific to CNR. In contrast, for CR-specific changes, numerous genes (1896 genes) were differentially expressed with other immune phenotypic characteristics being similar to those observed in the young. In general, CR and CNR shared very few differences with respect to the young, and of them few were previously associated with aging.

Elevated baseline levels and decreased cytokine responses in $CD8^+$ cells were common to both CR and CNR, though milder in CR. In addition, at higher q-value thresholds ($q\leq0.18$ for CNR vs. young and $q\leq0.3$ for CR vs. young) most measured serum cytokines significantly differed in their abundance in comparison to the young, likely reflecting increased inflammation (Franceschi et al., 2000) and large changes in cell subset composition. These results indicated that there is likely no common profile of immune aging. Instead it appeared that the immune system of CR and CNR were aging on different trajectories yielding a distinct immune system profile.

Example 7: Reduced Responses to Cytokine Stimulation are Primarily Due to Increased Basal Levels of Phosphorylated STAT Proteins and Alterations in Response Potential in the IL-6 and IFN-A Pathways The present studies confirm reports that cells of older individuals, particularly of CNRs, experience in vivo an increased inflammatory environment when compared to young individuals (Franceschi et al., 2000). The reduced response to cytokine stimulation, as observed in CNRs, may either be successful adaption to such an environment or resistance to signaling cues. Considering that the changes measured in the cytokine stimulation assays are relative to a baseline pre-stimulation measurement, there are four possible models that could explain the observed unresponsive cells phenotype: (1) an increased exposure to cytokines is leading to successful adaptation and a requirement of higher cytokine concentration, (2) a reaction defect, in which the signaling machinery of cells in the older subjects is leading to a lower response in the older subjects, (3) a baseline defect, in which elevation in baseline pSTAT levels leaves no protein left to phosphorylate and thus decreased pSTAT fold-change, or (4) a combination of both the baseline and reaction pathway defects (see FIG. 6A).

As the observed defected cytokine response occurred systematically in different cells, cytokines, and pSTATs, each may be attributed to a separate mechanism. In the single dose assay that was performed with all 29 individuals, the concentration, baseline and response differences could not be decoupled to identify the factors contributing to the observed reduced fold-change response. Indeed, plotting each subject's cytokine response fold-change levels to the measured baseline levels of the phosphoprotein revealed an inverse correlation with the fold-change response across many of the assays (see FIG. 6B and FIGS. 18A-18E), showing the importance of increased baseline pSTAT levels.

Discriminating between the above mentioned four models could be possible by reanalyzing the dose-response assay conducted in the present studies, which included two young and two old CNR subjects, measured at each of the 72 stimulation assays and baseline for five different doses per cytokine (see Experimental Procedures). A series of tests was applied to the dose-response assay data, using information from the single dose assay whenever possible. In the successful adaptation model (Model 1), the older subjects would be expected to respond similarly to the young at a higher dose of cytokines (see FIG. 6A, top left panel). Conversely, if the relative reduction in response to cytokine stimulation compared to that of the young remained, irrespective of the dose of cytokines, then the reduced response would result from signaling resistance (Models 2-4). These four models can be distinguished for each cell subset, cytokine, and pSTAT assay combination by following a decision tree (see FIG. 6C for a sketch and FIG. 19 for a full decision tree, also see Experimental Procedures).

The application of the decision tree (from FIG. 19) showed not a single case of adaptation. Of the 30 combinations of cell, cytokine, and pSTATs in which young and older subjects show differing responses, only the monocyte stimulations could be classified solely as a reaction defect, which suggested that these cell subsets-shown to be the main source of proinflammatory cytokines in CNR-might not be influenced in an autocrine manner insofar as showing elevated pSTAT baseline levels. All other cytokine responses showed a significant elevation in the older subjects' baseline pSTAT levels, with 11 due solely to a baseline elevation, and 14 to a combined baseline-reaction effect (Table S12). The combined baseline and response factor differences were predominantly seen in T cells stimulated by IL-6 or CD8+ T cells stimulated by IFN-a, whereas elevated baseline levels of pSTATs accounted for all of the observed differences in IL-10 stimulation in CD4+, CD8+ and B-cell and to a lesser extent those involving IL-21, IL-7 and IFN-a response differences. Thus, the reduced cytokine responses in older individuals can predominantly be attributed to an elevation of baseline phosphorylation levels of STAT proteins in cells and to an altered response potential in the IL-6 and IFN-a pathways.

Although the foregoing invention and its embodiments have been described in some detail by way of illustration and example for purposes of clarity of understanding, it is readily apparent to those of ordinary skill in the art in light of the teachings of this invention that certain changes and modifications may be made thereto without departing from the spirit or scope of the appended claims. Accordingly, the preceding merely illustrates the principles of the invention. It will be appreciated that those skilled in the art will be able to devise various arrangements which, although not explicitly described or shown herein, embody the principles of the invention and are included within its spirit and scope.

REFERENCES

ImmPort (2009)
Ademokun A et al. (2010). The ageing B cell population: composition and function. *Biogerontology* 11, 125-137.
Alon U (2007). An introduction to systems biology: design principles of biological circuits (Boca Raton, Fla.: Chapman & Hall/CRC).
Barrett T et al. (2007). NCBI GEO: mining tens of millions of expression profiles—database and tools update. *Nucleic Acids Res* 35, D760-765.
Choi J K et al. (2003). Combining multiple microarray studies and modeling interstudy variation. *Bioinformatics* 19 Suppl 1, i84-90.
Coudeville L et al. (2010). Relationship between haemagglutination-inhibiting antibody titres and clinical protection against influenza: development and application of a bayesian random-effects model. *BMC Med Res Methodol* 10, 18.
Davis M M (2008). A prescription for human immunology. *Immunity* 29, 835-838.
de Magalhaes J P et al. (2009). The Human Ageing Genomic Resources: online databases and tools for biogerontologists. *Aging Cell* 8, 65-72.
de Visser K E et al. (2006). Paradoxical roles of the immune system during cancer development. *Nat Rev Cancer* 6, 24-37.
Effros R B et al. (2005). The role of CD8+ T-cell replicative senescence in human aging. *Immunol Rev* 205, 147-157.
Evans E A et al. (2008). The DAF-2 insulin-like signaling pathway independently regulates aging and immunity in C. elegans. *Aging Cell* 7, 879-893.
Fagnoni F F et al. (1996). Expansion of cytotoxic CD8+ CD28− T cells in healthy ageing people, including centenarians. *Immunology* 88, 501-507.
Fagnoni F F et al. (2000). Shortage of circulating naïve CD8(+) T cells provides new insights on immunodeficiency in aging. *Blood* 95, 2860-2868.
Franceschi C et al. (2000). Inflamm-aging. An evolutionary perspective on immunosenescence. *Ann N Y Acad Sci* 908, 244-254.
Gernez Y et al. (2007). Altered phosphorylated signal transducer and activator of transcription profile of CD4+ CD161+ T cells in asthma: modulation by allergic status and oral corticosteroids. *J Allergy Clin Immunol* 120, 1441-1448.

Goodwin K et al. (2006). Antibody response to influenza vaccination in the elderly: a quantitative review. *Vaccine* 24, 1159-1169.

Hansson G K (2005). Inflammation, atherosclerosis, and coronary artery disease. *N Engl J Med* 352, 1685-1695.

Hobson D et al. (1972). The role of serum haemagglutination-inhibiting antibody in protection against challenge infection with influenza A2 and B viruses. *J Hyg* (Lund) 70, 767-777.

Irish J M et al. B-cell signaling networks reveal a negative prognostic human lymphoma cell subset that emerges during tumor progression. *Proc Natl Acad Sci USA* 107, 12747-12754.

Jones R G & Thompson C B (2007). Revving the engine: signal transduction fuels T cell activation. *Immunity* 27, 173-178.

Kirkwood T B (2002). Evolution of ageing. Mech Ageing Dev 123, 737-745.

Krutzik P O & Nolan G P (2006). Fluorescent cell barcoding in flow cytometry allows high-throughput drug screening and signaling profiling. *Nat Methods* 3, 361-368.

Langfelder P & Horvath S (2008). WGCNA: an R package for weighted correlation network analysis. *BMC Bioinformatics* 9, 559.

Lifson J D et al. (1985). Variables affecting T-lymphocyte subsets in a volunteer blood donor population. *Clin Immunol Immunopathol* 36, 151-160.

Perez O D and Nolan G P (2006). Phospho-proteomic immune analysis by flow cytometry: from mechanism to translational medicine at the single-cell level. *Immunol Rev* 210, 208-228.

Potter C W & Oxford J S. (1979). Determinants of immunity to influenza infection in man. *Br Med Bull* 35, 69-75.

Prevention, C.f.D.C.a. (1998). The 1998-99 WHO influenza reagent kit for the identification of influenza isolates. (Atlanta, Ga., Centers for Disease Control and Prevention).

Rodwell G E et al. (2004). A transcriptional profile of aging in the human kidney. *PLoS Biol* 2, e427.

Rojo L E et al. (2008). Neuroinflammation: implications for the pathogenesis and molecular diagnosis of Alzheimer's disease. *Arch Med Res* 39, 1-16.

Sarup P et al. (2011). Flies selected for longevity retain a young gene expression profile. *Age* (Dordr) 33, 69-80.

Shaw A C et al. (2010). Aging of the innate immune system. Curr Opin Immunol 22, 507-513.

Shen-Orr S S et al (2010). Cell type-specific gene expression differences in complex tissues. *Nat Methods* 7, 287-289.

Shurin G V et al. (2007). Dynamic alteration of soluble serum biomarkers in healthy aging. *Cytokine* 39, 123-129.

Southworth L K et al. (2009). Aging mice show a decreasing correlation of gene expression within genetic modules. *PLoS Genet* 5, e1000776.

Storey J D & Tibshirani R. (2003). Statistical significance for genomewide studies. *Proc Natl Acad Sci USA* 100, 9440-9445.

Strindhall J et al. (2007). No Immune Risk Profile among subjects who reach 100 years of age: findings from the Swedish NONA immune longitudinal study. *Exp Gerontol* 42, 753-761.

Tusher V G (2001). Significance analysis of microarrays applied to the ionizing radiation response. *Proc Natl Acad Sci USA* 98, 5116-5121.

Wassel C L et al. (2010). Association of circulating C-reactive protein and interleukin-6 with longevity into the 80s and 90s: The Rancho Bernardo Study. *J Clin Endocrinol Metab* 95, 4748-4755.

Weiskopf D et al. (2009). The aging of the immune system. *Transpl Int* 22, 1041-1050.

Wikby A et al. (2008). The immune risk profile is associated with age and gender: findings from three Swedish population studies of subjects 20-100 years of age. *Biogerontology* 9, 299-308.

Wikby A et al. (2006). The immune risk phenotype is associated with IL-6 in the terminal decline stage: findings from the Swedish NONA immune longitudinal study of very late life functioning. *Mech Ageing Dev* 127, 695-704.

Witten D M et al. (2009). A penalized matrix decomposition, with applications to sparse principal components and canonical correlation analysis. *Biostatistics* 10, 515-534.

APPENDICES

Appendix A—Table S1
Appendix B—Table S2
Appendix C—Table S3
Appendix D—Table S4
Appendix E—Table S5
Appendix F—Table S6
Appendix G—Table S7
Appendix H—Table S8
Appendix I—Table S9
Appendix J—Table S10
Appendix K—Table S11
Appendix L—Table S12

APPENDIX A

TABLE S1

Demographics Table

|  | Enrollment Category 18-30 years | Enrollment Category 60-79 years | Enrollment Category 80-100 years |
|---|---|---|---|
| Number enrolled | n = 10 | n = 11 | n = 8 |
| Gender |  |  |  |
| Female | 6 | 6 | 4 |
| Male | 4 | 5 | 4 |
| Age |  |  |  |
| Mean (yrs) | 24.42 | 64.21 | 85.44 |
| Range (yrs) | 21-28 | 60-74 | 83-96 |
| Ethnicity |  |  |  |
| Hispanic | 3 | 0 | 0 |
| Non-Hispanic | 7 | 11 | 8 |
| Race |  |  |  |
| White or Caucasian | 5 | 11 | 8 |
| Asian | 3 | 0 | 0 |
| American Indian/Alaska Native | 0 | 0 | 0 |
| Pacific Islander | 0 | 0 | 0 |
| Black/African Amer | 0 | 0 | 0 |
| More than one race | 1 | 0 | 0 (More than 1: Cauc/Asian) |
| Other Race | 1 | 0 | 0 (Other: not specified) |
| Declined to answer | 0 | 0 | 0 |

Note:
Demographics table displays enrollment as per original IRB. The enrollment category 60-79 yo included 10 subeject betweeen the ages of 60-65 and one individual that was 74 yo. That individual was visualized as within the oldest age group and considered within that group for all pertinent analyses

APPENDIX B

TABLE S2

Significant age-associated measurement from regression analysis of all individuals

| Cell subset - Name | Mean Yng | Mean Old | pAge | qAge | pGender | qGender |
|---|---|---|---|---|---|---|
| CD8 NAIVE | 71.62 | 48.33 | 0.005 | 0.15 | 0.14 | 0.42 |
| CD8 TERM DIFF EFFECTOR MEMORY | 14.68 | 28.47 | 0.065 | 0.175 | 0.155 | 0.4 |
| MONOCYTES | 26.91 | 33.86 | 0.07 | 0.175 | 0.28 | 0.45 |
| CD8+CD28− | 22.98 | 43.55 | 0.065 | 0.175 | 0.065 | 0.35 |
| CD4 TERM DIFF EFFECTOR MEMORY | 0.65 | 3.41 | 0.02 | 0.1875 | 0.265 | 0.45 |
| CD8 CENTRAL MEMORY | 11.78 | 18.48 | 0.095 | 0.214286 | 0.425 | 0.535714 |
| NK T CELLS | 5.76 | 9.89 | 0.12 | 0.225 | 0.275 | 0.45 |
| CD4+CD28− | 1.63 | 4.02 | 0.045 | 0.25 | 0.3 | 0.45 |

| Serum cytokines - Name | Mean Yng | Mean Old | pAge | qAge | pGender | qGender |
|---|---|---|---|---|---|---|
| EOTAXIN | 238 | 427.58 | 0.01 | 0.07875 | 0.715 | 0.933333 |
| IFN-G | 137.98 | 49.86 | 0.01 | 0.07875 | 0.12 | 0.458182 |
| IL-7 | 82.02 | 98.27 | 0.01 | 0.07875 | 0.12 | 0.458182 |
| MCP-3 | 121.81 | 162.92 | 0.01 | 0.07875 | 0.675 | 0.890909 |
| IL-12-P70 | 28.13 | 19.08 | 0.005 | 0.105 | 0.3 | 0.63 |
| IL-17 | 150.77 | 28.96 | 0.005 | 0.105 | 0.355 | 0.730435 |
| IL-4 | 55.63 | 98.19 | 0.005 | 0.105 | 0.455 | 0.724138 |
| TGF-a | 40.08 | 60.01 | 0.005 | 0.105 | 0.14 | 0.42 |
| IP10 | 462.3 | 1052.06 | 0.025 | 0.126 | 0.465 | 0.724138 |
| TNF-A | 26.09 | 42.98 | 0.025 | 0.126 | 0.02 | 0.35 |
| IFNA2 | 51.86 | 91.98 | 0.035 | 0.14 | 0.995 | 1 |
| IL-5 | 12.76 | 18.36 | 0.035 | 0.14 | 0.015 | 0.42 |

| Cytokine responses | Yng | Old | pAge | qAge | pGender | qGender |
|---|---|---|---|---|---|---|
| cd20_IL7_STAT3 | 0.99 | 1.04 | 0 | 0.027692 | 0.15 | 1.542857 |
| cd4_IFNa_STAT5 | 1.16 | 0.87 | 0 | 0.027692 | 0.295 | 1.661538 |
| cd4_IL6_STAT5 | 1.26 | 0.71 | 0 | 0.027692 | 0.83 | 0.952941 |
| cd4_IL21_STAT1 | 1.15 | 0.83 | 0 | 0.027692 | 0.515 | 1.004651 |
| cd4_IL21_STAT5 | 1.14 | 0.92 | 0 | 0.027692 | 0.74 | 0.9 |
| cd8_IFNa_STAT1 | 1.35 | 0.66 | 0 | 0.027692 | 0.64 | 0.916364 |
| cd8_IFNa_STAT3 | 1.15 | 0.79 | 0 | 0.027692 | 0.435 | 1.090909 |
| cd8_IFNa_STAT5 | 1.2 | 0.78 | 0 | 0.027692 | 0.415 | 1.090909 |
| cd8_IL6_STAT1 | 1.57 | 0.58 | 0 | 0.027692 | 0.265 | 1.661538 |
| cd8_IL6_STAT5 | 1.45 | 0.8 | 0 | 0.027692 | 0.42 | 1.090909 |
| cd8_IL21_STAT1 | 1.28 | 0.79 | 0 | 0.027692 | 0.74 | 0.9 |
| mono_IFNa_STAT1 | 1.13 | 0.87 | 0 | 0.027692 | 0.37 | 1.44 |
| mono_IL7_STAT5 | 1.09 | 0.95 | 0 | 0.027692 | 0.48 | 1.090909 |
| cd4_IL7_STAT5 | 1.08 | 1 | 0.005 | 0.036 | 0.72 | 0.9 |
| cd8_IFNg_STAT1 | 1.37 | 0.9 | 0.005 | 0.036 | 0.13 | 1.56 |
| cd8_IL7_STAT1 | 1.13 | 0.94 | 0.005 | 0.036 | 0.43 | 1.090909 |
| cd8_IL10_STAT1 | 1.19 | 0.91 | 0.005 | 0.036 | 0.61 | 0.916364 |
| cd8_IL21_STAT5 | 1.07 | 0.89 | 0.005 | 0.036 | 0.545 | 1.004651 |
| mono_IFNa_STAT3 | 1.08 | 0.78 | 0.005 | 0.036 | 0.945 | 1 |
| mono_IFNa_STAT5 | 1.04 | 0.81 | 0.005 | 0.036 | 0.7 | 0.916364 |
| cd4_IFNa_STAT1 | 1.19 | 0.78 | 0.01 | 0.045 | 0.785 | 0.9 |
| cd4_IFNa_STAT3 | 1.06 | 0.64 | 0.01 | 0.045 | 0.515 | 1.004651 |
| cd4_IL6_STAT1 | 1.27 | 0.77 | 0.01 | 0.045 | 0.74 | 0.9 |
| mono_IFNg_STAT3 | 1.07 | 0.89 | 0.01 | 0.045 | 0.8 | 0.9 |
| cd20_IFNa_STAT3 | 1.04 | 0.92 | 0.015 | 0.053333 | 0.53 | 1.004651 |
| cd8_IL6_STAT3 | 1.15 | 0.67 | 0.015 | 0.053333 | 0.275 | 1.661538 |
| mono_IL6_STAT3 | 1.09 | 0.7 | 0.015 | 0.053333 | 0.97 | 1 |
| cd4_IL6_STAT3 | 1.08 | 0.66 | 0.02 | 0.062069 | 0.595 | 1.004651 |
| cd4_IL21_STAT3 | 1.07 | 0.69 | 0.02 | 0.062069 | 0.485 | 1.090909 |
| cd8_IL7_STAT3 | 1.01 | 0.93 | 0.025 | 0.072 | 0.1 | 1.44 |
| cd4_IL10_STAT1 | 1.05 | 0.81 | 0.03 | 0.08129 | 0.615 | 0.916364 |
| cd20_IFNa_STAT1 | 1.01 | 0.79 | 0.035 | 0.087273 | 0.48 | 1.090909 |
| cd4_IL10_STAT3 | 1.03 | 0.69 | 0.035 | 0.087273 | 0.65 | 0.916364 |
| cd4_IL7_STAT3 | 1 | 0.9 | 0.045 | 0.105882 | 0.435 | 1.090909 |
| cd20_IFNg_STAT3 | 0.99 | 1.03 | 0.05 | 0.12 | 0.02 | 1.8 |
| mono_IL6_STAT1 | 1.06 | 1 | 0.05 | 0.12 | 0.555 | 1.004651 |

TABLE S2-continued

Significant age-associated measurement from regression analysis of all individuals

| | | | | | | |
|---|---|---|---|---|---|---|
| cd4_IFNg_STAT1 | 1.05 | 0.89 | 0.06 | 0.136216 | 0.325 | 1.44 |
| cd20_IFNa_STAT5 | 1.04 | 0.92 | 0.075 | 0.147692 | 0.82 | 0.952941 |
| mono_IFNg_STAT5 | 1.05 | 0.88 | 0.08 | 0.147692 | 0.81 | 0.952941 |

| Phophoprotein baseline | Yng | Old | pAge | qAge | pGender | qGender |
|---|---|---|---|---|---|---|
| cd20_Unstimulated_STAT1 | 0.96 | 1.69 | 0 | 0.03 | 0.94 | 1 |
| cd8_Unstimulated_STAT1 | 0.73 | 1.18 | 0 | 0.03 | 0.24 | 0.45 |
| cd4_Unstimulated_STAT1 | 0.87 | 1.55 | 0.005 | 0.04 | 0.17 | 0.432 |
| cd20_Unstimulated_STAT3 | 0.98 | 1.03 | 0.055 | 0.102857 | 0.075 | 0.32 |
| cd8_Unstimulated_STAT5 | 0.97 | 1.05 | 0.055 | 0.102857 | 0.095 | 0.3 |
| cd4_Unstimulated_STAT3 | 0.94 | 2.37 | 0.03 | 0.105 | 0.27 | 0.45 |
| cd4_Unstimulated_STAT5 | 0.97 | 1.02 | 0.04 | 0.108 | 0.055 | 0.36 |
| cd8_Unstimulated_STAT3 | 0.9 | 1.07 | 0.08 | 0.12 | 0.03 | 0.42 |

| Gene Expression | Entrez-Id | Probe-Id | Yng | Old | pAge | qAge | pGender | qGender | is-Aging |
|---|---|---|---|---|---|---|---|---|---|
| LRP10 | 26020 | A_24_P926770 | 7.16 | 7.31 | 0 | 0.1254-02 | 0.765 | 0.914885 | 0 |
| HLA-DRB5 | 3127 | A_23_P31006 | 9.05 | 9.7 | 0 | 0.1254-02 | 0.345 | 0.67843 | 0 |
| PSTPIP1 | 9051 | A_23_P48997 | 7.92 | 8.28 | 0 | 0.1254-02 | 0.52 | 0.811404 | 0 |
| GRB2 | 2885 | A_24_P407717 | 10.69 | 10.81 | 0 | 0.1254-02 | 0 | 0.242444 | 1 |
| HLA-J | 3137 | A_24_P418044 | 13.73 | 14.28 | 0 | 0.1254-02 | 0.735 | 0.914885 | 0 |
| PURB | 5814 | A_24_P286465 | 11.3 | 11.41 | 0 | 0.1254-02 | 0.54 | 0.811404 | 0 |
| CFD | 1675 | A_23_P119562 | 11.32 | 11.56 | 0 | 0.1254-02 | 0.05 | 0.337423 | 0 |
| LSP1 | 4046 | A_23_P13382 | 10.89 | 11.18 | 0 | 0.1254-02 | 0.13 | 0.409617 | 0 |
| NKX2-3 | 159296 | A_24_P38702 | 7.13 | 7.42 | 0 | 0.1254-02 | 0.715 | 0.914885 | 0 |
| MCL1 | 4170 | A_24_P336754 | 13.97 | 14.2 | 0 | 0.1254-02 | 0.655 | 0.864403 | 0 |
| FCGR2A | 2212 | A_23_P85716 | 8.04 | 8.16 | 0 | 0.1254-02 | 0.68 | 0.864403 | 0 |
| HLA-B | 3106 | A_24_P161933 | 13 | 13.46 | 0 | 0.1254-02 | 0.435 | 0.750602 | 0 |
| IRF1 | 3659 | A_23_P41765 | 9.11 | 9.46 | 0 | 0.1254-02 | 0.15 | 0.434661 | 0 |
| FPR1 | 2357 | A_23_P38795 | 9.55 | 10.52 | 0 | 0.1254-02 | 0.715 | 0.914885 | 0 |
| RAB18 | 22931 | A_23_P138376 | 10.64 | 10.84 | 0 | 0.1254-02 | 0.16 | 0.463385 | 0 |
| PTCRA | 171558 | A_23_P30755 | 7.6 | 7.88 | 0 | 0.1254-02 | 0.1 | 0.37395 | 0 |
| ARHGAP1 | 392 | A_23_P314070 | 12.76 | 12.9 | 0 | 0.1254-02 | 0.26 | 0.595091 | 1 |
| SDF4 | 51150 | A_23_P201338 | 12.71 | 12.89 | 0 | 0.1254-02 | 0.86 | 0.960763 | 0 |
| AMICA1 | 120425 | A_24_P192914 | 10.94 | 11.78 | 0 | 0.1254-02 | 0.535 | 0.811404 | 0 |
| CD79A | 973 | A_23_P107735 | 9.33 | 9.88 | 0 | 0.1254-02 | 0.13 | 0.409617 | 0 |
| CD4 | 920 | A_24_P295999 | 10.21 | 10.81 | 0 | 0.1254-02 | 0.18 | 0.479283 | 0 |
| CTNNB1 | 1499 | A_32_P187875 | 10.28 | 10.46 | 0 | 0.1254-02 | 0.525 | 0.811404 | 1 |
| IGF2AS | 51214 | A_23_P116435 | 7.78 | 7.93 | 0 | 0.1254-02 | 0.94 | 1 | 0 |
| XRCC6BP1 | 91419 | A_24_P927404 | 7.05 | 6.96 | 0 | 0.1254-02 | 0.955 | 1 | 0 |
| PAG1 | 55824 | A_32_P61684 | 8.54 | 8.38 | 0 | 0.1254-02 | 0.59 | 0.811404 | 0 |
| CCL3L3 | 414062 | A_24_P228130 | 7.16 | 6.96 | 0 | 0.1254-02 | 0.955 | 1 | 0 |
| DPP4 | 1803 | A_24_P97104 | 7.04 | 6.9 | 0 | 0.1254-02 | 0.32 | 0.67843 | 0 |
| TLN2 | 83660 | A_32_P170406 | 7.57 | 7.42 | 0 | 0.1254-02 | 0.345 | 0.67843 | 0 |
| RAC1 | 5879 | A_23_P215406 | 12.63 | 12.45 | 0 | 0.1254-02 | 0.05 | 0.337423 | 0 |

TABLE S2-continued

Significant age-associated measurement from regression analysis of all individuals

| Gene | ID | Probe | V1 | V2 | | p | | | |
|---|---|---|---|---|---|---|---|---|---|
| LOC731884 | 731884 | A_32_P132748 | 9.2 | 9.03 | 0 | 0.1254-02 | 0.575 | 0.811404 | 0 |
| PEA15 | 8682 | A_24_P410952 | 9.43 | 9.23 | 0 | 0.1254-02 | 0.435 | 0.750602 | 0 |
| PLG | 5340 | A_32_P206123 | 7.33 | 7.19 | 0 | 0.1254-02 | 0.86 | 0.960763 | 0 |
| CDH1 | 999 | A_23_P206359 | 11.32 | 11.1 | 0 | 0.1254-02 | 0.265 | 0.595091 | 0 |
| FKBP10 | 60681 | A_23_P15727 | 13.53 | 13.4 | 0 | 0.1254-02 | 0.37 | 0.67843 | 0 |
| RB1 | 5925 | A_24_P102636 | 7.64 | 7.49 | 0 | 0.1254-02 | 0.095 | 0.37395 | 1 |
| TAOK2 | 9344 | A_23_P308673 | 8.61 | 8.45 | 0 | 0.1254-02 | 0.38 | 0.67843 | 0 |
| DLL3 | 10683 | A_23_P16438 | 7.66 | 7.48 | 0 | 0.1254-02 | 0.275 | 0.595091 | 1 |
| MCAM | 4162 | A_23_P162171 | 10.61 | 10.45 | 0 | 0.1254-02 | 0.195 | 0.493665 | 0 |
| PTGR1 | 22949 | A_23_P157809 | 11.8 | 11.62 | 0 | 0.1254-02 | 0.65 | 0.864403 | 0 |
| TCTN3 | 26123 | A_32_P2738 | 11.84 | 11.62 | 0 | 0.1254-02 | 0.175 | 0.475209 | 0 |
| CTNNAL1 | 8727 | A_23_P157795 | 14.09 | 13.85 | 0 | 0.1254-02 | 0.6 | 0.811404 | 0 |
| IGBP1 | 3476 | A_23_P171255 | 10.06 | 9.93 | 0 | 0.1254-02 | 0.67 | 0.864403 | 0 |
| SEMA5A | 9037 | A_24_P912799 | 9.34 | 9.17 | 0 | 0.1254-02 | 0.58 | 0.811404 | 0 |
| CXCL12 | 6387 | A_24_P944054 | 6.77 | 6.65 | 0 | 0.1254-02 | 0.6 | 0.811404 | 0 |
| CMTM4 | 146223 | A_32_P84009 | 11.34 | 11.22 | 0 | 0.1254-02 | 0.58 | 0.811404 | 0 |
| APEX1 | 328 | A_23_P151649 | 12.82 | 12.64 | 0 | 0.1254-02 | 0.735 | 0.914885 | 1 |
| SLIT2 | 9353 | A_32_P106615 | 7.86 | 7.78 | 0 | 0.1254-02 | 0.475 | 0.750602 | 0 |
| CDH13 | 1012 | A_32_P85999 | 11.21 | 11.05 | 0 | 0.1254-02 | 0.04 | 0.307324 | 0 |
| SLTM | 79811 | A_23_P26094 | 11.67 | 11.5 | 0 | 0.1254-02 | 0.92 | 1 | 0 |
| NLGN4X | 57502 | A_23_P364592 | 6.8 | 6.65 | 0 | 0.1254-02 | 0.505 | 0.811404 | 0 |
| IFT140 | 9742 | A_23_P140725 | 8.99 | 8.91 | 0 | 0.1254-02 | 0.565 | 0.811404 | 0 |
| ATP5B | 506 | A_23_P33216 | 14.05 | 13.88 | 0 | 0.1254-02 | 0.965 | 1 | 0 |
| PSMA4 | 5685 | A_24_P124992 | 13.14 | 13.01 | 0 | 0.1254-02 | 0.15 | 0.434661 | 0 |
| CASP4 | 837 | A_23_P35912 | 12.63 | 12.75 | 0 | 0.1254-02 | 0.485 | 0.750602 | 0 |
| RRAGA | 10670 | A_23_P169117 | 12.88 | 12.77 | 0 | 0.1254-02 | 0.095 | 0.37395 | 0 |
| MYBPC3 | 4607 | A_23_P127385 | 7.09 | 7.34 | 0 | 0.1254-02 | 0.475 | 0.750602 | 0 |
| TREML1 | 340205 | A_23_P156550 | 6.85 | 7.1 | 0 | 0.1254-02 | 0.365 | 0.67843 | 0 |
| RARA | 5914 | A_23_P207842 | 7.76 | 8.06 | 0 | 0.1254-02 | 0.255 | 0.595091 | 0 |
| NRP1 | 8829 | A_23_P86390 | 6.93 | 7.05 | 0 | 0.1254-02 | 0.525 | 0.811404 | 0 |
| SARNP | 84324 | A_23_P43946 | 13.96 | 13.84 | 0 | 0.1254-02 | 0.225 | 0.595091 | 0 |
| IL17D | 53342 | A_23_P345692 | 8.47 | 8.37 | 0 | 0.1254-02 | 0.11 | 0.386195 | 0 |
| ASB1 | 51665 | A_32_P183609 | 9.87 | 9.79 | 0 | 0.1254-02 | 0.305 | 0.67843 | 0 |
| TYROBP | 7305 | A_23_P27994 | 11.41 | 12.64 | 0 | 0.1254-02 | 0.67 | 0.864403 | 0 |
| CASP9 | 842 | A_24_P111342 | 12.07 | 11.96 | 0 | 0.1254-02 | 0.425 | 0.750602 | 0 |
| IL13RA1 | 3597 | A_23_P137196 | 10.58 | 10.49 | 0 | 0.1254-02 | 0.13 | 0.409617 | 0 |
| HLA-B | 3106 | A_24_P113674 | 14.35 | 14.92 | 0 | 0.1254-02 | 0.87 | 0.960763 | 0 |
| EXOC6 | 54536 | A_32_P58280 | 7.2 | 7.09 | 0 | 0.1254-02 | 0.97 | 1 | 0 |
| BUB3 | 9184 | A_23_P46924 | 12.14 | 12.01 | 0 | 0.1254-02 | 0.81 | 0.960763 | 1 |

TABLE S2-continued

| Significant age-associated measurement from regression analysis of all individuals | | | | | | | | | |
|---|---|---|---|---|---|---|---|---|---|
| RTN4 | 57142 | A_23_P56933 | 12.98 | 12.87 | 0 | 0.1254-02 | 0.105 | 0.386195 | 0 |
| CADM3 | 57863 | A_23_P201156 | 7.24 | 7.49 | 0 | 0.1254-02 | 0.49 | 0.750602 | 0 |
| HIVEP3 | 59269 | A_24_P876734 | 6.93 | 6.79 | 0 | 0.1254-02 | 0.725 | 0.914885 | 0 |
| CLDN11 | 5010 | A_23_P29800 | 7.24 | 7.47 | 0 | 0.1254-02 | 0.265 | 0.595091 | 0 |
| MLL3 | 58508 | A_23_P168419 | 8.46 | 8.35 | 0 | 0.1254-02 | 0.01 | 0.260797 | 0 |
| PPFIBP1 | 8496 | A_23_P47867 | 8.84 | 8.73 | 0 | 0.1254-02 | 0.295 | 0.595091 | 0 |
| CFP | 5199 | A_23_P22444 | 9.84 | 10.77 | 0 | 0.1254-02 | 0.915 | 1 | 0 |
| IL16 | 3603 | A_24_P73599 | 7.24 | 7.15 | 0 | 0.1254-02 | 0.845 | 0.960763 | 0 |
| ACVR1B | 91 | A_24_P341897 | 8.19 | 8.45 | 0 | 0.1254-02 | 0.39 | 0.67843 | 0 |
| PTGER2 | 5732 | A_23_P151710 | 8.44 | 8.31 | 0 | 0.1254-02 | 0.745 | 0.914885 | 0 |
| BMP2 | 650 | A_23_P143331 | 8.54 | 8.42 | 0 | 0.1254-02 | 0.62 | 0.864403 | 0 |
| SON | 6651 | A_32_P36217 | 11.51 | 11.36 | 0 | 0.1254-02 | 0.84 | 0.960763 | 0 |
| FRK | 2444 | A_23_P133665 | 6.72 | 6.56 | 0 | 0.1254-02 | 0.11 | 0.386195 | 0 |
| TOPORS | 10210 | A_23_P32217 | 9.51 | 9.36 | 0 | 0.1254-02 | 0.26 | 0.595091 | 0 |
| DYRK2 | 8445 | A_24_P942786 | 8.8 | 8.66 | 0 | 0.1254-02 | 0.25 | 0.595091 | 0 |
| TSLP | 85480 | A_23_P121987 | 8.1 | 8.03 | 0 | 0.1254-02 | 0.655 | 0.864403 | 0 |
| CTNND1 | 1500 | A_24_P881527 | 7.66 | 7.59 | 0 | 0.1254-02 | 0.19 | 0.479283 | 0 |
| PRKG1 | 5592 | A_32_P6062 | 6.79 | 7.13 | 0 | 0.1254-02 | 0.1 | 0.37395 | 0 |
| C14orf153 | 84334 | A_24_P22174 | 6.77 | 6.66 | 0 | 0.1254-02 | 0.205 | 0.595091 | 0 |
| CD14 | 929 | A_24_P283189 | 8.14 | 8.67 | 0 | 0.1254-02 | 0.855 | 0.960763 | 0 |
| PLG | 5340 | A_23_P30693 | 7.28 | 7.15 | 0 | 0.1254-02 | 0.845 | 0.960763 | 0 |
| CDC42SE2 | 56990 | A_23_P430764 | 8.69 | 8.56 | 0 | 0.1254-02 | 0.31 | 0.67843 | 0 |
| BCAP29 | 55973 | A_32_P150735 | 7.74 | 7.62 | 0 | 0.1254-02 | 0.91 | 1 | 0 |
| PPARA | 5465 | A_23_P306730 | 7.39 | 7.29 | 0 | 0.1254-02 | 0.8 | 0.914885 | 1 |
| THBS2 | 7058 | A_23_P62021 | 13.96 | 13.8 | 0 | 0.1254-02 | 0.255 | 0.595091 | 0 |
| SEMA5A | 9037 | A_32_P72541 | 8.3 | 8.17 | 0 | 0.1254-02 | 0.775 | 0.914885 | 0 |
| CMTM8 | 152189 | A_23_P40880 | 9.13 | 8.93 | 0 | 0.1254-02 | 0.635 | 0.864403 | 0 |
| MIB1 | 57534 | A_32_P121651 | 7.54 | 7.42 | 0 | 0.1254-02 | 0.51 | 0.811404 | 0 |
| FXR1 | 8087 | A_24_P935252 | 9.31 | 9.18 | 0 | 0.1254-02 | 0.975 | 1 | 0 |
| RIMS2 | 9699 | A_23_P147786 | 7.39 | 7.22 | 0 | 0.1254-02 | 0.755 | 0.914885 | 0 |
| LY86 | 9450 | A_23_P70688 | 9.8 | 10.04 | 0 | 0.1254-02 | 0.185 | 0.479283 | 0 |
| CYCS | 54205 | A_24_P29665 | 8.22 | 8.1 | 0 | 0.1254-02 | 0.05 | 0.337423 | 0 |
| COL27A1 | 85301 | A_23_P158096 | 12.74 | 12.61 | 0 | 0.1254-02 | 0.965 | 1 | 0 |
| CRADD | 8738 | A_32_P29806 | 10.92 | 10.81 | 0 | 0.1254-02 | 0.95 | 1 | 0 |
| HLA-F | 3134 | A_23_P145264 | 12.36 | 12.67 | 0 | 0.1254-02 | 0.3 | 0.595091 | 0 |
| SLAMF7 | 57823 | A_24_P353638 | 8.47 | 8.35 | 0 | 0.1254-02 | 0.62 | 0.864403 | 0 |
| YWHAG | 7532 | A_24_P106681 | 14.51 | 14.33 | 0 | 0.1254-02 | 0.125 | 0.409617 | 0 |
| INCENP | 3619 | A_23_P116387 | 10.79 | 10.65 | 0 | 0.1254-02 | 0.805 | 0.960763 | 0 |
| DSTN | 11034 | A_23_P408095 | 13.7 | 13.58 | 0 | 0.1254-02 | 0.84 | 0.960763 | 0 |

TABLE S2-continued

| Significant age-associated measurement from regression analysis of all individuals | | | | | | | | | |
|---|---|---|---|---|---|---|---|---|---|
| JAKMIP1 | 152789 | A_23_P144274 | 9.85 | 9.78 | 0 | 0.1254-02 | 0.07 | 0.332405 | 0 |
| CBLB | 868 | A_23_P212715 | 9.84 | 9.71 | 0 | 0.1254-02 | 0.165 | 0.463385 | 0 |
| ERC1 | 23085 | A_23_P258377 | 7.1 | 6.97 | 0 | 0.1254-02 | 0.975 | 1 | 0 |
| FLJ23834 | 222256 | A_32_P197942 | 7.06 | 6.95 | 0 | 0.1254-02 | 0.35 | 0.67843 | 0 |
| FUT8 | 2530 | A_23_P313632 | 10.7 | 10.59 | 0 | 0.1254-02 | 0.35 | 0.67843 | 0 |
| FN1 | 2335 | A_24_P334130 | 8.71 | 8.6 | 0 | 0.1254-02 | 0.635 | 0.864403 | 0 |
| FCER1G | 2207 | A_23_P160849 | 9.27 | 9.76 | 0 | 0.1254-02 | 0.56 | 0.811404 | 0 |
| NF2 | 4771 | A_23_P325991 | 7.13 | 7 | 0 | 0.1254-02 | 0.145 | 0.434661 | 0 |
| PDCL3 | 79031 | A_32_P157539 | 11.76 | 11.66 | 0 | 0.1254-02 | 0.95 | 1 | 0 |
| IRS2 | 8660 | A_24_P207003 | 7.15 | 7.28 | 0 | 0.1254-02 | 0.19 | 0.479283 | 1 |
| TGM2 | 7052 | A_24_P923251 | 8.25 | 8.45 | 0 | 0.1254-02 | 0.81 | 0.960763 | 0 |
| COL15A1 | 1306 | A_23_P112554 | 9.36 | 9.18 | 0 | 0.1254-02 | 0.035 | 0.304111 | 0 |
| SMAD2 | 4087 | A_32_P109002 | 7.01 | 6.92 | 0 | 0.1254-02 | 0.86 | 0.960763 | 0 |
| E2F2 | 1870 | A_23_P125990 | 7.66 | 8.06 | 0 | 0.1254-02 | 0.14 | 0.421061 | 0 |
| ABL1 | 25 | A_24_P282416 | 7.51 | 7.42 | 0 | 0.1254-02 | 0.155 | 0.454288 | 1 |
| GLT25D2 | 23127 | A_24_P62505 | 8.45 | 8.57 | 0 | 0.1254-02 | 0.525 | 0.811404 | 0 |
| PRAM1 | 84106 | A_23_P165219 | 8.39 | 8.73 | 0 | 0.1254-02 | 0.66 | 0.864403 | 0 |
| PBX2 | 5089 | A_32_P141664 | 7.55 | 7.69 | 0 | 0.1254-02 | 0.885 | 0.960763 | 0 |
| EHD1 | 10938 | A_23_P52647 | 12.1 | 12.27 | 0 | 0.1254-02 | 0.345 | 0.67843 | 0 |
| ITFG3 | 83986 | A_23_P66117 | 11.9 | 12.03 | 0 | 0.1254-02 | 0.34 | 0.67843 | 0 |
| CNTNAP2 | 26047 | A_23_P84399 | 8.56 | 8.68 | 0 | 0.1254-02 | 0.75 | 0.914885 | 0 |
| THBS1 | 7057 | A_24_P142118 | 9.65 | 9.83 | 0 | 0.1254-02 | 0.705 | 0.914885 | 0 |
| UCP3 | 7352 | A_24_P292470 | 7.45 | 7.84 | 0 | 0.1254-02 | 0.065 | 0.332405 | 1 |
| SSTR3 | 6753 | A_23_P68910 | 7.15 | 7.35 | 0 | 0.1254-02 | 0.185 | 0.479283 | 1 |
| EXOC7 | 23265 | A_23_P100556 | 9.67 | 9.79 | 0 | 0.1254-02 | 0.58 | 0.811404 | 0 |
| CD300LB | 124599 | A_23_P15369 | 7.02 | 7.29 | 0 | 0.1254-02 | 0.685 | 0.864403 | 0 |
| LAMC2 | 3918 | A_23_P201636 | 7.78 | 7.88 | 0 | 0.1254-02 | 0.08 | 0.346006 | 0 |
| RUNX1 | 861 | A_24_P917783 | 7.47 | 7.84 | 0 | 0.1254-02 | 0.215 | 0.595091 | 0 |
| TUBB | 203068 | A_32_P78528 | 14.06 | 14.15 | 0 | 0.1254-02 | 0.54 | 0.811404 | 0 |
| B3GALNT1 | 8706 | A_23_P41166 | 9.33 | 9.47 | 0 | 0.1254-02 | 0.21 | 0.595091 | 0 |
| MPZL2 | 10205 | A_24_P278552 | 6.99 | 6.77 | 0 | 0.1254-02 | 0.84 | 0.960763 | 0 |
| SBDS | 51119 | A_32_P177024 | 10.42 | 10.51 | 0 | 0.1254-02 | 0.865 | 0.960763 | 0 |
| LAT2 | 7462 | A_23_P259621 | 10.67 | 10.96 | 0 | 0.1254-02 | 0.965 | 1 | 0 |
| MLLT6 | 4302 | A_32_P98683 | 11.01 | 11.16 | 0 | 0.1254-02 | 0.06 | 0.332405 | 0 |
| LALBA | 3906 | A_23_P116765 | 6.52 | 6.94 | 0 | 0.1254-02 | 0.275 | 0.595091 | 0 |
| PSMB2 | 5690 | A_24_P284893 | 12.84 | 12.93 | 0 | 0.1254-02 | 0.7 | 0.864403 | 0 |
| XRCC6 | 2547 | A_32_P230838 | 7 | 6.88 | 0 | 0.1254-02 | 0.185 | 0.479283 | 1 |
| NINJ2 | 4815 | A_23_P48109 | 8.93 | 9.09 | 0 | 0.1254-02 | 0.6 | 0.811404 | 0 |
| JAK3 | 3718 | A_24_P308096 | 7.6 | 7.98 | 0 | 0.1254-02 | 0.09 | 0.362659 | 0 |

TABLE S2-continued

Significant age-associated measurement from regression analysis of all individuals

| COL6A1 | 1291 | A_32_P72622 | 7.38 | 7.55 | 0 | 0.1254-02 | 0.11 | 0.386195 | 0 |
|---|---|---|---|---|---|---|---|---|---|
| LOC645166 | 645166 | A_32_P217655 | 11.01 | 11.1 | 0 | 0.1254-02 | 0.835 | 0.960763 | 0 |
| BCL6B | 255877 | A_23_P324813 | 6.7 | 6.62 | 0 | 0.1254-02 | 0.755 | 0.914885 | 0 |
| ERCC2 | 2068 | A_24_P401990 | 8.28 | 8.59 | 0 | 0.1254-02 | 0.09 | 0.362659 | 1 |
| FCGR3A | 2214 | A_23_P200728 | 9.6 | 10.62 | 0 | 0.1254-02 | 0.785 | 0.914885 | 0 |
| STX1A | 6804 | A_23_P82420 | 10.19 | 10.42 | 0 | 0.1254-02 | 0.01 | 0.260797 | 0 |
| UMOD | 7369 | A_23_P158775 | 7.1 | 7.32 | 0 | 0.1254-02 | 0.025 | 0.286477 | 0 |
| BNIP3L | 665 | A_23_P408708 | 11.6 | 11.74 | 0 | 0.1254-02 | 0.45 | 0.750602 | 0 |
| NID2 | 22795 | A_23_P163087 | 10.84 | 10.93 | 0 | 0.1254-02 | 0.57 | 0.811404 | 0 |
| PSMB2 | 5690 | A_23_P170058 | 11.96 | 12.16 | 0 | 0.1254-02 | 0.26 | 0.595091 | 0 |
| KIR2DL4 | 3805 | A_24_P288298 | 6.73 | 7.03 | 0 | 0.1254-02 | 0.32 | 0.67843 | 0 |
| RAC2 | 5880 | A_23_P218770 | 11.2 | 11.44 | 0 | 0.1254-02 | 0.405 | 0.750602 | 0 |
| RBP4 | 5950 | A_23_P75283 | 12.63 | 12.72 | 0 | 0.1254-02 | 0.49 | 0.750602 | 0 |
| PDGFRB | 5159 | A_32_P215404 | 7.4 | 7.66 | 0 | 0.1254-02 | 0.105 | 0.386195 | 1 |
| CDC42SE1 | 56882 | A_23_P320883 | 9.99 | 10.19 | 0 | 0.1254-02 | 0.42 | 0.750602 | 0 |
| FCN1 | 2219 | A_23_P157875 | 8.04 | 8.74 | 0 | 0.1254-02 | 0.42 | 0.750602 | 0 |
| IFITM2 | 10581 | A_24_P287043 | 12.34 | 12.53 | 0 | 0.1254-02 | 0.575 | 0.811404 | 0 |
| TNFAIP8L1 | 126282 | A_24_P134229 | 7.08 | 6.9 | 0 | 0.1254-02 | 0.79 | 0.914885 | 0 |
| TNFRSF11A | 8792 | A_23_P390518 | 7.39 | 7.19 | 0 | 0.1254-02 | 0.745 | 0.914885 | 0 |
| APOL2 | 23780 | A_24_P48898 | 11.23 | 11.51 | 0 | 0.1254-02 | 0.36 | 0.67843 | 0 |
| LITAF | 9516 | A_23_P3532 | 10.27 | 10.38 | 0 | 0.1254-02 | 0.72 | 0.914885 | 0 |
| TAOK2 | 9344 | A_23_P218269 | 8.79 | 9.25 | 0 | 0.1254-02 | 0.175 | 0.475209 | 0 |
| MINK1 | 50488 | A_23_P164307 | 8.15 | 8.44 | 0 | 0.1254-02 | 0.07 | 0.332405 | 0 |
| ITGB5 | 3693 | A_23_P166633 | 11.96 | 12.05 | 0 | 0.1254-02 | 0.53 | 0.811404 | 0 |
| CDSN | 1041 | A_23_P70520 | 7.17 | 7.46 | 0 | 0.1254-02 | 0.085 | 0.362659 | 0 |
| LRP10 | 26020 | A_23_P205499 | 11.57 | 11.66 | 0 | 0.1254-02 | 0.6 | 0.811404 | 0 |
| XCL2 | 6846 | A_23_P51534 | 6.93 | 6.79 | 0 | 0.1254-02 | 0.915 | 1 | 0 |
| RHOA | 387 | A_24_P174550 | 10.45 | 10.59 | 0 | 0.1254-02 | 0.705 | 0.914885 | 0 |
| HLA-DRB1 | 3123 | A_24_P343233 | 9.57 | 10.01 | 0.005 | 0.1484-35 | 0.69 | 0.864403 | 0 |
| FCN1 | 2219 | A_23_P157879 | 11.05 | 12.26 | 0.005 | 0.1484-35 | 0.78 | 0.914885 | 0 |
| 7-Sep | 989 | A_24_P291973 | 9.46 | 9.57 | 0.005 | 0.1484-35 | 0.36 | 0.67843 | 0 |
| MMP9 | 4318 | A_23_P40174 | 8.47 | 8.69 | 0.005 | 0.1484-35 | 0.5 | 0.750602 | 0 |
| MLXIPL | 51085 | A_24_P209389 | 8.89 | 9.37 | 0.005 | 0.1484-35 | 0.225 | 0.595091 | 0 |
| RPSA | 3921 | A_32_P222335 | 9.35 | 9.43 | 0.005 | 0.1484-35 | 0.565 | 0.811404 | 0 |
| HLA-A | 3105 | A_24_P376483 | 12.35 | 12.5 | 0.005 | 0.1484-35 | 0.11 | 0.386195 | 0 |
| PHF17 | 79960 | A_23_P167256 | 11.74 | 11.95 | 0.005 | 0.1484-35 | 0.015 | 0.266098 | 0 |
| HLA-C | 3107 | A_23_P113716 | 14.13 | 14.69 | 0.005 | 0.1484-35 | 0.365 | 0.67843 | 0 |
| CPLX2 | 10814 | A_23_P167537 | 8.98 | 9.36 | 0.005 | 0.1484-35 | 0.05 | 0.337423 | 0 |
| CASP8 | 841 | A_23_P209389 | 8.73 | 8.99 | 0.005 | 0.1484-35 | 0.15 | 0.434661 | 0 |

TABLE S2-continued

Significant age-associated measurement from regression analysis of all individuals

| BCL2 | 596 | A_23_P208132 | 8.72 | 9.27 | 0.005 | 0.1484-35 | 0.125 | 0.409617 | 1 |
| --- | --- | --- | --- | --- | --- | --- | --- | --- | --- |
| CACNB3 | 784 | A_23_P371794 | 7.97 | 8.29 | 0.005 | 0.1484-35 | 0.16 | 0.463385 | 0 |
| DGKZ | 8525 | A_23_P127627 | 9.41 | 9.61 | 0.005 | 0.1484-35 | 0.07 | 0.332405 | 0 |
| PRKCD | 5580 | A_23_P144054 | 10.09 | 10.29 | 0.005 | 0.1484-35 | 0.745 | 0.914885 | 1 |
| SMAD1 | 4086 | A_23_P334271 | 6.96 | 6.85 | 0.005 | 0.1484-35 | 0.035 | 0.304111 | 0 |
| SLFN5 | 162394 | A_23_P402899 | 7.66 | 7.57 | 0.005 | 0.1484-35 | 0.015 | 0.266098 | 0 |
| IGJ | 3512 | A_32_P43664 | 10.51 | 10.59 | 0.005 | 0.1484-35 | 0.43 | 0.750602 | 0 |
| CCR9 | 10803 | A_23_P212360 | 7.03 | 6.91 | 0.005 | 0.1484-35 | 0.245 | 0.595091 | 0 |
| PPP2R1A | 5518 | A_32_P200600 | 7.43 | 7.32 | 0.005 | 0.1484-35 | 0.485 | 0.750602 | 0 |
| DHRS2 | 10202 | A_23_P321501 | 15.21 | 15.06 | 0.005 | 0.1484-35 | 0.455 | 0.750602 | 0 |
| SGK1 | 6446 | A_23_P19673 | 13.31 | 13.18 | 0.005 | 0.1484-35 | 0.62 | 0.864403 | 0 |
| FNBP1L | 54874 | A_24_P366967 | 6.87 | 6.76 | 0.005 | 0.1484-35 | 0.115 | 0.395828 | 0 |
| IK | 3550 | A_32_P29759 | 12.94 | 12.87 | 0.005 | 0.1484-35 | 0.455 | 0.750602 | 0 |
| PSME1 | 5720 | A_23_P151614 | 9.58 | 9.38 | 0.005 | 0.1484-35 | 0.825 | 0.960763 | 0 |
| GPR98 | 84059 | A_23_P19134 | 9.02 | 8.85 | 0.005 | 0.1484-35 | 0.48 | 0.750602 | 0 |
| C1QTNF3 | 114899 | A_23_P122068 | 8.46 | 8.32 | 0.005 | 0.1484-35 | 0.64 | 0.864403 | 0 |
| IL2RG | 3561 | A_23_P148473 | 7.5 | 7.35 | 0.005 | 0.1484-35 | 0.345 | 0.67843 | 1 |
| SNUPN | 10073 | A_24_P27412 | 9.26 | 9.09 | 0.005 | 0.1484-35 | 0.31 | 0.67843 | 2 |
| STEAP2 | 261729 | A_23_P428260 | 8.13 | 7.93 | 0.005 | 0.1484-35 | 0.45 | 0.750602 | 0 |
| MAP4K4 | 9448 | A_23_P102192 | 9.71 | 9.45 | 0.005 | 0.1484-35 | 0.86 | 0.960763 | 0 |
| IFRD1 | 3475 | A_24_P137897 | 11.09 | 10.88 | 0.005 | 0.1484-35 | 0.82 | 0.960763 | 0 |
| NID1 | 4811 | A_23_P200928 | 8.55 | 8.43 | 0.005 | 0.1484-35 | 0.68 | 0.864403 | 0 |
| LPP | 4026 | A_23_P251118 | 8.44 | 8.3 | 0.005 | 0.1484-35 | 0.49 | 0.750602 | 0 |
| SMURF2 | 64750 | A_23_P100754 | 8.21 | 8.04 | 0.005 | 0.1484-35 | 0.665 | 0.864403 | 0 |
| CAMK2D | 817 | A_24_P114739 | 10.72 | 10.55 | 0.005 | 0.1484-35 | 0.86 | 0.960763 | 0 |
| TWIST1 | 7291 | A_23_P71067 | 9.22 | 9.12 | 0.005 | 0.1484-35 | 0.14 | 0.421061 | 0 |
| WNK1 | 65125 | A_24_P769359 | 12.08 | 11.89 | 0.005 | 0.1484-35 | 0.195 | 0.493665 | 0 |
| AP2S1 | 1175 | A_24_P113295 | 11.17 | 11.06 | 0.005 | 0.1484-35 | 0.99 | 1 | 0 |
| SIK1 | 150094 | A_23_P132115 | 10.02 | 9.93 | 0.005 | 0.1484-35 | 0.955 | 1 | 0 |
| PCDHB15 | 56121 | A_23_P121851 | 7.7 | 7.58 | 0.005 | 0.1484-35 | 0.055 | 0.337423 | 0 |
| PUF60 | 22827 | A_23_P9756 | 12.99 | 12.84 | 0.005 | 0.1484-35 | 0.26 | 0.595091 | 0 |
| RFFL | 117584 | A_23_P330209 | 7.82 | 7.71 | 0.005 | 0.1484-35 | 0.23 | 0.595091 | 0 |
| DDR2 | 4921 | A_32_P88965 | 8.18 | 8.07 | 0.005 | 0.1484-35 | 0.41 | 0.750602 | 0 |
| HLA-B | 3106 | A_23_P125107 | 13.6 | 13.89 | 0.005 | 0.1484-35 | 1 | 1 | 0 |
| FANCD2 | 2177 | A_23_P143994 | 9.92 | 9.82 | 0.005 | 0.1484-35 | 0.095 | 0.37395 | 0 |
| HDAC4 | 9759 | A_23_P210048 | 9.91 | 9.82 | 0.005 | 0.1484-35 | 0.6 | 0.811404 | 0 |
| ICAM3 | 3385 | A_23_P164691 | 11.88 | 12.15 | 0.005 | 0.1484-35 | 0.675 | 0.864403 | 0 |
| PHB | 5245 | A_23_P130040 | 11.56 | 11.48 | 0.005 | 0.1484-35 | 0.09 | 0.362659 | 0 |
| MUC4 | 4585 | A_24_P239183 | 7.16 | 7.53 | 0.005 | 0.1484-35 | 0.235 | 0.595091 | 0 |

TABLE S2-continued

Significant age-associated measurement from regression analysis of all individuals

| | | | | | | | | | |
|---|---|---|---|---|---|---|---|---|---|
| PURB | 5814 | A_23_P134517 | 10.53 | 10.42 | 0.005 | 0.1484-35 | 0.175 | 0.475209 | 0 |
| CLDN5 | 7122 | A_23_P6321 | 7.21 | 7.47 | 0.005 | 0.1484-35 | 0.295 | 0.595091 | 0 |
| SOCS4 | 122809 | A_24_P90637 | 6.99 | 6.84 | 0.005 | 0.1484-35 | 0.015 | 0.266098 | 0 |
| GHRHR | 2692 | A_24_P17048 | 7.16 | 7.44 | 0.005 | 0.1484-35 | 0.11 | 0.386195 | 1 |
| PTGR2 | 145482 | A_23_P48713 | 9.31 | 9.2 | 0.005 | 0.1484-35 | 0.785 | 0.914885 | 0 |
| LENG8 | 114823 | A_24_P40055 | 11.43 | 11.55 | 0.005 | 0.1484-35 | 0.555 | 0.811404 | 0 |
| HLA-DOA | 3111 | A_24_P354800 | 8.42 | 8.84 | 0.005 | 0.1484-35 | 0.415 | 0.750602 | 0 |
| ULBP2 | 80328 | A_23_P168259 | 7.8 | 7.69 | 0.005 | 0.1484-35 | 0.805 | 0.960763 | 0 |
| TGFB2 | 7042 | A_24_P402438 | 6.9 | 6.8 | 0.005 | 0.1484-35 | 0.44 | 0.750602 | 0 |
| MLLT1 | 4298 | A_24_P151295 | 7.57 | 7.73 | 0.005 | 0.1484-35 | 0.075 | 0.346006 | 0 |
| BCAM | 4059 | A_23_P398574 | 9.97 | 10.41 | 0.005 | 0.1484-35 | 0.165 | 0.463385 | 0 |
| NF2 | 4771 | A_23_P251051 | 13.22 | 13.1 | 0.005 | 0.1484-35 | 0.235 | 0.595091 | 0 |
| IFI30 | 10437 | A_23_P153745 | 12.68 | 12.85 | 0.005 | 0.1484-35 | 0.88 | 0.960763 | 0 |
| FEN1 | 2237 | A_24_P84898 | 11.69 | 11.6 | 0.005 | 0.1484-35 | 0.5 | 0.750602 | 1 |
| COL27A1 | 85301 | A_24_P363896 | 8.99 | 9.18 | 0.005 | 0.1484-35 | 0.055 | 0.337423 | 0 |
| POGK | 57645 | A_24_P285163 | 10.54 | 10.44 | 0.005 | 0.1484-35 | 0.115 | 0.395828 | 0 |
| MYADM | 91663 | A_24_P134195 | 7.97 | 8.16 | 0.005 | 0.1484-35 | 0.39 | 0.67843 | 0 |
| EFNB1 | 1947 | A_24_P365807 | 11.62 | 11.51 | 0.005 | 0.1484-35 | 0.25 | 0.595091 | 0 |
| TYMP | 1890 | A_23_P91802 | 10.56 | 10.89 | 0.005 | 0.1484-35 | 0.995 | 1 | 0 |
| TNFRSF19 | 55504 | A_23_P140057 | 6.72 | 6.64 | 0.005 | 0.1484-35 | 0.175 | 0.475209 | 0 |
| ADRBK1 | 156 | A_23_P202667 | 6.63 | 6.74 | 0.005 | 0.1484-35 | 0.765 | 0.914885 | 0 |
| EFNB2 | 1948 | A_24_P355944 | 9.56 | 9.47 | 0.005 | 0.1484-35 | 0.395 | 0.67843 | 0 |
| MRPS30 | 10884 | A_23_P252362 | 10.45 | 10.31 | 0.005 | 0.1484-35 | 0.06 | 0.332405 | 0 |
| FOXH1 | 8928 | A_23_P82959 | 7.57 | 7.77 | 0.005 | 0.1484-35 | 0.13 | 0.409617 | 0 |
| LAX1 | 54900 | A_24_P291278 | 7.64 | 7.92 | 0.005 | 0.1484-35 | 0.575 | 0.811404 | 0 |
| APOA4 | 337 | A_24_P252934 | 6.81 | 6.94 | 0.005 | 0.1484-35 | 0.13 | 0.409617 | 0 |
| HSPE1 | 3336 | A_23_P56922 | 16.02 | 15.89 | 0.005 | 0.1484-35 | 0.64 | 0.864403 | 0 |
| PLSCR1 | 5359 | A_23_P69109 | 10.23 | 10.13 | 0.005 | 0.1484-35 | 0.455 | 0.750602 | 0 |
| PEAR1 | 375033 | A_24_P385326 | 7.29 | 7.49 | 0.005 | 0.1484-35 | 0.095 | 0.37395 | 0 |
| DLC1 | 10395 | A_23_P252721 | 12.69 | 12.56 | 0.005 | 0.1484-35 | 0.76 | 0.914885 | 0 |
| SORL1 | 6653 | A_23_P87049 | 11.91 | 12.09 | 0.005 | 0.1484-35 | 0.38 | 0.67843 | 0 |
| CPLX1 | 10815 | A_24_P51909 | 7.27 | 7.16 | 0.005 | 0.1484-35 | 0.93 | 1 | 0 |
| B3GALNT1 | 8706 | A_24_P88870 | 7.22 | 7.12 | 0.005 | 0.1484-35 | 0.61 | 0.864403 | 0 |
| GYPC | 2995 | A_24_P139901 | 10.99 | 11.28 | 0.005 | 0.1484-35 | 0.52 | 0.811404 | 0 |
| B3GNT5 | 84002 | A_23_P18372 | 8.96 | 8.85 | 0.005 | 0.1484-35 | 0.05 | 0.337423 | 0 |
| ICA1L | 130026 | A_23_P17224 | 6.86 | 6.74 | 0.005 | 0.1484-35 | 0.095 | 0.37395 | 0 |
| C2 | 717 | A_32_P162187 | 9.49 | 9.63 | 0.005 | 0.1484-35 | 0.02 | 0.275505 | 0 |
| FCRL2 | 79368 | A_24_P319647 | 6.71 | 6.9 | 0.005 | 0.1484-35 | 0.965 | 1 | 0 |
| CCL24 | 6369 | A_23_P215491 | 9.84 | 10.29 | 0.005 | 0.1484-35 | 0.09 | 0.362659 | 0 |

TABLE S2-continued

Significant age-associated measurement from regression analysis of all individuals

| CDH16 | 1014 | A_23_P100240 | 7.15 | 7 | 0.005 | 0.1484-35 | 0.46 | 0.750602 | 0 |
|---|---|---|---|---|---|---|---|---|---|
| C9orf61 | 9413 | A_32_P43717 | 6.8 | 6.71 | 0.005 | 0.1484-35 | 0.56 | 0.811404 | 2 |
| SEMA3F | 6405 | A_23_P6878 | 6.92 | 7.18 | 0.005 | 0.1484-35 | 0.94 | 1 | 0 |
| VHL | 7428 | A_23_P132611 | 15.97 | 16.18 | 0.005 | 0.1484-35 | 0.965 | 1 | 0 |
| DIAPH2 | 1730 | A_23_P85004 | 8.32 | 8.25 | 0.005 | 0.1484-35 | 0.285 | 0.595091 | 0 |
| SNX3 | 8724 | A_23_P42498 | 13.08 | 13.2 | 0.005 | 0.1484-35 | 0.14 | 0.421061 | 0 |
| ZNF646 | 9726 | A_24_P181506 | 10.83 | 10.9 | 0.005 | 0.1484-35 | 0.31 | 0.67843 | 2 |
| PCDHB7 | 56129 | A_24_P243373 | 7.8 | 7.88 | 0.005 | 0.1484-35 | 0.255 | 0.595091 | 0 |
| SLC5A2 | 6524 | A_23_P411277 | 8.66 | 8.95 | 0.005 | 0.1484-35 | 0.065 | 0.332405 | 0 |
| AZU1 | 566 | A_23_P153741 | 6.6 | 6.7 | 0.005 | 0.1484-35 | 0.135 | 0.421061 | 0 |
| WNK1 | 65125 | A_23_P250701 | 10.85 | 10.95 | 0.005 | 0.1484-35 | 0.025 | 0.286477 | 0 |
| PGM5 | 5239 | A_24_P254949 | 6.79 | 6.97 | 0.005 | 0.1484-35 | 0.175 | 0.475209 | 0 |
| LTBR | 4055 | A_23_P53557 | 10.13 | 10.25 | 0.005 | 0.1484-35 | 0.215 | 0.595091 | 0 |
| PNN | 5411 | A_23_P99582 | 13.29 | 13.36 | 0.005 | 0.1484-35 | 0.165 | 0.463385 | 0 |
| HRH2 | 3274 | A_23_P7535 | 6.93 | 7.12 | 0.005 | 0.1484-35 | 0.045 | 0.319941 | 0 |
| PLEKHF1 | 79156 | A_24_P194068 | 7.81 | 7.99 | 0.005 | 0.1484-35 | 0.005 | 0.258225 | 0 |
| KYNU | 8942 | A_23_P56898 | 12.41 | 12.54 | 0.005 | 0.1484-35 | 0.44 | 0.750602 | 0 |
| PLG | 5340 | A_24_P240487 | 7.44 | 7.61 | 0.005 | 0.1484-35 | 0.02 | 0.275505 | 0 |
| MAP4K2 | 5871 | A_24_P50767 | 7.24 | 7.4 | 0.005 | 0.1484-35 | 0.045 | 0.319941 | 0 |
| CXCR5 | 643 | A_23_P203215 | 6.65 | 6.76 | 0.005 | 0.1484-35 | 0.05 | 0.337423 | 0 |
| SIGIRR | 59307 | A_23_P84344 | 10.53 | 10.68 | 0.005 | 0.1484-35 | 0.135 | 0.421061 | 0 |
| CEACAM19 | 56971 | A_23_P78526 | 8.66 | 9.03 | 0.005 | 0.1484-35 | 0.055 | 0.337423 | 0 |
| HLA-E | 3133 | A_32_P460973 | 13.29 | 13.67 | 0.005 | 0.1484-35 | 0.305 | 0.67843 | 0 |
| GZMM | 3004 | A_23_P130836 | 8.79 | 8.99 | 0.005 | 0.1484-35 | 0.01 | 0.260797 | 0 |
| MAPK7 | 5598 | A_23_P100704 | 9.67 | 9.81 | 0.005 | 0.1484-35 | 0.19 | 0.479283 | 0 |
| HLA-DPB1 | 3115 | A_23_P258769 | 10.52 | 10.72 | 0.005 | 0.1484-35 | 0.475 | 0.750602 | 0 |
| SIGLEC5 | 8778 | A_23_P15995 | 7.55 | 7.89 | 0.005 | 0.1484-35 | 0.945 | 1 | 0 |
| PCDH9 | 5101 | A_24_P187218 | 7.27 | 7.17 | 0.005 | 0.1484-35 | 0.555 | 0.811404 | 0 |
| STX1A | 6804 | A_23_P168556 | 10.12 | 10.25 | 0.005 | 0.1484-35 | 0.425 | 0.750602 | 0 |
| IGF2BP2 | 10644 | A_23_P95672 | 7.15 | 6.99 | 0.005 | 0.1484-35 | 0.24 | 0.595091 | 0 |
| HLA-DMB | 3109 | A_23_P259561 | 7.51 | 7.78 | 0.005 | 0.1484-35 | 0.925 | 1 | 0 |

APPENDIX C

TABLE S3

GEO Datasets used in meta-analysis of aging gene expression data

| GEO Data Set or Series | Title | Species | Pubmed ID | Source | Number Chips |
|---|---|---|---|---|---|
| GDS1278 | Age effect on laryngeal muscle | *Rattus norvegicus* | | McMullen CA, et al. | 6 |

TABLE S3-continued

GEO Datasets used in meta-analysis of aging gene expression data

| GEO Data Set or Series | Title | Species | Pubmed ID | Source | Number Chips |
|---|---|---|---|---|---|
| GDS1279 | Age effect on extraocular muscles | Rattus norvegicus | | McMullen CA, et al. | 16 |
| GDS1280 | Age effect on central and peripheral nervous | Rattus norvegicus | | McMullen CA, et al. | 12 |
| GDS1311 | Age effect on lipopolysaccharide-induced neuroinflammation and | Mus musculus | 15919760 | Godbout JP, et al. | 12 |
| GDS156 | Muscle function and aging (HG-U95A) | Homo sapiens | 12204100 | Welle S, et al. | 12 |
| GDS1961 | Male and female thymi response to aging and caloric restriction (A) | Mus musculus | 17499630 | Lustig A, et al. | 40 |
| GDS2019 | Age effect on livers of long-lived Snell dwarf | Mus musculus | | DeFord JH, et al. | 14 |
| GDS2082 | Age effect on the hippocampus | Mus musculus | 15169854 | Verbitsky M, et al. | 23 |
| GDS2612 | Caloric restriction effect on aged skeletal muscle | Mus musculus | 17381838 | Edwards MG, et al. | 10 |
| GDS2639 | Aging and cognitive impairment: hippocampus | Rattus norvegicus | 17376971 | Rowe WB, et al. | 78 |
| GDS2654 | Neurological aging models: retinas and | Mus musculus | 15960800 | Carter TA, et al. | 9 |
| GDS2681 | Caloric restriction effect on aged cochlea | Mus musculus | 16890326 | Someya S, et al. | 6 |
| GDS287 | Muscle function and aging - male (HG-U133A) | Homo sapiens | 12783983 | Welle S, et al. | 15 |
| GDS288 | Muscle function and aging - male (HG-U133B) | Homo sapiens | 12783983 | Welle S, et al. | 15 |
| GDS2929 | Aging lungs and genetic background | Mus musculus | 17726092 | Misra V, et al. | 15 |
| GDS2962 | Male and female thymi response to aging and caloric restriction (B) | Mus musculus | 18081424 | Lustig A, et al. | 40 |
| GDS355 | Calorie restriction and aging (Mu11K-A) | Mus musculus | | Kayo T, et al. | 10 |
| GDS356 | Calorie restriction and aging (Mu11K-B) | Mus musculus | | Kayo T, et al. | 10 |
| GDS399 | Cardiac aging | Rattus | 12902548 | Dobson JG, et al. | 11 |
| GDS40 | Cardiac development, maturation and aging | Mus musculus | | Schinke M, et al. | 15 |
| GDS472 | Muscle function and aging - female (HG-U133A) | Homo sapiens | | Welle, et al. | 15 |
| GDS473 | Muscle function and aging - female (HG-U133B) | Homo sapiens | | Welle, et al. | 15 |
| GDS520 | Hippocampal aging and cognitive impairment | Rattus norvegicus | 12736351 | Blalock EM, et al. | 19 |
| GDS583 | Aging time course, normal adult | Caenorhabditis elegans | 14730301 | McCarroll SA, et al. | 6 |
| GDS707 | Aging brain: frontal cortex expression profiles at various ages | Homo sapiens | 15190254 | Lu T, et al. | 22 |
| GSE11097 | Coordinated Changes in Xenobiotic Metabolizing Enzyme Gene Expression in Aging Male Rats: Brown Norway and F344 | Rattus norvegicus | | Lee JS, et al. | 21 |
| GSE11291 | Effect of age, calorie restriction and resveratrol on gene expression in mouse heart, brain, and skeletal muscle | Mus musculus | 18523577 | Barger JL, et al. | 30 |
| GSE11546 | Age-related changes in the expression of schizophrenia susceptibility genes in the | Homo sapiens | 18470533 | Colantuoni C, et al. | 33 |
| GSE12168 | Aging Time course | Caenorhabditis elegans | 18662544 | Budovskaya YV, et al. | 16 |
| GSE12290 | Age-related behaviors have distinct transcriptional profiles in | Caenorhabditis elegans | 18778409 | Golden TR, et al. | 70 |
| GSE12872 | Drosophila melanogaster transcriptional profiling over life span: Indy vs. | Drosophila melanogaster | 19164521 | Neretti N, et al. | 25 |

TABLE S3-continued

GEO Datasets used in meta-analysis of aging gene expression data

| GEO Data Set or Series | Title | Species | Pubmed ID | Source | Number Chips |
|---|---|---|---|---|---|
| GSE13496 | Aging hematopoietic progenitor/stem cells | Homo sapiens | 18596738 | Stirewelt DL, et al. | 10 |
| GSE3150 | Aging Liver Profiles of the Long Lived Prop-1 Mutant Mouse (Ames) and Wild Type Controls | Mus musculus | | DeFord JH, et al. | 21 |
| GSE3531 | LTM in CA1 Aged versus young rats | Rattus norvegicus | 16829144 | Burger C, et al. | 79 |
| GSE4821 | Identification of putative learning and memory genes in the dentate gyrus of aged rats following the Morris Water Maze | Rattus norvegicus | | Burger C, et al. | 79 |
| GSE5086 | Transcriptional profile of aging human muscle | Homo sapiens | 16789832 | Zahn JM, et al. | 40 |
| GSE6314 | Temporal and Spatial Transcriptional Profiles of Aging in Drosophila | Drosophila melanogaster | | Yamaza H, et al. | 55 |
| GSE6718 | Transcriptional Response to Aging and Caloric Restriction in Heart and | Rattus norvegicus | 17874999 | Linford NJ, et al. | 25 |
| GSE8409 | Age Map, Cerebellum (A) | Mus musculus | 17988385 | Zahn JM, et al. | 40 |
| GSE8410 | Age Map, Cerebral Cortex | Mus musculus | 17988385 | Zahn JM, et al. | 40 |
| GSE8412 | Age Map, Spinal Cord (A) | Mus musculus | 17988385 | Zahn JM, et al. | 38 |
| GSE8414 | Age Map, Cerebellum (B) | Mus musculus | 17988385 | Zahn JM, et al. | 39 |
| GSE8415 | Age Map, Cerebral Cortex | Mus musculus | 17988385 | Zahn JM, et al. | 38 |
| GSE8418 | Age Map, Spinal Cord (B) | Mus musculus | 17988385 | Zahn JM, et al. | 41 |
| GSE8419 | Age Map, Striatum (B) | Mus musculus | 17988385 | Zahn JM, et al. | 40 |
| GSE8479 | Resistance Exercise Reverses Aging in Human Skeletal Muscle | Homo sapiens | 17520024 | Melov S, et al. | 51 |
| GSE9103 | Skeletal Muscle Transcript Profiles in Trained or Sedentary Young and Old Subjects | Homo sapiens | | Asmann YW, et al. | 40 |
| GSE9419 | The skeletal muscle transcript profile reflects responses to inadequate protein intake in younger | Homo sapiens | 17490972 | Campbell WW, et al. | 66 |
| GSE9895 | AGEMAP_Adrenals | Mus musculus | 16789832 | Zahn JM, et al. | 80 |
| GSE9898 | AGEMAP_Bone_Marrow | Mus musculus | 18081424 | Zahn JM, et al. | 72 |
| GSE9900 | AGEMAP_Eye | Mus musculus | 18081424 | Zahn JM, et al. | 80 |
| GSE9901 | AGEMAP_Gonads | Mus musculus | 16789832 | Zahn JM, et al. | 77 |
| GSE9902 | AGEMAP_Heart | Mus musculus | 16789832 | Zahn JM, et al. | 76 |
| GSE9904 | AGEMAP_Kidney | Mus musculus | 16789832 | Zahn JM, et al. | 80 |
| GSE9905 | AGEMAP_Liver | Mus musculus | 18081424 | Zahn JM, et al. | 64 |
| GSE9906 | AGEMAP_Lung | Mus musculus | 16789832 | Zahn JM, et al. | 80 |
| GSE9907 | AGEMAP_Skeletal_Muscle | Mus musculus | 18081424 | Zahn JM, et al. | 80 |
| GSE9908 | AGEMAP_Spleen | Mus musculus | 18081424 | Zahn JM, et al. | 80 |

APPENDIX D

TABLE S4

Genes found to be significantly associated with age in the meta-analysis

| Entrez ID | Name | MetaEffect | pvalFisher |
|---|---|---|---|
| 68031 | C3 | 0.337698315 | 1.10E−54 |
| 7750 | RT1-Ba | 0.196164486 | 1.06E−41 |
| 1880 | Gpnmb | 0.643641429 | 1.01E−37 |
| 2974 | Fcgr2b | 0.243994532 | 2.05E−34 |
| 16958 | Igj | 0.226477271 | 3.56E−32 |
| 17012 | 1100001E04Rik | 0.849789673 | 4.49E−32 |
| 20867 | Ctss | 0.152554449 | 3.55E−31 |
| 9962 | CXorf57 | 0.325268282 | 6.96E−27 |
| 86179 | EG665378 | 1.104731656 | 9.48E−27 |
| 1603 | RT1-Bb | 0.160732706 | 2.23E−25 |
| 36030 | C4b | 0.261099138 | 5.33E−24 |
| 56810 | Lrp1b | 0.30257626 | 5.74E−24 |
| 5109 | Adamts5 | 0.251108456 | 6.79E−24 |
| 68066 | Hbb | 0.164149192 | 7.36E−24 |
| 90902 | Usp54 | 0.186061881 | 3.01E−23 |
| 14126 | Il33 | 0.215106418 | 6.57E−23 |
| 7924 | S100a4 | 0.208560953 | 1.86E−21 |
| 7839 | Mlf1 | −0.259261704 | 8.04E−21 |
| 113759 | C21orf7 | 0.768001812 | 7.61E−20 |
| 115591 | LOC259246 | −0.154435161 | 1.27E−19 |
| 23032 | Fam46a | 0.180448732 | 1.38E−19 |
| 1431 | Ctgf | 0.183450344 | 5.03E−18 |
| 31070 | Glra2 | −0.157278315 | 5.78E−18 |
| 49424 | CCDC69 | −0.204656005 | 1.73E−16 |
| 7986 | Tyrobp | 0.281565935 | 1.99E−16 |
| 2000 | Plek | 0.182525947 | 2.35E−16 |
| 23519 | Acsf2 | −0.367179713 | 2.72E−16 |

TABLE S4-continued

Genes found to be significantly associated with age in the meta-analysis

| Entrez ID | Name | MetaEffect | pvalFisher |
|---|---|---|---|
| 37584 | Hoxb2 | −0.285938235 | 1.51E−15 |
| 49543 | ZNF415 | −0.255270555 | 2.94E−15 |
| 122149 | HMGN2 | 0.278687741 | 8.90E−15 |
| 88734 | MT1X | 0.304942233 | 9.85E−15 |
| 108195 | NPIP | 0.210485047 | 2.02E−14 |
| 2086 | Pros28.1 | 0.212491471 | 2.18E−14 |
| 69153 | Ptpla | −0.341833039 | 4.75E−14 |
| 89678 | LOC685001 | 1.084414575 | 4.78E−14 |
| 120336 | LOC499782 | 0.216224302 | 5.11E−14 |
| 49694 | Cxcl16 | 0.218628389 | 6.86E−14 |
| 82588 | RGD1559909 | −0.154209952 | 7.29E−14 |
| 56300 | CG13384 | 0.278803929 | 1.05E−13 |
| 7309 | Mpzl2 | 0.176061389 | 2.81E−13 |
| 65299 | Tmtc1 | 0.154398135 | 3.08E−13 |
| 74448 | LOC286911 | −0.181577041 | 4.15E−13 |
| 41282 | Erbb2ip | 0.168449838 | 4.66E−13 |
| 49949 | COL21A1 | 0.199777973 | 8.60E−13 |
| 88747 | C10orf16 | 0.380945602 | 2.17E−12 |
| 38171 | Ifi30 | 0.262554903 | 2.20E−12 |
| 104063 | UQCRH | −0.271384989 | 3.75E−12 |
| 9413 | Clec4a3 | 0.635951202 | 4.74E−12 |
| 88538 | 1700034I23Rik | −0.197783627 | 5.48E−12 |
| 5782 | Lace1 | −0.197067324 | 8.82E−12 |
| 2236 | Clec11a | −0.185486672 | 1.25E−11 |
| 1209 | Irf7 | 0.177331413 | 1.36E−11 |
| 17048 | Ttc18 | 0.200712085 | 1.49E−11 |
| 76450 | Cml3 | 0.36115736 | 2.07E−11 |
| 15446 | Asb12 | −0.365859356 | 3.52E−11 |
| 477 | Fcgr3a | 0.320924509 | 3.61E−11 |
| 20453 | Cfd | 0.162628176 | 3.63E−11 |
| 90224 | 1500009L16Rik | 0.225854306 | 9.44E−11 |
| 17057 | Spata18 | 0.155521865 | 9.97E−11 |
| 115689 | Plscr2 | 0.437399565 | 2.77E−10 |
| 9294 | Pla1a | 0.151688359 | 3.57E−10 |
| 18882 | Paqr9 | −0.198906882 | 3.82E−10 |
| 40707 | Opn3 | −0.176913022 | 3.90E−10 |
| 89046 | RGD1564174 | 0.185419884 | 4.30E−10 |
| 7945 | Slfn2 | 0.421614816 | 4.39E−10 |
| 121641 | His3.3A | 0.219066526 | 4.64E−10 |
| 79796 | LOC689755 | −0.259319102 | 8.52E−10 |
| 8332 | Hook2 | −0.170591301 | 1.29E−09 |
| 108191 | MT1H | 0.210737894 | 1.72E−09 |
| 16012 | Frmd3 | −0.161818085 | 1.91E−09 |
| 35310 | 3-Mar | −0.154297586 | 2.06E−09 |
| 87124 | Pcdhb9 | 0.254572988 | 3.36E−09 |
| 105677 | YWHAQ | 0.171385197 | 4.10E−09 |
| 11093 | Fn3krp | 0.202668204 | 4.37E−09 |
| 11509 | Ccdc28b | −0.216748469 | 4.68E−09 |
| 87898 | ISCA1 | −0.195551567 | 5.40E−09 |
| 45124 | Gcom1 | 0.169362212 | 5.83E−09 |
| 74413 | E2f3 | −0.155122336 | 8.46E−09 |
| 48326 | G1p2 | 0.329823574 | 1.10E−08 |
| 37689 | PTMA | 0.166331587 | 1.20E−08 |
| 9135 | TRIM58 | 0.237072147 | 1.31E−08 |
| 23499 | Synpo2l | 0.24111956 | 1.49E−08 |
| 9574 | Pcdh12 | −0.224426147 | 1.78E−08 |
| 27392 | Cpne2 | 0.233138906 | 1.79E−08 |
| 12698 | Ddit4l | −0.163908824 | 2.06E−08 |
| 75853 | Cyp4x1 | 0.219081962 | 2.92E−08 |
| 114241 | RGD1559482 | 0.469297715 | 3.25E−08 |
| 72226 | Zfp454 | 0.29786873 | 3.38E−08 |
| 55916 | S100a11 | 0.157104104 | 5.53E−08 |
| 14286 | Galntl2 | 0.219172594 | 7.10E−08 |
| 294 | Sox9 | 0.252846332 | 8.50E−08 |
| 104370 | ZNF492 | 0.238974473 | 9.47E−08 |
| 122101 | C14orf2 | −0.1545888 | 1.10E−07 |
| 121604 | DUSP13 | −0.315450904 | 1.13E−07 |
| 62161 | Vangl2 | −0.184049867 | 1.44E−07 |
| 19108 | Dhrs7c | −0.215088035 | 1.55E−07 |
| 45432 | Slfn8 | 0.243086196 | 2.01E−07 |
| 48388 | MT2A | 0.299104826 | 3.01E−07 |
| 5353 | Pdss1 | −0.150879199 | 3.71E−07 |
| 77713 | LOC360228 | 0.150600586 | 3.98E−07 |
| 8835 | FAM38A | 0.252755946 | 4.57E−07 |
| 25079 | TPPP2 | −0.162143162 | 7.69E−07 |
| 86882 | Fmo2 | 0.23321182 | 7.99E−07 |
| 49517 | TRMT61B | −0.201215511 | 1.07E−06 |
| 123533 | RGD1310159 | −0.400765479 | 1.11E−06 |
| 19274 | 4933405L10Rik | −0.240828861 | 1.12E−06 |
| 86733 | MGC108823 | 0.279660777 | 1.37E−06 |
| 56783 | LOC310721 | 0.267238671 | 1.65E−06 |
| 10073 | Pnmal1 | 0.295057188 | 2.08E−06 |
| 89164 | isg12(b) | 0.189563208 | 2.15E−06 |
| 10641 | CTNNBIP1 | −0.253945736 | 2.27E−06 |
| 39074 | Nmnat1 | −0.156890572 | 2.51E−06 |
| 66117 | MYH7B | 0.323225125 | 3.03E−06 |
| 48468 | H28 | 0.194466507 | 3.23E−06 |
| 74438 | Ifi204 | 0.216986862 | 3.34E−06 |
| 7014 | EG226654 | 0.267725488 | 3.80E−06 |
| 85555 | 1700019N12Rik | −0.351845158 | 4.34E−06 |
| 19952 | Efcab7 | 0.15813991 | 4.69E−06 |
| 8024 | Hcst | 0.172404007 | 5.13E−06 |
| 7392 | Kcnu1 | −0.278737565 | 5.23E−06 |
| 23217 | Plscr4 | 0.20548157 | 5.91E−06 |
| 17562 | Ankle1 | 0.217270121 | 9.29E−06 |
| 68443 | CLEC2B | 0.204602687 | 9.30E−06 |
| 826 | RGD1310507 | 0.170957726 | 9.55E−06 |
| 9927 | Fam70a | 0.159236473 | 9.96E−06 |
| 86122 | ISOC2 | −0.219663119 | 1.04E−05 |
| 4665 | Ubd | 0.158771035 | 1.06E−05 |
| 103871 | RGD1307935 | −0.181586721 | 1.43E−05 |
| 122195 | 1700054F22Rik | −0.171224127 | 1.49E−05 |
| 45975 | RGD1309350 | 0.188776766 | 1.61E−05 |
| 28424 | Rasef | 0.185265697 | 1.66E−05 |
| 70768 | Herc6 | 0.164936064 | 1.86E−05 |
| 16320 | Cthrc1 | −0.229051149 | 2.18E−05 |
| 118004 | 1700019G17Rik | 0.192558616 | 2.52E−05 |
| 88921 | C1qtnf3 | −0.265651382 | 4.28E−05 |
| 117949 | Fcn1 | 0.296439068 | 4.59E−05 |
| 121796 | Krtap4-2 | −0.486548637 | 4.66E−05 |
| 86269 | Stfa2l3 | 0.539695764 | 5.11E−05 |
| 8908 | Galnac4s-6st | −0.150046526 | 5.67E−05 |
| 22708 | Itgb1bp2 | −0.184686403 | 5.89E−05 |
| 12732 | Tmem177 | −0.15887907 | 8.44E−05 |
| 56944 | Rtp4 | 0.160669645 | 8.54E−05 |
| 18680 | Tmem52 | 0.194064654 | 8.72E−05 |
| 17571 | Kbtbd5 | 0.316607601 | 9.22E−05 |
| 85034 | OTTMUSG0000000-8561 | −0.153816472 | 9.44E−05 |
| 9726 | Gramd1c | 0.157603931 | 9.59E−05 |
| 10813 | Alpk3 | 0.1854543 | 0.000117326 |
| 84858 | Cd209b | 0.231577687 | 0.000130483 |
| 49905 | 1700074P13Rik | −0.301791964 | 0.00014641 |
| 76446 | Tsga13 | −0.163833253 | 0.00014714 |
| 86705 | LOC691170 | −0.224121255 | 0.000155202 |
| 114502 | LOC685157 | 0.394921169 | 0.000164994 |
| 18252 | Fsd2 | −0.16439316 | 0.000168398 |
| 71779 | Rsph4a | 0.255594277 | 0.000191545 |
| 34940 | Arid5a | 0.156559299 | 0.000252817 |
| 16823 | CG9996 | 0.232308435 | 0.000255029 |
| 77416 | Mlkl | −0.168997471 | 0.000344719 |
| 12257 | 4930547C10Rik | 1.950401446 | 0.000481826 |
| 41271 | Arhgap15 | 0.159114218 | 0.000489405 |
| 19144 | Fam171a2 | −0.18584737 | 0.000520793 |
| 49710 | TTC31 | 0.179167307 | 0.000588967 |
| 79726 | Doxl1 | −0.197224641 | 0.000610383 |
| 117975 | ZNF432 | 0.213393951 | 0.000628027 |
| 110822 | Klra5 | 0.18662964 | 0.000675574 |
| 89168 | ZNF323 | 0.222940842 | 0.00070422 |
| 9555 | Ninj2 | 0.154045269 | 0.0007144 |
| 35542 | E030049G20Rik | −0.326818364 | 0.000785296 |
| 69257 | ERMAP | 0.172273481 | 0.000788985 |
| 50475 | Alpk2 | 0.152879973 | 0.000856753 |
| 117700 | ZNF267 | 0.1545496 | 0.000870494 |
| 18691 | 6430537H07Rik | 0.153146801 | 0.000945891 |
| 17794 | Klre1 | −0.16554649 | 0.00098146 |
| 78018 | Lrrc69 | 0.152806524 | 0.001081192 |
| 10471 | MOSPD1 | −0.150832941 | 0.001171416 |
| 108186 | HMGN1 | 0.170483349 | 0.001187045 |
| 28471 | RGD1563109 | 0.177024178 | 0.001259499 |

TABLE S4-continued

Genes found to be significantly associated with age in the meta-analysis

| Entrez ID | Name | MetaEffect | pvalFisher |
|---|---|---|---|
| 10590 | 1810011O10Rik | −0.189298682 | 0.001305993 |
| 10416 | 4933403G14Rik | −0.300796963 | 0.001328408 |
| 75166 | Pmaip1 | 0.390056763 | 0.001375651 |
| 18842 | 2310010M20Rik | −0.166178609 | 0.001478701 |
| 65996 | BC046404 | −0.187618646 | 0.001579988 |
| 65257 | Ip6k3 | 0.183436928 | 0.001737446 |
| 22993 | Gypc | −0.158924665 | 0.001907036 |
| 81055 | Slc16a12 | 0.173590885 | 0.002046819 |
| 48124 | Ppp1r3a | −0.167230437 | 0.002095651 |
| 119893 | Ces6 | −0.150311233 | 0.002125614 |
| 18692 | Dpy19l3 | −0.156477327 | 0.002143708 |
| 56428 | Ppm1a | −0.150286052 | 0.002179903 |
| 8897 | Tecpr2 | 0.191902469 | 0.002519878 |
| 88945 | BC043301 | −0.153636401 | 0.002607832 |
| 86703 | Ng23 | −0.19533328 | 0.002670184 |
| 47588 | MGC116202 | −0.194928701 | 0.00274781 |
| 113783 | Itgb1bp3 | 0.316801607 | 0.002899996 |
| 41378 | Olfr1509 | −0.189842453 | 0.003121475 |
| 104345 | LOC680230 | 0.420756428 | 0.00325828 |
| 114519 | Cd209g | 0.224085149 | 0.003413665 |
| 27072 | A330049M08Rik | 0.215087101 | 0.003484588 |
| 12281 | RGD1308059 | −0.214931361 | 0.003972846 |
| 77326 | Zfp52 | 0.33674368 | 0.003985404 |
| 99855 | Agmat | −0.150177637 | 0.004717601 |
| 110478 | Olfr672 | 0.482514016 | 0.004994427 |
| 35234 | Pddc1 | 0.160100112 | 0.005408099 |
| 75198 | Ankrd36 | 0.35318104 | 0.005921352 |
| 11488 | Smtnl1 | 0.207571119 | 0.005971935 |
| 18544 | Rnf222 | 0.531926369 | 0.007282176 |
| 110771 | Svs3 | −0.210425649 | 0.00775244 |
| 10957 | Cd200r1 | 0.33606348 | 0.008209761 |
| 84597 | Tusc1 | −0.210561393 | 0.008264043 |
| 103867 | 4933415F23Rik | 0.174474914 | 0.008405947 |
| 77918 | 1700065l17Rik | −0.252317071 | 0.008703318 |
| 122178 | Cyp2j5 | 0.168201503 | 0.008708446 |
| 23416 | Slco1a6 | −0.184593022 | 0.009385085 |
| 104304 | Psbpc1 | −0.243828288 | 0.009507612 |
| 32697 | Nphp3 | 0.178084932 | 0.009524546 |

APPENDIX E

TABLE S5

| Network cluster membership | Serum cytokines | Chemokines |
|---|---|---|
| TH1 | INF-A2 | Eotaxin |
|  | INF-G | IL-12p40 |
| Th2 | Il-4 | IP-10 |
|  | IL-5 |  |
|  | IL-7 |  |

| Gene Expression | Probe ID | Entrez Gene ID | Gene Symbol | Description |
|---|---|---|---|---|
| GC1 | A_23_P107735 | 973 | CD79A | CD79a molecule, immunoglobulin-associated alpha |
|  | A_23_P116387 | 3619 | INCENP | inner centromere protein antigens 135/155 kDa |
|  | A_23_P116765 | 3906 | LALBA | lactalbumin, alpha- |
|  | A_23_P125990 | 1870 | E2F2 | E2F transcription factor 2 |
|  | A_23_P127385 | 4607 | MYBPC3 | myosin binding protein C, cardiac |
|  | A_23_P130836 | 3004 | GZMM | granzyme M (lymphocyte metase 1) |
|  | A_23_P132115 | 150094 | SIK1 | salt-inducible kinase 1 |
|  | A_23_P133665 | 2444 | FRK | fyn-related kinase |
|  | A_23_P140057 | 55504 | TNFRSF19 | tumor necrosis factor receptor superfamily, member 19 |
|  | A_23_P145264 | 3134 | HLA-F | major histocompatibility complex, class I, F |
|  | A_23_P15369 | 124599 | CD300LB | CD300 molecule-like family member b |
|  | A_23_P156550 | 340205 | TREML1 | triggering receptor expressed on myeloid cells-like 1 |
|  | A_23_P158775 | 7369 | UMOD | uromodulin |
|  | A_23_P160849 | 2207 | FCER1G | Fc fragment of IgE, high affinity I, receptor for; gamma polypeptide |
|  | A_23_P164307 | 50488 | MINK1 | misshapen-like kinase 1 (zebrafish) |
|  | A_23_P167537 | 10814 | CPLX2 | complexin 2 |
|  | A_23_P17224 | 130026 | ICA1L | islet cell autoantigen 1, 69 kDa-like |
|  | A_23_P201156 | 57863 | CADM3 | cell adhesion molecule 3 |
|  | A_23_P202667 | 156 | ADRBK1 | adrenergic, beta, receptor kinase 1 |

TABLE S5-continued

| | | | |
|---|---|---|---|
| A_23_P203215 | 643 | CXCR5 | chemokine (C—X—C motif) receptor 5 |
| A_23_P207842 | 5914 | RARA | retinoic acid receptor, alpha |
| A_23_P208132 | 596 | BCL2 | B-cell CLL/lymphoma 2 |
| A_23_P209389 | 841 | CASP8 | caspase 8, apoptosis-related cysteine peptidase |
| A_23_P215491 | 6369 | CCL24 | chemokine (C-C motif) ligand 24 |
| A_23_P218269 | 9344 | TAOK2 | TAO kinase 2 |
| A_23_P258377 | 23085 | ERC1 | ELKS/RAB6-interacting/CAST family member 1 |
| A_23_P29800 | 5010 | CLDN11 | claudin 11 |
| A_23_P306730 | 5465 | PPARA | peroxisome proliferator-activated receptor alpha |
| A_23_P30755 | 171558 | PTCRA | pre T-cell antigen receptor alpha |
| A_23_P324813 | 255877 | BCL6B | B-cell CLL/lymphoma 6, member B (zinc finger protein) |
| A_23_P325991 | 4771 | NF2 | neurofibromin 2 (merlin) |
| A_23_P334271 | 4086 | SMAD1 | SMAD family member 1 |
| A_23_P364592 | 57502 | NLGN4X | neuroligin 4, X-linked |
| A_23_P371794 | 784 | CACNB3 | calcium channel, voltage-dependent, beta 3 subunit |
| A_23_P390518 | 8792 | TNFRSF11A | tumor necrosis factor receptor superfamily, member 11a, NFKB activator |
| A_23_P398574 | 4059 | BCAM | basal cell adhesion molecule (Lutheran blood group) |
| A_23_P402899 | 162394 | SLFN5 | schlafen family member 5 |
| A_23_P408095 | 11034 | DSTN | destrin (actin depolymerizing factor) |
| A_23_P411277 | 6524 | SLC5A2 | solute carrier family 5 (sodium/glucose cotransporter), member 2 |
| A_23_P41166 | 8706 | B3GALNT1 | beta-1,3-N-acetylgalactosaminyltransferase 1 (globoside blood group) |
| A_23_P430764 | 56990 | CDC42SE2 | CDC42 small effector 2 |
| A_23_P48109 | 4815 | NINJ2 | ninjurin 2 |
| A_23_P6321 | 7122 | CLDN5 | claudin 5 |
| A_23_P68910 | 6753 | SSTR3 | somatostatin receptor 3 |
| A_23_P70520 | 1041 | CDSN | corneodesmosin |
| A_23_P7535 | 3274 | HRH2 | histamine receptor H2 |
| A_23_P78526 | 56971 | CEACAM19 | carcinoembryonic antigen-related cell adhesion molecule 19 |
| A_23_P82959 | 8928 | FOXH1 | forkhead box H1 |
| A_23_P86390 | 8829 | NRP1 | neuropilin 1 |
| A_23_P95672 | 10644 | IGF2BP2 | insulin-like growth factor 2 mRNA binding protein 2 |
| A_24_P134195 | 91663 | MYADM | myeloid-associated differentiation marker |
| A_24_P139901 | 2995 | GYPC | glycophorin C (Gerbich blood group) |
| A_24_P151295 | 4298 | MLLT1 | myeloid/lymphoid or mixed-lineage leukemia (trithorax homolog, *Drosophila*); translocated to, 1 |
| A_24_P17048 | 2692 | GHRHR | growth hormone releasing hormone receptor |
| A_24_P194068 | 79156 | PLEKHF1 | pleckstrin homology domain containing, family F (with FYVE domain) member 1 |
| A_24_P207003 | 8660 | IRS2 | insulin receptor substrate 2 |
| A_24_P209389 | 51085 | MLXIPL | MLX interacting protein-like |
| A_24_P22174 | 84334 | C14orf153 | chromosome 14 open reading frame 153 |

TABLE S5-continued

|  | | | | |
|---|---|---|---|---|
| | A_24_P239183 | 4585 | MUC4 | mucin 4, cell surface associated |
| | A_24_P240487 | 5340 | PLG | plasminogen |
| | A_24_P252934 | 337 | APOA4 | apolipoprotein A-IV |
| | A_24_P282416 | 25 | ABL1 | c-abl oncogene 1, receptor tyrosine kinase |
| | A_24_P288298 | 3805 | KIR2DL4 | killer cell immunoglobulin-like receptor, two domains, long cytoplasmic tail, 4 |
| | A_24_P291278 | 54900 | LAX1 | lymphocyte transmembrane adaptor 1 |
| | A_24_P292470 | 7352 | UCP3 | uncoupling protein 3 (mitochondrial, proton carrier) |
| | A_24_P295999 | 920 | CD4 | CD4 molecule |
| | A_24_P308096 | 3718 | JAK3 | Janus kinase 3 |
| | A_24_P341897 | 91 | ACVR1B | activin A receptor, type IB |
| | A_24_P354800 | 3111 | HLA-DOA | major histocompatibility complex, class II, DO alpha |
| | A_24_P363896 | 85301 | COL27A1 | collagen, type XXVII, alpha 1 |
| | A_24_P366967 | 54874 | FNBP1L | formin binding protein 1-like |
| | A_24_P385326 | 375033 | PEAR1 | platelet endothelial aggregation receptor 1 |
| | A_24_P38702 | 159296 | NKX2-3 | NK2 transcription factor related, locus 3 (*Drosophila*) |
| | A_24_P401990 | 2068 | ERCC2 | excision repair cross-complementing rodent repair deficiency, complementation group 2 |
| | A_24_P50767 | 5871 | MAP4K2 | mitogen-activated protein kinase kinase kinase kinase 2 |
| | A_24_P881527 | 1500 | CTNND1 | catenin (cadherin-associated protein), delta |
| | A_24_P917783 | 861 | RUNX1 | runt-related transcription factor 1 |
| | A_32_P150735 | 55973 | BCAP29 | B-cell receptor-associated protein 29 |
| | A_32_P183609 | 51665 | ASB1 | ankyrin repeat and SOCS box-containing 1 |
| | A_32_P187875 | 1499 | CTNNB1 | catenin (cadherin-associated protein), beta 1, 88 kDa |
| | A_32_P197942 | 222256 | FLJ23834 | hypothetical protein FLJ23834 |
| | A_32_P215404 | 5159 | PDGFRB | platelet-derived growth factor receptor, beta polypeptide |
| | A_32_P460973 | 3133 | HLA-E | major histocompatibility complex, class I, E |
| | A_32_P6062 | 5592 | PRKG1 | protein kinase, cGMP-dependent, type I |
| | A_32_P72622 | 1291 | COL6A1 | collagen, type VI, alpha 1 |
| GC2 | A_23_P100704 | 5598 | MAPK7 | mitogen-activated protein kinase 7 |
| | A_23_P102192 | 9448 | MAP4K4 | mitogen-activated protein kinase kinase kinase kinase 4 |
| | A_23_P112554 | 1306 | COL15A1 | collagen, type XV, alpha 1 |
| | A_23_P119562 | 1675 | CFD | complement factor D (adipsin) |
| | A_23_P127627 | 8525 | DGKZ | diacylglycerol kinase, zeta 104 kDa |
| | A_23_P134517 | 5814 | PURB | purine-rich element binding protein B |
| | A_23_P144054 | 5580 | PRKCD | protein kinase C, delta |
| | A_23_P164691 | 3385 | ICAM3 | intercellular adhesion molecule 3 |
| | A_23_P166633 | 3693 | ITGB5 | integrin, beta 5 |
| | A_23_P168419 | 58508 | MLL3 | myeloid/lymphoid or mixed-lineage leukemia 3 |
| | A_23_P168556 | 6804 | STX1A | syntaxin 1A (brain) |
| | A_23_P169117 | 10670 | RRAGA | Ras-related GTP binding A |

TABLE S5-continued

| | | | |
|---|---|---|---|
| A_23_P170058 | 5690 | PSMB2 | proteasome (prosome, macropain) subunit, beta type, 2 |
| A_23_P18372 | 84002 | B3GNT5 | UDP-GlcNAc:betaGal beta-1,3-N-acetylglucosaminyltransferase 5 |
| A_23_P19134 | 84059 | GPR98 | G protein-coupled receptor 98 |
| A_23_P201636 | 3918 | LAMC2 | laminin, gamma 2 |
| A_23_P205499 | 26020 | LRP10 | low density lipoprotein receptor-related protein 10 |
| A_23_P206359 | 999 | CDH1 | cadherin 1, type 1, E-cadherin (epithelial) |
| A_23_P212360 | 10803 | CCR9 | chemokine (C-C motif) receptor 9 |
| A_23_P218770 | 5880 | RAC2 | ras-related C3 botulinum toxin substrate 2 (rho family, small GTP binding protein Rac2) |
| A_23_P250701 | 65125 | WNK1 | WNK lysine deficient protein kinase 1 |
| A_23_P251051 | 4771 | NF2 | neurofibromin 2 (merlin) |
| A_23_P252362 | 10884 | MRPS30 | mitochondrial ribosomal protein S30 |
| A_23_P35912 | 837 | CASP4 | caspase 4, apoptosis-related cysteine peptidase |
| A_23_P40174 | 4318 | MMP9 | matrix metallopeptidase 9 (gelatinase B, 92 kDa gelatinase, 92 kDa type IV collagenase) |
| A_23_P428260 | 261729 | STEAP2 | six transmembrane epithelial antigen of the prostate 2 |
| A_23_P47867 | 8496 | PPFIBP1 | PTPRF interacting protein, binding protein 1 (liprin beta 1) |
| A_23_P52647 | 10938 | EHD1 | EH-domain containing 1 |
| A_23_P53557 | 4055 | LTBR | lymphotoxin beta receptor (TNFR superfamily, member 3) |
| A_23_P56898 | 8942 | KYNU | kynureninase (L-kynurenine hydrolase) |
| A_23_P56933 | 57142 | RTN4 | reticulon 4 |
| A_23_P6878 | 6405 | SEMA3F | sema domain, immunoglobulin domain (Ig), short basic domain, secreted, (semaphorin) 3F |
| A_23_P75283 | 5950 | RBP4 | retinol binding protein 4, plasma |
| A_23_P82420 | 6804 | STX1A | syntaxin 1A (brain) |
| A_23_P84344 | 59307 | SIGIRR | single immunoglobulin and toll-interleukin 1 receptor (TIR) domain |
| A_23_P84399 | 26047 | CNTNAP2 | contactin associated protein-like 2 |
| A_23_P87049 | 6653 | SORL1 | sortilin-related receptor, L(DLR class) A repeats-containing |
| A_23_P91802 | 1890 | TYMP | thymidine phosphorylase |
| A_24_P102636 | 5925 | RB1 | retinoblastoma 1 |
| A_24_P106681 | 7532 | YWHAG | tyrosine 3-monooxygenase/tryptophan 5-monooxygenase activation protein, gamma polypeptide |
| A_24_P137897 | 3475 | IFRD1 | interferon-related developmental regulator 1 |
| A_24_P174550 | 387 | RHOA | ras homolog gene family, member A |
| A_24_P187218 | 5101 | PCDH9 | protocadherin 9 |
| A_24_P243373 | 56129 | PCDHB7 | protocadherin beta 7 |
| A_24_P254949 | 5239 | PGM5 | phosphoglucomutase 5 |
| A_24_P287043 | 10581 | IFITM2 | interferon induced transmembrane protein 2 (1-8D) |
| A_24_P376483 | 3105 | HLA-A | major histocompatibility complex, class I, A |

TABLE S5-continued

| | | | | |
|---|---|---|---|---|
| | A_24_P402438 | 7042 | TGFB2 | transforming growth factor, beta 2 |
| | A_24_P407717 | 2885 | GRB2 | growth factor receptor-bound protein 2 |
| | A_24_P48898 | 23780 | APOL2 | apolipoprotein L, 2 |
| | A_24_P62505 | 23127 | GLT25D2 | glycosyltransferase 25 domain containing 2 |
| | A_24_P769359 | 65125 | WNK1 | WNK lysine deficient protein kinase 1 |
| | A_24_P90637 | 122809 | SOCS4 | suppressor of cytokine signaling 4 |
| | A_24_P926770 | 26020 | LRP10 | low density lipoprotein receptor-related protein 10 |
| | A_24_P944054 | 6387 | CXCL12 | chemokine (C—X—C motif) ligand 12 (stromal cell-derived factor 1) |
| | A_24_P97104 | 1803 | DPP4 | dipeptidyl-peptidase 4 |
| | A_32_P109002 | 4087 | SMAD2 | SMAD family member 2 |
| | A_32_P132748 | 731884 | LOC731884 | similar to programmed cell death 6 interacting protein |
| | A_32_P162187 | 717 | C2 | complement component 2 |
| | A_32_P206123 | 5340 | PLG | plasminogen |
| | A_32_P43664 | 3512 | IGJ | immunoglobulin J polypeptide, linker protein for immunoglobulin alpha and mu polypeptides |
| | A_32_P61684 | 55824 | PAG1 | phosphoprotein associated with glycosphingolipid microdomains 1 |
| | A_32_P78528 | 203068 | TUBB | tubulin, beta |
| | A_32_P85999 | 1012 | CDH13 | cadherin 13, H-cadherin (heart) |
| | A_32_P98683 | 4302 | MLLT6 | myeloid/lymphoid or mixed-lineage leukemia (trithorax homolog, *Drosophila*); translocated to, 6 |
| GC3 | A_23_P100556 | 23265 | EXOC7 | exocyst complex component 7 |
| | A_23_P116435 | 51214 | IGF2AS | insulin-like growth factor 2 antisense |
| | A_23_P121851 | 56121 | PCDHB15 | protocadherin beta 15 |
| | A_23_P130040 | 5245 | PHB | prohibitin |
| | A_23_P137196 | 3597 | IL13RA1 | interleukin 13 receptor, alpha 1 |
| | A_23_P143994 | 2177 | FANCD2 | Fanconi anemia, complementation group D2 |
| | A_23_P144274 | 152789 | JAKMIP1 | Janus kinase and microtubule interacting protein 1 |
| | A_23_P151710 | 5732 | PTGER2 | prostaglandin E receptor 2 (subtype EP2), 53 kDa |
| | A_23_P153741 | 566 | AZU1 | azurocidin 1 |
| | A_23_P15727 | 60681 | FKBP10 | FK506 binding protein 10, 65 kDa |
| | A_23_P171255 | 3476 | IGBP1 | immunoglobulin (CD79A) binding protein 1 |
| | A_23_P210048 | 9759 | HDAC4 | histone deacetylase 4 |
| | A_23_P212715 | 868 | CBLB | Cas-Br-M (murine) ecotropic retroviral transforming sequence b |
| | A_23_P215406 | 5879 | RAC1 | ras-related C3 botulinum toxin substrate 1 (rho family, small GTP binding protein Rac1) |
| | A_23_P30693 | 5340 | PLG | plasminogen |
| | A_23_P313632 | 2530 | FUT8 | fucosyltransferase 8 (alpha (1,6) fucosyltransferase) |
| | A_23_P32217 | 10210 | TOPORS | topoisomerase I binding, arginine/serine-rich |
| | A_23_P345692 | 53342 | IL17D | interleukin 17D |
| | A_23_P40880 | 152189 | CMTM8 | CKLF-like MARVEL transmembrane domain containing 8 |

TABLE S5-continued

| | | | | |
|---|---|---|---|---|
| | A_23_P43946 | 84324 | SARNP | SAP domain containing ribonucleoprotein |
| | A_23_P46924 | 9184 | BUB3 | budding uninhibited by benzimidazoles 3 homolog (yeast) |
| | A_23_P48713 | 145482 | PTGR2 | prostaglandin reductase 2 |
| | A_23_P56922 | 3336 | HSPE1 | heat shock 10 kDa protein 1 (chaperonin 10) |
| | A_23_P62021 | 7058 | THBS2 | thrombospondin 2 |
| | A_23_P69109 | 5359 | PLSCR1 | phospholipid scramblase 1 |
| | A_23_P70688 | 9450 | LY86 | lymphocyte antigen 86 |
| | A_23_P85004 | 1730 | DIAPH2 | diaphanous homolog 2 (*Drosophila*) |
| | A_24_P111342 | 842 | CASP9 | caspase 9, apoptosis-related cysteine peptidase |
| | A_24_P124992 | 5685 | PSMA4 | proteasome (prosome, macropain) subunit, alpha type, 4 |
| | A_24_P142118 | 7057 | THBS1 | thrombospondin 1 |
| | A_24_P161933 | 3106 | HLA-B | major histocompatibility complex, class I, B |
| | A_24_P228130 | 414062 | CCL3L3 | chemokine (C-C motif) ligand 3-like 3 |
| | A_24_P286465 | 5814 | PURB | purine-rich element binding protein B |
| | A_24_P291973 | 989 | 7-Sep | septin 7 |
| | A_24_P29665 | 54205 | CYCS | cytochrome c, somatic |
| | A_24_P319647 | 79368 | FCRL2 | Fc receptor-like 2 |
| | A_24_P353638 | 57823 | SLAMF7 | SLAM family member 7 |
| | A_24_P355944 | 1948 | EFNB2 | ephrin-B2 |
| | A_24_P40055 | 114823 | LENG8 | leukocyte receptor cluster (LRC) member 8 |
| | A_24_P876734 | 59269 | HIVEP3 | human immunodeficiency virus type I enhancer binding protein 3 |
| | A_24_P923251 | 7052 | TGM2 | transglutaminase 2 (C polypeptide, protein-glutamine-gamma-glutamyltransferase) |
| | A_24_P942786 | 8445 | DYRK2 | dual-specificity tyrosine-(Y)-phosphorylation regulated kinase 2 |
| | A_32_P141664 | 5089 | PBX2 | pre-B-cell leukemia homeobox 2 |
| | A_32_P222335 | 3921 | RPSA | ribosomal protein SA |
| | A_32_P230838 | 2547 | XRCC6 | X-ray repair complementing defective repair in Chinese hamster cells 6 |
| | A_32_P29759 | 3550 | IK | IK cytokine, down-regulator of HLA II |
| | A_32_P36217 | 6651 | SON | SON DNA binding protein |
| | A_32_P58280 | 54536 | EXOC6 | exocyst complex component 6 |
| GC4 | A_23_P100754 | 64750 | SMURF2 | SMAD specific E3 ubiquitin protein ligase 2 |
| | A_23_P113716 | 3107 | HLA-C | major histocompatibility complex, class I, C |
| | A_23_P122068 | 114899 | C1QTNF3 | C1q and tumor necrosis factor related protein 3 |
| | A_23_P125107 | 3106 | HLA-B | major histocompatibility complex, class I, B |
| | A_23_P132611 | 7428 | VHL | von Hippel-Lindau tumor suppressor |
| | A_23_P148473 | 3561 | IL2RG | interleukin 2 receptor, gamma (severe combined immunodeficiency) |
| | A_23_P151614 | 5720 | PSME1 | proteasome (prosome, macropain) activator subunit 1 (PA28 alpha) |
| | A_23_P151649 | 328 | APEX1 | APEX nuclease (multifunctional DNA repair enzyme) 1 |
| | A_23_P157795 | 8727 | CTNNAL1 | catenin (cadherin-associated protein), alpha-like 1 |
| | A_23_P157809 | 22949 | PTGR1 | prostaglandin reductase 1 |
| | A_23_P162171 | 4162 | MCAM | melanoma cell adhesion molecule |

TABLE S5-continued

| | | | | |
|---|---|---|---|---|
| | A_23_P163087 | 22795 | NID2 | nidogen 2 (osteonidogen) |
| | A_23_P16438 | 10683 | DLL3 | delta-like 3 (*Drosophila*) |
| | A_23_P19673 | 6446 | SGK1 | serum/glucocorticoid regulated kinase 1 |
| | A_23_P200928 | 4811 | NID1 | nidogen 1 |
| | A_23_P201338 | 51150 | SDF4 | stromal cell derived factor 4 |
| | A_23_P251118 | 4026 | LPP | LIM domain containing preferred translocation partner in lipoma |
| | A_23_P258769 | 3115 | HLA-DPB1 | major histocompatibility complex, class II, DP beta 1 |
| | A_23_P26094 | 79811 | SLTM | SAFB-like, transcription modulator |
| | A_23_P308673 | 9344 | TAOK2 | TAO kinase 2 |
| | A_23_P314070 | 392 | ARHGAP1 | Rho GTPase activating protein 1 |
| | A_23_P320883 | 56882 | CDC42SE1 | CDC42 small effector 1 |
| | A_23_P321501 | 10202 | DHRS2 | dehydrogenase/reductase (SDR family) member 2 |
| | A_23_P330209 | 117584 | RFFL | ring finger and FYVE-like domain containing 1 |
| | A_23_P33216 | 506 | ATP5B | ATP synthase, H+ transporting, mitochondrial F1 complex, beta polypeptide |
| | A_23_P3532 | 9516 | LITAF | lipopolysaccharide-induced TNF factor |
| | A_23_P408708 | 665 | BNIP3L | BCL2/adenovirus E1B 19 kDa interacting protein 3-like |
| | A_23_P42498 | 8724 | SNX3 | sorting nexin 3 |
| | A_23_P71067 | 7291 | TWIST1 | twist homolog 1 (*Drosophila*) |
| | A_23_P9756 | 22827 | PUF60 | poly-U binding splicing factor 60 KDa |
| | A_23_P99582 | 5411 | PNN | pinin, desmosome associated protein |
| | A_24_P113674 | 3106 | HLA-B | major histocompatibility complex, class I, B |
| | A_24_P114739 | 817 | CAMK2D | calcium/calmodulin-dependent protein kinase II delta |
| | A_24_P181506 | 9726 | ZNF646 | zinc finger protein 646 |
| | A_24_P27412 | 10073 | SNUPN | snurportin 1 |
| | A_24_P284893 | 5690 | PSMB2 | proteasome (prosome, macropain) subunit, beta type, 2 |
| | A_24_P336754 | 4170 | MCL1 | myeloid cell leukemia sequence 1 (BCL2-related) |
| | A_24_P410952 | 8682 | PEA15 | phosphoprotein enriched in astrocytes 15 |
| | A_24_P418044 | 3137 | HLA-J | major histocompatibility complex, class I, J (pseudogene) |
| | A_24_P73599 | 3603 | IL16 | interleukin 16 (lymphocyte chemoattractant factor) |
| | A_24_P912799 | 9037 | SEMA5A | sema domain, seven thrombospondin repeats (type 1 and type 1-like), transmembrane domain (TM) and short cytoplasmic domain, (semaphorin) 5A |
| | A_24_P927404 | 91419 | XRCC6BP1 | XRCC6 binding protein 1 |
| | A_32_P170406 | 83660 | TLN2 | talin 2 |
| | A_32_P177024 | 51119 | SBDS | Shwachman-Bodian-Diamond syndrome |
| | A_32_P217655 | 645166 | LOC645166 | lymphocyte-specific protein 1 pseudogene |
| | A_32_P2738 | 26123 | TCTN3 | tectonic family member 3 |
| | A_32_P88965 | 4921 | DDR2 | discoidin domain receptor tyrosine kinase 2 |
| GC5 | A_23_P13382 | 4046 | LSP1 | lymphocyte-specific protein 1 |
| | A_23_P138376 | 22931 | RAB18 | RAB18, member RAS oncogene family |

TABLE S5-continued

| | | | | |
|---|---|---|---|---|
| | A_23_P140725 | 9742 | IFT140 | intraflagellar transport 140 homolog (*Chlamydomonas*) |
| | A_23_P157875 | 2219 | FCN1 | ficolin (collagen/fibrinogen domain containing) 1 |
| | A_23_P157879 | 2219 | FCN1 | ficolin (collagen/fibrinogen domain containing) 1 |
| | A_23_P15995 | 8778 | SIGLEC5 | sialic acid binding Ig-like lectin 5 |
| | A_23_P165219 | 84106 | PRAM1 | PML-RARA regulated adaptor molecule 1 |
| | A_23_P167256 | 79960 | PHF17 | PHD finger protein 17 |
| | A_23_P200728 | 2214 | FCGR3A | Fc fragment of IgG, low affinity IIIa, receptor (CD16a) |
| | A_23_P22444 | 5199 | CFP | complement factor properdin |
| | A_23_P259561 | 3109 | HLA-DMB | major histocompatibility complex, class II, DM beta |
| | A_23_P259621 | 7462 | LAT2 | linker for activation of T cells family, member 2 |
| | A_23_P27994 | 7305 | TYROBP | TYRO protein tyrosine kinase binding protein |
| | A_23_P31006 | 3127 | HLA-DRB5 | major histocompatibility complex, class II, DR beta 5 |
| | A_23_P38795 | 2357 | FPR1 | formyl peptide receptor 1 |
| | A_23_P41765 | 3659 | IRF1 | interferon regulatory factor 1 |
| | A_23_P48997 | 9051 | PSTPIP1 | proline-serine-threonine phosphatase interacting protein 1 |
| | A_23_P51534 | 6846 | XCL2 | chemokine (C motif) ligand 2 |
| | A_23_P85716 | 2212 | FCGR2A | Fc fragment of IgG, low affinity IIa, receptor (CD32) |
| | A_24_P134229 | 126282 | TNFAIP8L1 | tumor necrosis factor, alpha-induced protein 8-like 1 |
| | A_24_P192914 | 120425 | AMICA1 | adhesion molecule, interacts with CXADR antigen 1 |
| | A_24_P283189 | 929 | CD14 | CD14 molecule |
| | A_24_P343233 | 3123 | HLA-DRB1 | major histocompatibility complex, class II, DR beta 1 |
| | A_24_P365807 | 1947 | EFNB1 | ephrin-B1 |
| GC6 | A_23_P100240 | 1014 | CDH16 | cadherin 16, KSP-cadherin |
| | A_23_P121987 | 85480 | TSLP | thymic stromal lymphopoietin |
| | A_23_P143331 | 650 | BMP2 | bone morphogenetic protein 2 |
| | A_23_P147786 | 9699 | RIMS2 | regulating synaptic membrane exocytosis 2 |
| | A_23_P158096 | 85301 | COL27A1 | collagen, type XXVII, alpha 1 |
| | A_23_P168259 | 80328 | ULBP2 | UL16 binding protein 2 |
| | A_23_P252721 | 10395 | DLC1 | deleted in liver cancer 1 |
| | A_23_P66117 | 83986 | ITFG3 | integrin alpha FG-GAP repeat containing 3 |
| | A_24_P113295 | 1175 | AP2S1 | adaptor-related protein complex 2, sigma 1 subunit |
| | A_24_P285163 | 57645 | POGK | pogo transposable element with KRAB domain |
| | A_24_P334130 | 2335 | FN1 | fibronectin 1 |
| | A_24_P51909 | 10815 | CPLX1 | complexin 1 |
| | A_24_P84898 | 2237 | FEN1 | flap structure-specific endonuclease 1 |
| | A_24_P88870 | 8706 | B3GALNT1 | beta-1,3-N-acetylgalactosaminyltransferase 1 (globoside blood group) |
| | A_24_P935252 | 8087 | FXR1 | fragile X mental retardation, autosomal homolog 1 |
| | A_32_P106615 | 9353 | SLIT2 | slit homolog 2 (*Drosophila*) |

TABLE S5-continued

| | | | |
|---|---|---|---|
| A_32_P121651 | 57534 | MIB1 | mindbomb homolog 1 (*Drosophila*) |
| A_32_P157539 | 79031 | PDCL3 | phosducin-like 3 |
| A_32_P200600 | 5518 | PPP2R1A | protein phosphatase 2 (formerly 2A), regulatory subunit A, alpha isoform |
| A_32_P29806 | 8738 | CRADD | CASP2 and RIPK1 domain containing adaptor with death domain |
| A_32_P43717 | 9413 | C9orf61 | chromosome 9 open reading frame 61 |
| A_32_P72541 | 9037 | SEMA5A | sema domain, seven thrombospondin repeats (type 1 and type 1-like), transmembrane domain (TM) and short cytoplasmic domain, (semaphorin) 5A |
| A_32_P84009 | 146223 | CMTM4 | CKLF-like MARVEL transmembrane domain containing 4 |

APPENDIX F

TABLE S6

| | Weights of sparse CCA | | | |
|---|---|---|---|---|
| Cytokine responses | B-cells | CD8 | CD4 | Monocytes |
| Correlation Factors | 0.9 | 0.88 | 0.87 | 0.75 |
| Baseline-B-cells | −0.9 | −0.88 | −0.95 | −0.75 |
| Baseline-CD4 | −0.76 | −0.68 | −0.79 | −0.36 |
| CD8 Naive | 0.76 | 0.72 | 0.6 | 0.49 |
| CD8 TDEM | −0.67 | −0.65 | −0.65 | −0.49 |
| CD8+CD28− | 0.81 | 0.6 | 0.7 | 0.32 |
| CD4 TDEM | −0.35 | −0.59 | −0.56 | −0.63 |
| CD4+CD28− | 0.19 | 0.55 | 0.39 | 0.65 |
| GC 6 | 0.52 | 0.46 | 0.4 | 0.26 |
| GC 1 | −0.21 | −0.39 | −0.38 | −0.54 |
| NK T | −0.4 | −0.41 | −0.42 | −0.18 |
| GC 5 | −0.21 | −0.32 | −0.27 | −0.49 |
| GC 3 | 0.24 | 0.15 | 0.24 | 0.24 |
| Baseline-cd8 | −0.42 | −0.22 | −0.23 | −0.02 |
| IL-17 | 0.38 | 0 | 0.16 | 0 |
| GC 4 | 0.25 | 0.18 | 0.05 | 0 |
| MPZL2 (A_24_P278552 mono | 0 | 0.08 | 0.05 | 0.18 |
| | 0 | −0.01 | 0 | −0.21 |
| IFI30 (A_23_P153745) | −0.06 | −0.01 | −0.05 | −0.07 |
| GC 2 | 0 | 0 | −0.02 | −0.17 |
| TGF-a | 0 | 0.05 | 0.1 | 0 |
| Th1 | −0.15 | 0 | 0 | 0 |
| MCP-3 | 0 | 0.06 | 0.06 | 0 |
| Th2 | 0 | 0.07 | 0 | 0 |
| TNF-a | 0 | −0.02 | 0 | −0.01 |
| chemokines | 0 | 0 | 0 | 0 |
| CD8 CenMem | 0 | 0 | 0 | 0 |

APPENDIX G

TABLE S7

| | Significant differences between CR and CNR | | | | | |
|---|---|---|---|---|---|---|
| | Fold-change CNR vs CR | Cytokine response | | Age: 60-65 yo vs 74+ yo | | Gender |
| | | p-value | q-value | p-value | q-value | p-value | q-value |
| Cytokine stimulation response | | | | | | | |
| cd4_IFNa_STAT3 | 4 | 0 | 0 | 0.947037 | 0.460211 | 0.153556 | 0.376565 |
| cd4_IL6_STAT3 | 6.28 | 0 | 0 | 0.900331 | 0.443676 | 0.299048 | 0.482754 |
| cd4_IL21_STAT3 | 4.08 | 0 | 0 | 0.829489 | 0.428303 | 0.13378 | 0.376565 |
| cd4_IL10_STAT3 | 3.8 | 0 | 0.000001 | 0.802164 | 0.428303 | 0.340265 | 0.482754 |
| mono_IFNg_STAT3 | 1.54 | 0.000006 | 0.000025 | 0.714285 | 0.420019 | 0.70903 | 0.702136 |
| cd8_IL7_STAT1 | 1.25 | 0.000015 | 0.000047 | 0.135552 | 0.420019 | 0.060505 | 0.291589 |
| mono_IL6_STAT3 | 3.59 | 0.000015 | 0.000047 | 0.684827 | 0.420019 | 0.776648 | 0.702136 |
| cd8_IFNg_STAT1 | 2.45 | 0.000023 | 0.000064 | 0.290331 | 0.420019 | 0.014834 | 0.291589 |
| cd8_IL6_STAT3 | 4.35 | 0.000034 | 0.000083 | 0.24283 | 0.420019 | 0.065875 | 0.291589 |
| cd4_IL6_STAT1 | 6.81 | 0.000039 | 0.000085 | 0.345614 | 0.420019 | 0.310418 | 0.482754 |
| cd4_IFNa_STAT1 | 3.16 | 0.000057 | 0.000106 | 0.493856 | 0.420019 | 0.166634 | 0.380318 |
| mono_IFNa_STAT5 | 1.62 | 0.000058 | 0.000106 | 0.319297 | 0.420019 | 0.977993 | 0.725487 |
| cd4_IL6_STAT5 | 2.93 | 0.00007 | 0.000119 | 0.53263 | 0.420019 | 0.822851 | 0.708112 |
| mono_IFNa_STAT3 | 1.75 | 0.000095 | 0.000149 | 0.37638 | 0.420019 | 0.995002 | 0.725487 |
| cd4_IFNg_STAT1 | 2.22 | 0.000121 | 0.000177 | 0.198227 | 0.420019 | 0.092476 | 0.373417 |
| cd8_IFNa_STAT3 | 1.78 | 0.000156 | 0.000215 | 0.381077 | 0.420019 | 0.066656 | 0.291589 |

TABLE S7-continued

Significant differences between CR and CNR

| | | Fold-change CNR vs CR | Cytokine response | | Age: 60-65 yo vs 74+ yo | | Gender | | |
|---|---|---|---|---|---|---|---|---|---|
| | | | p-value | q-value | p-value | q-value | p-value | q-value | |
| cd4_IL7_STAT3 | | 1.31 | 0.00019 | 0.000241 | 0.39983 | 0.420019 | 0.405702 | 0.519438 | |
| cd8_IL6_STAT1 | | 7.41 | 0.000197 | 0.000241 | 0.340202 | 0.420019 | 0.049192 | 0.291589 | |
| cd4_IL21_STAT1 | | 1.83 | 0.000217 | 0.000251 | 0.555918 | 0.420019 | 0.108496 | 0.376565 | |
| cd8_IFNa_STAT1 | | 2.79 | 0.000262 | 0.000288 | 0.218327 | 0.420019 | 0.137566 | 0.376565 | |
| mono_IFNg_STAT5 | | 1.65 | 0.000303 | 0.000318 | 0.457462 | 0.420019 | 0.664712 | 0.691429 | |
| cd8_IL7_STAT3 | | 1.17 | 0.000936 | 0.000936 | 0.730943 | 0.420019 | 0.03782 | 0.291589 | |
| mono_IL7_STAT5 | | 1.17 | 0.001112 | 0.001063 | 0.41378 | 0.420019 | 0.505697 | 0.63205 | |
| cd20_IFNa_STAT1 | | 2.42 | 0.001232 | 0.00113 | 0.427269 | 0.420019 | 0.784512 | 0.702136 | |
| cd4_IL10_STAT1 | | 1.83 | 0.001462 | 0.001287 | 0.840156 | 0.428303 | 0.958775 | 0.725487 | |
| cd20_IFNg_STAT1 | | 2.05 | 0.001556 | 0.001317 | 0.618695 | 0.420019 | 0.791049 | 0.702136 | |
| cd4_IFNg_STAT3 | | 1.13 | 0.001933 | 0.001575 | 0.514195 | 0.420019 | 0.113051 | 0.376565 | |
| mono_IFNa_STAT1 | | 1.71 | 0.003477 | 0.002732 | 0.37889 | 0.420019 | 0.839715 | 0.710969 | |
| cd8_IL10_STAT1 | | 1.57 | 0.003883 | 0.002947 | 0.091318 | 0.420019 | 0.97801 | 0.725487 | |
| cd8_IFNa_STAT5 | | 2.02 | 0.004273 | 0.003134 | 0.253498 | 0.420019 | 0.042724 | 0.291589 | |
| cd8_IL6_STAT5 | | 1.85 | 0.005126 | 0.003525 | 0.493479 | 0.420019 | 0.193612 | 0.423479 | |
| cd8_IL21_STAT1 | | 1.51 | 0.005003 | 0.003525 | 0.58113 | 0.420019 | 0.133924 | 0.376565 | |
| mono_IFNg_STAT1 | | 1.55 | 0.009067 | 0.006046 | 0.634593 | 0.420019 | 0.802532 | 0.702136 | |
| cd20_IL21_STAT1 | | 1.46 | 0.010978 | 0.007106 | 0.330071 | 0.420019 | 0.338943 | 0.482754 | |
| mono_IL10_STAT3 | | 1.16 | 0.028449 | 0.017863 | 0.558034 | 0.420019 | 0.995066 | 0.725487 | |
| mono_IL21_STAT3 | | 1.11 | 0.029221 | 0.017863 | 0.744283 | 0.420019 | 0.315413 | 0.482754 | |
| cd20_IL21_STAT3 | | 1.15 | 0.042992 | 0.02557 | 0.641946 | 0.420019 | 0.117569 | 0.376565 | |
| cd8_IL7_STAT5 | | 1.22 | 0.044731 | 0.025904 | 0.069506 | 0.420019 | 0.157816 | 0.376565 | |
| cd8_IFNg_STAT5 | | 1.1 | 0.049497 | 0.02793 | 0.682996 | 0.420019 | 0.059991 | 0.291589 | |
| cd20_IFNa_STAT3 | | 1.17 | 0.051587 | 0.028381 | 0.337448 | 0.420019 | 0.033475 | 0.291589 | |
| cd4_IL7_STAT1 | | 1.19 | 0.05989 | 0.032146 | 0.375291 | 0.420019 | 0.629986 | 0.691429 | |
| cd4_IL21_STAT5 | | 1.18 | 0.080319 | 0.042084 | 0.856894 | 0.428303 | 0.155441 | 0.376565 | |
| cd4_IFNa_STAT5 | | 1.33 | 0.092694 | 0.047439 | 0.633135 | 0.420019 | 0.785958 | 0.702136 | |
| cd8_IL21_STAT5 | | 1.18 | 0.114836 | 0.057435 | 0.718208 | 0.420019 | 0.03049 | 0.291589 | |
| cd20_IFNg_STAT3 | | −1.05 | 0.14128 | 0.069091 | 0.594073 | 0.420019 | 0.061708 | 0.291589 | |
| cd4_IFNg_STAT5 | | 1.03 | 0.154626 | 0.073974 | 0.58423 | 0.420019 | 0.335123 | 0.482754 | |
| cd20_IL7_STAT1 | | 1.1 | 0.17748 | 0.0831 | 0.471045 | 0.420019 | 0.958544 | 0.725487 | |
| cd8_IL10_STAT5 | | 1.13 | 0.215206 | 0.098212 | 0.462871 | 0.420019 | 0.684921 | 0.691429 | |
| cd8_IL21_STAT3 | | 1.1 | 0.21868 | 0.098212 | 0.744099 | 0.420019 | 0.86352 | 0.719519 | |
| phosphoprotein baseline | | | | | | | | | |
| cd20_Unstimulated_STAT1 | | −2.57 | 0.000117 | 0.000644 | 0.373293 | 0.777023 | 0.619702 | 0.308798 | |
| cd4_Unstimulated_STAT3 | | −4.2 | 0.000273 | 0.000753 | 0.485768 | 0.777023 | 0.062525 | 0.066939 | |
| cd20_Unstimulated_STAT5 | | −1.11 | 0.076648 | 0.070499 | 0.33538 | 0.777023 | 0.841783 | 0.349551 | |
| cd20_Unstimulated_STAT3 | | −1.11 | 0.007217 | 0.009957 | 0.57577 | 0.777023 | 0.024649 | 0.040941 | |
| cd4_Unstimulated_STAT1 | | −2.15 | 0.006027 | 0.009957 | 0.812278 | 0.777023 | 0.010133 | 0.025246 | |
| cd4_Unstimulated_STAT5 | | −1.05 | 0.090487 | 0.071338 | 0.296912 | 0.777023 | 0.00931 | 0.025246 | |
| mono_Unstimulated_STAT1 | | −1.2 | 0.019564 | 0.021594 | 0.433673 | 0.777023 | 0.379235 | 0.20997 | |
| Cell subsets | | | | | | | | | |
| CD8+CD28− | | −4.21 | 0.000008 | 0.000032 | 0.630348 | 0.607903 | 0.005759 | 0.037864 | |
| CD8 TERM DIFF EFFECTOR MEMORY | | −9.49 | 0.000032 | 0.000068 | 0.389149 | 0.585539 | 0.039951 | 0.058839 | |
| CD8 NAIVE | | 2.14 | 0.001718 | 0.002449 | 0.694365 | 0.618129 | 0.032877 | 0.058839 | |
| B CELLS | | 3.54 | 0.004612 | 0.004932 | 0.817871 | 0.630998 | 0.541342 | 0.237297 | |
| CD4 EFFECTOR MEMORY | | −5.62 | 0.012042 | 0.010302 | 0.477152 | 0.585539 | 0.457482 | 0.231389 | |
| CD4 NAIVE | | 1.48 | 0.019374 | 0.013811 | 0.519746 | 0.585539 | 0.111156 | 0.117433 | |
| CD4 TERM DIFF EFFECTOR MEMORY | | −53.39 | 0.024124 | 0.014741 | 0.556562 | 0.585539 | 0.378876 | 0.217652 | |
| NK T CELLS | | −6.67 | 0.034716 | 0.018562 | 0.163185 | 0.585539 | 0.246943 | 0.202964 | |
| CD8 CENTRAL MEMORY | | 1.92 | 0.053228 | 0.023628 | 0.549683 | 0.585539 | 0.291454 | 0.208139 | |
| CD4+CD28− | | −31.87 | 0.055239 | 0.023628 | 0.319976 | 0.585539 | 0.523354 | 0.237297 | |
| GAMMA DELTA CELLS | | −2.58 | 0.164423 | 0.063936 | 0.215857 | 0.585539 | 0.044742 | 0.058839 | |
| CD4 CENTRAL MEMORY | | −1.2 | 0.303572 | 0.099883 | 0.751379 | 0.621106 | 0.031656 | 0.058839 | |
| CD8 EFFECTOR MEMORY | | −2.44 | 0.294813 | 0.099883 | 0.3442 | 0.585539 | 0.39722 | 0.217652 | |
| Gene expression | | | | | | | | | |
| CNTFR | 1271 A_23_P9402 | 1.42 | 0.000002 | 0.003052 | 0.468716 | 0.999497 | 0.681992 | 0.999623 | 0 |
| CD33 | 945 A_24_P301655 | 1.55 | 0.000019 | 0.014378 | 0.65498 | 0.999497 | 0.569891 | 0.999623 | 0 |

TABLE S7-continued

Significant differences between CR and CNR

| | | Fold-change CNR vs CR | Cytokine response | | Age: 60-65 yo vs 74+ yo | | Gender | | |
|---|---|---|---|---|---|---|---|---|---|
| | | | p-value | q-value | p-value | q-value | p-value | q-value | |
| CCL5 | 6352 A_23_P152838 | −8.16 | 0.000025 | 0.014378 | 0.852489 | 0.999497 | 0.771658 | 0.999623 | 0 |
| UBE2I | 7329 A_23_P152107 | 1.59 | 0.001915 | 0.036104 | 0.935523 | 0.999497 | 0.9852 | 0.999623 | 1 |
| NAE1 | 8883 A_23_P77459 | −1.72 | 0.000889 | 0.036104 | 0.528884 | 0.999497 | 0.609482 | 0.999623 | 0 |
| F5 | 2153 A_32_P41604 | 1.48 | 0.001425 | 0.036104 | 0.401274 | 0.999497 | 0.503965 | 0.999623 | 0 |
| PGM5 | 5239 A_24_P120907 | 1.41 | 0.001015 | 0.036104 | 0.327167 | 0.999497 | 0.051766 | 0.999623 | 0 |
| CRYAB | 1410 A_24_P206776 | 1.71 | 0.001353 | 0.036104 | 0.870361 | 0.999497 | 0.77123 | 0.999623 | 0 |
| FOS | 2353 A_23_P106194 | 1.66 | 0.001921 | 0.036104 | 0.630412 | 0.999497 | 0.655547 | 0.999623 | 1 |
| NUPR1 | 26471 A_24_P270728 | 1.72 | 0.001261 | 0.036104 | 0.544316 | 0.999497 | 0.86663 | 0.999623 | 0 |
| COL6A2 | 1292 A_23_P211233 | 2.12 | 0.001914 | 0.036104 | 0.443149 | 0.999497 | 0.685136 | 0.999623 | 0 |
| ACTN4 | 81 A_23_P315241 | 2 | 0.001969 | 0.036104 | 0.477143 | 0.999497 | 0.541507 | 0.999623 | 0 |
| NOG | 9241 A_23_P341938 | 1.9 | 0.000533 | 0.036104 | 0.851653 | 0.999497 | 0.264467 | 0.999623 | 1 |
| CAPN10 | 11132 A_23_P312217 | 1.93 | 0.001745 | 0.036104 | 0.113584 | 0.999497 | 0.295294 | 0.999623 | 0 |
| HDAC5 | 10014 A_23_P26916 | 1.85 | 0.001396 | 0.036104 | 0.755511 | 0.999497 | 0.244218 | 0.999623 | 0 |
| CUTA | 51596 A_23_P214678 | 1.6 | 0.000807 | 0.036104 | 0.612211 | 0.999497 | 0.241352 | 0.999623 | 0 |
| TGFB1I1 | 7041 A_23_P141055 | 1.99 | 0.000809 | 0.036104 | 0.822061 | 0.999497 | 0.246581 | 0.999623 | 0 |
| SOD1 | 6647 A_23_P154840 | 1.62 | 0.001546 | 0.036104 | 0.662823 | 0.999497 | 0.535483 | 0.999623 | 1 |
| NRP2 | 8828 A_24_P50801 | 1.72 | 0.001623 | 0.036104 | 0.952429 | 0.999497 | 0.133472 | 0.999623 | 0 |
| FOLR1 | 2348 A_23_P53176 | 1.93 | 0.000554 | 0.036104 | 0.892212 | 0.999497 | 0.193482 | 0.999623 | 0 |
| MKNK2 | 2872 A_24_P938135 | 1.74 | 0.001284 | 0.036104 | 0.769347 | 0.999497 | 0.224105 | 0.999623 | 0 |
| RAMP3 | 10268 A_23_P111737 | 1.86 | 0.000877 | 0.036104 | 0.846338 | 0.999497 | 0.58297 | 0.999623 | 0 |
| IGF1R | 3480 A_23_P205986 | 1.67 | 0.000913 | 0.036104 | 0.644569 | 0.999497 | 0.996777 | 0.999623 | 1 |
| FXYD5 | 53827 A_24_P194081 | 1.65 | 0.000561 | 0.036104 | 0.387527 | 0.999497 | 0.632614 | 0.999623 | 0 |
| ZNF346 | 23567 A_23_P400887 | 1.55 | 0.001565 | 0.036104 | 0.956026 | 0.999497 | 0.621718 | 0.999623 | 0 |
| CIAPIN1 | 57019 A_23_P88781 | 1.4 | 0.000741 | 0.036104 | 0.91067 | 0.999497 | 0.828879 | 0.999623 | 0 |
| DAB2 | 1601 A_23_P257871 | 1.65 | 0.001499 | 0.036104 | 0.734123 | 0.999497 | 0.216778 | 0.999623 | 0 |
| CEACAM1 | 634 A_24_P382319 | −2.09 | 0.00171 | 0.036104 | 0.818157 | 0.999497 | 0.367309 | 0.999623 | 0 |
| LSP1 | 4046 A_32_P111098 | 1.38 | 0.001183 | 0.036104 | 0.858935 | 0.999497 | 0.539176 | 0.999623 | 0 |
| CCL3 | 6348 A_23_P373017 | 1.47 | 0.00082 | 0.036104 | 0.753777 | 0.999497 | 0.835003 | 0.999623 | 0 |
| HIC1 | 3090 A_23_P129856 | 1.39 | 0.001829 | 0.036104 | 0.756911 | 0.999497 | 0.266203 | 0.999623 | 1 |
| RICTOR | 253260 A_32_P193322 | −3.17 | 0.000688 | 0.036104 | 0.892103 | 0.999497 | 0.896246 | 0.999623 | 0 |
| LOC731884 | 731884 A_32_P132748 | −1.52 | 0.000346 | 0.036104 | 0.546338 | 0.999497 | 0.970792 | 0.999623 | 0 |
| C11orf82 | 220042 A_23_P429491 | −1.83 | 0.000382 | 0.036104 | 0.969107 | 0.999497 | 0.454269 | 0.999623 | 0 |
| ADH5 | 128 A_24_P260346 | −1.83 | 0.000181 | 0.036104 | 0.991188 | 0.999497 | 0.537529 | 0.999623 | 0 |
| LRP12 | 29967 A_23_P8906 | −2.5 | 0.001269 | 0.036104 | 0.615746 | 0.999497 | 0.632577 | 0.999623 | 0 |
| RIMS4 | 140730 A_24_P374532 | −1.89 | 0.000957 | 0.036104 | 0.922956 | 0.999497 | 0.49328 | 0.999623 | 0 |
| BMI1 | 648 A_23_P314115 | −5.23 | 0.001737 | 0.036104 | 0.47677 | 0.999497 | 0.588522 | 0.999623 | 1 |
| FNBP1L | 54874 A_23_P417942 | −2.18 | 0.000321 | 0.036104 | 0.592882 | 0.999497 | 0.4161 | 0.999623 | 0 |
| KCNMA1 | 3778 A_32_P192692 | 1.28 | 0.001967 | 0.036104 | 0.735474 | 0.999497 | 0.411288 | 0.999623 | 0 |
| SCRN1 | 9805 A_23_P366366 | 1.51 | 0.001041 | 0.036104 | 0.413517 | 0.999497 | 0.643565 | 0.999623 | 0 |
| NRTN | 4902 A_23_P90359 | 2.19 | 0.001956 | 0.036104 | 0.480441 | 0.999497 | 0.274495 | 0.999623 | 0 |
| GZMH | 2999 A_23_P128993 | −20.32 | 0.000372 | 0.036104 | 0.48478 | 0.999497 | 0.732471 | 0.999623 | 0 |
| MAP4K2 | 5871 A_24_P287075 | 2.04 | 0.00125 | 0.036104 | 0.95867 | 0.999497 | 0.783462 | 0.999623 | 0 |
| PCDHB11 | 56125 A_23_P167401 | 1.62 | 0.001861 | 0.036104 | 0.644295 | 0.999497 | 0.471202 | 0.999623 | 0 |
| HCG18 | 414777 A_32_P181722 | 1.93 | 0.001725 | 0.036104 | 0.718093 | 0.999497 | 0.310781 | 0.999623 | 0 |
| FSCN1 | 6624 A_23_P168532 | 2.08 | 0.000886 | 0.036104 | 0.959932 | 0.999497 | 0.756668 | 0.999623 | 0 |
| MUC5AC | 4586 A_24_P743708 | 1.91 | 0.000211 | 0.036104 | 0.565104 | 0.999497 | 0.972325 | 0.999623 | 0 |
| NINJ1 | 4814 A_23_P169137 | 1.97 | 0.001275 | 0.036104 | 0.954106 | 0.999497 | 0.255055 | 0.999623 | 0 |
| PSMD4 | 5710 A_23_P12168 | 1.62 | 0.00196 | 0.036104 | 0.662586 | 0.999497 | 0.272692 | 0.999623 | 0 |
| CLN3 | 1201 A_24_P187651 | 1.62 | 0.001455 | 0.036104 | 0.84645 | 0.999497 | 0.546117 | 0.999623 | 0 |
| PYCARD | 29108 A_23_P26629 | 1.46 | 0.001903 | 0.036104 | 0.995796 | 0.999497 | 0.50099 | 0.999623 | 0 |
| UTP14A | 10813 A_24_P170538 | −1.96 | 0.001041 | 0.036104 | 0.973791 | 0.999497 | 0.634985 | 0.999623 | 2 |
| RPS3A | 6189 A_32_P196483 | −1.64 | 0.001684 | 0.036104 | 0.741683 | 0.999497 | 0.677281 | 0.999623 | 0 |
| TYMP | 1890 A_23_P91802 | 1.88 | 0.000299 | 0.036104 | 0.963687 | 0.999497 | 0.535271 | 0.999623 | 0 |
| PLD2 | 5338 A_23_P4308 | 1.43 | 0.001952 | 0.036104 | 0.59288 | 0.999497 | 0.9276 | 0.999623 | 0 |
| FGFR1 | 2260 A_24_P4171 | 1.75 | 0.001282 | 0.036104 | 0.510266 | 0.999497 | 0.702185 | 0.999623 | 1 |
| TGM2 | 7052 A_24_P923251 | 1.44 | 0.001857 | 0.036104 | 0.406185 | 0.999497 | 0.678772 | 0.999623 | 0 |
| AP2A1 | 160 A_23_P4885 | 1.54 | 0.001371 | 0.036104 | 0.657812 | 0.999497 | 0.805783 | 0.999623 | 0 |
| C16orf5 | 29965 A_23_P15247 | 1.45 | 0.000499 | 0.036104 | 0.79947 | 0.999497 | 0.456699 | 0.999623 | 0 |
| AREG | 374 A_23_P259071 | 1.6 | 0.00181 | 0.036104 | 0.425941 | 0.999497 | 0.55855 | 0.999623 | 0 |
| CHST10 | 9486 A_23_P102351 | 1.56 | 0.000695 | 0.036104 | 0.524686 | 0.999497 | 0.752694 | 0.999623 | 0 |
| LOC91316 | 91316 A_24_P915446 | 1.35 | 0.000436 | 0.036104 | 0.512559 | 0.999497 | 0.65309 | 0.999623 | 0 |
| ARHGEF11 | 9826 A_23_P426809 | 1.58 | 0.001814 | 0.036104 | 0.829165 | 0.999497 | 0.794249 | 0.999623 | 0 |
| IL3RA | 3563 A_23_P253081 | 1.7 | 0.000099 | 0.036104 | 0.95942 | 0.999497 | 0.34963 | 0.999623 | 0 |
| YKT6 | 10652 A_24_P372048 | 1.72 | 0.000851 | 0.036104 | 0.917946 | 0.999497 | 0.584568 | 0.999623 | 0 |
| PEX5 | 5830 A_24_P372932 | 1.71 | 0.001585 | 0.036104 | 0.832499 | 0.999497 | 0.935308 | 0.999623 | 1 |
| RAB5B | 5869 A_23_P162238 | 1.44 | 0.000215 | 0.036104 | 0.605261 | 0.999497 | 0.777266 | 0.999623 | 0 |
| TCTA | 6988 A_24_P123166 | 1.8 | 0.000417 | 0.036104 | 0.272418 | 0.999497 | 0.520236 | 0.999623 | 0 |
| TRAP1 | 10131 A_23_P3849 | 1.44 | 0.001417 | 0.036104 | 0.249931 | 0.999497 | 0.377573 | 0.999623 | 0 |
| KYNU | 8942 A_23_P56898 | 1.42 | 0.001445 | 0.036104 | 0.582003 | 0.999497 | 0.598451 | 0.999623 | 0 |
| FN1 | 2335 A_32_P92642 | 1.81 | 0.000524 | 0.036104 | 0.77332 | 0.999497 | 0.2 | 0.999623 | 0 |
| TRIP10 | 9322 A_23_P50349 | 1.78 | 0.00032 | 0.036104 | 0.476946 | 0.999497 | 0.552793 | 0.999623 | 0 |
| PIN1 | 5300 A_23_P67162 | 1.67 | 0.001732 | 0.036104 | 0.8874 | 0.999497 | 0.272875 | 0.999623 | 1 |

TABLE S7-continued

Significant differences between CR and CNR

| | | Fold-change CNR vs CR | Cytokine response | | Age: 60-65 yo vs 74+ yo | | Gender | | |
|---|---|---|---|---|---|---|---|---|---|
| | | | p-value | q-value | p-value | q-value | p-value | q-value | |
| RIN2 | 54453 A_23_P91379 | 1.64 | 0.000727 | 0.036104 | 0.689161 | 0.999497 | 0.820036 | 0.999623 | 0 |
| BSCL2 | 26580 A_24_P244442 | 1.72 | 0.00045 | 0.036104 | 0.692057 | 0.999497 | 0.61986 | 0.999623 | 1 |
| PCDHA1 | 56147 A_24_P146138 | 1.62 | 0.000977 | 0.036104 | 0.526039 | 0.999497 | 0.447015 | 0.999623 | 0 |
| ZNF346 | 23567 A_23_P400884 | 1.58 | 0.000724 | 0.036104 | 0.490382 | 0.999497 | 0.592862 | 0.999623 | 0 |
| CCND1 | 595 A_24_P193011 | 1.75 | 0.001864 | 0.036104 | 0.703558 | 0.999497 | 0.411183 | 0.999623 | 0 |
| EPO | 2056 A_23_P145669 | 1.76 | 0.000322 | 0.036104 | 0.959527 | 0.999497 | 0.840031 | 0.999623 | 0 |
| FAT1 | 2195 A_23_P69586 | 1.39 | 0.000235 | 0.036104 | 0.646189 | 0.999497 | 0.852769 | 0.999623 | 0 |
| DBNL | 28988 A_23_P168692 | 1.87 | 0.000995 | 0.036104 | 0.74013 | 0.999497 | 0.345923 | 0.999623 | 0 |
| PDLIM7 | 9260 A_23_P144896 | 1.58 | 0.001505 | 0.036104 | 0.818648 | 0.999497 | 0.993117 | 0.999623 | 0 |
| SNCG | 6623 A_23_P251293 | 1.66 | 0.001516 | 0.036104 | 0.519845 | 0.999497 | 0.314046 | 0.999623 | 1 |
| PTPRF | 5792 A_23_P200984 | 2.14 | 0.000486 | 0.036104 | 0.898652 | 0.999497 | 0.867885 | 0.999623 | 0 |
| FOXO1 | 2308 A_24_P222079 | 1.43 | 0.001 | 0.036104 | 0.289655 | 0.999497 | 0.979632 | 0.999623 | 1 |
| SNAPIN | 23557 A_23_P161022 | 1.32 | 0.000764 | 0.036104 | 0.738372 | 0.999497 | 0.441884 | 0.999623 | 0 |
| BAALC | 79870 A_23_P134663 | 1.61 | 0.001112 | 0.036104 | 0.338482 | 0.999497 | 0.795973 | 0.999623 | 0 |
| GSS | 2937 A_23_P210920 | 1.36 | 0.001469 | 0.036104 | 0.798475 | 0.999497 | 0.45919 | 0.999623 | 1 |
| ADAL | 161823 A_32_P221694 | 1.5 | 0.001468 | 0.036104 | 0.931525 | 0.999497 | 0.881205 | 0.999623 | 0 |
| MLF1 | 4291 A_23_P143906 | 1.46 | 0.000909 | 0.036104 | 0.453641 | 0.999497 | 0.677062 | 0.999623 | 0 |
| FOXO4 | 4303 A_24_P379165 | 1.27 | 0.000497 | 0.036104 | 0.56281 | 0.999497 | 0.274221 | 0.999623 | 1 |
| EMILIN1 | 11117 A_32_P71518 | 1.43 | 0.000714 | 0.036104 | 0.986821 | 0.999497 | 0.646397 | 0.999623 | 0 |
| C1QTNF1 | 114897 A_23_P3956 | 1.54 | 0.001265 | 0.036104 | 0.881114 | 0.999497 | 0.746563 | 0.999623 | 0 |
| CD99L2 | 83692 A_23_P253052 | 1.71 | 0.004014 | 0.036799 | 0.523831 | 0.999497 | 0.828093 | 0.999623 | 0 |
| CLSTN3 | 9746 A_23_P53724 | 1.47 | 0.003655 | 0.036799 | 0.552344 | 0.999497 | 0.995555 | 0.999623 | 0 |
| PI4KB | 5298 A_23_P314726 | 1.76 | 0.003335 | 0.036799 | 0.678786 | 0.999497 | 0.727324 | 0.999623 | 0 |
| LAMA5 | 3911 A_23_P109269 | 2.03 | 0.003997 | 0.036799 | 0.943309 | 0.999497 | 0.531834 | 0.999623 | 0 |
| FEZ2 | 9637 A_23_P39718 | 1.24 | 0.002046 | 0.036799 | 0.626235 | 0.999497 | 0.372874 | 0.999623 | 0 |
| PPP1R15A | 23645 A_23_P90172 | 1.72 | 0.003598 | 0.036799 | 0.672479 | 0.999497 | 0.386734 | 0.999623 | 0 |
| PPIG | 9360 A_23_P154411 | −1.81 | 0.00368 | 0.036799 | 0.584021 | 0.999497 | 0.704251 | 0.999623 | 0 |
| NKG7 | 4818 A_23_P119042 | −8.38 | 0.002739 | 0.036799 | 0.96245 | 0.999497 | 0.65534 | 0.999623 | 0 |
| RAB3B | 5865 A_24_P933319 | −1.34 | 0.002854 | 0.036799 | 0.977899 | 0.999497 | 0.311996 | 0.999623 | 0 |
| MAP4K4 | 9448 A_23_P90804 | −1.63 | 0.003976 | 0.036799 | 0.708133 | 0.999497 | 0.50406 | 0.999623 | 0 |
| NOS3 | 4846 A_23_P70849 | 1.66 | 0.002663 | 0.036799 | 0.64946 | 0.999497 | 0.911586 | 0.999623 | 0 |
| TCL1A | 8115 A_23_P357717 | 3.84 | 0.003301 | 0.036799 | 0.250558 | 0.999497 | 0.449763 | 0.999623 | 0 |
| LTBP2 | 4053 A_23_P218144 | 1.66 | 0.00387 | 0.036799 | 0.502699 | 0.999497 | 0.480426 | 0.999623 | 0 |
| MGMT | 4255 A_23_P104323 | 1.62 | 0.002836 | 0.036799 | 0.833298 | 0.999497 | 0.295631 | 0.999623 | 0 |
| PARVB | 29780 A_23_P40718 | 1.57 | 0.002688 | 0.036799 | 0.348734 | 0.999497 | 0.503429 | 0.999623 | 0 |
| ERBB2 | 2064 A_23_P89249 | 2.17 | 0.002514 | 0.036799 | 0.750799 | 0.999497 | 0.790942 | 0.999623 | 1 |
| RRAD | 6236 A_23_P88849 | 2.06 | 0.003003 | 0.036799 | 0.685343 | 0.999497 | 0.202877 | 0.999623 | 0 |
| ACIN1 | 22985 A_23_P14389 | 1.75 | 0.002299 | 0.036799 | 0.917116 | 0.999497 | 0.446935 | 0.999623 | 0 |
| FANCC | 2176 A_23_P32021 | 1.5 | 0.002675 | 0.036799 | 0.903823 | 0.999497 | 0.727957 | 0.999623 | 0 |
| RSPH3 | 83861 A_23_P59397 | 1.39 | 0.002969 | 0.036799 | 0.564778 | 0.999497 | 0.330631 | 0.999623 | 0 |
| MYC | 4609 A_24_P38363 | 1.62 | 0.003476 | 0.036799 | 0.72846 | 0.999497 | 0.515281 | 0.999623 | 1 |
| HDAC5 | 10014 A_24_P125283 | 1.64 | 0.00221 | 0.036799 | 0.787224 | 0.999497 | 0.351233 | 0.999623 | 0 |
| PRKRA | 8575 A_23_P91019 | −2.37 | 0.002484 | 0.036799 | 0.819817 | 0.999497 | 0.404809 | 0.999623 | 0 |
| CD276 | 80381 A_23_P54313 | 1.56 | 0.00329 | 0.036799 | 0.407954 | 0.999497 | 0.530047 | 0.999623 | 0 |
| ITGB8 | 3696 A_24_P759477 | −3.02 | 0.003897 | 0.036799 | 0.766779 | 0.999497 | 0.530018 | 0.999623 | 0 |
| DDR1 | 780 A_24_P367289 | 1.65 | 0.003704 | 0.036799 | 0.831862 | 0.999497 | 0.19632 | 0.999623 | 0 |
| DCTN3 | 11258 A_23_P158024 | 1.39 | 0.003757 | 0.036799 | 0.734811 | 0.999497 | 0.13659 | 0.999623 | 0 |
| CSNK1E | 1454 A_24_P918436 | 1.49 | 0.002487 | 0.036799 | 0.842292 | 0.999497 | 0.311868 | 0.999623 | 1 |
| ADRA1B | 147 A_23_P33326 | 1.77 | 0.002217 | 0.036799 | 0.434475 | 0.999497 | 0.939526 | 0.999623 | 0 |
| LGALS12 | 85329 A_23_P139198 | 1.9 | 0.002282 | 0.036799 | 0.50909 | 0.999497 | 0.705245 | 0.999623 | 0 |
| HLA-C | 3107 A_23_P70539 | 1.88 | 0.00371 | 0.036799 | 0.691174 | 0.999497 | 0.597814 | 0.999623 | 0 |
| RALA | 5898 A_24_P192262 | −1.44 | 0.003584 | 0.036799 | 0.711675 | 0.999497 | 0.240291 | 0.999623 | 0 |
| C1QTNF4 | 114900 A_23_P52597 | 1.53 | 0.00299 | 0.036799 | 0.70973 | 0.999497 | 0.560858 | 0.999623 | 0 |
| HSPA8 | 3312 A_32_P13728 | −2.16 | 0.003663 | 0.036799 | 0.893335 | 0.999497 | 0.511234 | 0.999623 | 1 |
| IFNA4 | 3441 A_24_P403459 | −2.8 | 0.003451 | 0.036799 | 0.638658 | 0.999497 | 0.312166 | 0.999623 | 0 |
| RAB18 | 22931 A_24_P132787 | −1.67 | 0.003088 | 0.036799 | 0.567201 | 0.999497 | 0.417807 | 0.999623 | 0 |
| LRP12 | 29967 A_24_P415012 | −2.71 | 0.00382 | 0.036799 | 0.939237 | 0.999497 | 0.323012 | 0.999623 | 0 |
| CD320 | 51293 A_23_P119698 | 1.66 | 0.003495 | 0.036799 | 0.933906 | 0.999497 | 0.526329 | 0.999623 | 0 |
| NEDD4L | 23327 A_23_P27279 | 1.29 | 0.003033 | 0.036799 | 0.387082 | 0.999497 | 0.016414 | 0.999623 | 0 |
| GH1 | 2688 A_23_P207194 | −1.87 | 0.002357 | 0.036799 | 0.478376 | 0.999497 | 0.26117 | 0.999623 | 1 |
| PSMG2 | 56984 A_24_P399362 | −1.66 | 0.002488 | 0.036799 | 0.448467 | 0.999497 | 0.467237 | 0.999623 | 0 |
| NLGN1 | 22871 A_23_P18123 | −1.44 | 0.003168 | 0.036799 | 0.926995 | 0.999497 | 0.723127 | 0.999623 | 0 |
| LIN7C | 55327 A_24_P98723 | −3.08 | 0.002742 | 0.036799 | 0.310595 | 0.999497 | 0.185406 | 0.999623 | 0 |
| CXADR | 1525 A_24_P374943 | −1.93 | 0.003767 | 0.036799 | 0.895248 | 0.999497 | 0.420753 | 0.999623 | 0 |
| HLA-C | 3107 A_32_P143980 | −1.95 | 0.003887 | 0.036799 | 0.944433 | 0.999497 | 0.981696 | 0.999623 | 0 |
| MUC5AC | 4586 A_24_P548274 | −2.44 | 0.002238 | 0.036799 | 0.456842 | 0.999497 | 0.190606 | 0.999623 | 0 |
| COL14A1 | 7373 A_24_P222591 | −2.69 | 0.003725 | 0.036799 | 0.873298 | 0.999497 | 0.607016 | 0.999623 | 0 |
| 5-Sep | 5413 A_23_P17724 | 1.73 | 0.002616 | 0.036799 | 0.661674 | 0.999497 | 0.262184 | 0.999623 | 0 |
| SKAP2 | 8935 A_24_P813550 | 1.46 | 0.002665 | 0.036799 | 0.171854 | 0.999497 | 0.504189 | 0.999623 | 0 |
| BCL2L12 | 83596 A_23_P50477 | 1.61 | 0.003724 | 0.036799 | 0.384718 | 0.999497 | 0.243259 | 0.999623 | 0 |
| FXYD5 | 53827 A_23_P130995 | 1.83 | 0.003836 | 0.036799 | 0.379437 | 0.999497 | 0.559681 | 0.999623 | 0 |
| TMX1 | 81542 A_23_P76951 | 1.39 | 0.002725 | 0.036799 | 0.673962 | 0.999497 | 0.601861 | 0.999623 | 0 |

TABLE S7-continued

Significant differences between CR and CNR

| | | Fold-change CNR vs CR | Cytokine response | | Age: 60-65 yo vs 74+ yo | | Gender | | |
|---|---|---|---|---|---|---|---|---|---|
| | | | p-value | q-value | p-value | q-value | p-value | q-value | |
| IL3RA | 3563 A_32_P217750 | 1.93 | 0.003195 | 0.036799 | 0.619472 | 0.999497 | 0.483508 | 0.999623 | 0 |
| PKD1 | 5310 A_24_P477127 | 1.53 | 0.003118 | 0.036799 | 0.562036 | 0.999497 | 0.723101 | 0.999623 | 0 |
| CX3CL1 | 6376 A_23_P377727 | 2.01 | 0.003135 | 0.036799 | 0.972373 | 0.999497 | 0.800236 | 0.999623 | 0 |
| BMF | 90427 A_23_P379649 | 1.76 | 0.00305 | 0.036799 | 0.854947 | 0.999497 | 0.599953 | 0.999623 | 0 |
| NFATC1 | 4772 A_23_P300150 | 1.96 | 0.003188 | 0.036799 | 0.744964 | 0.999497 | 0.38305 | 0.999623 | 0 |
| KEL | 3792 A_23_P252758 | 1.47 | 0.002375 | 0.036799 | 0.521584 | 0.999497 | 0.723356 | 0.999623 | 0 |
| CTSD | 1509 A_23_P52556 | 2.11 | 0.00327 | 0.036799 | 0.689915 | 0.999497 | 0.102454 | 0.999623 | 0 |
| LOC644297 | 644297 A_23_P164316 | 1.74 | 0.002326 | 0.036799 | 0.966498 | 0.999497 | 0.123516 | 0.999623 | 0 |
| EMD | 2010 A_23_P85171 | 2.27 | 0.003097 | 0.036799 | 0.973726 | 0.999497 | 0.271842 | 0.999623 | 1 |
| CD1A | 909 A_23_P402670 | 1.49 | 0.002533 | 0.036799 | 0.824906 | 0.999497 | 0.720479 | 0.999623 | 0 |
| GZMA | 3001 A_23_P133445 | -2.87 | 0.003841 | 0.036799 | 0.484362 | 0.999497 | 0.997193 | 0.999623 | 0 |
| UCP2 | 7351 A_23_P47704 | 1.96 | 0.002975 | 0.036799 | 0.739123 | 0.999497 | 0.455132 | 0.999623 | 1 |
| WFS1 | 7466 A_23_P121499 | 1.68 | 0.002796 | 0.036799 | 0.803433 | 0.999497 | 0.543886 | 0.999623 | 0 |
| RAB22A | 57403 A_32_P179258 | 1.49 | 0.003676 | 0.036799 | 0.943042 | 0.999497 | 0.874004 | 0.999623 | 0 |
| PCDHB2 | 56133 A_24_P251962 | 1.35 | 0.00383 | 0.036799 | 0.993183 | 0.999497 | 0.174231 | 0.999623 | 0 |
| BECN1 | 8678 A_23_P433071 | -1.27 | 0.002554 | 0.036799 | 0.580946 | 0.999497 | 0.957391 | 0.999623 | 0 |
| PRDX2 | 7001 A_24_P168416 | 1.66 | 0.003664 | 0.036799 | 0.452472 | 0.999497 | 0.979373 | 0.999623 | 0 |
| TTRAP | 51567 A_23_P8311 | -2.25 | 0.003941 | 0.036799 | 0.751661 | 0.999497 | 0.841923 | 0.999623 | 0 |
| MRPS30 | 10884 A_23_P252362 | -1.33 | 0.002741 | 0.036799 | 0.57551 | 0.999497 | 0.400199 | 0.999623 | 0 |
| IL17RD | 54756 A_32_P188860 | -1.88 | 0.002724 | 0.036799 | 0.927843 | 0.999497 | 0.664638 | 0.999623 | 0 |
| AIF1 | 199 A_23_P214627 | 1.94 | 0.004012 | 0.036799 | 0.461864 | 0.999497 | 0.348074 | 0.999623 | 0 |
| RNF216 | 54476 A_24_P469641 | -1.6 | 0.002874 | 0.036799 | 0.780076 | 0.999497 | 0.8195 | 0.999623 | 0 |
| HMGB1 | 3146 A_23_P99980 | -2.4 | 0.002061 | 0.036799 | 0.561096 | 0.999497 | 0.275322 | 0.999623 | 1 |
| BSG | 682 A_32_P232825 | 1.71 | 0.003834 | 0.036799 | 0.971549 | 0.999497 | 0.157925 | 0.999623 | 0 |
| ERBB3 | 2065 A_23_P349416 | 1.64 | 0.002964 | 0.036799 | 0.997041 | 0.999497 | 0.505466 | 0.999623 | 0 |
| TNFRSF10B | 8795 A_23_P169030 | 1.47 | 0.003361 | 0.036799 | 0.72306 | 0.999497 | 0.811524 | 0.999623 | 0 |
| PLD1 | 5337 A_23_P398774 | 1.49 | 0.002554 | 0.036799 | 0.264221 | 0.999497 | 0.791086 | 0.999623 | 0 |
| MYST4 | 23522 A_23_P388855 | 1.57 | 0.002953 | 0.036799 | 0.942193 | 0.999497 | 0.829364 | 0.999623 | 0 |
| COL16A1 | 1307 A_23_P160318 | 1.39 | 0.003366 | 0.036799 | 0.120822 | 0.999497 | 0.934672 | 0.999623 | 0 |
| BMP1 | 649 A_23_P33277 | 1.86 | 0.003944 | 0.036799 | 0.63638 | 0.999497 | 0.629346 | 0.999623 | 0 |
| RAB3D | 9545 A_23_P404678 | 1.39 | 0.003287 | 0.036799 | 0.446421 | 0.999497 | 0.2315 | 0.999623 | 0 |
| DCHS1 | 8642 A_23_P98645 | 1.82 | 0.002777 | 0.036799 | 0.650747 | 0.999497 | 0.391191 | 0.999623 | 0 |
| AQP3 | 360 A_23_P112482 | 1.53 | 0.002361 | 0.036799 | 0.643996 | 0.999497 | 0.807047 | 0.999623 | 0 |
| B3GNTL1 | 146712 A_24_P181672 | 1.71 | 0.002961 | 0.036799 | 0.83054 | 0.999497 | 0.598684 | 0.999623 | 0 |
| COL24A1 | 255631 A_23_P74701 | 1.81 | 0.003256 | 0.036799 | 0.933385 | 0.999497 | 0.785361 | 0.999623 | 0 |
| LAMA1 | 284217 A_23_P118967 | 1.82 | 0.002498 | 0.036799 | 0.546325 | 0.999497 | 0.524802 | 0.999623 | 0 |
| HMGB3 | 3149 A_23_P217236 | 1.42 | 0.002816 | 0.036799 | 0.61878 | 0.999497 | 0.89304 | 0.999623 | 0 |
| IGSF8 | 93185 A_23_P137423 | 1.68 | 0.00376 | 0.036799 | 0.999039 | 0.999497 | 0.719943 | 0.999623 | 0 |
| MMP12 | 4321 A_23_P340698 | 1.29 | 0.002657 | 0.036799 | 0.592962 | 0.999497 | 0.921481 | 0.999623 | 0 |
| HSPA8 | 3312 A_24_P287129 | -1.98 | 0.003382 | 0.036799 | 0.119957 | 0.999497 | 0.901493 | 0.999623 | 1 |
| ARVCF | 421 A_23_P109393 | 1.59 | 0.002613 | 0.036799 | 0.759477 | 0.999497 | 0.366938 | 0.999623 | 0 |
| PVR | 5817 A_23_P141894 | 1.4 | 0.003357 | 0.036799 | 0.491225 | 0.999497 | 0.474115 | 0.999623 | 0 |
| HIF1A | 3091 A_23_P48637 | -1.71 | 0.004371 | 0.036858 | 0.92804 | 0.999497 | 0.387877 | 0.999623 | 1 |
| TRAF1 | 7185 A_23_P216970 | 1.99 | 0.004122 | 0.036858 | 0.978755 | 0.999497 | 0.699893 | 0.999623 | 0 |
| SECTM1 | 6398 A_24_P335656 | 2.07 | 0.004322 | 0.036858 | 0.821937 | 0.999497 | 0.82145 | 0.999623 | 0 |
| PRKCD | 5580 A_23_P144054 | 1.47 | 0.004481 | 0.036858 | 0.914646 | 0.999497 | 0.799097 | 0.999623 | 1 |
| RAB5C | 5878 A_23_P107214 | 1.49 | 0.004129 | 0.036858 | 0.503106 | 0.999497 | 0.673735 | 0.999623 | 0 |
| SERPINB2 | 5055 A_23_P153185 | 1.88 | 0.004089 | 0.036858 | 0.428911 | 0.999497 | 0.152952 | 0.999623 | 0 |
| VPREB3 | 29802 A_23_P166371 | 1.45 | 0.004403 | 0.036858 | 0.980636 | 0.999497 | 0.644839 | 0.999623 | 0 |
| TOLLIP | 54472 A_24_P923704 | -2.02 | 0.004345 | 0.036858 | 0.688941 | 0.999497 | 0.146524 | 0.999623 | 0 |
| MIB1 | 57534 A_24_P943156 | -1.49 | 0.00443 | 0.036858 | 0.540753 | 0.999497 | 0.639846 | 0.999623 | 0 |
| NEIL3 | 55247 A_23_P155711 | -4.87 | 0.004452 | 0.036858 | 0.608058 | 0.999497 | 0.360265 | 0.999623 | 0 |
| MLXIPL | 51085 A_23_P145786 | 1.62 | 0.004438 | 0.036858 | 0.447741 | 0.999497 | 0.220519 | 0.999623 | 0 |
| GYPA | 2993 A_23_P45180 | -1.56 | 0.004533 | 0.036858 | 0.923595 | 0.999497 | 0.225265 | 0.999623 | 0 |
| PACSIN3 | 29763 A_24_P381136 | 1.69 | 0.004502 | 0.036858 | 0.847646 | 0.999497 | 0.868742 | 0.999623 | 0 |
| BAT2 | 7916 A_24_P641130 | 2.13 | 0.004534 | 0.036858 | 0.612267 | 0.999497 | 0.871152 | 0.999623 | 0 |
| EIF5A | 1984 A_24_P31235 | 1.46 | 0.004298 | 0.036858 | 0.272048 | 0.999497 | 0.639329 | 0.999623 | 0 |
| RIN1 | 9610 A_23_P64102 | 2.09 | 0.004233 | 0.036858 | 0.606987 | 0.999497 | 0.933581 | 0.999623 | 0 |
| CPXM1 | 56265 A_23_P6066 | 1.76 | 0.004096 | 0.036858 | 0.420615 | 0.999497 | 0.996511 | 0.999623 | 0 |
| OXSR1 | 9943 A_24_P26114 | 1.77 | 0.004221 | 0.036858 | 0.876339 | 0.999497 | 0.879169 | 0.999623 | 0 |
| THBS4 | 7060 A_24_P260443 | 1.41 | 0.004154 | 0.036858 | 0.881901 | 0.999497 | 0.417252 | 0.999623 | 0 |
| DOK1 | 1796 A_23_P5610 | 1.29 | 0.004495 | 0.036858 | 0.978146 | 0.999497 | 0.650775 | 0.999623 | 0 |
| FLNA | 2316 A_23_P96568 | 1.41 | 0.00425 | 0.036858 | 0.596631 | 0.999497 | 0.761419 | 0.999623 | 0 |
| MDM2 | 4193 A_23_P309545 | 1.4 | 0.004394 | 0.036858 | 0.764841 | 0.999497 | 0.521728 | 0.999623 | 1 |
| NCAM1 | 4684 A_23_P1740 | 1.47 | 0.004492 | 0.036858 | 0.542844 | 0.999497 | 0.155061 | 0.999623 | 0 |
| MAPK13 | 5603 A_24_P406132 | 1.52 | 0.004418 | 0.036858 | 0.852344 | 0.999497 | 0.867762 | 0.999623 | 0 |
| CD8A | 925 A_32_P163247 | -4.02 | 0.004597 | 0.036918 | 0.582391 | 0.999497 | 0.425898 | 0.999623 | 0 |
| FIS1 | 51024 A_24_P277955 | 1.38 | 0.004627 | 0.036918 | 0.625394 | 0.999497 | 0.756806 | 0.999623 | 0 |
| RAB13 | 5872 A_23_P46369 | -1.89 | 0.004574 | 0.036918 | 0.738182 | 0.999497 | 0.778696 | 0.999623 | 0 |
| PDLIM7 | 9260 A_24_P41882 | 1.38 | 0.004608 | 0.036918 | 0.081496 | 0.999497 | 0.470102 | 0.999623 | 0 |
| BGLAP | 632 A_24_P336551 | 1.79 | 0.004673 | 0.036962 | 0.879465 | 0.999497 | 0.252697 | 0.999623 | 0 |
| DDIT4 | 54541 A_23_P104318 | 1.48 | 0.004676 | 0.036962 | 0.988634 | 0.999497 | 0.783134 | 0.999623 | 0 |

TABLE S7-continued

Significant differences between CR and CNR

| | | Fold-change CNR vs CR | Cytokine response p-value | Cytokine response q-value | Age: 60-65 yo vs 74+ yo p-value | Age: 60-65 yo vs 74+ yo q-value | Gender p-value | Gender q-value | |
|---|---|---|---|---|---|---|---|---|---|
| HRAS | 3265 A_23_P98183 | 1.44 | 0.004932 | 0.036987 | 0.329159 | 0.999497 | 0.667962 | 0.999623 | 1 |
| NAIP | 4671 A_23_P110473 | -2.54 | 0.004925 | 0.036987 | 0.75741 | 0.999497 | 0.648142 | 0.999623 | 0 |
| C7 | 730 A_23_P213857 | -2.26 | 0.004791 | 0.036987 | 0.790559 | 0.999497 | 0.249087 | 0.999623 | 0 |
| TRGV5 | 6978 A_24_P927432 | -2.17 | 0.004796 | 0.036987 | 0.932939 | 0.999497 | 0.694945 | 0.999623 | 0 |
| HAPLN3 | 145864 A_23_P14754 | 1.44 | 0.004737 | 0.036987 | 0.337781 | 0.999497 | 0.514733 | 0.999623 | 0 |
| HDAC4 | 9759 A_24_P359859 | 1.58 | 0.00483 | 0.036987 | 0.924326 | 0.999497 | 0.332864 | 0.999623 | 0 |
| FN1 | 2335 A_24_P85539 | 1.86 | 0.004957 | 0.036987 | 0.330315 | 0.999497 | 0.353643 | 0.999623 | 0 |
| P2RX7 | 5027 A_24_P319113 | 1.6 | 0.004958 | 0.036987 | 0.491895 | 0.999497 | 0.473055 | 0.999623 | 0 |
| DEFB4 | 1673 A_23_P157628 | -1.54 | 0.004745 | 0.036987 | 0.642515 | 0.999497 | 0.472583 | 0.999623 | 0 |
| LSM14B | 149986 A_23_P323783 | 1.52 | 0.004897 | 0.036987 | 0.57233 | 0.999497 | 0.670692 | 0.999623 | 0 |
| TCTA | 6988 A_23_P58002 | 1.79 | 0.004727 | 0.036987 | 0.92342 | 0.999497 | 0.754902 | 0.999623 | 0 |
| NAB2 | 4665 A_23_P368187 | 1.72 | 0.004896 | 0.036987 | 0.188646 | 0.999497 | 0.784659 | 0.999623 | 2 |
| PODXL2 | 50512 A_23_P121037 | 1.38 | 0.004862 | 0.036987 | 0.458616 | 0.999497 | 0.688154 | 0.999623 | 0 |
| GDF6 | 392255 A_32_P140489 | -2.06 | 0.005064 | 0.037134 | 0.945682 | 0.999497 | 0.567596 | 0.999623 | 0 |
| SCD5 | 79966 A_24_P417546 | -1.62 | 0.005043 | 0.037134 | 0.845392 | 0.999497 | 0.33532 | 0.999623 | 0 |
| ITGA11 | 22801 A_23_P206022 | 1.95 | 0.005028 | 0.037134 | 0.972503 | 0.999497 | 0.807434 | 0.999623 | 0 |
| CD38 | 952 A_23_P167328 | 1.55 | 0.00501 | 0.037134 | 0.468403 | 0.999497 | 0.769658 | 0.999623 | 0 |
| N-PAC | 84656 A_23_P218302 | 1.55 | 0.00517 | 0.037756 | 0.19692 | 0.999497 | 0.622897 | 0.999623 | 0 |
| CLDN14 | 23562 A_23_P91512 | 2.03 | 0.005196 | 0.037781 | 0.831003 | 0.999497 | 0.563221 | 0.999623 | 0 |
| SDF2L1 | 23753 A_23_P6344 | 1.79 | 0.005308 | 0.038434 | 0.840802 | 0.999497 | 0.951897 | 0.999623 | 0 |
| HOXB7 | 3217 A_23_P49810 | 1.62 | 0.005445 | 0.038772 | 0.89319 | 0.999497 | 0.47444 | 0.999623 | 1 |
| HSPA5 | 3309 A_24_P98411 | 1.47 | 0.005433 | 0.038772 | 0.42492 | 0.999497 | 0.453205 | 0.999623 | 0 |
| PDGFC | 56034 A_23_P58396 | -1.64 | 0.005383 | 0.038772 | 0.92027 | 0.999497 | 0.698472 | 0.999623 | 0 |
| TNFSF13 | 8741 A_23_P152620 | 1.43 | 0.005431 | 0.038772 | 0.119195 | 0.999497 | 0.94806 | 0.999623 | 0 |
| ATP6V1H | 51606 A_24_P363679 | -2.05 | 0.005562 | 0.039126 | 0.885499 | 0.999497 | 0.39461 | 0.999623 | 0 |
| BAX | 581 A_23_P208706 | 1.42 | 0.005542 | 0.039126 | 0.168214 | 0.999497 | 0.648696 | 0.999623 | 1 |
| NEIL2 | 252969 A_32_P126846 | 1.43 | 0.005523 | 0.039126 | 0.239915 | 0.999497 | 0.303618 | 0.999623 | 0 |
| EPN2 | 22905 A_23_P89310 | 1.6 | 0.005599 | 0.039227 | 0.403423 | 0.999497 | 0.729579 | 0.999623 | 0 |
| CXCL14 | 9547 A_23_P213745 | 1.27 | 0.005651 | 0.039425 | 0.959343 | 0.999497 | 0.967797 | 0.999623 | 0 |
| BOC | 91653 A_23_P257763 | 1.49 | 0.005835 | 0.039662 | 0.962864 | 0.999497 | 0.925063 | 0.999623 | 0 |
| AKAP11 | 11215 A_23_P204929 | -1.85 | 0.00588 | 0.039662 | 0.851873 | 0.999497 | 0.590879 | 0.999623 | 0 |
| 3-Sep | 55964 A_23_P503127 | 1.56 | 0.005927 | 0.039662 | 0.768511 | 0.999497 | 0.969072 | 0.999623 | 0 |
| N-PAC | 84656 A_32_P743407 | 1.84 | 0.006007 | 0.039662 | 0.81878 | 0.999497 | 0.609 | 0.999623 | 0 |
| SEMA3C | 10512 A_23_P256473 | -1.79 | 0.00588 | 0.039662 | 0.797983 | 0.999497 | 0.995553 | 0.999623 | 0 |
| C3orf38 | 285237 A_23_P44177 | -1.99 | 0.005996 | 0.039662 | 0.086769 | 0.999497 | 0.901564 | 0.999623 | 0 |
| PRSS2 | 5645 A_23_P310274 | 1.55 | 0.005948 | 0.039662 | 0.710419 | 0.999497 | 0.131909 | 0.999623 | 0 |
| WNK1 | 65125 A_24_P769359 | -1.81 | 0.005813 | 0.039662 | 0.265821 | 0.999497 | 0.292153 | 0.999623 | 0 |
| DOCK7 | 85440 A_23_P331348 | -1.73 | 0.00582 | 0.039662 | 0.580693 | 0.999497 | 0.140506 | 0.999623 | 0 |
| IGHV1-69 | 28461 A_24_P367432 | 1.71 | 0.005994 | 0.039662 | 0.818702 | 0.999497 | 0.768258 | 0.999623 | 0 |
| ASB1 | 51665 A_23_P165360 | 1.68 | 0.005896 | 0.039662 | 0.63158 | 0.999497 | 0.474956 | 0.999623 | 0 |
| AP1B1 | 162 A_23_P6398 | 1.56 | 0.005872 | 0.039662 | 0.593906 | 0.999497 | 0.053772 | 0.999623 | 0 |
| PRKCQ | 5588 A_23_P1374 | 1.25 | 0.005884 | 0.039662 | 0.268524 | 0.999497 | 0.118193 | 0.999623 | 0 |
| RAE1 | 8480 A_23_P346206 | 1.27 | 0.006 | 0.039662 | 0.574388 | 0.999497 | 0.441716 | 0.999623 | 1 |
| CFL1 | 1072 A_23_P35820 | 1.57 | 0.006039 | 0.039725 | 0.834753 | 0.999497 | 0.423084 | 0.999623 | 0 |
| CISH | 1154 A_24_P97465 | 1.75 | 0.006192 | 0.039811 | 0.957882 | 0.999497 | 0.838468 | 0.999623 | 0 |
| NFKBIL1 | 4795 A_23_P145301 | 2.06 | 0.006091 | 0.039811 | 0.666764 | 0.999497 | 0.296183 | 0.999623 | 0 |
| BMP1 | 649 A_24_P60930 | 1.48 | 0.00623 | 0.039811 | 0.765526 | 0.999497 | 0.075354 | 0.999623 | 0 |
| TRIB3 | 57761 A_24_P305541 | 1.87 | 0.006237 | 0.039811 | 0.566477 | 0.999497 | 0.47545 | 0.999623 | 0 |
| PLAGL2 | 5326 A_23_P6151 | -1.68 | 0.006188 | 0.039811 | 0.79153 | 0.999497 | 0.351673 | 0.999623 | 0 |
| CDH16 | 1014 A_23_P100240 | 1.58 | 0.006166 | 0.039811 | 0.613212 | 0.999497 | 0.481024 | 0.999623 | 0 |
| HTT | 3064 A_23_P212749 | 1.72 | 0.006125 | 0.039811 | 0.759241 | 0.999497 | 0.135237 | 0.999623 | 1 |
| CROP | 51747 A_23_P207493 | 1.32 | 0.0062 | 0.039811 | 0.233464 | 0.999497 | 0.201247 | 0.999623 | 0 |
| RP11-138L21.1 | 389722 A_24_P652609 | 1.28 | 0.00632 | 0.039896 | 0.569351 | 0.999497 | 0.38752 | 0.999623 | 0 |
| INHBC | 3626 A_24_P155502 | -2.23 | 0.006301 | 0.039896 | 0.239035 | 0.999497 | 0.254386 | 0.999623 | 0 |
| TNXB | 7148 A_23_P156708 | 1.8 | 0.006276 | 0.039896 | 0.24883 | 0.999497 | 0.190948 | 0.999623 | 0 |
| GLT25D2 | 23127 A_24_P62505 | 1.25 | 0.006343 | 0.039897 | 0.665854 | 0.999497 | 0.624613 | 0.999623 | 0 |
| CD163L1 | 283316 A_23_P61466 | 1.79 | 0.006394 | 0.040067 | 0.597613 | 0.999497 | 0.974297 | 0.999623 | 0 |
| PEX5 | 5830 A_23_P48246 | 1.57 | 0.006757 | 0.040193 | 0.55322 | 0.999497 | 0.393006 | 0.999623 | 1 |
| TP53 | 7157 A_23_P26810 | 1.45 | 0.006693 | 0.040193 | 0.329323 | 0.999497 | 0.229693 | 0.999623 | 1 |
| EGF | 1950 A_23_P155979 | 1.54 | 0.006706 | 0.040193 | 0.380675 | 0.999497 | 0.847549 | 0.999623 | 1 |
| WDR59 | 79726 A_23_P206856 | 1.46 | 0.006684 | 0.040193 | 0.643522 | 0.999497 | 0.658962 | 0.999623 | 2 |
| STXBP2 | 6813 A_24_P934487 | 1.53 | 0.006513 | 0.040193 | 0.997036 | 0.999497 | 0.248488 | 0.999623 | 0 |
| SLIT2 | 9353 A_23_P144348 | 1.78 | 0.006488 | 0.040193 | 0.411598 | 0.999497 | 0.557526 | 0.999623 | 0 |
| GPR98 | 84059 A_23_P19134 | -1.54 | 0.006643 | 0.040193 | 0.388514 | 0.999497 | 0.809156 | 0.999623 | 0 |
| HDAC4 | 9759 A_23_P210048 | -1.33 | 0.006618 | 0.040193 | 0.060507 | 0.999497 | 0.79865 | 0.999623 | 0 |
| ICAM3 | 3385 A_23_P164691 | 1.73 | 0.006764 | 0.040193 | 0.503806 | 0.999497 | 0.315636 | 0.999623 | 0 |
| LMLN | 89782 A_23_P43786 | 1.46 | 0.006627 | 0.040193 | 0.514015 | 0.999497 | 0.949942 | 0.999623 | 0 |
| TNFRSF6B | 8771 A_23_P218646 | 1.65 | 0.006541 | 0.040193 | 0.474909 | 0.999497 | 0.401812 | 0.999623 | 0 |
| ARF6 | 382 A_24_P472455 | -2.6 | 0.00665 | 0.040193 | 0.295516 | 0.999497 | 0.157962 | 0.999623 | 0 |
| JUB | 84962 A_23_P54055 | -1.4 | 0.006721 | 0.040193 | 0.665982 | 0.999497 | 0.635921 | 0.999623 | 0 |
| ELMOD3 | 84173 A_23_P154256 | 1.47 | 0.006751 | 0.040193 | 0.76838 | 0.999497 | 0.690694 | 0.999623 | 0 |
| CD59 | 966 A_24_P639441 | 1.89 | 0.006571 | 0.040193 | 0.178875 | 0.999497 | 0.711986 | 0.999623 | 0 |

TABLE S7-continued

Significant differences between CR and CNR

| | | Fold-change CNR vs CR | Cytokine response | | Age: 60-65 yo vs 74+ yo | | Gender | | |
|---|---|---|---|---|---|---|---|---|---|
| | | | p-value | q-value | p-value | q-value | p-value | q-value | |
| DLG1 | 1739 A_24_P131752 | -1.84 | 0.006882 | 0.040756 | 0.858759 | 0.999497 | 0.640739 | 0.999623 | 0 |
| COL14A1 | 7373 A_32_P80850 | 1.76 | 0.007048 | 0.040877 | 0.599642 | 0.999497 | 0.416598 | 0.999623 | 0 |
| CAV3 | 859 A_24_P251599 | -1.31 | 0.007088 | 0.040877 | 0.305798 | 0.999497 | 0.317434 | 0.999623 | 0 |
| TGM2 | 7052 A_32_P86763 | 1.42 | 0.007119 | 0.040877 | 0.831014 | 0.999497 | 0.131657 | 0.999623 | 0 |
| TNIP1 | 10318 A_23_P30435 | 1.53 | 0.007087 | 0.040877 | 0.947415 | 0.999497 | 0.046481 | 0.999623 | 0 |
| MEN1 | 4221 A_23_P75453 | 1.68 | 0.007056 | 0.040877 | 0.911128 | 0.999497 | 0.159982 | 0.999623 | 0 |
| ARRB2 | 409 A_23_P158829 | 1.59 | 0.007077 | 0.040877 | 0.779283 | 0.999497 | 0.615331 | 0.999623 | 0 |
| CTNND2 | 1501 A_23_P110624 | 1.56 | 0.00707 | 0.040877 | 0.759584 | 0.999497 | 0.73204 | 0.999623 | 0 |
| THBS2 | 7058 A_23_P62021 | -1.48 | 0.007122 | 0.040877 | 0.533028 | 0.999497 | 0.934161 | 0.999623 | 0 |
| PBX2 | 5089 A_32_P141664 | 1.25 | 0.00714 | 0.040877 | 0.428924 | 0.999497 | 0.430511 | 0.999623 | 0 |
| CSNK2B | 1460 A_24_P804263 | 1.29 | 0.007037 | 0.040877 | 0.538916 | 0.999497 | 0.391645 | 0.999623 | 0 |
| CLDN23 | 137075 A_23_P134854 | 1.56 | 0.007175 | 0.040946 | 0.308815 | 0.999497 | 0.041708 | 0.999623 | 0 |
| THBS1 | 7057 A_23_P206212 | 1.44 | 0.007267 | 0.040951 | 0.561238 | 0.999497 | 0.402662 | 0.999623 | 0 |
| DCBLD2 | 131566 A_24_P137434 | -1.63 | 0.007231 | 0.040951 | 0.684511 | 0.999497 | 0.780267 | 0.999623 | 0 |
| CBX4 | 8535 A_23_P89621 | 1.65 | 0.007227 | 0.040951 | 0.721296 | 0.999497 | 0.873026 | 0.999623 | 0 |
| ISG20L2 | 81875 A_23_P126457 | 1.39 | 0.007271 | 0.040951 | 0.949767 | 0.999497 | 0.722942 | 0.999623 | 0 |
| LY75 | 4065 A_23_P334173 | -2.1 | 0.007393 | 0.0411 | 0.280371 | 0.999497 | 0.554946 | 0.999623 | 0 |
| ARHGDIA | 396 A_24_P366989 | 1.65 | 0.007441 | 0.0411 | 0.381574 | 0.999497 | 0.805743 | 0.999623 | 0 |
| CCL16 | 6360 A_23_P207582 | 1.44 | 0.007347 | 0.0411 | 0.660933 | 0.999497 | 0.812475 | 0.999623 | 0 |
| EMILIN2 | 84034 A_23_P27315 | 1.43 | 0.007433 | 0.0411 | 0.873004 | 0.999497 | 0.924728 | 0.999623 | 0 |
| MAF | 4094 A_23_P397376 | 1.62 | 0.007349 | 0.0411 | 0.280531 | 0.999497 | 0.933361 | 0.999623 | 0 |
| MYBPH | 4608 A_23_P148737 | 2.2 | 0.00741 | 0.0411 | 0.381457 | 0.999497 | 0.449587 | 0.999623 | 0 |
| ULBP2 | 80328 A_23_P145485 | 1.82 | 0.007477 | 0.041165 | 0.673118 | 0.999497 | 0.267142 | 0.999623 | 0 |
| FBF1 | 85302 A_24_P73848 | 1.81 | 0.007547 | 0.041205 | 0.530159 | 0.999497 | 0.324689 | 0.999623 | 0 |
| TCIRG1 | 10312 A_23_P75369 | 1.75 | 0.007515 | 0.041205 | 0.807329 | 0.999497 | 0.336722 | 0.999623 | 0 |
| CUL2 | 8453 A_24_P252794 | -2.44 | 0.007571 | 0.041205 | 0.833332 | 0.999497 | 0.548846 | 0.999623 | 0 |
| FOXO3 | 2309 A_32_P102062 | 1.22 | 0.00758 | 0.041205 | 0.993458 | 0.999497 | 0.821457 | 0.999623 | 1 |
| FKBP8 | 23770 A_23_P39336 | 1.49 | 0.007665 | 0.041315 | 0.359148 | 0.999497 | 0.380361 | 0.999623 | 0 |
| IFT172 | 26160 A_23_P406135 | 1.53 | 0.00772 | 0.041315 | 0.703408 | 0.999497 | 0.597845 | 0.999623 | 0 |
| RFX2 | 5990 A_23_P502350 | 1.5 | 0.007694 | 0.041315 | 0.645075 | 0.999497 | 0.75437 | 0.999623 | 0 |
| STX1A | 6804 A_23_P82420 | 1.46 | 0.007702 | 0.041315 | 0.364024 | 0.999497 | 0.258177 | 0.999623 | 0 |
| BNIP1 | 662 A_23_P7655 | 1.57 | 0.007629 | 0.041315 | 0.947384 | 0.999497 | 0.241845 | 0.999623 | 0 |
| DAPK2 | 23604 A_24_P10233 | 1.45 | 0.007805 | 0.041645 | 0.836353 | 0.999497 | 0.040823 | 0.999623 | 0 |
| DYRK2 | 8445 A_23_P204048 | 1.27 | 0.007862 | 0.04169 | 0.993595 | 0.999497 | 0.593907 | 0.999623 | 0 |
| BBC3 | 27113 A_23_P382775 | 1.49 | 0.007854 | 0.04169 | 0.652506 | 0.999497 | 0.695162 | 0.999623 | 0 |
| FUT4 | 2526 A_24_P295609 | 1.5 | 0.007921 | 0.041874 | 0.756507 | 0.999497 | 0.805845 | 0.999623 | 0 |
| TH1L | 51497 A_24_P222126 | 1.38 | 0.008004 | 0.04218 | 0.570652 | 0.999497 | 0.640054 | 0.999623 | 0 |
| CYTH2 | 9266 A_23_P119377 | 1.51 | 0.008084 | 0.042473 | 0.265899 | 0.999497 | 0.921536 | 0.999623 | 0 |
| MFAP4 | 4239 A_23_P164057 | 1.62 | 0.008144 | 0.042661 | 0.820137 | 0.999497 | 0.810928 | 0.999623 | 0 |
| IGFALS | 3483 A_23_P14892 | 1.76 | 0.008414 | 0.042748 | 0.869832 | 0.999497 | 0.649025 | 0.999623 | 0 |
| CLDN4 | 1364 A_24_P115183 | 2.13 | 0.008418 | 0.042748 | 0.578741 | 0.999497 | 0.743621 | 0.999623 | 0 |
| RPS3A | 6189 A_32_P135818 | -6.71 | 0.008272 | 0.042748 | 0.339463 | 0.999497 | 0.302119 | 0.999623 | 0 |
| BIN3 | 55909 A_24_P115443 | 1.69 | 0.008205 | 0.042748 | 0.221195 | 0.999497 | 0.308429 | 0.999623 | 0 |
| BSG | 682 A_24_P202769 | 1.83 | 0.008386 | 0.042748 | 0.358983 | 0.999497 | 0.36206 | 0.999623 | 0 |
| PCSK9 | 255738 A_32_P142440 | -2.31 | 0.008448 | 0.042748 | 0.87887 | 0.999497 | 0.858256 | 0.999623 | 0 |
| YWHAG | 7532 A_24_P106681 | -1.57 | 0.008284 | 0.042748 | 0.692692 | 0.999497 | 0.900717 | 0.999623 | 0 |
| BCL2A1 | 597 A_23_P152002 | -2.14 | 0.008483 | 0.042748 | 0.894468 | 0.999497 | 0.539085 | 0.999623 | 0 |
| CFB | 629 A_23_P156687 | 1.47 | 0.00835 | 0.042748 | 0.467483 | 0.999497 | 0.918707 | 0.999623 | 0 |
| CROP | 51747 A_24_P920693 | -2.88 | 0.008461 | 0.042748 | 0.799301 | 0.999497 | 0.839386 | 0.999623 | 0 |
| MSLN | 10232 A_23_P77529 | 1.42 | 0.008228 | 0.042748 | 0.306015 | 0.999497 | 0.280281 | 0.999623 | 0 |
| WWP2 | 11060 A_23_P206684 | 1.46 | 0.008446 | 0.042748 | 0.560331 | 0.999497 | 0.465721 | 0.999623 | 0 |
| CD200 | 4345 A_23_P121480 | 1.63 | 0.008448 | 0.042748 | 0.25547 | 0.999497 | 0.901291 | 0.999623 | 0 |
| PSMD12 | 5718 A_23_P77876 | -2.08 | 0.008603 | 0.043102 | 0.958158 | 0.999497 | 0.63048 | 0.999623 | 0 |
| CCND3 | 896 A_23_P361773 | 1.45 | 0.008629 | 0.043102 | 0.930372 | 0.999497 | 0.318564 | 0.999623 | 0 |
| COL15A1 | 1306 A_24_P315120 | 1.59 | 0.00862 | 0.043102 | 0.62621 | 0.999497 | 0.777929 | 0.999623 | 0 |
| RAB3B | 5865 A_32_P18668 | 1.3 | 0.008685 | 0.043133 | 0.63651 | 0.999497 | 0.247465 | 0.999623 | 0 |
| AIFM2 | 84883 A_32_P75094 | 1.58 | 0.008675 | 0.043133 | 0.448982 | 0.999497 | 0.746676 | 0.999623 | 0 |
| RPS6KA1 | 6195 A_24_P396650 | 1.8 | 0.008792 | 0.043542 | 0.844551 | 0.999497 | 0.859124 | 0.999623 | 0 |
| HIP1 | 3092 A_23_P71033 | 1.42 | 0.00884 | 0.043652 | 0.984356 | 0.999497 | 0.706868 | 0.999623 | 0 |
| ICAM2 | 3384 A_23_P152655 | 1.38 | 0.008886 | 0.043754 | 0.574412 | 0.999497 | 0.773073 | 0.999623 | 0 |
| ISLR2 | 57611 A_32_P379467 | -1.56 | 0.008919 | 0.043789 | 0.293109 | 0.999497 | 0.275047 | 0.999623 | 0 |
| AGGF1 | 55109 A_24_P256513 | 1.34 | 0.009025 | 0.043934 | 0.9808 | 0.999497 | 0.920873 | 0.999623 | 0 |
| LIF | 3976 A_24_P122137 | 1.7 | 0.00901 | 0.043934 | 0.684537 | 0.999497 | 0.304884 | 0.999623 | 0 |
| CDH7 | 1005 A_23_P153146 | 1.3 | 0.009022 | 0.043934 | 0.744671 | 0.999497 | 0.93517 | 0.999623 | 0 |
| GMDS | 2762 A_23_P72068 | 1.45 | 0.009147 | 0.04414 | 0.190757 | 0.999497 | 0.953153 | 0.999623 | 0 |
| HSPA1A | 3303 A_24_P123616 | 1.75 | 0.009119 | 0.04414 | 0.770009 | 0.999497 | 0.281256 | 0.999623 | 1 |
| ACSF3 | 197322 A_23_P259797 | 1.47 | 0.009182 | 0.04414 | 0.7574 | 0.999497 | 0.979474 | 0.999623 | 0 |
| SFRS17A | 8227 A_24_P16856 | 1.3 | 0.009348 | 0.04414 | 0.899318 | 0.999497 | 0.841563 | 0.999623 | 0 |
| RBM4 | 5936 A_23_P13033 | 1.64 | 0.009269 | 0.04414 | 0.686055 | 0.999497 | 0.901274 | 0.999623 | 0 |
| XAF1 | 54739 A_23_P4286 | 1.29 | 0.009205 | 0.04414 | 0.571241 | 0.999497 | 0.278729 | 0.999623 | 0 |
| CD2BP2 | 10421 A_23_P61551 | 2.43 | 0.009285 | 0.04414 | 0.864105 | 0.999497 | 0.924686 | 0.999623 | 0 |
| TUBB | 203068 A_23_P387057 | -1.27 | 0.009241 | 0.04414 | 0.701621 | 0.999497 | 0.433631 | 0.999623 | 0 |

TABLE S7-continued

Significant differences between CR and CNR

| | | Fold-change CNR vs CR | Cytokine response | | Age: 60-65 yo vs 74+ yo | | Gender | | |
|---|---|---|---|---|---|---|---|---|---|
| | | | p-value | q-value | p-value | q-value | p-value | q-value | |
| WFIKKN1 | 117166 A_23_P163666 | 1.79 | 0.009333 | 0.04414 | 0.882626 | 0.999497 | 0.983759 | 0.999623 | 0 |
| MARK4 | 57787 A_23_P107714 | 1.72 | 0.009295 | 0.04414 | 0.610972 | 0.999497 | 0.849994 | 0.999623 | 0 |
| DOCK3 | 1795 A_24_P272845 | −2.09 | 0.009349 | 0.04414 | 0.99466 | 0.999497 | 0.096042 | 0.999623 | 0 |
| TRAF7 | 84231 A_23_P206474 | 1.68 | 0.009411 | 0.044311 | 0.612181 | 0.999497 | 0.292044 | 0.999623 | 0 |
| HGF | 3082 A_23_P93787 | 1.52 | 0.009569 | 0.044882 | 0.198441 | 0.999497 | 0.50498 | 0.999623 | 0 |
| EEF1A2 | 1917 A_23_P256033 | 2.02 | 0.009584 | 0.044882 | 0.534017 | 0.999497 | 0.417562 | 0.999623 | 0 |
| RAD9A | 5883 A_23_P12920 | 1.36 | 0.009796 | 0.044899 | 0.420983 | 0.999497 | 0.774342 | 0.999623 | 0 |
| NDUFS1 | 4719 A_23_P131363 | −3.13 | 0.009784 | 0.044899 | 0.562165 | 0.999497 | 0.668457 | 0.999623 | 0 |
| TAGAP | 117289 A_23_P253145 | −3.04 | 0.009658 | 0.044899 | 0.280321 | 0.999497 | 0.521664 | 0.999623 | 0 |
| TAX1BP1 | 8887 A_24_P95029 | −1.23 | 0.009719 | 0.044899 | 0.469163 | 0.999497 | 0.420653 | 0.999623 | 0 |
| CD109 | 135228 A_23_P331928 | −2.13 | 0.009739 | 0.044899 | 0.814845 | 0.999497 | 0.336296 | 0.999623 | 0 |
| TOLLIP | 54472 A_23_P75903 | 1.69 | 0.009629 | 0.044899 | 0.652502 | 0.999497 | 0.944066 | 0.999623 | 0 |
| BCL11B | 64919 A_23_P205738 | 1.36 | 0.009749 | 0.044899 | 0.353575 | 0.999497 | 0.943937 | 0.999623 | 0 |
| RTN3 | 10313 A_24_P335221 | 1.38 | 0.009788 | 0.044899 | 0.58224 | 0.999497 | 0.571566 | 0.999623 | 0 |
| PVRL3 | 25945 A_23_P80759 | −1.62 | 0.009854 | 0.045045 | 0.330796 | 0.999497 | 0.450665 | 0.999623 | 0 |
| ERBB3 | 2065 A_24_P919096 | 1.37 | 0.009892 | 0.045098 | 0.444707 | 0.999497 | 0.606208 | 0.999623 | 0 |
| TTYH1 | 57348 A_23_P50817 | 1.81 | 0.01008 | 0.04524 | 0.513414 | 0.999497 | 0.981078 | 0.999623 | 0 |
| TCF3 | 6929 A_24_P365365 | 1.64 | 0.009991 | 0.04524 | 0.628151 | 0.999497 | 0.54057 | 0.999623 | 1 |
| PCMT1 | 5110 A_24_P140827 | −1.81 | 0.010046 | 0.04524 | 0.841975 | 0.999497 | 0.613309 | 0.999623 | 1 |
| NLGN3 | 54413 A_23_P62298 | 1.44 | 0.010021 | 0.04524 | 0.535075 | 0.999497 | 0.603253 | 0.999623 | 0 |
| NRXN2 | 9379 A_24_P261470 | 1.44 | 0.01008 | 0.04524 | 0.623422 | 0.999497 | 0.420966 | 0.999623 | 0 |
| GTF2H2 | 2966 A_24_P274640 | −1.57 | 0.009963 | 0.04524 | 0.661375 | 0.999497 | 0.218962 | 0.999623 | 1 |
| GNA12 | 2768 A_23_P215265 | 1.45 | 0.010123 | 0.045312 | 0.603611 | 0.999497 | 0.392406 | 0.999623 | 0 |
| TNFRSF1A | 7132 A_24_P364363 | 1.71 | 0.010194 | 0.045513 | 0.669489 | 0.999497 | 0.685361 | 0.999623 | 0 |
| PTGIS | 5740 A_24_P48723 | −2.43 | 0.010325 | 0.045576 | 0.652291 | 0.999497 | 0.282921 | 0.999623 | 0 |
| AXIN1 | 8312 A_24_P22488 | 1.58 | 0.010341 | 0.045576 | 0.652531 | 0.999497 | 0.43497 | 0.999623 | 0 |
| C9orf61 | 9413 A_24_P209710 | 1.31 | 0.010306 | 0.045576 | 0.14166 | 0.999497 | 0.930086 | 0.999623 | 2 |
| CCL17 | 6361 A_23_P26325 | 1.39 | 0.010272 | 0.045576 | 0.764709 | 0.999497 | 0.247562 | 0.999623 | 0 |
| TSTA3 | 7264 A_23_P94301 | 1.47 | 0.010236 | 0.045576 | 0.571615 | 0.999497 | 0.867314 | 0.999623 | 0 |
| BOK | 666 A_23_P253029 | 1.79 | 0.010547 | 0.045815 | 0.590899 | 0.999497 | 0.212588 | 0.999623 | 0 |
| MLLT1 | 4298 A_24_P418126 | 1.52 | 0.010509 | 0.045815 | 0.785998 | 0.999497 | 0.587068 | 0.999623 | 0 |
| CMKLR1 | 1240 A_24_P766716 | 1.55 | 0.010444 | 0.045815 | 0.723016 | 0.999497 | 0.43937 | 0.999623 | 0 |
| MST1R | 4486 A_23_P256312 | 1.81 | 0.010581 | 0.045815 | 0.49545 | 0.999497 | 0.541623 | 0.999623 | 0 |
| FGFR3 | 2261 A_23_P500501 | 1.33 | 0.010471 | 0.045815 | 0.591985 | 0.999497 | 0.728747 | 0.999623 | 0 |
| C1QTNF6 | 114904 A_24_P211565 | 1.86 | 0.010542 | 0.045815 | 0.797733 | 0.999497 | 0.521666 | 0.999623 | 0 |
| ITFG2 | 55846 A_24_P196038 | 1.52 | 0.010559 | 0.045815 | 0.872446 | 0.999497 | 0.184621 | 0.999623 | 0 |
| KCNH3 | 23416 A_23_P87917 | 1.49 | 0.010616 | 0.045853 | 0.716099 | 0.999497 | 0.361986 | 0.999623 | 2 |
| AGPAT2 | 10555 A_32_P26103 | 2.16 | 0.011394 | 0.046008 | 0.883506 | 0.999497 | 0.932464 | 0.999623 | 1 |
| MACF1 | 23499 A_24_P418637 | 1.24 | 0.011639 | 0.046008 | 0.413313 | 0.999497 | 0.755876 | 0.999623 | 2 |
| MAMDC4 | 158056 A_23_P71790 | 1.69 | 0.01093 | 0.046008 | 0.885796 | 0.999497 | 0.33709 | 0.999623 | 0 |
| ITGB2 | 3689 A_23_P329573 | −2.6 | 0.011337 | 0.046008 | 0.577022 | 0.999497 | 0.1366 | 0.999623 | 0 |
| DGKZ | 8525 A_24_P103952 | 1.75 | 0.011766 | 0.046008 | 0.683759 | 0.999497 | 0.658028 | 0.999623 | 0 |
| SLC26A6 | 65010 A_23_P109895 | 1.44 | 0.010777 | 0.046008 | 0.990628 | 0.999497 | 0.929937 | 0.999623 | 0 |
| AP2A2 | 161 A_24_P339974 | 1.3 | 0.011777 | 0.046008 | 0.758622 | 0.999497 | 0.071888 | 0.999623 | 0 |
| LAIR1 | 3903 A_23_P209135 | 1.3 | 0.011816 | 0.046008 | 0.798188 | 0.999497 | 0.445371 | 0.999623 | 0 |
| SIX4 | 51804 A_23_P326885 | 1.31 | 0.011577 | 0.046008 | 0.662808 | 0.999497 | 0.967053 | 0.999623 | 0 |
| 7-Sep | 989 A_32_P79584 | −2.54 | 0.011163 | 0.046008 | 0.707334 | 0.999497 | 0.548829 | 0.999623 | 0 |
| IL23A | 51561 A_23_P76078 | 2.19 | 0.011657 | 0.046008 | 0.795485 | 0.999497 | 0.601849 | 0.999623 | 0 |
| CLDN12 | 9069 A_23_P157268 | −1.75 | 0.011527 | 0.046008 | 0.952433 | 0.999497 | 0.187921 | 0.999623 | 0 |
| NFE2L3 | 9603 A_23_P42718 | −2.04 | 0.011594 | 0.046008 | 0.30672 | 0.999497 | 0.699681 | 0.999623 | 0 |
| AR | 367 A_23_P113111 | 1.41 | 0.011739 | 0.046008 | 0.722581 | 0.999497 | 0.845551 | 0.999623 | 1 |
| FGFR1 | 2260 A_23_P301304 | −4.3 | 0.011933 | 0.046008 | 0.416966 | 0.999497 | 0.640217 | 0.999623 | 1 |
| FASTKD2 | 22868 A_23_P345830 | −2.68 | 0.011045 | 0.046008 | 0.644005 | 0.999497 | 0.302389 | 0.999623 | 0 |
| MYH9 | 4627 A_23_P57497 | 1.76 | 0.011765 | 0.046008 | 0.422758 | 0.999497 | 0.886066 | 0.999623 | 0 |
| SLPI | 6590 A_23_P91230 | 1.43 | 0.011265 | 0.046008 | 0.209007 | 0.999497 | 0.089489 | 0.999623 | 0 |
| LATS2 | 26524 A_24_P70002 | 1.39 | 0.011702 | 0.046008 | 0.492726 | 0.999497 | 0.538383 | 0.999623 | 0 |
| RPS6KA2 | 6196 A_23_P335920 | 1.52 | 0.011932 | 0.046008 | 0.780008 | 0.999497 | 0.445324 | 0.999623 | 0 |
| CD19 | 930 A_23_P113572 | 2.19 | 0.010793 | 0.046008 | 0.213669 | 0.999497 | 0.834861 | 0.999623 | 0 |
| CD3EAP | 10849 A_23_P208310 | 1.73 | 0.011621 | 0.046008 | 0.718564 | 0.999497 | 0.703033 | 0.999623 | 0 |
| ADAR | 103 A_23_P200439 | 1.71 | 0.011759 | 0.046008 | 0.872095 | 0.999497 | 0.997358 | 0.999623 | 0 |
| PRKACA | 5566 A_24_P399630 | 1.82 | 0.011515 | 0.046008 | 0.936106 | 0.999497 | 0.030038 | 0.999623 | 0 |
| C1QTNF2 | 114898 A_23_P92903 | 1.56 | 0.011866 | 0.046008 | 0.975072 | 0.999497 | 0.524615 | 0.999623 | 0 |
| FIS1 | 51024 A_23_P20183 | 2.08 | 0.010736 | 0.046008 | 0.956333 | 0.999497 | 0.517864 | 0.999623 | 0 |
| MST1 | 4485 A_24_P148796 | 1.48 | 0.011737 | 0.046008 | 0.520318 | 0.999497 | 0.219025 | 0.999623 | 0 |
| MYD88 | 4615 A_23_P92140 | 1.66 | 0.011705 | 0.046008 | 0.627416 | 0.999497 | 0.473691 | 0.999623 | 0 |
| CLDN3 | 1365 A_23_P71017 | 1.73 | 0.011827 | 0.046008 | 0.959934 | 0.999497 | 0.150042 | 0.999623 | 0 |
| FCGRT | 2217 A_23_P55936 | 1.49 | 0.010887 | 0.046008 | 0.871968 | 0.999497 | 0.733417 | 0.999623 | 0 |
| PLAUR | 5329 A_23_P16469 | 1.72 | 0.011721 | 0.046008 | 0.913173 | 0.999497 | 0.959682 | 0.999623 | 0 |
| NFAT5 | 10725 A_23_P359647 | −1.59 | 0.01097 | 0.046008 | 0.927355 | 0.999497 | 0.231058 | 0.999623 | 0 |
| RNF130 | 55819 A_23_P41734 | −1.54 | 0.011328 | 0.046008 | 0.624961 | 0.999497 | 0.199011 | 0.999623 | 0 |
| JMY | 133746 A_32_P176550 | −1.6 | 0.010749 | 0.046008 | 0.993441 | 0.999497 | 0.897651 | 0.999623 | 0 |
| PHLDA1 | 22822 A_24_P943597 | −1.65 | 0.011663 | 0.046008 | 0.623252 | 0.999497 | 0.22338 | 0.999623 | 0 |

TABLE S7-continued

Significant differences between CR and CNR

| | | Fold-change CNR vs CR | Cytokine response | | Age: 60-65 yo vs 74+ yo | | Gender | | |
|---|---|---|---|---|---|---|---|---|---|
| | | | p-value | q-value | p-value | q-value | p-value | q-value | |
| UBE2Z | 65264 A_24_P339305 | -1.4 | 0.011561 | 0.046008 | 0.35366 | 0.999497 | 0.76336 | 0.999623 | 0 |
| EHD1 | 10938 A_23_P52647 | 1.19 | 0.011932 | 0.046008 | 0.556726 | 0.999497 | 0.933536 | 0.999623 | 0 |
| RFX5 | 5993 A_24_P20032 | -1.43 | 0.011832 | 0.046008 | 0.714182 | 0.999497 | 0.443883 | 0.999623 | 0 |
| LTBR | 4055 A_23_P53557 | 1.35 | 0.010873 | 0.046008 | 0.74031 | 0.999497 | 0.870839 | 0.999623 | 0 |
| SNX17 | 9784 A_23_P28238 | 1.37 | 0.011097 | 0.046008 | 0.678232 | 0.999497 | 0.817956 | 0.999623 | 0 |
| GDF15 | 9518 A_23_P16523 | 1.62 | 0.011923 | 0.046008 | 0.701642 | 0.999497 | 0.446223 | 0.999623 | 0 |
| NME3 | 4832 A_23_P152115 | 1.57 | 0.011402 | 0.046008 | 0.626596 | 0.999497 | 0.245007 | 0.999623 | 0 |
| TBX21 | 30009 A_23_P141555 | -1.38 | 0.011205 | 0.046008 | 0.593257 | 0.999497 | 0.823812 | 0.999623 | 0 |
| SOCS3 | 9021 A_23_P351069 | 1.28 | 0.011613 | 0.046008 | 0.839539 | 0.999497 | 0.088534 | 0.999623 | 0 |
| WISP1 | 8840 A_23_P354694 | 1.49 | 0.010885 | 0.046008 | 0.685025 | 0.999497 | 0.867964 | 0.999623 | 0 |
| CDC2L2 | 728642 A_24_P937644 | 1.32 | 0.010948 | 0.046008 | 0.942452 | 0.999497 | 0.499853 | 0.999623 | 0 |
| YWHAZ | 7534 A_32_P97489 | -1.79 | 0.010923 | 0.046008 | 0.39737 | 0.999497 | 0.535257 | 0.999623 | 1 |
| MAPK7 | 5598 A_23_P100704 | 1.5 | 0.01148 | 0.046008 | 0.334768 | 0.999497 | 0.64556 | 0.999623 | 0 |
| CDC2L1 | 984 A_23_P501460 | 1.72 | 0.011987 | 0.046113 | 0.709495 | 0.999497 | 0.893553 | 0.999623 | 0 |
| PIWIL4 | 143689 A_23_P427760 | 1.51 | 0.012061 | 0.046291 | 0.854777 | 0.999497 | 0.737882 | 0.999623 | 0 |
| ADRB3 | 155 A_23_P168993 | -1.31 | 0.012105 | 0.046359 | 0.665715 | 0.999497 | 0.527794 | 0.999623 | 0 |
| DDIT4 | 54541 A_32_P232327 | 1.48 | 0.01217 | 0.0464 | 0.785068 | 0.999497 | 0.665712 | 0.999623 | 0 |
| CALR | 811 A_24_P610375 | 1.28 | 0.012168 | 0.0464 | 0.048403 | 0.999497 | 0.792997 | 0.999623 | 0 |
| SOCS7 | 30837 A_32_P43711 | 1.72 | 0.012371 | 0.046958 | 0.968504 | 0.999497 | 0.879769 | 0.999623 | 0 |
| METTL11A | 28989 A_23_P71904 | 1.48 | 0.012369 | 0.046958 | 0.474362 | 0.999497 | 0.648279 | 0.999623 | 0 |
| TNFAIP3 | 7128 A_24_P157926 | -1.59 | 0.012484 | 0.047179 | 0.670444 | 0.999497 | 0.430055 | 0.999623 | 0 |
| EP300 | 2033 A_23_P40693 | -2.34 | 0.012471 | 0.047179 | 0.102764 | 0.999497 | 0.444003 | 0.999623 | 1 |
| LYST | 1130 A_23_P354074 | -2.23 | 0.012682 | 0.047422 | 0.643012 | 0.999497 | 0.597959 | 0.999623 | 0 |
| PACSIN1 | 29993 A_24_P149266 | 1.44 | 0.012592 | 0.047422 | 0.810806 | 0.999497 | 0.319026 | 0.999623 | 0 |
| IGHMBP2 | 3508 A_23_P393713 | 1.86 | 0.012685 | 0.047422 | 0.536694 | 0.999497 | 0.559356 | 0.999623 | 0 |
| POLM | 27434 A_24_P934245 | 1.73 | 0.012615 | 0.047422 | 0.74306 | 0.999497 | 0.630574 | 0.999623 | 0 |
| LRP4 | 4038 A_24_P403561 | -1.89 | 0.01267 | 0.047422 | 0.385702 | 0.999497 | 0.259541 | 0.999623 | 0 |
| NLK | 51701 A_23_P15647 | 1.57 | 0.012716 | 0.047431 | 0.959462 | 0.999497 | 0.362725 | 0.999623 | 0 |
| RAG1AP1 | 55974 A_24_P88565 | 1.63 | 0.012996 | 0.047513 | 0.825239 | 0.999497 | 0.72817 | 0.999623 | 0 |
| RAF1 | 5894 A_23_P40952 | 1.4 | 0.013268 | 0.047513 | 0.604929 | 0.999497 | 0.864017 | 0.999623 | 0 |
| LEFTY2 | 7044 A_23_P137573 | 1.35 | 0.013316 | 0.047513 | 0.835132 | 0.999497 | 0.79175 | 0.999623 | 0 |
| KLRF1 | 51348 A_32_P158966 | -2.47 | 0.013194 | 0.047513 | 0.094166 | 0.999497 | 0.497135 | 0.999623 | 0 |
| BAT3 | 7917 A_23_P111141 | 1.44 | 0.013123 | 0.047513 | 0.830021 | 0.999497 | 0.605435 | 0.999623 | 0 |
| GADD45B | 4616 A_23_P142506 | 1.67 | 0.013118 | 0.047513 | 0.418033 | 0.999497 | 0.561697 | 0.999623 | 0 |
| ITGB4 | 3691 A_23_P66355 | 1.88 | 0.012977 | 0.047513 | 0.884416 | 0.999497 | 0.850481 | 0.999623 | 0 |
| NDRG1 | 10397 A_24_P38387 | 1.39 | 0.013316 | 0.047513 | 0.431376 | 0.999497 | 0.338149 | 0.999623 | 0 |
| FOXL2 | 668 A_23_P110052 | 1.4 | 0.01325 | 0.047513 | 0.623953 | 0.999497 | 0.756941 | 0.999623 | 0 |
| CRKL | 1399 A_24_P935009 | -3.21 | 0.013096 | 0.047513 | 0.989163 | 0.999497 | 0.618805 | 0.999623 | 0 |
| FKBP5 | 2289 A_23_P111206 | 1.48 | 0.013028 | 0.047513 | 0.805064 | 0.999497 | 0.180509 | 0.999623 | 0 |
| L1CAM | 3897 A_24_P207995 | 1.48 | 0.012946 | 0.047513 | 0.948151 | 0.999497 | 0.973372 | 0.999623 | 0 |
| BAG3 | 9531 A_23_P52552 | -1.99 | 0.013304 | 0.047513 | 0.889016 | 0.999497 | 0.9404 | 0.999623 | 0 |
| RHOA | 387 A_23_P69493 | 1.53 | 0.01318 | 0.047513 | 0.672895 | 0.999497 | 0.646367 | 0.999623 | 0 |
| SMAD6 | 4091 A_23_P65812 | 1.71 | 0.012827 | 0.047513 | 0.844195 | 0.999497 | 0.658975 | 0.999623 | 0 |
| GPR98 | 84059 A_24_P119702 | -1.41 | 0.012977 | 0.047513 | 0.684207 | 0.999497 | 0.179322 | 0.999623 | 0 |
| IRS2 | 8660 A_23_P53838 | 1.5 | 0.012997 | 0.047513 | 0.942002 | 0.999497 | 0.602622 | 0.999623 | 1 |
| PML | 5371 A_24_P198598 | 1.3 | 0.013099 | 0.047513 | 0.879069 | 0.999497 | 0.92629 | 0.999623 | 1 |
| PACS2 | 23241 A_24_P393372 | 1.75 | 0.013226 | 0.047513 | 0.433797 | 0.999497 | 0.355999 | 0.999623 | 0 |
| PSMD9 | 5715 A_23_P203994 | 1.31 | 0.013234 | 0.047513 | 0.457114 | 0.999497 | 0.757866 | 0.999623 | 0 |
| SOCS1 | 8651 A_23_P420196 | 1.25 | 0.012857 | 0.047513 | 0.596738 | 0.999497 | 0.43267 | 0.999623 | 0 |
| EP300 | 2033 A_24_P7887 | 1.29 | 0.013457 | 0.047522 | 0.518843 | 0.999497 | 0.836977 | 0.999623 | 1 |
| MLL5 | 55904 A_24_P196704 | -2.12 | 0.013431 | 0.047522 | 0.853142 | 0.999497 | 0.367771 | 0.999623 | 0 |
| SH2D1A | 4068 A_24_P203103 | -1.53 | 0.013432 | 0.047522 | 0.354116 | 0.999497 | 0.768015 | 0.999623 | 0 |
| UBP1 | 7342 A_23_P211738 | -1.91 | 0.013397 | 0.047522 | 0.864577 | 0.999497 | 0.584273 | 0.999623 | 0 |
| CLN8 | 2055 A_23_P253738 | 1.35 | 0.013435 | 0.047522 | 0.97432 | 0.999497 | 0.823165 | 0.999623 | 0 |
| NOL3 | 8996 A_23_P206371 | 1.28 | 0.01352 | 0.047649 | 0.885717 | 0.999497 | 0.216732 | 0.999623 | 0 |
| MKL1 | 57591 A_23_P348138 | 1.28 | 0.013636 | 0.047959 | 0.213954 | 0.999497 | 0.218478 | 0.999623 | 0 |
| PSMB2 | 5690 A_23_P170058 | 1.66 | 0.013703 | 0.048095 | 0.172869 | 0.999497 | 0.889876 | 0.999623 | 0 |
| IBTK | 25998 A_23_P358995 | -1.49 | 0.013747 | 0.048101 | 0.847817 | 0.999497 | 0.427783 | 0.999623 | 0 |
| CAT | 847 A_23_P105138 | 1.32 | 0.01376 | 0.048101 | 0.349021 | 0.999497 | 0.498228 | 0.999623 | 1 |
| NTN1 | 9423 A_32_P53524 | 1.57 | 0.013797 | 0.04813 | 0.625534 | 0.999497 | 0.525615 | 0.999623 | 0 |
| TNF | 7124 A_24_P50759 | 1.42 | 0.013975 | 0.048193 | 0.496325 | 0.999497 | 0.252806 | 0.999623 | 1 |
| DBNL | 28988 A_24_P43681 | 1.87 | 0.013971 | 0.048193 | 0.962298 | 0.999497 | 0.497226 | 0.999623 | 0 |
| RABEP1 | 9135 A_23_P78158 | -2.29 | 0.014175 | 0.048193 | 0.230644 | 0.999497 | 0.897774 | 0.999623 | 2 |
| HFE | 3077 A_23_P145204 | -2.54 | 0.014178 | 0.048193 | 0.90836 | 0.999497 | 0.616177 | 0.999623 | 0 |
| POLD1 | 5424 A_23_P50456 | 1.54 | 0.01398 | 0.048193 | 0.577717 | 0.999497 | 0.748243 | 0.999623 | 1 |
| DDR1 | 780 A_23_P93311 | 1.81 | 0.014078 | 0.048193 | 0.549439 | 0.999497 | 0.982262 | 0.999623 | 0 |
| ZFYVE9 | 9372 A_23_P33768 | 1.31 | 0.014041 | 0.048193 | 0.24404 | 0.999497 | 0.234146 | 0.999623 | 0 |
| SNAP29 | 9342 A_23_P29141 | -2.08 | 0.013989 | 0.048193 | 0.833414 | 0.999497 | 0.455003 | 0.999623 | 0 |
| AQP3 | 360 A_23_P112481 | 1.54 | 0.014039 | 0.048193 | 0.469185 | 0.999497 | 0.622415 | 0.999623 | 0 |
| PSMF1 | 9491 A_24_P122050 | 1.26 | 0.014135 | 0.048193 | 0.850782 | 0.999497 | 0.82084 | 0.999623 | 0 |
| PBX4 | 80714 A_23_P90419 | 1.33 | 0.013989 | 0.048193 | 0.228749 | 0.999497 | 0.538604 | 0.999623 | 0 |
| BDNF | 627 A_23_P127891 | 1.41 | 0.014073 | 0.048193 | 0.323296 | 0.999497 | 0.764656 | 0.999623 | 1 |

TABLE S7-continued

Significant differences between CR and CNR

|  |  | Fold-change CNR vs CR | Cytokine response | | Age: 60-65 yo vs 74+ yo | | Gender | | |
|---|---|---|---|---|---|---|---|---|---|
|  |  |  | p-value | q-value | p-value | q-value | p-value | q-value |  |
| COL7A1 | 1294 A_23_P144071 | 1.66 | 0.014106 | 0.048193 | 0.54834 | 0.999497 | 0.460984 | 0.999623 | 0 |
| ATP2A2 | 488 A_24_P141786 | 1.32 | 0.014283 | 0.048454 | 0.164309 | 0.999497 | 0.215689 | 0.999623 | 0 |
| SRPK1 | 6732 A_23_P19543 | -1.64 | 0.014417 | 0.048811 | 0.938567 | 0.999497 | 0.575052 | 0.999623 | 0 |
| NISCH | 11188 A_24_P925709 | 1.46 | 0.014487 | 0.048916 | 0.914042 | 0.999497 | 0.524538 | 0.999623 | 0 |
| AMOTL1 | 154810 A_23_P138796 | 1.7 | 0.014504 | 0.048916 | 0.441658 | 0.999497 | 0.566352 | 0.999623 | 0 |
| PKN2 | 5586 A_24_P387869 | -1.51 | 0.014633 | 0.049157 | 0.651112 | 0.999497 | 0.540453 | 0.999623 | 0 |
| ICAM5 | 7087 A_24_P254079 | 1.64 | 0.014627 | 0.049157 | 0.709284 | 0.999497 | 0.406186 | 0.999623 | 0 |
| LTBP2 | 4053 A_23_P405129 | 1.55 | 0.014726 | 0.049278 | 0.78761 | 0.999497 | 0.050492 | 0.999623 | 0 |
| PDCD10 | 11235 A_23_P18325 | -2.23 | 0.014706 | 0.049278 | 0.219256 | 0.999497 | 0.625871 | 0.999623 | 0 |
| EMR1 | 2015 A_23_P27556 | 1.39 | 0.014778 | 0.049356 | 0.461514 | 0.999497 | 0.088336 | 0.999623 | 0 |
| HSPB1 | 3315 A_24_P86537 | 1.64 | 0.014813 | 0.049377 | 0.895272 | 0.999497 | 0.507419 | 0.999623 | 0 |
| RAB4A | 5867 A_24_P122682 | -1.9 | 0.014942 | 0.049477 | 0.68528 | 0.999497 | 0.805571 | 0.999623 | 0 |
| PSMG3 | 84262 A_24_P21044 | 1.33 | 0.014935 | 0.049477 | 0.509811 | 0.999497 | 0.910752 | 0.999623 | 0 |
| CD86 | 942 A_23_P109988 | -2.1 | 0.015025 | 0.049477 | 0.47095 | 0.999497 | 0.349895 | 0.999623 | 0 |
| COTL1 | 23406 A_23_P83624 | 1.63 | 0.015133 | 0.049477 | 0.104524 | 0.999497 | 0.467965 | 0.999623 | 0 |
| TUBB | 203068 A_23_P81912 | 1.34 | 0.015187 | 0.049477 | 0.24464 | 0.999497 | 0.530503 | 0.999623 | 0 |
| COL6A1 | 1291 A_32_P32254 | 1.43 | 0.015105 | 0.049477 | 0.427278 | 0.999497 | 0.481937 | 0.999623 | 0 |
| CEACAM19 | 56971 A_23_P78518 | 1.84 | 0.01516 | 0.049477 | 0.546633 | 0.999497 | 0.168758 | 0.999623 | 0 |
| UBE2Z | 65264 A_24_P378506 | 1.77 | 0.015088 | 0.049477 | 0.981491 | 0.999497 | 0.894359 | 0.999623 | 0 |
| ENG | 2022 A_23_P83328 | 1.56 | 0.01488 | 0.049477 | 0.853209 | 0.999497 | 0.622503 | 0.999623 | 0 |
| NAIF1 | 203245 A_24_P89911 | 1.59 | 0.014961 | 0.049477 | 0.447055 | 0.999497 | 0.609572 | 0.999623 | 0 |
| FAM3C | 10447 A_23_P157365 | -1.83 | 0.015015 | 0.049477 | 0.979811 | 0.999497 | 0.749666 | 0.999623 | 0 |
| SCFD2 | 152579 A_23_P92543 | 1.67 | 0.015134 | 0.049477 | 0.884615 | 0.999497 | 0.762606 | 0.999623 | 0 |
| FOXC1 | 2296 A_23_P390504 | 1.56 | 0.015239 | 0.049551 | 0.742861 | 0.999497 | 0.263313 | 0.999623 | 0 |
| RPS3 | 6188 A_23_P139376 | 1.39 | 0.01535 | 0.049784 | 0.6263 | 0.999497 | 0.27172 | 0.999623 | 0 |
| PNN | 5411 A_32_P212578 | 1.9 | 0.015455 | 0.049784 | 0.701619 | 0.999497 | 0.099695 | 0.999623 | 0 |
| LPP | 4026 A_24_P114551 | -1.89 | 0.0154 | 0.049784 | 0.3246 | 0.999497 | 0.596791 | 0.999623 | 0 |
| YWHAZ | 7534 A_32_P198923 | -1.55 | 0.015381 | 0.049784 | 0.564362 | 0.999497 | 0.865171 | 0.999623 | 1 |
| TAPBPL | 55080 A_23_P36700 | 1.47 | 0.015437 | 0.049784 | 0.46879 | 0.999497 | 0.870077 | 0.999623 | 0 |
| PYDC1 | 260434 A_23_P407614 | 1.55 | 0.015517 | 0.049856 | 0.859028 | 0.999497 | 0.294833 | 0.999623 | 0 |
| MAP2K3 | 5606 A_24_P296698 | 1.96 | 0.015535 | 0.049856 | 0.576898 | 0.999497 | 0.357913 | 0.999623 | 0 |
| DOCK11 | 139818 A_23_P148584 | -1.9 | 0.015696 | 0.049953 | 0.636569 | 0.999497 | 0.855811 | 0.999623 | 0 |
| HTATIP2 | 10553 A_23_P64129 | -1.58 | 0.015739 | 0.049953 | 0.869306 | 0.999497 | 0.459502 | 0.999623 | 0 |
| SRF | 6722 A_24_P337657 | -2.44 | 0.015601 | 0.049953 | 0.792965 | 0.999497 | 0.702688 | 0.999623 | 0 |
| HDAC4 | 9759 A_24_P8892 | -2.51 | 0.015763 | 0.049953 | 0.362259 | 0.999497 | 0.877712 | 0.999623 | 0 |
| SP3 | 6670 A_23_P347198 | -1.77 | 0.015825 | 0.049953 | 0.80038 | 0.999497 | 0.197154 | 0.999623 | 0 |
| MAP1S | 55201 A_23_P67583 | 1.81 | 0.01571 | 0.049953 | 0.549605 | 0.999497 | 0.360408 | 0.999623 | 0 |
| FEN1 | 2237 A_24_P73158 | 1.5 | 0.015928 | 0.049953 | 0.634676 | 0.999497 | 0.246327 | 0.999623 | 1 |
| NISCH | 11188 A_24_P405621 | 1.68 | 0.015908 | 0.049953 | 0.53073 | 0.999497 | 0.589713 | 0.999623 | 0 |
| HAX1 | 10456 A_23_P115223 | 1.51 | 0.015846 | 0.049953 | 0.520141 | 0.999497 | 0.27338 | 0.999623 | 0 |
| RASSF5 | 83593 A_24_P171268 | -1.42 | 0.015661 | 0.049953 | 0.617751 | 0.999497 | 0.722341 | 0.999623 | 0 |
| GNLY | 10578 A_23_P209954 | -3.67 | 0.015862 | 0.049953 | 0.540932 | 0.999497 | 0.6485 | 0.999623 | 0 |
| STK17A | 9263 A_23_P82550 | 1.19 | 0.015943 | 0.049953 | 0.186936 | 0.999497 | 0.471213 | 0.999623 | 0 |
| THAP3 | 90326 A_23_P340890 | 1.84 | 0.015971 | 0.049953 | 0.340718 | 0.999497 | 0.544535 | 0.999623 | 0 |
| TREML2 | 79865 A_23_P7932 | 2.03 | 0.015817 | 0.049953 | 0.440179 | 0.999497 | 0.775578 | 0.999623 | 0 |
| HMGB1 | 3146 A_24_P801264 | -1.38 | 0.016067 | 0.050069 | 0.52182 | 0.999497 | 0.148462 | 0.999623 | 1 |
| MYO18A | 399687 A_23_P78122 | 1.29 | 0.016065 | 0.050069 | 0.998903 | 0.999497 | 0.324238 | 0.999623 | 0 |
| DUB3 | 377630 A_24_P227917 | -1.85 | 0.016161 | 0.050192 | 0.196264 | 0.999497 | 0.491006 | 0.999623 | 0 |
| XRCC5 | 7520 A_24_P345498 | -1.63 | 0.016194 | 0.050192 | 0.659552 | 0.999497 | 0.398873 | 0.999623 | 1 |
| PDCD6IP | 10015 A_24_P945194 | -2.76 | 0.01618 | 0.050192 | 0.720101 | 0.999497 | 0.279458 | 0.999623 | 0 |
| PANX1 | 24145 A_23_P47155 | 1.41 | 0.016242 | 0.050251 | 0.417255 | 0.999497 | 0.488458 | 0.999623 | 0 |
| CD40 | 958 A_23_P57036 | 1.54 | 0.016274 | 0.050262 | 0.589716 | 0.999497 | 0.824097 | 0.999623 | 0 |
| PAFAH1B1 | 5048 A_24_P356406 | -1.47 | 0.016423 | 0.050509 | 0.567136 | 0.999497 | 0.712043 | 0.999623 | 0 |
| EFS | 10278 A_23_P48561 | 1.45 | 0.016397 | 0.050509 | 0.59346 | 0.999497 | 0.817169 | 0.999623 | 0 |
| LMNA | 4000 A_24_P162718 | 1.41 | 0.016472 | 0.050509 | 0.591051 | 0.999497 | 0.698601 | 0.999623 | 1 |
| GDF3 | 9573 A_23_P72817 | 1.76 | 0.016448 | 0.050509 | 0.454274 | 0.999497 | 0.873001 | 0.999623 | 0 |
| MLL4 | 9757 A_23_P142421 | 1.81 | 0.01651 | 0.050536 | 0.663526 | 0.999497 | 0.484866 | 0.999623 | 0 |
| RABEP2 | 79874 A_23_P61100 | 1.62 | 0.016647 | 0.050686 | 0.72717 | 0.999497 | 0.505663 | 0.999623 | 0 |
| IRAK1BP1 | 134728 A_32_P21474 | -1.63 | 0.016622 | 0.050686 | 0.873052 | 0.999497 | 0.271013 | 0.999623 | 0 |
| EPS15L1 | 58513 A_23_P38941 | 1.37 | 0.016609 | 0.050686 | 0.558181 | 0.999497 | 0.997655 | 0.999623 | 0 |
| SERPINF2 | 5345 A_23_P89270 | 1.78 | 0.016727 | 0.050841 | 0.751593 | 0.999497 | 0.417585 | 0.999623 | 0 |
| RACGAP1 | 29127 A_32_P186474 | -2.21 | 0.016765 | 0.050865 | 0.333038 | 0.999497 | 0.999402 | 0.999623 | 0 |
| AP3B2 | 8120 A_23_P77304 | 1.52 | 0.01684 | 0.051003 | 0.851386 | 0.999497 | 0.57374 | 0.999623 | 0 |
| GYG2 | 8908 A_32_P111701 | 1.45 | 0.016875 | 0.05102 | 0.530844 | 0.999497 | 0.142388 | 0.999623 | 2 |
| CBL | 867 A_23_P339191 | 1.56 | 0.016983 | 0.051041 | 0.806197 | 0.999497 | 0.899872 | 0.999623 | 0 |
| SYNJ2BP | 55333 A_24_P201919 | 1.51 | 0.016967 | 0.051041 | 0.798666 | 0.999497 | 0.981506 | 0.999623 | 0 |
| DLC1 | 10395 A_24_P940115 | -1.95 | 0.017 | 0.051041 | 0.843286 | 0.999497 | 0.450104 | 0.999623 | 0 |
| CREBBP | 1387 A_24_P322025 | -2.25 | 0.016942 | 0.051041 | 0.817713 | 0.999497 | 0.419253 | 0.999623 | 1 |
| DST | 667 A_23_P59388 | 1.41 | 0.017075 | 0.051142 | 0.296653 | 0.999497 | 0.711256 | 0.999623 | 0 |
| CELSR3 | 1951 A_23_P92093 | 1.4 | 0.017093 | 0.051142 | 0.982517 | 0.999497 | 0.820933 | 0.999623 | 0 |
| LRDD | 55367 A_32_P117145 | 1.67 | 0.017205 | 0.051298 | 0.928012 | 0.999497 | 0.404034 | 0.999623 | 0 |
| HIVEP3 | 59269 A_24_P876734 | 1.4 | 0.017179 | 0.051298 | 0.892249 | 0.999497 | 0.356162 | 0.999623 | 0 |

TABLE S7-continued

Significant differences between CR and CNR

|  |  | Fold-change CNR vs CR | Cytokine response | | Age: 60-65 yo vs 74+ yo | | Gender | |  |
| --- | --- | --- | --- | --- | --- | --- | --- | --- | --- |
|  |  |  | p-value | q-value | p-value | q-value | p-value | q-value |  |
| ITIH1 | 3697 A_23_P18223 | 1.37 | 0.01738 | 0.051376 | 0.611713 | 0.999497 | 0.22151 | 0.999623 | 0 |
| SPG7 | 6687 A_24_P5305 | 1.49 | 0.01738 | 0.051376 | 0.689204 | 0.999497 | 0.774355 | 0.999623 | 0 |
| BMP4 | 652 A_23_P54144 | 1.46 | 0.017375 | 0.051376 | 0.348872 | 0.999497 | 0.686438 | 0.999623 | 0 |
| HLA-DMA | 3108 A_23_P42306 | 1.72 | 0.017325 | 0.051376 | 0.270348 | 0.999497 | 0.921517 | 0.999623 | 0 |
| CUL4A | 8451 A_24_P61467 | -1.51 | 0.017319 | 0.051376 | 0.427646 | 0.999497 | 0.363818 | 0.999623 | 0 |
| S100B | 6285 A_23_P143526 | -2.33 | 0.017479 | 0.051579 | 0.383508 | 0.999497 | 0.47419 | 0.999623 | 1 |
| HIPK2 | 28996 A_24_P681011 | -2.02 | 0.017655 | 0.051664 | 0.880894 | 0.999497 | 0.189806 | 0.999623 | 0 |
| TRIP6 | 7205 A_24_P4054 | 1.32 | 0.017616 | 0.051664 | 0.224741 | 0.999497 | 0.413981 | 0.999623 | 0 |
| RPSA | 3921 A_24_P375949 | -2.29 | 0.017658 | 0.051664 | 0.689339 | 0.999497 | 0.494854 | 0.999623 | 0 |
| TNFRSF8 | 943 A_23_P500614 | 1.47 | 0.01763 | 0.051664 | 0.713048 | 0.999497 | 0.355213 | 0.999623 | 0 |
| DHCR24 | 1718 A_23_P379475 | -1.44 | 0.017589 | 0.051664 | 0.997665 | 0.999497 | 0.603534 | 0.999623 | 0 |
| GCNT2 | 2651 A_24_P397489 | -2.02 | 0.017693 | 0.051681 | 0.851155 | 0.999497 | 0.51601 | 0.999623 | 0 |
| ACSF3 | 197322 A_32_P218332 | 1.4 | 0.017722 | 0.05185 | 0.800768 | 0.999497 | 0.64634 | 0.999623 | 0 |
| LRIG1 | 26018 A_23_P109636 | 1.46 | 0.01779 | 0.05185 | 0.625735 | 0.999497 | 0.191008 | 0.999623 | 0 |
| UBL7 | 84993 A_23_P117778 | 1.61 | 0.017843 | 0.051854 | 0.592493 | 0.999497 | 0.553974 | 0.999623 | 0 |
| NEDD4L | 23327 A_24_P108311 | -1.48 | 0.017927 | 0.051924 | 0.54472 | 0.999497 | 0.482055 | 0.999623 | 0 |
| TRAF2 | 7186 A_23_P169331 | 1.64 | 0.017906 | 0.051924 | 0.661343 | 0.999497 | 0.861379 | 0.999623 | 0 |
| CXCL12 | 6387 A_23_P202448 | 1.34 | 0.018001 | 0.05205 | 0.543554 | 0.999497 | 0.423963 | 0.999623 | 0 |
| DPT | 1805 A_23_P200741 | -1.63 | 0.018103 | 0.05217 | 0.605565 | 0.999497 | 0.072208 | 0.999623 | 0 |
| MFGE8 | 4240 A_23_P48951 | 1.43 | 0.018092 | 0.05217 | 0.64808 | 0.999497 | 0.524613 | 0.999623 | 0 |
| C1RL | 51279 A_23_P363968 | -1.83 | 0.01829 | 0.052194 | 0.975317 | 0.999497 | 0.171012 | 0.999623 | 0 |
| JAK1 | 3716 A_23_P97005 | 1.29 | 0.018292 | 0.052194 | 0.796622 | 0.999497 | 0.631485 | 0.999623 | 0 |
| HDAC3 | 8841 A_23_P7388 | 1.46 | 0.018293 | 0.052194 | 0.745046 | 0.999497 | 0.560529 | 0.999623 | 1 |
| NF2 | 4771 A_23_P251051 | -1.31 | 0.018246 | 0.052194 | 0.953115 | 0.999497 | 0.791877 | 0.999623 | 0 |
| PPIH | 10465 A_23_P200940 | 1.37 | 0.018156 | 0.052194 | 0.800519 | 0.999497 | 0.687063 | 0.999623 | 0 |
| DAP | 1611 A_24_P243278 | 1.68 | 0.018176 | 0.052194 | 0.254917 | 0.999497 | 0.998228 | 0.999623 | 0 |
| RASSF5 | 83593 A_24_P336584 | 1.42 | 0.018386 | 0.052374 | 0.217375 | 0.999497 | 0.6456 | 0.999623 | 0 |
| FGB | 2244 A_23_P136125 | -1.76 | 0.018452 | 0.052473 | 0.941636 | 0.999497 | 0.641752 | 0.999623 | 0 |
| COL9A1 | 1297 A_24_P311856 | 1.73 | 0.018791 | 0.052571 | 0.535609 | 0.999497 | 0.292217 | 0.999623 | 0 |
| MIA3 | 375056 A_24_P256692 | -1.52 | 0.018669 | 0.052571 | 0.963688 | 0.999497 | 0.563596 | 0.999623 | 0 |
| AGGF1 | 55109 A_23_P250554 | -1.57 | 0.018757 | 0.052571 | 0.525892 | 0.999497 | 0.321101 | 0.999623 | 0 |
| ANLN | 54443 A_23_P356684 | -1.83 | 0.018522 | 0.052571 | 0.911901 | 0.999497 | 0.453283 | 0.999623 | 0 |
| PKN3 | 29941 A_23_P258982 | 1.55 | 0.018662 | 0.052571 | 0.967297 | 0.999497 | 0.534119 | 0.999623 | 0 |
| CES1 | 1066 A_23_P206733 | 1.28 | 0.018566 | 0.052571 | 0.989327 | 0.999497 | 0.31266 | 0.999623 | 0 |
| PSMD2 | 5708 A_24_P42681 | 1.3 | 0.018693 | 0.052571 | 0.734936 | 0.999497 | 0.85722 | 0.999623 | 0 |
| CDK5 | 1020 A_23_P8400 | 1.36 | 0.018722 | 0.052571 | 0.948372 | 0.999497 | 0.902436 | 0.999623 | 0 |
| RAB7A | 7879 A_24_P234572 | 1.38 | 0.018778 | 0.052571 | 0.685641 | 0.999497 | 0.748355 | 0.999623 | 0 |
| SH3GL2 | 6456 A_23_P169351 | 1.26 | 0.018774 | 0.052571 | 0.99059 | 0.999497 | 0.3713 | 0.999623 | 0 |
| LENG9 | 94059 A_32_P493225 | -1.43 | 0.018823 | 0.052573 | 0.995231 | 0.999497 | 0.049609 | 0.999623 | 0 |
| MNDA | 4332 A_23_P137935 | -3.26 | 0.019013 | 0.052678 | 0.201131 | 0.999497 | 0.820534 | 0.999623 | 0 |
| GZMB | 3002 A_23_P117602 | -4.13 | 0.01891 | 0.052678 | 0.95404 | 0.999497 | 0.727099 | 0.999623 | 0 |
| TMBIM6 | 7009 A_23_P204702 | 1.65 | 0.018934 | 0.052678 | 0.912088 | 0.999497 | 0.730606 | 0.999623 | 0 |
| EXOC4 | 60412 A_24_P7946 | -1.32 | 0.018975 | 0.052678 | 0.297355 | 0.999497 | 0.26402 | 0.999623 | 0 |
| BAG4 | 9530 A_24_P930926 | -2.5 | 0.018999 | 0.052678 | 0.909919 | 0.999497 | 0.568578 | 0.999623 | 0 |
| LTBP4 | 8425 A_23_P1412946 | 1.75 | 0.019121 | 0.052893 | 0.663471 | 0.999497 | 0.710995 | 0.999623 | 0 |
| DHCR24 | 1718 A_23_P217820 | 1.81 | 0.019155 | 0.052901 | 0.890871 | 0.999497 | 0.400115 | 0.999623 | 0 |
| COL8A1 | 1295 A_23_P69030 | 1.36 | 0.019206 | 0.052957 | 0.791072 | 0.999497 | 0.614035 | 0.999623 | 0 |
| INHBB | 3625 A_23_P153964 | 1.23 | 0.019281 | 0.053079 | 0.403749 | 0.999497 | 0.971628 | 0.999623 | 0 |
| RPS3A | 6189 A_24_P383999 | -1.67 | 0.019398 | 0.053231 | 0.794357 | 0.999497 | 0.502794 | 0.999623 | 0 |
| CLCF1 | 23529 A_23_P138760 | 1.52 | 0.019385 | 0.053231 | 0.826001 | 0.999497 | 0.909078 | 0.999623 | 0 |
| DGKE | 8526 A_32_P540991 | 1.56 | 0.019464 | 0.053328 | 0.972552 | 0.999497 | 0.771683 | 0.999623 | 0 |
| AKT1 | 207 A_23_P2960 | 1.7 | 0.019564 | 0.053495 | 0.786708 | 0.999497 | 0.686243 | 0.999623 | 1 |
| SMAD4 | 4089 A_23_P27346 | -1.7 | 0.019649 | 0.053495 | 0.502666 | 0.999497 | 0.175732 | 0.999623 | 0 |
| GPR77 | 27202 A_23_P164943 | 1.57 | 0.019626 | 0.053495 | 0.491916 | 0.999497 | 0.410461 | 0.999623 | 0 |
| RABEP1 | 9135 A_24_P945147 | -1.66 | 0.01964 | 0.053495 | 0.612789 | 0.999497 | 0.396126 | 0.999623 | 2 |
| CDC42 | 998 A_23_P200560 | -1.77 | 0.019749 | 0.053533 | 0.22318 | 0.999497 | 0.780298 | 0.999623 | 1 |
| RTN3 | 10313 A_32_P61729 | 1.39 | 0.019788 | 0.053533 | 0.690649 | 0.999497 | 0.264794 | 0.999623 | 0 |
| LOC728613 | 728613 A_24_P59632 | 1.34 | 0.019784 | 0.053533 | 0.217679 | 0.999497 | 0.20341 | 0.999623 | 0 |
| SHB | 6461 A_23_P257743 | 1.48 | 0.019711 | 0.053533 | 0.841275 | 0.999497 | 0.778223 | 0.999623 | 0 |
| ELMO2 | 63916 A_24_P187993 | 1.56 | 0.019866 | 0.053541 | 0.768714 | 0.999497 | 0.638768 | 0.999623 | 0 |
| DGCR6 | 8214 A_24_P202948 | 1.55 | 0.019884 | 0.053541 | 0.942565 | 0.999497 | 0.58851 | 0.999623 | 0 |
| CCR6 | 1235 A_24_P234921 | -2.17 | 0.019826 | 0.053541 | 0.156564 | 0.999497 | 0.297857 | 0.999623 | 0 |
| LAMA5 | 3911 A_32_P175321 | 1.79 | 0.01993 | 0.053582 | 0.84655 | 0.999497 | 0.81709 | 0.999623 | 0 |
| PRKAR1B | 5575 A_32_P72394 | 1.71 | 0.020007 | 0.053624 | 0.626371 | 0.999497 | 0.149768 | 0.999623 | 0 |
| AMIGO1 | 57463 A_24_P302506 | 1.27 | 0.020008 | 0.053624 | 0.7741 | 0.999497 | 0.90952 | 0.999623 | 0 |
| KRAS | 3845 A_23_P45140 | -1.85 | 0.020192 | 0.054035 | 0.391977 | 0.999497 | 0.399416 | 0.999623 | 0 |
| KNG1 | 3827 A_23_P212258 | 1.29 | 0.020374 | 0.054369 | 0.984157 | 0.999497 | 0.945638 | 0.999623 | 0 |
| LDLRAP1 | 26119 A_32_P216548 | 1.59 | 0.020381 | 0.054369 | 0.413619 | 0.999497 | 0.848391 | 0.999623 | 0 |
| PSME3 | 10197 A_24_P344307 | 1.47 | 0.020416 | 0.054381 | 0.134221 | 0.999497 | 0.588152 | 0.999623 | 0 |
| RAB35 | 11021 A_23_P204484 | 1.41 | 0.020663 | 0.054867 | 0.925716 | 0.999497 | 0.900051 | 0.999623 | 0 |
| CCL27 | 10850 A_23_P135248 | 1.32 | 0.020634 | 0.054867 | 0.555063 | 0.999497 | 0.607125 | 0.999623 | 0 |
| FNBP1 | 23048 A_24_P205130 | -1.59 | 0.020837 | 0.054915 | 0.943748 | 0.999497 | 0.374231 | 0.999623 | 0 |

TABLE S7-continued

Significant differences between CR and CNR

| | | Fold-change CNR vs CR | Cytokine response | | Age: 60-65 yo vs 74+ yo | | Gender | | |
|---|---|---|---|---|---|---|---|---|---|
| | | | p-value | q-value | p-value | q-value | p-value | q-value | |
| HIF1A | 3091 A_24_P56388 | -2.63 | 0.020904 | 0.054915 | 0.506111 | 0.999497 | 0.425761 | 0.999623 | 1 |
| MIF | 4282 A_23_P91619 | 2.35 | 0.020884 | 0.054915 | 0.9379 | 0.999497 | 0.170699 | 0.999623 | 0 |
| IFRD1 | 3475 A_24_P137897 | -2.06 | 0.020772 | 0.054915 | 0.481302 | 0.999497 | 0.634188 | 0.999623 | 0 |
| MARK3 | 4140 A_23_P140111 | 1.19 | 0.020904 | 0.054915 | 0.495457 | 0.999497 | 0.35198 | 0.999623 | 0 |
| CASP8AP2 | 9994 A_23_P58898 | -1.67 | 0.020872 | 0.054915 | 0.960732 | 0.999497 | 0.48113 | 0.999623 | 0 |
| BCL6B | 255877 A_23_P324813 | 1.32 | 0.02081 | 0.054915 | 0.396926 | 0.999497 | 0.719695 | 0.999623 | 0 |
| BCL9L | 283149 A_24_P134816 | 1.51 | 0.021124 | 0.055409 | 0.748984 | 0.999497 | 0.274008 | 0.999623 | 0 |
| BTBD9 | 114781 A_32_P94722 | 1.64 | 0.021164 | 0.055417 | 0.738167 | 0.999497 | 0.28085 | 0.999623 | 0 |
| RAB26 | 25837 A_23_P54709 | 1.63 | 0.021191 | 0.055417 | 0.93245 | 0.999497 | 0.670129 | 0.999623 | 0 |
| HIP1 | 3092 A_24_P916314 | -1.85 | 0.02134 | 0.055721 | 0.575538 | 0.999497 | 0.250488 | 0.999623 | 0 |
| TERF1 | 7013 A_24_P192434 | -2.32 | 0.021372 | 0.055721 | 0.515626 | 0.999497 | 0.892773 | 0.999623 | 1 |
| GATA2 | 2624 A_24_P165998 | 1.63 | 0.021461 | 0.055826 | 0.764621 | 0.999497 | 0.351429 | 0.999623 | 0 |
| COL6A2 | 1292 A_23_P310956 | 1.99 | 0.021477 | 0.055826 | 0.796434 | 0.999497 | 0.64886 | 0.999623 | 0 |
| MAP4K4 | 9448 A_23_P102192 | -1.87 | 0.021568 | 0.055977 | 0.877988 | 0.999497 | 0.58069 | 0.999623 | 0 |
| PXN | 5829 A_32_P41574 | 2 | 0.021875 | 0.056142 | 0.938061 | 0.999497 | 0.319663 | 0.999623 | 0 |
| IGKC | 3514 A_32_P148122 | 1.69 | 0.022022 | 0.056142 | 0.701558 | 0.999497 | 0.329592 | 0.999623 | 0 |
| TLX2 | 3196 A_23_P389987 | 1.7 | 0.021845 | 0.056142 | 0.775794 | 0.999497 | 0.77374 | 0.999623 | 0 |
| NTSR1 | 4923 A_23_P371039 | 1.39 | 0.021794 | 0.056142 | 0.614617 | 0.999497 | 0.235568 | 0.999623 | 0 |
| NFATC3 | 4775 A_23_P77440 | 1.87 | 0.021799 | 0.056142 | 0.819628 | 0.999497 | 0.865093 | 0.999623 | 0 |
| JAK3 | 3718 A_24_P59667 | 1.59 | 0.021816 | 0.056142 | 0.490451 | 0.999497 | 0.687042 | 0.999623 | 0 |
| PTPRS | 5802 A_23_P56163 | 1.33 | 0.021992 | 0.056142 | 0.073697 | 0.999497 | 0.028188 | 0.999623 | 0 |
| SEMA4C | 54910 A_23_P9677 | 1.45 | 0.02197 | 0.056142 | 0.748578 | 0.999497 | 0.521656 | 0.999623 | 0 |
| IFT81 | 28981 A_23_P72680 | -1.72 | 0.021961 | 0.056142 | 0.815794 | 0.999497 | 0.46504 | 0.999623 | 0 |
| WWTR1 | 25937 A_23_P29769 | 1.19 | 0.021808 | 0.056142 | 0.267907 | 0.999497 | 0.815463 | 0.999623 | 0 |
| MSN | 4478 A_24_P186370 | 1.55 | 0.021903 | 0.056142 | 0.463843 | 0.999497 | 0.300839 | 0.999623 | 0 |
| IL4I1 | 259307 A_23_P502520 | 1.43 | 0.021876 | 0.056142 | 0.798508 | 0.999497 | 0.4201 | 0.999623 | 0 |
| NFKBIB | 4793 A_24_P161086 | 1.65 | 0.022342 | 0.056377 | 0.878305 | 0.999497 | 0.860706 | 0.999623 | 0 |
| MAG | 4099 A_24_P279704 | 1.39 | 0.022377 | 0.056377 | 0.568829 | 0.999497 | 0.090688 | 0.999623 | 0 |
| ARHGAP27 | 201176 A_23_P141335 | 1.5 | 0.022406 | 0.056377 | 0.316929 | 0.999497 | 0.27609 | 0.999623 | 0 |
| PTPRU | 10076 A_23_P149064 | 1.51 | 0.022407 | 0.056377 | 0.669712 | 0.999497 | 0.772528 | 0.999623 | 0 |
| HSPB1 | 3315 A_23_P257704 | 1.66 | 0.022296 | 0.056377 | 0.800525 | 0.999497 | 0.236396 | 0.999623 | 0 |
| MAL | 4118 A_23_P17134 | 1.38 | 0.022409 | 0.056377 | 0.240071 | 0.999497 | 0.979282 | 0.999623 | 0 |
| SPIN2B | 474343 A_23_P125553 | 1.29 | 0.022305 | 0.056377 | 0.56812 | 0.999497 | 0.280096 | 0.999623 | 0 |
| MED1 | 5469 A_23_P425704 | 1.93 | 0.022333 | 0.056377 | 0.70843 | 0.999497 | 0.564714 | 0.999623 | 1 |
| RHOT2 | 89941 A_23_P15067 | 1.5 | 0.022339 | 0.056377 | 0.901844 | 0.999497 | 0.343098 | 0.999623 | 0 |
| PAG1 | 55824 A_32_P61684 | -1.44 | 0.022711 | 0.056646 | 0.96324 | 0.999497 | 0.93506 | 0.999623 | 0 |
| STEAP2 | 261729 A_23_P428260 | -1.5 | 0.022586 | 0.056646 | 0.482959 | 0.999497 | 0.664367 | 0.999623 | 0 |
| NPTN | 27020 A_24_P95822 | 1.48 | 0.022781 | 0.056646 | 0.703564 | 0.999497 | 0.976427 | 0.999623 | 0 |
| ORM2 | 5005 A_23_P9485 | 1.48 | 0.023091 | 0.056646 | 0.593209 | 0.999497 | 0.171531 | 0.999623 | 0 |
| MATN3 | 4148 A_23_P102058 | -3.17 | 0.023056 | 0.056646 | 0.897744 | 0.999497 | 0.944137 | 0.999623 | 0 |
| RNF216 | 54476 A_24_P235131 | 2.64 | 0.022954 | 0.056646 | 0.399745 | 0.999497 | 0.961986 | 0.999623 | 0 |
| CP110 | 9738 A_24_P373286 | -1.8 | 0.023131 | 0.056646 | 0.422223 | 0.999497 | 0.281232 | 0.999623 | 0 |
| ATP2A2 | 488 A_24_P73290 | -2.67 | 0.023137 | 0.056646 | 0.914603 | 0.999497 | 0.625231 | 0.999623 | 0 |
| ICK | 22858 A_23_P344988 | -1.33 | 0.022649 | 0.056646 | 0.40055 | 0.999497 | 0.663226 | 0.999623 | 0 |
| ELMO1 | 9844 A_23_P122937 | 1.22 | 0.02263 | 0.056646 | 0.408629 | 0.999497 | 0.935388 | 0.999623 | 0 |
| CLPTM1L | 81037 A_32_P133464 | 1.84 | 0.023171 | 0.056646 | 0.856714 | 0.999497 | 0.241929 | 0.999623 | 0 |
| GLRX2 | 51022 A_23_P160503 | -1.33 | 0.023121 | 0.056646 | 0.904378 | 0.999497 | 0.293382 | 0.999623 | 0 |
| RUNX3 | 864 A_23_P51231 | -1.2 | 0.022822 | 0.056646 | 0.742994 | 0.999497 | 0.58824 | 0.999623 | 0 |
| VCP | 7415 A_23_P83045 | 1.46 | 0.022818 | 0.056646 | 0.736891 | 0.999497 | 0.715977 | 0.999623 | 1 |
| LOC645166 | 645166 A_32_P217655 | 1.25 | 0.022817 | 0.056646 | 0.15421 | 0.999497 | 0.685198 | 0.999623 | 0 |
| PRKCDBP | 112464 A_23_P203475 | 2.92 | 0.022754 | 0.056646 | 0.405562 | 0.999497 | 0.190765 | 0.999623 | 0 |
| RAC2 | 5880 A_23_P218770 | 1.39 | 0.023173 | 0.056646 | 0.440046 | 0.999497 | 0.937421 | 0.999623 | 0 |
| ILF2 | 3608 A_23_P257956 | 1.8 | 0.022875 | 0.056646 | 0.556435 | 0.999497 | 0.867959 | 0.999623 | 0 |
| DBN1 | 1627 A_24_P97849 | 1.81 | 0.022907 | 0.056646 | 0.889694 | 0.999497 | 0.669193 | 0.999623 | 1 |
| NFKBIL2 | 4796 A_23_P216355 | 1.58 | 0.022988 | 0.056646 | 0.858402 | 0.999497 | 0.269339 | 0.999623 | 0 |
| NFE2L1 | 4779 A_23_P78302 | 1.54 | 0.023301 | 0.056759 | 0.855912 | 0.999497 | 0.650591 | 0.999623 | 0 |
| PCDH1 | 5097 A_23_P213359 | 1.53 | 0.023351 | 0.056759 | 0.751946 | 0.999497 | 0.205484 | 0.999623 | 0 |
| CEACAM7 | 1087 A_24_P228302 | 1.35 | 0.023344 | 0.056759 | 0.21966 | 0.999497 | 0.269926 | 0.999623 | 0 |
| TAF8 | 129685 A_23_P133807 | 1.31 | 0.023253 | 0.056759 | 0.835292 | 0.999497 | 0.422309 | 0.999623 | 0 |
| FASTK | 10922 A_23_P215140 | 1.73 | 0.023404 | 0.056806 | 0.863451 | 0.999497 | 0.740462 | 0.999623 | 0 |
| STAT5A | 6776 A_24_P173088 | 1.83 | 0.023464 | 0.056872 | 0.602291 | 0.999497 | 0.704537 | 0.999623 | 1 |
| PPM1D | 8493 A_32_P150030 | 1.13 | 0.023563 | 0.056876 | 0.662459 | 0.999497 | 0.92021 | 0.999623 | 1 |
| TLN2 | 83660 A_24_P347566 | 1.29 | 0.023582 | 0.056876 | 0.134377 | 0.999497 | 0.241966 | 0.999623 | 0 |
| APOA4 | 337 A_23_P87036 | 1.47 | 0.023597 | 0.056876 | 0.826018 | 0.999497 | 0.23829 | 0.999623 | 0 |
| IGF2 | 3481 A_23_P421379 | 1.9 | 0.023596 | 0.056876 | 0.367862 | 0.999497 | 0.560618 | 0.999623 | 1 |
| EDA | 1896 A_23_P34045 | 1.39 | 0.023641 | 0.056901 | 0.810786 | 0.999497 | 0.664527 | 0.999623 | 0 |
| TNFRSF25 | 8718 A_23_P126844 | 1.41 | 0.023674 | 0.056902 | 0.440383 | 0.999497 | 0.327934 | 0.999623 | 0 |
| TPT1 | 7178 A_24_P306726 | -2.01 | 0.024225 | 0.057014 | 0.989532 | 0.999497 | 0.763209 | 0.999623 | 0 |
| EXOC6 | 54536 A_23_P169576 | 1.27 | 0.02423 | 0.057014 | 0.090174 | 0.999497 | 0.834501 | 0.999623 | 0 |
| TAX1BP3 | 30851 A_23_P38468 | 1.74 | 0.023911 | 0.057014 | 0.632985 | 0.999497 | 0.689932 | 0.999623 | 0 |
| SHISA5 | 51246 A_23_P212475 | -1.36 | 0.023864 | 0.057014 | 0.666164 | 0.999497 | 0.623782 | 0.999623 | 0 |
| NME2 | 4831 A_23_P141405 | -1.65 | 0.02417 | 0.057014 | 0.575399 | 0.999497 | 0.259454 | 0.999623 | 0 |

TABLE S7-continued

Significant differences between CR and CNR

| | | Fold-change CNR vs CR | Cytokine response | | Age: 60-65 yo vs 74+ yo | | Gender | | |
|---|---|---|---|---|---|---|---|---|---|
| | | | p-value | q-value | p-value | q-value | p-value | q-value | |
| PPIL2 | 23759 A_24_P923591 | -2.02 | 0.024157 | 0.057014 | 0.666113 | 0.999497 | 0.369511 | 0.999623 | 0 |
| IGJ | 3512 A_23_P167168 | -1.38 | 0.023992 | 0.057014 | 0.537089 | 0.999497 | 0.514473 | 0.999623 | 0 |
| FCHO2 | 115548 A_23_P349083 | -1.6 | 0.023998 | 0.057014 | 0.696781 | 0.999497 | 0.197378 | 0.999623 | 0 |
| CAPN10 | 11132 A_23_P341349 | -5.87 | 0.023902 | 0.057014 | 0.397217 | 0.999497 | 0.886854 | 0.999623 | 0 |
| NHEJ1 | 79840 A_24_P251381 | -1.68 | 0.023847 | 0.057014 | 0.69479 | 0.999497 | 0.90056 | 0.999623 | 0 |
| GREM2 | 64388 A_23_P97181 | -1.48 | 0.023944 | 0.057014 | 0.858879 | 0.999497 | 0.551297 | 0.999623 | 0 |
| PML | 5371 A_23_P306148 | 1.74 | 0.024224 | 0.057014 | 0.994814 | 0.999497 | 0.683126 | 0.999623 | 1 |
| CTSK | 1513 A_23_P34744 | 1.42 | 0.024268 | 0.057014 | 0.731985 | 0.999497 | 0.504504 | 0.999623 | 0 |
| PPIL2 | 23759 A_24_P284783 | 1.85 | 0.024349 | 0.057014 | 0.814733 | 0.999497 | 0.900514 | 0.999623 | 0 |
| IFT122 | 55764 A_23_P212447 | 1.45 | 0.024348 | 0.057014 | 0.738761 | 0.999497 | 0.848825 | 0.999623 | 0 |
| MAEA | 10296 A_23_P18490 | -1.52 | 0.024173 | 0.057014 | 0.791352 | 0.999497 | 0.275621 | 0.999623 | 0 |
| DLL3 | 10683 A_24_P57047 | 1.48 | 0.023761 | 0.057014 | 0.317412 | 0.999497 | 0.865777 | 0.999623 | 1 |
| CTNNA1 | 1495 A_24_P80633 | 1.68 | 0.024278 | 0.057014 | 0.961889 | 0.999497 | 0.590684 | 0.999623 | 0 |
| XRCC1 | 7515 A_23_P153692 | 1.72 | 0.024315 | 0.057014 | 0.415487 | 0.999497 | 0.941061 | 0.999623 | 0 |
| BAT5 | 7920 A_23_P156697 | 1.79 | 0.024507 | 0.057306 | 0.406512 | 0.999497 | 0.268181 | 0.999623 | 0 |
| GSR | 2936 A_23_P146084 | 1.43 | 0.024587 | 0.057414 | 0.447782 | 0.999497 | 0.402011 | 0.999623 | 1 |
| CSNK2B | 1460 A_24_P97931 | 1.41 | 0.024627 | 0.05743 | 0.872929 | 0.999497 | 0.423811 | 0.999623 | 0 |
| IL1RN | 3557 A_23_P209995 | 1.26 | 0.024757 | 0.057565 | 0.325441 | 0.999497 | 0.662672 | 0.999623 | 0 |
| ELMO2 | 63916 A_24_P322635 | 2.07 | 0.024782 | 0.057565 | 0.608839 | 0.999497 | 0.153068 | 0.999623 | 0 |
| XRCC6 | 2547 A_32_P230838 | 1.2 | 0.024785 | 0.057565 | 0.653775 | 0.999497 | 0.046736 | 0.999623 | 1 |
| TP63 | 8626 A_23_P327380 | 1.31 | 0.024828 | 0.057588 | 0.359601 | 0.999497 | 0.427082 | 0.999623 | 1 |
| UACA | 55075 A_23_P360340 | -2.36 | 0.024868 | 0.057601 | 0.96785 | 0.999497 | 0.599824 | 0.999623 | 0 |
| CD1B | 910 A_23_P351844 | 1.25 | 0.024905 | 0.05761 | 0.838072 | 0.999497 | 0.64236 | 0.999623 | 0 |
| TIRAP | 114609 A_23_P202905 | 1.45 | 0.024995 | 0.057741 | 0.623572 | 0.999497 | 0.353426 | 0.999623 | 0 |
| C8A | 731 A_23_P46639 | 1.39 | 0.025118 | 0.057856 | 0.338603 | 0.999497 | 0.088464 | 0.999623 | 0 |
| IFI27L1 | 122509 A_23_P53976 | 1.55 | 0.025112 | 0.057856 | 0.915004 | 0.999497 | 0.643707 | 0.999623 | 0 |
| CDKN1B | 1027 A_23_P204696 | 1.57 | 0.025145 | 0.057856 | 0.311175 | 0.999497 | 0.756093 | 0.999623 | 0 |
| APOA4 | 337 A_24_P252934 | -1.41 | 0.025181 | 0.057862 | 0.53623 | 0.999497 | 0.197791 | 0.999623 | 0 |
| FKBPL | 63943 A_23_P70566 | 1.53 | 0.025326 | 0.057892 | 0.560314 | 0.999497 | 0.128645 | 0.999623 | 0 |
| SERPINB9 | 5272 A_24_P295010 | -1.65 | 0.025329 | 0.057892 | 0.568829 | 0.999497 | 0.58219 | 0.999623 | 0 |
| COL6A2 | 1292 A_32_P22750 | 1.46 | 0.025261 | 0.057892 | 0.872014 | 0.999497 | 0.418784 | 0.999623 | 0 |
| TSLP | 85480 A_23_P121987 | 1.23 | 0.02532 | 0.057892 | 0.147663 | 0.999497 | 0.78859 | 0.999623 | 0 |
| KRAS | 3845 A_23_P306507 | -1.81 | 0.025434 | 0.057925 | 0.350719 | 0.999497 | 0.395689 | 0.999623 | 0 |
| APAF1 | 317 A_23_P36611 | -1.98 | 0.025489 | 0.057925 | 0.284157 | 0.999497 | 0.889888 | 0.999623 | 0 |
| VSIG2 | 23584 A_23_P36018 | -1.31 | 0.025512 | 0.057925 | 0.857542 | 0.999497 | 0.311081 | 0.999623 | 0 |
| COL13A1 | 1305 A_24_P9005 | -1.33 | 0.0255 | 0.057925 | 0.451096 | 0.999497 | 0.824942 | 0.999623 | 0 |
| TPD52 | 7163 A_23_P216257 | -1.85 | 0.025495 | 0.057925 | 0.84194 | 0.999497 | 0.600095 | 0.999623 | 0 |
| GHSR | 2693 A_23_P109864 | -1.83 | 0.025652 | 0.058093 | 0.655901 | 0.999497 | 0.755184 | 0.999623 | 0 |
| COL15A1 | 1306 A_23_P112554 | -1.52 | 0.02565 | 0.058091 | 0.381867 | 0.999497 | 0.461919 | 0.999623 | 0 |
| GNA13 | 10672 A_24_P941441 | -2.38 | 0.025698 | 0.058119 | 0.708494 | 0.999497 | 0.176524 | 0.999623 | 0 |
| PRKCB | 5579 A_23_P420281 | -1.39 | 0.02578 | 0.058161 | 0.19234 | 0.999497 | 0.531901 | 0.999623 | 0 |
| DCTN3 | 11258 A_24_P209765 | 1.59 | 0.025784 | 0.058161 | 0.526632 | 0.999497 | 0.357129 | 0.999623 | 0 |
| CKAP2 | 26586 A_23_P151405 | -1.36 | 0.025879 | 0.058196 | 0.603597 | 0.999497 | 0.885128 | 0.999623 | 0 |
| ULBP2 | 80328 A_23_P168259 | 1.47 | 0.025877 | 0.058196 | 0.716694 | 0.999497 | 0.949984 | 0.999623 | 0 |
| PAFAH1B3 | 5050 A_23_P16078 | 1.33 | 0.025901 | 0.058196 | 0.765951 | 0.999497 | 0.813546 | 0.999623 | 0 |
| CD248 | 57124 A_23_P52697 | 1.52 | 0.025939 | 0.058205 | 0.740171 | 0.999497 | 0.263471 | 0.999623 | 0 |
| ATP2A2 | 488 A_23_P53603 | 1.45 | 0.025984 | 0.058231 | 0.855788 | 0.999497 | 0.825546 | 0.999623 | 0 |
| CFLAR | 8837 A_23_P209394 | -1.4 | 0.026045 | 0.058288 | 0.395349 | 0.999497 | 0.96893 | 0.999623 | 0 |
| PSMF1 | 9491 A_23_P79911 | -1.34 | 0.026111 | 0.058288 | 0.349748 | 0.999497 | 0.867932 | 0.999623 | 0 |
| FBLIM1 | 54751 A_23_P23457 | 1.37 | 0.026085 | 0.058288 | 0.122642 | 0.999497 | 0.2457 | 0.999623 | 0 |
| TUSC4 | 10641 A_23_P18267 | 1.48 | 0.026168 | 0.058339 | 0.40297 | 0.999497 | 0.075194 | 0.999623 | 2 |
| SART3 | 9733 A_23_P87664 | 1.57 | 0.026244 | 0.058434 | 0.933546 | 0.999497 | 0.69472 | 0.999623 | 0 |
| ITFG2 | 55846 A_23_P204417 | 1.99 | 0.026393 | 0.058689 | 0.727136 | 0.999497 | 0.651347 | 0.999623 | 0 |
| CSF2RB | 1439 A_23_P120899 | 1.47 | 0.026635 | 0.059 | 0.786508 | 0.999497 | 0.977127 | 0.999623 | 0 |
| ADAM22 | 53616 A_24_P243741 | 1.25 | 0.026632 | 0.059 | 0.431297 | 0.999497 | 0.690916 | 0.999623 | 0 |
| RACGAP1 | 29127 A_23_P65110 | -1.86 | 0.026629 | 0.059 | 0.398668 | 0.999497 | 0.839477 | 0.999623 | 0 |
| RRAGC | 64121 A_23_P97623 | -1.71 | 0.026678 | 0.059018 | 0.188304 | 0.999497 | 0.043924 | 0.999623 | 0 |
| ZFR2 | 23217 A_23_P332713 | 1.38 | 0.026762 | 0.059052 | 0.222351 | 0.999497 | 0.435681 | 0.999623 | 2 |
| BCL7A | 605 A_32_P704982 | 1.51 | 0.026748 | 0.059052 | 0.75426 | 0.999497 | 0.516311 | 0.999623 | 0 |
| SNPH | 9751 A_23_P102706 | 1.43 | 0.027005 | 0.059512 | 0.744087 | 0.999497 | 0.358138 | 0.999623 | 0 |
| EXOC2 | 55770 A_23_P214354 | 1.16 | 0.027117 | 0.059532 | 0.182019 | 0.999497 | 0.422793 | 0.999623 | 0 |
| FANCG | 2189 A_23_P71644 | 1.63 | 0.027117 | 0.059532 | 0.67724 | 0.999497 | 0.863808 | 0.999623 | 0 |
| LTBP2 | 4053 A_24_P167668 | 1.62 | 0.027107 | 0.059532 | 0.918361 | 0.999497 | 0.34478 | 0.999623 | 0 |
| VEZF1 | 7716 A_24_P924591 | -3.39 | 0.027161 | 0.059551 | 0.2347 | 0.999497 | 0.459209 | 0.999623 | 0 |
| BCAP31 | 10134 A_32_P4364 | 1.3 | 0.0272 | 0.059561 | 0.828339 | 0.999497 | 0.814044 | 0.999623 | 0 |
| TYK2 | 7297 A_23_P141917 | 1.61 | 0.02731 | 0.059651 | 0.718789 | 0.999497 | 0.305446 | 0.999623 | 0 |
| DNAJB6 | 10049 A_24_P63827 | -2.94 | 0.027306 | 0.059651 | 0.768705 | 0.999497 | 0.601868 | 0.999623 | 0 |
| PRSS2 | 5645 A_32_P94444 | 1.48 | 0.027445 | 0.059718 | 0.254523 | 0.999497 | 0.123377 | 0.999623 | 0 |
| ATP2A1 | 487 A_23_P72462 | 1.33 | 0.027434 | 0.059718 | 0.390992 | 0.999497 | 0.439009 | 0.999623 | 0 |
| BBS7 | 55212 A_23_P252913 | 1.26 | 0.027395 | 0.059718 | 0.679015 | 0.999497 | 0.781101 | 0.999623 | 0 |
| KLRC2 | 3822 A_23_P22232 | -1.96 | 0.027513 | 0.05979 | 0.523282 | 0.999497 | 0.263981 | 0.999623 | 0 |
| VPS45 | 11311 A_23_P23719 | 1.57 | 0.027561 | 0.059821 | 0.486518 | 0.999497 | 0.948904 | 0.999623 | 0 |

TABLE S7-continued

Significant differences between CR and CNR

| | | Fold-change CNR vs CR | Cytokine response | | Age: 60-65 yo vs 74+ yo | | Gender | | |
|---|---|---|---|---|---|---|---|---|---|
| | | | p-value | q-value | p-value | q-value | p-value | q-value | |
| PLDN | 26258 A_23_P205808 | -2.14 | 0.027632 | 0.059822 | 0.271162 | 0.999497 | 0.807566 | 0.999623 | 0 |
| MLL2 | 8085 A_24_P212559 | -1.5 | 0.027605 | 0.059822 | 0.925297 | 0.999497 | 0.438707 | 0.999623 | 0 |
| UTP11L | 51118 A_23_P11774 | -1.65 | 0.027951 | 0.060438 | 0.712349 | 0.999497 | 0.341129 | 0.999623 | 0 |
| WDR92 | 116143 A_32_P165113 | 1.35 | 0.028014 | 0.060499 | 0.959143 | 0.999497 | 0.631753 | 0.999623 | 0 |
| LY6E | 4061 A_24_P317762 | 1.67 | 0.028104 | 0.06054 | 0.639579 | 0.999497 | 0.801153 | 0.999623 | 0 |
| SPG7 | 6687 A_24_P205120 | 1.32 | 0.028103 | 0.06054 | 0.815515 | 0.999497 | 0.187053 | 0.999623 | 0 |
| SBDS | 51119 A_23_P70867 | -1.81 | 0.028224 | 0.060572 | 0.637322 | 0.999497 | 0.855503 | 0.999623 | 0 |
| PTX3 | 5806 A_23_P121064 | -1.54 | 0.028185 | 0.060572 | 0.545358 | 0.999497 | 0.666942 | 0.999623 | 0 |
| ACVRL1 | 94 A_24_P945113 | 1.28 | 0.028223 | 0.060572 | 0.399627 | 0.999497 | 0.675879 | 0.999623 | 0 |
| MLL3 | 58508 A_32_P209472 | 1.26 | 0.028549 | 0.060651 | 0.55675 | 0.999497 | 0.778025 | 0.999623 | 0 |
| CCR10 | 2826 A_23_P141367 | 1.65 | 0.028465 | 0.060651 | 0.753723 | 0.999497 | 0.189758 | 0.999623 | 0 |
| PTPN12 | 5782 A_23_P8763 | -1.71 | 0.028409 | 0.060651 | 0.672264 | 0.999497 | 0.445015 | 0.999623 | 2 |
| POSTN | 10631 A_24_P347411 | -1.6 | 0.028613 | 0.060651 | 0.648284 | 0.999497 | 0.020574 | 0.999623 | 0 |
| GPR126 | 57211 A_23_P214756 | 1.13 | 0.028563 | 0.060651 | 0.132732 | 0.999497 | 0.306654 | 0.999623 | 0 |
| SEMA3B | 7869 A_24_P294419 | 1.65 | 0.028588 | 0.060651 | 0.551926 | 0.999497 | 0.365382 | 0.999623 | 0 |
| BIRC3 | 330 A_23_P98350 | -1.39 | 0.028389 | 0.060651 | 0.273709 | 0.999497 | 0.675393 | 0.999623 | 0 |
| CUL5 | 8065 A_23_P203009 | -1.59 | 0.028487 | 0.060651 | 0.69055 | 0.999497 | 0.612001 | 0.999623 | 0 |
| TOPORS | 10210 A_23_P32217 | -1.36 | 0.02849 | 0.060651 | 0.561509 | 0.999497 | 0.941162 | 0.999623 | 0 |
| FAF1 | 11124 A_23_P96853 | 1.17 | 0.028357 | 0.060651 | 0.814361 | 0.999497 | 0.964896 | 0.999623 | 0 |
| MLF2 | 8079 A_23_P13873 | 1.35 | 0.028813 | 0.060753 | 0.542433 | 0.999497 | 0.705194 | 0.999623 | 0 |
| IGSF1 | 3547 A_23_P125303 | 1.47 | 0.028819 | 0.060753 | 0.842061 | 0.999497 | 0.602729 | 0.999623 | 0 |
| SCARB1 | 949 A_23_P203900 | 1.36 | 0.028837 | 0.060753 | 0.945806 | 0.999497 | 0.666927 | 0.999623 | 0 |
| KLF10 | 7071 A_23_P168828 | -2.07 | 0.02879 | 0.060753 | 0.957562 | 0.999497 | 0.434456 | 0.999623 | 0 |
| CBR1 | 873 A_23_P29046 | -1.65 | 0.028769 | 0.060753 | 0.302828 | 0.999497 | 0.13344 | 0.999623 | 0 |
| RAB5C | 5878 A_23_P107211 | 1.36 | 0.028886 | 0.060781 | 0.398687 | 0.999497 | 0.499714 | 0.999623 | 0 |
| TNFRSF13B | 23495 A_23_P84705 | 1.5 | 0.028959 | 0.060839 | 0.468352 | 0.999497 | 0.202085 | 0.999623 | 0 |
| PTGS1 | 5742 A_23_P216966 | 1.59 | 0.028984 | 0.060839 | 0.850501 | 0.999497 | 0.911628 | 0.999623 | 0 |
| RHCE | 6006 A_23_P62634 | -1.28 | 0.029031 | 0.060864 | 0.372412 | 0.999497 | 0.659916 | 0.999623 | 0 |
| BBC3 | 27113 A_24_P305312 | 1.42 | 0.02926 | 0.061195 | 0.922857 | 0.999497 | 0.755122 | 0.999623 | 0 |
| TXLNA | 200081 A_32_P83305 | 1.48 | 0.029249 | 0.061195 | 0.719249 | 0.999497 | 0.62894 | 0.999623 | 0 |
| FEZ1 | 9638 A_23_P202881 | 1.3 | 0.029481 | 0.061583 | 0.302527 | 0.999497 | 0.741929 | 0.999623 | 0 |
| IL27RA | 9466 A_23_P27606 | 1.47 | 0.029555 | 0.061663 | 0.096732 | 0.999497 | 0.219257 | 0.999623 | 0 |
| PCDHB5 | 26167 A_23_P69863 | -1.28 | 0.029601 | 0.061683 | 0.519939 | 0.999497 | 0.243401 | 0.999623 | 0 |
| MLLT4 | 4301 A_23_P256603 | 1.36 | 0.029685 | 0.061784 | 0.292715 | 0.999497 | 0.339017 | 0.999623 | 0 |
| HSPD1 | 3329 A_32_P76091 | -3.09 | 0.029737 | 0.061817 | 0.515284 | 0.999497 | 0.494684 | 0.999623 | 1 |
| MRC2 | 9902 A_23_P49627 | 1.82 | 0.029815 | 0.061906 | 0.428232 | 0.999497 | 0.834295 | 0.999623 | 0 |
| PPP2R1A | 5518 A_23_P107661 | 1.52 | 0.029953 | 0.062117 | 0.912085 | 0.999497 | 0.216815 | 0.999623 | 0 |
| TCF3 | 6929 A_23_P67708 | 1.55 | 0.030032 | 0.062206 | 0.51389 | 0.999497 | 0.401865 | 0.999623 | 1 |
| MAPK8 | 5599 A_23_P356152 | 1.45 | 0.030224 | 0.062529 | 0.869519 | 0.999497 | 0.374373 | 0.999623 | 1 |
| SYTL1 | 84958 A_32_P217773 | 1.58 | 0.030264 | 0.062537 | 0.999751 | 0.999957 | 0.236159 | 0.999623 | 0 |
| TNFRSF1A | 7132 A_23_P139722 | -2.64 | 0.030305 | 0.062546 | 0.650778 | 0.999497 | 0.384675 | 0.999623 | 0 |
| TLR9 | 54106 A_23_P132654 | 1.57 | 0.030412 | 0.06261 | 0.804853 | 0.999497 | 0.838006 | 0.999623 | 0 |
| LAMC2 | 3918 A_23_P201636 | 1.28 | 0.030445 | 0.06261 | 0.947975 | 0.999497 | 0.332588 | 0.999623 | 0 |
| ERC1 | 23085 A_24_P249784 | 1.23 | 0.030398 | 0.06261 | 0.486291 | 0.999497 | 0.561453 | 0.999623 | 0 |
| PRKCA | 5578 A_23_P55099 | 1.41 | 0.030626 | 0.062682 | 0.763036 | 0.999497 | 0.313272 | 0.999623 | 1 |
| MSH3 | 4437 A_23_P122001 | -1.28 | 0.030547 | 0.062682 | 0.245368 | 0.999497 | 0.945702 | 0.999623 | 0 |
| 5-Sep | 5413 A_24_P297166 | 1.55 | 0.030596 | 0.062682 | 0.715949 | 0.999497 | 0.459014 | 0.999623 | 0 |
| NDUFA13 | 51079 A_23_P119627 | 1.6 | 0.030558 | 0.062682 | 0.782875 | 0.999497 | 0.274226 | 0.999623 | 0 |
| CYFIP2 | 26999 A_23_P156117 | 1.66 | 0.030695 | 0.06275 | 0.368667 | 0.999497 | 0.634073 | 0.999623 | 0 |
| BID | 637 A_23_P154929 | 1.85 | 0.030794 | 0.062877 | 0.661313 | 0.999497 | 0.84687 | 0.999623 | 0 |
| PARVA | 55742 A_23_P47642 | 1.25 | 0.030877 | 0.062897 | 0.959506 | 0.999497 | 0.920002 | 0.999623 | 0 |
| MAGED1 | 9500 A_24_P391526 | 1.29 | 0.030857 | 0.062897 | 0.369865 | 0.999497 | 0.287833 | 0.999623 | 0 |
| RAB18 | 22931 A_23_P138376 | 1.19 | 0.031017 | 0.063095 | 0.577327 | 0.999497 | 0.285604 | 0.999623 | 0 |
| CDKN1A | 1026 A_24_P89457 | 1.49 | 0.031197 | 0.063095 | 0.788278 | 0.999497 | 0.200461 | 0.999623 | 0 |
| CEBPA | 1050 A_24_P224727 | 1.5 | 0.031126 | 0.063095 | 0.306921 | 0.999497 | 0.188434 | 0.999623 | 1 |
| ADAM33 | 80332 A_23_P210731 | 1.55 | 0.031097 | 0.063095 | 0.485134 | 0.999497 | 0.592091 | 0.999623 | 0 |
| MYBPC3 | 4607 A_23_P127385 | -2.51 | 0.03123 | 0.063095 | 0.456002 | 0.999497 | 0.385035 | 0.999623 | 0 |
| CCL4 | 6351 A_23_P207564 | -2.79 | 0.031197 | 0.063095 | 0.360911 | 0.999497 | 0.22704 | 0.999623 | 0 |
| IL21R | 50615 A_24_P227927 | 1.39 | 0.031176 | 0.063095 | 0.765221 | 0.999497 | 0.826481 | 0.999623 | 0 |
| CYBA | 1535 A_23_P163506 | 1.48 | 0.031498 | 0.063104 | 0.820061 | 0.999497 | 0.40144 | 0.999623 | 0 |
| CHRNB2 | 1141 A_23_P368624 | 1.49 | 0.031385 | 0.063104 | 0.585591 | 0.999497 | 0.645168 | 0.999623 | 0 |
| TNNC2 | 7125 A_23_P131825 | 1.45 | 0.031527 | 0.063104 | 0.945366 | 0.999497 | 0.610019 | 0.999623 | 0 |
| TFPT | 29844 A_23_P27573 | 1.53 | 0.03146 | 0.063104 | 0.883172 | 0.999497 | 0.350379 | 0.999623 | 0 |
| EHD2 | 30846 A_24_P156113 | 1.5 | 0.031355 | 0.063104 | 0.993684 | 0.999497 | 0.734683 | 0.999623 | 0 |
| CDH18 | 1016 A_23_P84118 | 1.29 | 0.031368 | 0.063104 | 0.828265 | 0.999497 | 0.679675 | 0.999623 | 0 |
| LTBP3 | 4054 A_24_P298360 | 1.53 | 0.031475 | 0.063104 | 0.902998 | 0.999497 | 0.95695 | 0.999623 | 0 |
| CD63 | 967 A_23_P139476 | 1.5 | 0.031524 | 0.063104 | 0.441376 | 0.999497 | 0.107585 | 0.999623 | 0 |
| EIF5A | 1984 A_24_P375609 | 1.55 | 0.031679 | 0.063261 | 0.263799 | 0.999497 | 0.594688 | 0.999623 | 0 |
| AEBP1 | 165 A_23_P145916 | 1.46 | 0.031645 | 0.063261 | 0.442664 | 0.999497 | 0.395607 | 0.999623 | 0 |
| LENG1 | 79165 A_23_P208523 | 1.47 | 0.031818 | 0.063414 | 0.646664 | 0.999497 | 0.933681 | 0.999623 | 0 |
| SIRT6 | 51548 A_23_P208847 | 1.34 | 0.031903 | 0.063414 | 0.522245 | 0.999497 | 0.421646 | 0.999623 | 1 |
| AP1S1 | 1174 A_24_P63950 | 1.3 | 0.031872 | 0.063414 | 0.711261 | 0.999497 | 0.504707 | 0.999623 | 0 |

TABLE S7-continued

Significant differences between CR and CNR

| | | Fold-change CNR vs CR | Cytokine response | | Age: 60-65 yo vs 74+ yo | | Gender | | |
|---|---|---|---|---|---|---|---|---|---|
| | | | p-value | q-value | p-value | q-value | p-value | q-value | |
| TIMP2 | 7077 A_23_P107401 | 1.54 | 0.031872 | 0.063414 | 0.882487 | 0.999497 | 0.207987 | 0.999623 | 0 |
| GULP1 | 51454 A_23_P332399 | −1.93 | 0.031986 | 0.063433 | 0.689299 | 0.999497 | 0.543041 | 0.999623 | 0 |
| DAPK1 | 1612 A_23_P252163 | 1.29 | 0.031953 | 0.063433 | 0.505182 | 0.999497 | 0.564311 | 0.999623 | 0 |
| SFRS17A | 8227 A_23_P342668 | 1.25 | 0.032068 | 0.063445 | 0.082378 | 0.999497 | 0.492234 | 0.999623 | 0 |
| PRKAR2B | 5577 A_23_P42975 | −2.2 | 0.032103 | 0.063445 | 0.7629 | 0.999497 | 0.300333 | 0.999623 | 0 |
| PSMA1 | 5682 A_23_P150286 | −1.37 | 0.032058 | 0.063445 | 0.299438 | 0.999497 | 0.527897 | 0.999623 | 0 |
| LEPR | 3953 A_24_P231104 | −1.96 | 0.032218 | 0.063527 | 0.785813 | 0.999497 | 0.410247 | 0.999623 | 1 |
| MYBPC2 | 4606 A_23_P16262 | 1.43 | 0.032212 | 0.063527 | 0.949079 | 0.999497 | 0.137534 | 0.999623 | 0 |
| NPM1 | 4869 A_32_P49423 | −1.94 | 0.032263 | 0.063534 | 0.902419 | 0.999497 | 0.467736 | 0.999623 | 0 |
| CCND3 | 896 A_23_P214464 | 1.52 | 0.032295 | 0.063534 | 0.878017 | 0.999497 | 0.72382 | 0.999623 | 0 |
| THOC5 | 8563 A_23_P109470 | 1.29 | 0.032341 | 0.063551 | 0.962271 | 0.999497 | 0.941392 | 0.999623 | 0 |
| ALDH1A3 | 220 A_23_P205959 | −1.32 | 0.032482 | 0.063565 | 0.750488 | 0.999497 | 0.270208 | 0.999623 | 0 |
| PKD1 | 5310 A_23_P77502 | 1.83 | 0.032532 | 0.063565 | 0.408551 | 0.999497 | 0.973099 | 0.999623 | 0 |
| MAF | 4094 A_32_P213103 | 1.62 | 0.032459 | 0.063565 | 0.794258 | 0.999497 | 0.936076 | 0.999623 | 0 |
| VCP | 7415 A_24_P295412 | 1.22 | 0.032519 | 0.063565 | 0.346933 | 0.999497 | 0.608681 | 0.999623 | 1 |
| FCRLB | 127943 A_23_P350574 | 1.73 | 0.032444 | 0.063565 | 0.429888 | 0.999497 | 0.416771 | 0.999623 | 0 |
| CTSB | 1508 A_23_P215944 | −1.47 | 0.032578 | 0.063581 | 0.488009 | 0.999497 | 0.977433 | 0.999623 | 0 |
| FGB | 2244 A_24_P550411 | 1.4 | 0.03266 | 0.06367 | 0.497199 | 0.999497 | 0.559463 | 0.999623 | 0 |
| CTSC | 1075 A_24_P115762 | −1.61 | 0.033185 | 0.063796 | 0.995805 | 0.999497 | 0.615207 | 0.999623 | 0 |
| BBS9 | 27241 A_23_P82351 | 1.19 | 0.033317 | 0.063796 | 0.31653 | 0.999497 | 0.913647 | 0.999623 | 0 |
| ARHGDIA | 396 A_24_P133933 | 1.51 | 0.033156 | 0.063796 | 0.840647 | 0.999497 | 0.773433 | 0.999623 | 0 |
| FGFR3 | 2261 A_23_P212830 | 1.59 | 0.033108 | 0.063796 | 0.881589 | 0.999497 | 0.496839 | 0.999623 | 0 |
| TNFRSF21 | 27242 A_23_P42065 | 1.46 | 0.032849 | 0.063796 | 0.278269 | 0.999497 | 0.846903 | 0.999623 | 0 |
| HCFC1R1 | 54985 A_23_P26534 | 1.54 | 0.033024 | 0.063796 | 0.748762 | 0.999497 | 0.205968 | 0.999623 | 0 |
| VEGFA | 7422 A_24_P179400 | 1.71 | 0.032983 | 0.063796 | 0.944173 | 0.999497 | 0.703621 | 0.999623 | 1 |
| HBP1 | 26959 A_24_P204971 | −1.59 | 0.033215 | 0.063796 | 0.798522 | 0.999497 | 0.245275 | 0.999623 | 1 |
| BBS2 | 583 A_23_P106835 | 1.23 | 0.033285 | 0.063796 | 0.1723 | 0.999497 | 0.261281 | 0.999623 | 0 |
| PTGFR | 5737 A_24_P302172 | 1.25 | 0.033071 | 0.063796 | 0.619445 | 0.999497 | 0.938937 | 0.999623 | 0 |
| NGFR | 4804 A_23_P389897 | 1.44 | 0.033202 | 0.063796 | 0.810191 | 0.999497 | 0.472641 | 0.999623 | 1 |
| FBLIM1 | 54751 A_24_P94222 | 1.48 | 0.032872 | 0.063796 | 0.768085 | 0.999497 | 0.76898 | 0.999623 | 0 |
| ADAMTS7 | 11173 A_23_P37624 | 1.33 | 0.033246 | 0.063796 | 0.514772 | 0.999497 | 0.250831 | 0.999623 | 0 |
| SIVA1 | 10572 A_24_P116351 | 1.43 | 0.033253 | 0.063796 | 0.825935 | 0.999497 | 0.482239 | 0.999623 | 0 |
| FCGR3B | 2215 A_23_P126298 | −3.65 | 0.032777 | 0.063796 | 0.504655 | 0.999497 | 0.63578 | 0.999623 | 0 |
| XPA | 7507 A_23_P60283 | 1.31 | 0.033168 | 0.063796 | 0.973303 | 0.999497 | 0.318812 | 0.999623 | 1 |
| TAPBP | 6892 A_23_P365719 | 1.35 | 0.033357 | 0.063801 | 0.617357 | 0.999497 | 0.52104 | 0.999623 | 0 |
| COL18A1 | 80781 A_24_P57426 | 2.23 | 0.033707 | 0.064009 | 0.369159 | 0.999497 | 0.785081 | 0.999623 | 0 |
| COL20A1 | 57642 A_32_P185637 | 1.32 | 0.03358 | 0.064009 | 0.48373 | 0.999497 | 0.239762 | 0.999623 | 0 |
| RNF34 | 80196 A_32_P70420 | −1.41 | 0.033591 | 0.064009 | 0.916876 | 0.999497 | 0.090264 | 0.999623 | 0 |
| C9orf127 | 51754 A_23_P216522 | −1.35 | 0.033696 | 0.064009 | 0.301834 | 0.999497 | 0.387275 | 0.999623 | 0 |
| TXLNA | 200081 A_23_P51361 | 1.51 | 0.033687 | 0.064009 | 0.919058 | 0.999497 | 0.794959 | 0.999623 | 0 |
| MALL | 7851 A_24_P80204 | 1.45 | 0.033716 | 0.064009 | 0.838832 | 0.999497 | 0.614491 | 0.999623 | 0 |
| TBXAS1 | 6916 A_32_P212886 | 1.29 | 0.033725 | 0.064009 | 0.476815 | 0.999497 | 0.497037 | 0.999623 | 0 |
| NFATC1 | 4772 A_24_P258846 | 2.31 | 0.033788 | 0.064058 | 0.484876 | 0.999497 | 0.188787 | 0.999623 | 0 |
| TERT | 7015 A_23_P110851 | 2.15 | 0.033887 | 0.064123 | 0.904127 | 0.999497 | 0.891923 | 0.999623 | 1 |
| ZFYVE16 | 9765 A_24_P286054 | −2.49 | 0.033909 | 0.064123 | 0.562591 | 0.999497 | 0.318679 | 0.999623 | 0 |
| FUT3 | 2525 A_23_P360316 | 1.53 | 0.033934 | 0.064123 | 0.875302 | 0.999497 | 0.621745 | 0.999623 | 0 |
| HAPLN4 | 404037 A_23_P430842 | 1.37 | 0.033975 | 0.06413 | 0.492467 | 0.999497 | 0.118386 | 0.999623 | 0 |
| VAV1 | 7409 A_23_P38959 | 1.61 | 0.034064 | 0.064213 | 0.380843 | 0.999497 | 0.861607 | 0.999623 | 0 |
| HRK | 8739 A_23_P25194 | 1.36 | 0.034093 | 0.064213 | 0.54629 | 0.999497 | 0.493787 | 0.999623 | 0 |
| IFI27L2 | 83982 A_23_P140146 | 1.53 | 0.034226 | 0.064345 | 0.542263 | 0.999497 | 0.208311 | 0.999623 | 0 |
| TOM1 | 10043 A_23_P103084 | 1.49 | 0.034294 | 0.064345 | 0.422176 | 0.999497 | 0.643378 | 0.999623 | 0 |
| SLPI | 6590 A_24_P190472 | 1.44 | 0.034284 | 0.064345 | 0.255446 | 0.999497 | 0.596129 | 0.999623 | 0 |
| FKBP1A | 2280 A_23_P154667 | 1.65 | 0.034313 | 0.064345 | 0.355904 | 0.999497 | 0.748701 | 0.999623 | 0 |
| TERF1 | 7013 A_32_P220696 | −1.78 | 0.034374 | 0.064348 | 0.606755 | 0.999497 | 0.565852 | 0.999623 | 1 |
| IRF7 | 3665 A_24_P378019 | 1.33 | 0.034412 | 0.064348 | 0.398343 | 0.999497 | 0.717063 | 0.999623 | 0 |
| C2 | 717 A_32_P162187 | 1.31 | 0.034427 | 0.064348 | 0.742981 | 0.999497 | 0.353564 | 0.999623 | 0 |
| RRAD | 6236 A_24_P262127 | 1.41 | 0.03452 | 0.064453 | 0.301818 | 0.999497 | 0.626374 | 0.999623 | 0 |
| ICOSLG | 23308 A_23_P6272 | −1.56 | 0.034668 | 0.064659 | 0.789295 | 0.999497 | 0.107452 | 0.999623 | 0 |
| EEF2 | 1938 A_24_P87763 | 1.45 | 0.034707 | 0.064661 | 0.296008 | 0.999497 | 0.285848 | 0.999623 | 1 |
| CHRNA7 | 1139 A_23_P163390 | 1.55 | 0.034872 | 0.064724 | 0.58819 | 0.999497 | 0.408751 | 0.999623 | 0 |
| SCD5 | 79966 A_23_P213288 | 1.45 | 0.034902 | 0.064724 | 0.6819 | 0.999497 | 0.314801 | 0.999623 | 0 |
| ATHL1 | 80162 A_23_P98686 | 1.47 | 0.034966 | 0.064724 | 0.318446 | 0.999497 | 0.427014 | 0.999623 | 0 |
| GCLM | 2730 A_23_P103996 | −1.49 | 0.034959 | 0.064724 | 0.924876 | 0.999497 | 0.331781 | 0.999623 | 1 |
| MLLT6 | 4302 A_32_P98683 | 1.29 | 0.034953 | 0.064724 | 0.825453 | 0.999497 | 0.568063 | 0.999623 | 0 |
| WWTR1 | 25937 A_32_P6868 | 1.36 | 0.034797 | 0.064724 | 0.323648 | 0.999497 | 0.863363 | 0.999623 | 0 |
| PRDX1 | 5052 A_23_P11995 | 1.34 | 0.035081 | 0.064868 | 0.231794 | 0.999497 | 0.6463 | 0.999623 | 1 |
| PXN | 5829 A_23_P409355 | 1.56 | 0.035123 | 0.064876 | 0.842538 | 0.999497 | 0.30583 | 0.999623 | 0 |
| PRKCSH | 5589 A_24_P396197 | 1.79 | 0.035235 | 0.065012 | 0.531771 | 0.999497 | 0.921556 | 0.999623 | 0 |
| BCLAF1 | 9774 A_24_P89512 | −1.8 | 0.035453 | 0.065255 | 0.846611 | 0.999497 | 0.829268 | 0.999623 | 0 |
| TNFAIP8L1 | 126282 A_23_P428875 | 1.56 | 0.035448 | 0.065255 | 0.483639 | 0.999497 | 0.701125 | 0.999623 | 0 |
| BAT2L | 84726 A_24_P95198 | 1.5 | 0.03548 | 0.065255 | 0.301971 | 0.999497 | 0.432894 | 0.999623 | 0 |
| RTKN | 6242 A_23_P120056 | 1.46 | 0.035523 | 0.065265 | 0.457554 | 0.999497 | 0.302307 | 0.999623 | 0 |

TABLE S7-continued

Significant differences between CR and CNR

| | | Fold-change CNR vs CR | Cytokine response | | Age: 60-65 yo vs 74+ yo | | Gender | | |
|---|---|---|---|---|---|---|---|---|---|
| | | | p-value | q-value | p-value | q-value | p-value | q-value | |
| CTNND1 | 1500 A_23_P251316 | −1.41 | 0.03565 | 0.065286 | 0.7144 | 0.999497 | 0.245176 | 0.999623 | 0 |
| MYST3 | 7994 A_23_P407628 | 1.22 | 0.035735 | 0.065286 | 0.59063 | 0.999497 | 0.520196 | 0.999623 | 0 |
| MLL | 4297 A_24_P922909 | 1.74 | 0.035679 | 0.065286 | 0.678586 | 0.999497 | 0.972241 | 0.999623 | 0 |
| CSRNP1 | 64651 A_23_P121011 | 1.27 | 0.035762 | 0.065286 | 0.224143 | 0.999497 | 0.960358 | 0.999623 | 0 |
| LY6K | 54742 A_32_P202214 | 1.24 | 0.035583 | 0.065286 | 0.750624 | 0.999497 | 0.45165 | 0.999623 | 0 |
| PLDN | 26258 A_23_P205801 | 1.21 | 0.035698 | 0.065286 | 0.259189 | 0.999497 | 0.033897 | 0.999623 | 0 |
| IGBP1 | 3476 A_23_P171249 | −1.68 | 0.035812 | 0.065308 | 0.628936 | 0.999497 | 0.43381 | 0.999623 | 0 |
| CLDN1 | 9076 A_24_P165949 | 1.28 | 0.035893 | 0.065323 | 0.672177 | 0.999497 | 0.017062 | 0.999623 | 0 |
| LY86 | 9450 A_23_P70688 | 1.27 | 0.035896 | 0.065323 | 0.634683 | 0.999497 | 0.73318 | 0.999623 | 0 |
| SEMA3B | 7869 A_23_P132718 | 1.19 | 0.035945 | 0.065344 | 0.237064 | 0.999497 | 0.408716 | 0.999623 | 0 |
| IGF2BP1 | 10642 A_23_P83498 | 1.4 | 0.036054 | 0.065472 | 0.208519 | 0.999497 | 0.335448 | 0.999623 | 0 |
| FANCI | 55215 A_23_P375104 | −2.62 | 0.036106 | 0.065499 | 0.475677 | 0.999497 | 0.588487 | 0.999623 | 0 |
| GRN | 2896 A_23_P49708 | 1.49 | 0.036236 | 0.065559 | 0.410007 | 0.999497 | 0.210933 | 0.999623 | 0 |
| SMOC1 | 64093 A_24_P150466 | 1.54 | 0.036368 | 0.065559 | 0.751552 | 0.999497 | 0.588362 | 0.999623 | 0 |
| CBARA1 | 10367 A_23_P46907 | −1.24 | 0.036358 | 0.065559 | 0.275835 | 0.999497 | 0.97784 | 0.999623 | 0 |
| BGLAP | 632 A_23_P160638 | 1.54 | 0.036338 | 0.065559 | 0.658997 | 0.999497 | 0.331015 | 0.999623 | 0 |
| AP1S2 | 8905 A_24_P10804 | −1.44 | 0.036294 | 0.065559 | 0.09235 | 0.999497 | 0.358259 | 0.999623 | 0 |
| UACA | 55075 A_24_P290585 | 1.47 | 0.03622 | 0.065559 | 0.31198 | 0.999497 | 0.39171 | 0.999623 | 0 |
| AATK | 9625 A_23_P159169 | 1.31 | 0.036427 | 0.065597 | 0.473991 | 0.999497 | 0.956776 | 0.999623 | 0 |
| MAP3K5 | 4217 A_23_P134125 | −2.36 | 0.036467 | 0.065601 | 0.494233 | 0.999497 | 0.366173 | 0.999623 | 1 |
| CD5 | 921 A_24_P364221 | 1.3 | 0.036675 | 0.065905 | 0.814369 | 0.999497 | 0.292644 | 0.999623 | 0 |
| PTK2B | 2185 A_23_P168836 | 2.03 | 0.037067 | 0.06621 | 0.339483 | 0.999497 | 0.265766 | 0.999623 | 1 |
| SRC | 6714 A_23_P308603 | 1.35 | 0.037344 | 0.06621 | 0.627243 | 0.999497 | 0.955467 | 0.999623 | 0 |
| IMPDH1 | 3614 A_24_P89708 | 1.59 | 0.037174 | 0.06621 | 0.659222 | 0.999497 | 0.612172 | 0.999623 | 0 |
| LIMS1 | 3987 A_23_P210358 | −1.55 | 0.037261 | 0.06621 | 0.629349 | 0.999497 | 0.549508 | 0.999623 | 0 |
| CD4 | 920 A_24_P295999 | −2.75 | 0.037125 | 0.06621 | 0.966905 | 0.999497 | 0.286739 | 0.999623 | 0 |
| FRAP1 | 2475 A_23_P34606 | 1.46 | 0.037277 | 0.06621 | 0.809112 | 0.999497 | 0.566189 | 0.999623 | 1 |
| HSPA1A | 3303 A_24_P682285 | 1.59 | 0.036909 | 0.06621 | 0.887857 | 0.999497 | 0.415038 | 0.999623 | 1 |
| PRDX2 | 7001 A_32_P227525 | 1.84 | 0.03694 | 0.06621 | 0.555601 | 0.999497 | 0.861216 | 0.999623 | 0 |
| VAMP3 | 9341 A_23_P97532 | 1.36 | 0.037161 | 0.06621 | 0.864031 | 0.999497 | 0.65595 | 0.999623 | 0 |
| TOP2B | 7155 A_23_P121095 | −1.33 | 0.037062 | 0.06621 | 0.941946 | 0.999497 | 0.51165 | 0.999623 | 1 |
| ERCC1 | 2067 A_23_P107701 | 1.35 | 0.037233 | 0.06621 | 0.873782 | 0.999497 | 0.66258 | 0.999623 | 1 |
| PHB | 5245 A_24_P262355 | 1.17 | 0.037113 | 0.06621 | 0.633978 | 0.999497 | 0.067449 | 0.999623 | 0 |
| YWHAZ | 7534 A_32_P233860 | −1.43 | 0.037331 | 0.06621 | 0.607754 | 0.999497 | 0.720726 | 0.999623 | 1 |
| UBE2N | 7334 A_32_P11499 | −1.28 | 0.03743 | 0.066295 | 0.543764 | 0.999497 | 0.42914 | 0.999623 | 0 |
| C8orf4 | 56892 A_23_P253350 | −1.86 | 0.037619 | 0.066561 | 0.725317 | 0.999497 | 0.615774 | 0.999623 | 0 |
| CD97 | 976 A_23_P502314 | 1.5 | 0.037696 | 0.066629 | 0.966568 | 0.999497 | 0.409637 | 0.999623 | 0 |
| CBLB | 868 A_23_P29830 | 1.23 | 0.037782 | 0.066677 | 0.200474 | 0.999497 | 0.518392 | 0.999623 | 0 |
| GP1BB | 2812 A_23_P29124 | 2.12 | 0.037967 | 0.066677 | 0.49344 | 0.999497 | 0.479874 | 0.999623 | 0 |
| WWTR1 | 25937 A_24_P944390 | −1.68 | 0.037822 | 0.066677 | 0.866945 | 0.999497 | 0.547464 | 0.999623 | 0 |
| DNASE1L3 | 1776 A_23_P257993 | 1.14 | 0.038125 | 0.066677 | 0.317968 | 0.999497 | 0.493312 | 0.999623 | 0 |
| PPP1R13B | 23368 A_23_P205273 | 1.44 | 0.038021 | 0.066677 | 0.546261 | 0.999497 | 0.8945 | 0.999623 | 0 |
| EBI3 | 10148 A_23_P119478 | 1.14 | 0.037841 | 0.066677 | 0.730837 | 0.999497 | 0.16421 | 0.999623 | 0 |
| CEBPB | 1051 A_23_P143242 | 1.43 | 0.038082 | 0.066677 | 0.414807 | 0.999497 | 0.430171 | 0.999623 | 1 |
| OSCAR | 126014 A_23_P50374 | 1.3 | 0.038096 | 0.066677 | 0.501881 | 0.999497 | 0.970502 | 0.999623 | 0 |
| SGPL1 | 8879 A_23_P75325 | 1.32 | 0.038128 | 0.066677 | 0.569951 | 0.999497 | 0.507742 | 0.999623 | 0 |
| ADAM12 | 8038 A_23_P202327 | 1.34 | 0.037935 | 0.066677 | 0.050751 | 0.999497 | 0.627833 | 0.999623 | 0 |
| PDZD2 | 23037 A_23_P7402 | 1.44 | 0.038149 | 0.066677 | 0.26995 | 0.999497 | 0.301539 | 0.999623 | 0 |
| TEK | 7010 A_23_P374695 | 1.48 | 0.038188 | 0.066678 | 0.218137 | 0.999497 | 0.415731 | 0.999623 | 0 |
| FLVCR1 | 28982 A_23_P12113 | 1.33 | 0.038289 | 0.066786 | 0.676007 | 0.999497 | 0.815572 | 0.999623 | 0 |
| PSMA3 | 5684 A_23_P140301 | −1.33 | 0.038396 | 0.066838 | 0.429774 | 0.999497 | 0.404923 | 0.999623 | 0 |
| CSF1 | 1435 A_23_P407012 | 1.19 | 0.038392 | 0.066838 | 0.262292 | 0.999497 | 0.194732 | 0.999623 | 0 |
| CD68 | 968 A_23_P15394 | 1.64 | 0.038438 | 0.066843 | 0.186404 | 0.999497 | 0.619938 | 0.999623 | 0 |
| PCDHB7 | 56129 A_24_P243373 | 1.19 | 0.038495 | 0.066853 | 0.903951 | 0.999497 | 0.426421 | 0.999623 | 0 |
| JAG1 | 182 A_23_P210763 | −1.4 | 0.038521 | 0.066853 | 0.379778 | 0.999497 | 0.349641 | 0.999623 | 0 |
| ELF1 | 1997 A_24_P78590 | −2.17 | 0.038608 | 0.066868 | 0.648052 | 0.999497 | 0.404488 | 0.999623 | 0 |
| COL18A1 | 80781 A_23_P211212 | 1.37 | 0.038572 | 0.066868 | 0.316143 | 0.999497 | 0.97801 | 0.999623 | 0 |
| MSRA | 4482 A_23_P61426 | 1.27 | 0.038699 | 0.066894 | 0.889898 | 0.999497 | 0.940286 | 0.999623 | 1 |
| FGFR1 | 2260 A_23_P372923 | 1.46 | 0.0387 | 0.066894 | 0.912491 | 0.999497 | 0.213834 | 0.999623 | 1 |
| IGF2BP2 | 10644 A_23_P250156 | 1.25 | 0.039017 | 0.067051 | 0.205824 | 0.999497 | 0.856667 | 0.999623 | 0 |
| FERMT2 | 10979 A_23_P88347 | −1.47 | 0.039058 | 0.067051 | 0.449805 | 0.999497 | 0.327004 | 0.999623 | 0 |
| METTL1 | 4234 A_23_P47790 | 1.45 | 0.038859 | 0.067051 | 0.816033 | 0.999497 | 0.583595 | 0.999623 | 0 |
| PECR | 55825 A_23_P91140 | 1.51 | 0.038948 | 0.067051 | 0.884259 | 0.999497 | 0.820681 | 0.999623 | 0 |
| CCRL2 | 9034 A_23_P69310 | 1.28 | 0.039102 | 0.067051 | 0.734989 | 0.999497 | 0.392005 | 0.999623 | 0 |
| ISG20 | 3669 A_23_P32404 | 1.46 | 0.03902 | 0.067051 | 0.330731 | 0.999497 | 0.806808 | 0.999623 | 0 |
| VEGFB | 7423 A_24_P55971 | 1.68 | 0.039039 | 0.067051 | 0.796219 | 0.999497 | 0.472839 | 0.999623 | 0 |
| SMOC2 | 64094 A_23_P70307 | 1.22 | 0.039102 | 0.067051 | 0.58029 | 0.999497 | 0.428484 | 0.999623 | 0 |
| PRF1 | 5551 A_23_P1473 | −2.85 | 0.039259 | 0.067197 | 0.250656 | 0.999497 | 0.651678 | 0.999623 | 0 |
| CALR | 811 A_23_P67288 | 1.6 | 0.039265 | 0.067197 | 0.331002 | 0.999497 | 0.554073 | 0.999623 | 0 |
| SFN | 2810 A_23_P63254 | 1.4 | 0.039388 | 0.06734 | 0.756443 | 0.999497 | 0.927541 | 0.999623 | 0 |
| RPH3AL | 9501 A_23_P94819 | 1.48 | 0.039521 | 0.067366 | 0.35573 | 0.999497 | 0.808914 | 0.999623 | 0 |
| AIRE | 326 A_23_P68740 | −1.41 | 0.039517 | 0.067366 | 0.619415 | 0.999497 | 0.551874 | 0.999623 | 0 |

TABLE S7-continued

Significant differences between CR and CNR

|  |  | Fold-change CNR vs CR | Cytokine response | | Age: 60-65 yo vs 74+ yo | | Gender | | |
| --- | --- | --- | --- | --- | --- | --- | --- | --- | --- |
|  |  |  | p-value | q-value | p-value | q-value | p-value | q-value |  |
| ADORA2A | 135 A_24_P237270 | 1.68 | 0.03951 | 0.067366 | 0.570034 | 0.999497 | 0.813103 | 0.999623 | 0 |
| MTCH1 | 23787 A_24_P235012 | 1.34 | 0.039611 | 0.067394 | 0.45622 | 0.999497 | 0.917992 | 0.999623 | 0 |
| GSG2 | 83903 A_23_P66732 | 1.35 | 0.039615 | 0.067394 | 0.10052 | 0.999497 | 0.844113 | 0.999623 | 0 |
| TM2D1 | 83941 A_23_P148959 | -2.07 | 0.039693 | 0.06746 | 0.872628 | 0.999497 | 0.986858 | 0.999623 | 0 |
| NFATC2IP | 84901 A_23_P125157 | 1.21 | 0.039962 | 0.06785 | 0.31469 | 0.999497 | 0.910653 | 0.999623 | 0 |
| IRF3 | 3661 A_23_P27677 | 1.66 | 0.040046 | 0.067925 | 0.741216 | 0.999497 | 0.098662 | 0.999623 | 0 |
| TGFB1 | 7040 A_24_P79054 | 1.7 | 0.040109 | 0.067965 | 0.797209 | 0.999497 | 0.292058 | 0.999623 | 1 |
| EEF1A1 | 1915 A_32_P44316 | -1.87 | 0.040328 | 0.068109 | 0.900192 | 0.999497 | 0.92053 | 0.999623 | 1 |
| FOXP1 | 27086 A_24_P362737 | -1.58 | 0.040352 | 0.068109 | 0.3515 | 0.999497 | 0.899575 | 0.999623 | 0 |
| CBLB | 868 A_23_P212715 | -1.33 | 0.040295 | 0.068109 | 0.534774 | 0.999497 | 0.943076 | 0.999623 | 0 |
| HLA-DOB | 3112 A_23_P30736 | 1.49 | 0.040279 | 0.068109 | 0.300797 | 0.999497 | 0.332659 | 0.999623 | 0 |
| BAT4 | 7918 A_23_P13923 | 1.25 | 0.040486 | 0.068269 | 0.351473 | 0.999497 | 0.412532 | 0.999623 | 0 |
| NOSTRIN | 115677 A_23_P79360 | 1.48 | 0.040846 | 0.068541 | 0.163568 | 0.999497 | 0.198707 | 0.999623 | 0 |
| NPM1 | 4869 A_24_P826646 | 1.33 | 0.04083 | 0.068541 | 0.441115 | 0.999497 | 0.290941 | 0.999623 | 0 |
| PCDHGA8 | 9708 A_23_P354734 | 1.39 | 0.040769 | 0.068541 | 0.358886 | 0.999497 | 0.639883 | 0.999623 | 0 |
| WISP2 | 8839 A_23_P102611 | 2.1 | 0.040729 | 0.068541 | 0.752003 | 0.999497 | 0.762391 | 0.999623 | 0 |
| SIPA1 | 6494 A_23_P127460 | 1.44 | 0.040756 | 0.068541 | 0.753914 | 0.999497 | 0.69068 | 0.999623 | 0 |
| HIVEP2 | 3097 A_23_P214766 | 1.58 | 0.040923 | 0.068604 | 0.735097 | 0.999497 | 0.43867 | 0.999623 | 0 |
| FKBP9 | 11328 A_23_P376211 | 1.16 | 0.04097 | 0.068615 | 0.739192 | 0.999497 | 0.737438 | 0.999623 | 0 |
| BTG1 | 694 A_32_P225870 | 1.35 | 0.041055 | 0.068625 | 0.89781 | 0.999497 | 0.103594 | 0.999623 | 0 |
| MAST1 | 22983 A_23_P101480 | 1.34 | 0.041027 | 0.068625 | 0.689448 | 0.999497 | 0.320766 | 0.999623 | 0 |
| SERPING1 | 710 A_23_P139123 | 1.48 | 0.041165 | 0.068629 | 0.537946 | 0.999497 | 0.585445 | 0.999623 | 0 |
| IRAK1 | 3654 A_23_P73780 | 1.82 | 0.041217 | 0.068629 | 0.346895 | 0.999497 | 0.397119 | 0.999623 | 0 |
| PTGES3 | 10728 A_24_P263623 | -1.7 | 0.041217 | 0.068629 | 0.400474 | 0.999497 | 0.899976 | 0.999623 | 0 |
| ARHGDIA | 396 A_23_P207766 | 1.42 | 0.041146 | 0.068629 | 0.937183 | 0.999497 | 0.797306 | 0.999623 | 0 |
| PTCD2 | 79810 A_24_P191847 | -2.25 | 0.041264 | 0.068641 | 0.804729 | 0.999497 | 0.312599 | 0.999623 | 0 |
| CYTIP | 9595 A_23_P90626 | -1.43 | 0.041387 | 0.068658 | 0.402373 | 0.999497 | 0.26584 | 0.999623 | 0 |
| BIRC7 | 79444 A_23_P79769 | 1.39 | 0.041362 | 0.068658 | 0.826231 | 0.999497 | 0.932431 | 0.999623 | 0 |
| CDH4 | 1002 A_23_P28999 | 1.27 | 0.041394 | 0.068658 | 0.984845 | 0.999497 | 0.506975 | 0.999623 | 0 |
| RYBP | 23429 A_23_P305711 | 1.25 | 0.041476 | 0.068729 | 0.973564 | 0.999497 | 0.950795 | 0.999623 | 0 |
| ABCA1 | 19 A_24_P235429 | -1.44 | 0.041522 | 0.068737 | 0.994963 | 0.999497 | 0.233991 | 0.999623 | 0 |
| TRAF7 | 84231 A_24_P53150 | -2.6 | 0.041571 | 0.068754 | 0.998076 | 0.999497 | 0.560697 | 0.999623 | 0 |
| DCBLD1 | 285761 A_23_P409462 | 1.23 | 0.041836 | 0.068772 | 0.305884 | 0.999497 | 0.724295 | 0.999623 | 0 |
| PSMC1 | 5700 A_24_P347488 | -1.31 | 0.042055 | 0.068772 | 0.799563 | 0.999497 | 0.530682 | 0.999623 | 0 |
| NFASC | 23114 A_24_P350656 | 1.27 | 0.041644 | 0.068772 | 0.087798 | 0.999497 | 0.296733 | 0.999623 | 0 |
| RAD9A | 5883 A_24_P21715 | 1.33 | 0.041975 | 0.068772 | 0.962305 | 0.999497 | 0.558778 | 0.999623 | 0 |
| TAL2 | 6887 A_23_P409449 | 1.31 | 0.042007 | 0.068772 | 0.264624 | 0.999497 | 0.304782 | 0.999623 | 0 |
| UCP3 | 7352 A_23_P203601 | 1.51 | 0.042132 | 0.068772 | 0.694175 | 0.999497 | 0.234801 | 0.999623 | 1 |
| MAMDC2 | 256691 A_32_P47222 | 1.38 | 0.041863 | 0.068772 | 0.79643 | 0.999497 | 0.633976 | 0.999623 | 0 |
| SDF2 | 6388 A_23_P107313 | 1.41 | 0.042031 | 0.068772 | 0.399052 | 0.999497 | 0.635088 | 0.999623 | 0 |
| CD81 | 975 A_23_P13425 | 1.56 | 0.04191 | 0.068772 | 0.419469 | 0.999497 | 0.762805 | 0.999623 | 0 |
| STK17A | 9263 A_24_P337796 | -1.64 | 0.042013 | 0.068772 | 0.847399 | 0.999497 | 0.358757 | 0.999623 | 0 |
| AURKC | 6795 A_23_P50232 | 1.4 | 0.042006 | 0.068772 | 0.480049 | 0.999497 | 0.54651 | 0.999623 | 0 |
| ITGA7 | 3679 A_23_P128084 | 1.47 | 0.041848 | 0.068772 | 0.710712 | 0.999497 | 0.283288 | 0.999623 | 0 |
| PSMD14 | 10213 A_23_P165691 | -1.36 | 0.042141 | 0.068772 | 0.458016 | 0.999497 | 0.274646 | 0.999623 | 0 |
| FSCN1 | 6624 A_23_P168531 | 1.5 | 0.042083 | 0.068772 | 0.689746 | 0.999497 | 0.849582 | 0.999623 | 0 |
| MAPK9 | 5601 A_23_P167692 | -1.71 | 0.042221 | 0.068773 | 0.745508 | 0.999497 | 0.424412 | 0.999623 | 1 |
| HSP90AA1 | 3320 A_32_P199252 | -2.34 | 0.042189 | 0.068773 | 0.970412 | 0.999497 | 0.777715 | 0.999623 | 1 |
| ICAM4 | 3386 A_23_P130537 | 1.54 | 0.042372 | 0.068887 | 0.865075 | 0.999497 | 0.326853 | 0.999623 | 0 |
| CXCR3 | 2833 A_23_P114299 | -2.58 | 0.042355 | 0.068887 | 0.823285 | 0.999497 | 0.314022 | 0.999623 | 0 |
| RIN2 | 54453 A_23_P120572 | 1.39 | 0.04255 | 0.069112 | 0.172327 | 0.999497 | 0.654862 | 0.999623 | 0 |
| PSEN1 | 5663 A_23_P205686 | 1.37 | 0.042646 | 0.069203 | 0.374946 | 0.999497 | 0.988842 | 0.999623 | 1 |
| SECTM1 | 6398 A_24_P48204 | -1.59 | 0.042703 | 0.06923 | 0.402995 | 0.999497 | 0.507383 | 0.999623 | 0 |
| LYAR | 55646 A_23_P41327 | -1.53 | 0.042853 | 0.069343 | 0.318999 | 0.999497 | 0.799633 | 0.999623 | 0 |
| GRK5 | 2869 A_23_P12884 | 1.21 | 0.042815 | 0.069343 | 0.325056 | 0.999497 | 0.974853 | 0.999623 | 0 |
| ROM1 | 6094 A_23_P105002 | 1.52 | 0.042908 | 0.069366 | 0.721971 | 0.999497 | 0.489213 | 0.999623 | 0 |
| SH2D1A | 4068 A_23_P45248 | -1.65 | 0.042988 | 0.069431 | 0.23822 | 0.999497 | 0.86803 | 0.999623 | 0 |
| CLN3 | 1201 A_24_P296424 | 1.36 | 0.043199 | 0.069433 | 0.609698 | 0.999497 | 0.494394 | 0.999623 | 0 |
| ANGPTL4 | 51129 A_23_P159325 | 1.8 | 0.043231 | 0.069433 | 0.562689 | 0.999497 | 0.654075 | 0.999623 | 0 |
| FUT4 | 2526 A_23_P12965 | 1.33 | 0.04319 | 0.069433 | 0.189847 | 0.999497 | 0.331627 | 0.999623 | 0 |
| ENPP2 | 5168 A_23_P94338 | 1.24 | 0.043185 | 0.069433 | 0.397435 | 0.999497 | 0.822373 | 0.999623 | 0 |
| BMPR1A | 657 A_24_P418717 | 1.28 | 0.043121 | 0.069433 | 0.941555 | 0.999497 | 0.637727 | 0.999623 | 0 |
| EI24 | 9538 A_24_P4661 | 1.39 | 0.043099 | 0.069433 | 0.592521 | 0.999497 | 0.708771 | 0.999623 | 0 |
| CROP | 51747 A_24_P382113 | -1.85 | 0.043511 | 0.069568 | 0.878013 | 0.999497 | 0.49499 | 0.999623 | 0 |
| SERPINA3 | 12 A_23_P162918 | 1.2 | 0.043506 | 0.069568 | 0.194155 | 0.999497 | 0.539888 | 0.999623 | 0 |
| EXOC4 | 60412 A_23_P135437 | 1.14 | 0.043431 | 0.069568 | 0.460005 | 0.999497 | 0.739296 | 0.999623 | 0 |
| PDCL3 | 79031 A_32_P157531 | -1.31 | 0.043597 | 0.069568 | 0.82953 | 0.999497 | 0.882052 | 0.999623 | 0 |
| CDC42SE2 | 56990 A_23_P430758 | 1.65 | 0.043592 | 0.069568 | 0.941825 | 0.999497 | 0.973747 | 0.999623 | 0 |
| TGFBR2 | 7048 A_23_P337242 | 1.32 | 0.043564 | 0.069568 | 0.445034 | 0.999497 | 0.962719 | 0.999623 | 0 |
| CRYAA | 1409 A_23_P306755 | 1.3 | 0.043526 | 0.069568 | 0.977503 | 0.999497 | 0.456865 | 0.999623 | 0 |
| ATL1 | 51062 A_23_P88351 | 1.33 | 0.043673 | 0.069624 | 0.350602 | 0.999497 | 0.46682 | 0.999623 | 0 |
| MZF1 | 7593 A_23_P130455 | 1.51 | 0.0439 | 0.06992 | 0.688516 | 0.999497 | 0.935398 | 0.999623 | 0 |

TABLE S7-continued

Significant differences between CR and CNR

| | | Fold-change CNR vs CR | Cytokine response | | Age: 60-65 yo vs 74+ yo | | Gender | | |
|---|---|---|---|---|---|---|---|---|---|
| | | | p-value | q-value | p-value | q-value | p-value | q-value | |
| FNDC3A | 22862 A_23_P25503 | -2.64 | 0.044282 | 0.070403 | 0.592107 | 0.999497 | 0.609437 | 0.999623 | 0 |
| CDC2L2 | 728642 A_24_P96709 | 1.55 | 0.044284 | 0.070403 | 0.861503 | 0.999497 | 0.991662 | 0.999623 | 0 |
| 3-Mar | 115123 A_23_P321511 | 1.32 | 0.044347 | 0.070438 | 0.293459 | 0.999497 | 0.650932 | 0.999623 | 0 |
| SIRPA | 140885 A_24_P259083 | 1.44 | 0.044492 | 0.07055 | 0.560109 | 0.999497 | 0.249875 | 0.999623 | 0 |
| PTPRF | 5792 A_24_P385313 | -1.32 | 0.0445 | 0.07055 | 0.454858 | 0.999497 | 0.764493 | 0.999623 | 0 |
| GSTP1 | 2950 A_23_P202658 | 1.39 | 0.044573 | 0.070602 | 0.828026 | 0.999497 | 0.13349 | 0.999623 | 1 |
| FKBP1A | 2280 A_32_P50522 | -1.53 | 0.044868 | 0.070777 | 0.65713 | 0.999497 | 0.745111 | 0.999623 | 0 |
| PCNA | 5111 A_23_P28886 | -1.51 | 0.045095 | 0.070777 | 0.728671 | 0.999497 | 0.361769 | 0.999623 | 1 |
| ATF2 | 1386 A_24_P246467 | 1.32 | 0.045028 | 0.070777 | 0.69581 | 0.999497 | 0.63401 | 0.999623 | 1 |
| MNT | 4335 A_24_P350969 | -1.72 | 0.045044 | 0.070777 | 0.382325 | 0.999497 | 0.327378 | 0.999623 | 0 |
| ATP5O | 539 A_23_P143474 | 1.31 | 0.044989 | 0.070777 | 0.171139 | 0.999497 | 0.592729 | 0.999623 | 1 |
| APIP | 51074 A_23_P2066 | -1.43 | 0.045078 | 0.070777 | 0.129824 | 0.999497 | 0.3636 | 0.999623 | 0 |
| CD36 | 948 A_23_P111583 | 1.41 | 0.044796 | 0.070777 | 0.969281 | 0.999497 | 0.152155 | 0.999623 | 0 |
| NME5 | 8382 A_23_P156402 | 1.3 | 0.045049 | 0.070777 | 0.500561 | 0.999497 | 0.34537 | 0.999623 | 0 |
| HCG18 | 414777 A_24_P567944 | 1.43 | 0.044934 | 0.070777 | 0.879112 | 0.999497 | 0.293233 | 0.999623 | 0 |
| MUC4 | 4585 A_24_P208825 | 1.63 | 0.044783 | 0.070777 | 0.742799 | 0.999497 | 0.495826 | 0.999623 | 0 |
| PDGFRL | 5157 A_23_P60146 | -1.44 | 0.045146 | 0.070794 | 0.615637 | 0.999497 | 0.330274 | 0.999623 | 0 |
| TOLLIP | 54472 A_24_P287189 | -1.71 | 0.045435 | 0.071067 | 0.933862 | 0.999497 | 0.453475 | 0.999623 | 0 |
| GNL1 | 2794 A_23_P145289 | 1.5 | 0.045377 | 0.071067 | 0.949038 | 0.999497 | 0.420492 | 0.999623 | 0 |
| DGCR8 | 54487 A_23_P211355 | 1.48 | 0.045444 | 0.071067 | 0.466895 | 0.999497 | 0.44656 | 0.999623 | 0 |
| PPFIBP1 | 8496 A_23_P373724 | -3.99 | 0.045722 | 0.071192 | 0.813694 | 0.999497 | 0.676853 | 0.999623 | 0 |
| TXN | 7295 A_24_P175519 | -1.35 | 0.045731 | 0.071192 | 0.527585 | 0.999497 | 0.140613 | 0.999623 | 1 |
| OPA1 | 4976 A_23_P211797 | 1.3 | 0.045702 | 0.071192 | 0.968662 | 0.999497 | 0.768005 | 0.999623 | 0 |
| SOCS1 | 8651 A_24_P48014 | 1.31 | 0.045645 | 0.071192 | 0.619718 | 0.999497 | 0.206638 | 0.999623 | 0 |
| ALG9 | 79796 A_32_P49188 | 1.62 | 0.045727 | 0.071192 | 0.255926 | 0.999497 | 0.353473 | 0.999623 | 2 |
| CUL5 | 8065 A_32_P134167 | 1.2 | 0.045806 | 0.071244 | 0.386454 | 0.999497 | 0.95481 | 0.999623 | 0 |
| IKBKAP | 8518 A_23_P169189 | -1.91 | 0.045952 | 0.071388 | 0.954821 | 0.999497 | 0.806443 | 0.999623 | 0 |
| DDX41 | 51428 A_23_P122116 | 1.31 | 0.045981 | 0.071388 | 0.843995 | 0.999497 | 0.810098 | 0.999623 | 0 |
| PIWIL2 | 55124 A_23_P253074 | 1.33 | 0.046063 | 0.071429 | 0.826224 | 0.999497 | 0.283979 | 0.999623 | 0 |
| COL6A1 | 1291 A_24_P515815 | 1.41 | 0.04609 | 0.071429 | 0.903557 | 0.999497 | 0.13481 | 0.999623 | 0 |
| PRKRIR | 5612 A_23_P203686 | 1.21 | 0.04619 | 0.07152 | 0.215995 | 0.999497 | 0.415878 | 0.999623 | 0 |
| ASGR1 | 432 A_23_P118722 | 1.4 | 0.046274 | 0.071585 | 0.328991 | 0.999497 | 0.511678 | 0.999623 | 0 |
| SIRPA | 140885 A_23_P210708 | 1.53 | 0.046507 | 0.071762 | 0.666027 | 0.999497 | 0.589137 | 0.999623 | 0 |
| SHFM1 | 7979 A_23_P42664 | -1.37 | 0.046459 | 0.071762 | 0.515968 | 0.999497 | 0.69132 | 0.999623 | 0 |
| PCDHGA3 | 56112 A_24_P334529 | 1.25 | 0.046513 | 0.071762 | 0.258594 | 0.999497 | 0.137665 | 0.999623 | 0 |
| SCYE1 | 9255 A_23_P121686 | -1.56 | 0.04672 | 0.071766 | 0.812198 | 0.999497 | 0.315334 | 0.999623 | 0 |
| MYC | 4609 A_24_P178011 | -1.59 | 0.046802 | 0.071766 | 0.977739 | 0.999497 | 0.296596 | 0.999623 | 1 |
| IL17RA | 23765 A_23_P17706 | 1.32 | 0.046815 | 0.071766 | 0.371759 | 0.999497 | 0.118861 | 0.999623 | 0 |
| PAGE1 | 8712 A_24_P314337 | 1.16 | 0.046785 | 0.071766 | 0.935663 | 0.999497 | 0.550923 | 0.999623 | 0 |
| ZAK | 51776 A_23_P318300 | -1.44 | 0.046667 | 0.071766 | 0.777675 | 0.999497 | 0.567119 | 0.999623 | 0 |
| CALM3 | 808 A_24_P219785 | 1.5 | 0.04675 | 0.071766 | 0.811511 | 0.999497 | 0.194461 | 0.999623 | 0 |
| CD55 | 1604 A_24_P188377 | -1.26 | 0.046892 | 0.071766 | 0.259449 | 0.999497 | 0.884425 | 0.999623 | 0 |
| H2AFX | 3014 A_24_P38895 | 1.36 | 0.046959 | 0.071766 | 0.095474 | 0.999497 | 0.293479 | 0.999623 | 1 |
| CP110 | 9738 A_23_P26501 | -1.72 | 0.04697 | 0.071766 | 0.549938 | 0.999497 | 0.930941 | 0.999623 | 0 |
| ITGA9 | 3680 A_24_P607904 | 1.31 | 0.046745 | 0.071766 | 0.221123 | 0.999497 | 0.285706 | 0.999623 | 0 |
| DNM2 | 1785 A_23_P407074 | 1.61 | 0.046974 | 0.071766 | 0.952938 | 0.999497 | 0.614731 | 0.999623 | 0 |
| CD96 | 10225 A_23_P44154 | 1.25 | 0.047027 | 0.071784 | 0.20498 | 0.999497 | 0.086648 | 0.999623 | 0 |
| TNIP2 | 79155 A_23_P258418 | 1.45 | 0.047183 | 0.071939 | 0.655112 | 0.999497 | 0.999335 | 0.999623 | 0 |
| ALG1 | 56052 A_32_P169131 | 1.3 | 0.047213 | 0.071939 | 0.572971 | 0.999497 | 0.61471 | 0.999623 | 0 |
| SCYE1 | 9255 A_24_P354523 | -1.68 | 0.047277 | 0.071973 | 0.766268 | 0.999497 | 0.57458 | 0.999623 | 0 |
| MCL1 | 4170 A_24_P336759 | -2.16 | 0.047418 | 0.072053 | 0.889888 | 0.999497 | 0.381535 | 0.999623 | 0 |
| PRKAR1A | 5573 A_24_P356592 | -1.64 | 0.047401 | 0.072053 | 0.511529 | 0.999497 | 0.177114 | 0.999623 | 0 |
| IGF2BP3 | 10643 A_23_P19987 | 1.26 | 0.047454 | 0.072053 | 0.591045 | 0.999497 | 0.864679 | 0.999623 | 0 |
| MLH1 | 4292 A_23_P69058 | -1.63 | 0.047976 | 0.072653 | 0.630992 | 0.999497 | 0.122333 | 0.999623 | 1 |
| FLRT3 | 23767 A_23_P166109 | 1.37 | 0.047953 | 0.072653 | 0.838091 | 0.999497 | 0.790526 | 0.999623 | 0 |
| PBX1 | 5087 A_23_P62953 | 1.33 | 0.047962 | 0.072653 | 0.359381 | 0.999497 | 0.59874 | 0.999623 | 0 |
| RELA | 5970 A_23_P104689 | 1.49 | 0.048214 | 0.072949 | 0.73911 | 0.999497 | 0.263018 | 0.999623 | 1 |
| FOXC1 | 2296 A_32_P205110 | -1.56 | 0.048476 | 0.073281 | 0.387431 | 0.999497 | 0.900154 | 0.999623 | 0 |
| MLLT1 | 4298 A_23_P153827 | 1.52 | 0.048922 | 0.073693 | 0.648386 | 0.999497 | 0.211593 | 0.999623 | 0 |
| PDIA3 | 2923 A_32_P63182 | -1.79 | 0.049133 | 0.073693 | 0.20452 | 0.999497 | 0.609904 | 0.999623 | 0 |
| CYCS | 54205 A_32_P174083 | 1.48 | 0.049129 | 0.073693 | 0.639667 | 0.999497 | 0.26236 | 0.999623 | 0 |
| NFE2L2 | 4780 A_24_P936444 | 1.32 | 0.049107 | 0.073693 | 0.266244 | 0.999497 | 0.239128 | 0.999623 | 0 |
| HTATSF1 | 27336 A_23_P45345 | -1.49 | 0.048971 | 0.073693 | 0.359184 | 0.999497 | 0.214235 | 0.999623 | 0 |
| TRIB3 | 57761 A_23_P210690 | 1.48 | 0.048901 | 0.073693 | 0.970463 | 0.999497 | 0.565315 | 0.999623 | 0 |
| FOXP1 | 27086 A_23_P155257 | -1.19 | 0.048856 | 0.073693 | 0.732264 | 0.999497 | 0.857483 | 0.999623 | 0 |
| ADAM11 | 4185 A_23_P502158 | -1.3 | 0.049132 | 0.073693 | 0.710373 | 0.999497 | 0.858642 | 0.999623 | 0 |
| CCL28 | 56477 A_23_P503072 | -1.49 | 0.04885 | 0.073693 | 0.585233 | 0.999497 | 0.981947 | 0.999623 | 0 |
| PPM1F | 9647 A_24_P125894 | 1.54 | 0.049182 | 0.073702 | 0.605032 | 0.999497 | 0.477826 | 0.999623 | 0 |
| TIMP3 | 7078 A_23_P399078 | 1.64 | 0.049266 | 0.073763 | 0.465532 | 0.999497 | 0.707186 | 0.999623 | 0 |
| F7 | 2155 A_23_P117298 | 1.39 | 0.049347 | 0.073821 | 0.59254 | 0.999497 | 0.236397 | 0.999623 | 0 |
| COPG | 22820 A_23_P44617 | 1.24 | 0.049474 | 0.073946 | 0.858751 | 0.999497 | 0.54968 | 0.999623 | 0 |
| PDIA3 | 2923 A_24_P101201 | -1.31 | 0.049589 | 0.074054 | 0.522978 | 0.999497 | 0.684458 | 0.999623 | 0 |

TABLE S7-continued

Significant differences between CR and CNR

| | | Fold-change CNR vs CR | Cytokine response | | Age: 60-65 yo vs 74+ yo | | Gender | | |
|---|---|---|---|---|---|---|---|---|---|
| | | | p-value | q-value | p-value | q-value | p-value | q-value | |
| PTPN11 | 5781 A_23_P99027 | 1.46 | 0.049759 | 0.074116 | 0.711278 | 0.999497 | 0.902129 | 0.999623 | 1 |
| CX3CL1 | 6376 A_24_P390495 | 1.58 | 0.049724 | 0.074116 | 0.934763 | 0.999497 | 0.728325 | 0.999623 | 0 |
| IL6ST | 3572 A_23_P502470 | 1.36 | 0.049726 | 0.074116 | 0.821297 | 0.999497 | 0.75394 | 0.999623 | 0 |
| MPZL3 | 196264 A_24_P270033 | -1.49 | 0.049947 | 0.074236 | 0.804556 | 0.999497 | 0.184604 | 0.999623 | 0 |
| PCDHB8 | 56128 A_23_P41599 | 1.33 | 0.049969 | 0.074236 | 0.987622 | 0.999497 | 0.506273 | 0.999623 | 0 |
| DLG5 | 9231 A_24_P129632 | -1.79 | 0.0499 | 0.074236 | 0.744695 | 0.999497 | 0.188498 | 0.999623 | 0 |
| CDH23 | 64072 A_24_P943180 | 1.53 | 0.05054 | 0.074955 | 0.938805 | 0.999497 | 0.522084 | 0.999623 | 0 |
| BCL2 | 596 A_23_P352266 | -1.75 | 0.050506 | 0.074955 | 0.490873 | 0.999497 | 0.477736 | 0.999623 | 1 |
| ICA1 | 3382 A_24_P372012 | 1.45 | 0.050587 | 0.07496 | 0.828191 | 0.999497 | 0.836975 | 0.999623 | 0 |
| ITGB3BP | 23421 A_23_P23765 | 1.35 | 0.050776 | 0.075175 | 0.500913 | 0.999497 | 0.901291 | 0.999623 | 0 |
| MAPK11 | 5600 A_23_P502274 | 1.6 | 0.050917 | 0.075319 | 0.626765 | 0.999497 | 0.385447 | 0.999623 | 0 |
| CDKN2C | 1031 A_23_P85460 | 1.33 | 0.051088 | 0.075378 | 0.50526 | 0.999497 | 0.343098 | 0.999623 | 0 |
| DOCK4 | 9732 A_23_P59637 | -1.98 | 0.051014 | 0.075378 | 0.929724 | 0.999497 | 0.373991 | 0.999623 | 0 |
| KIAA0368 | 23392 A_23_P146431 | -1.4 | 0.051049 | 0.075378 | 0.47502 | 0.999497 | 0.675111 | 0.999623 | 0 |
| CLN3 | 1201 A_32_P53713 | -1.47 | 0.051216 | 0.075502 | 0.916349 | 0.999497 | 0.984168 | 0.999623 | 0 |
| ADAM15 | 8751 A_23_P159227 | 1.45 | 0.051276 | 0.075526 | 0.519439 | 0.999497 | 0.246545 | 0.999623 | 0 |
| EDN1 | 1906 A_23_P214821 | 1.37 | 0.051411 | 0.075661 | 0.803693 | 0.999497 | 0.664785 | 0.999623 | 0 |
| FCGBP | 8857 A_32_P23960 | -1.73 | 0.051757 | 0.075976 | 0.704005 | 0.999497 | 0.552795 | 0.999623 | 0 |
| BICD2 | 23299 A_24_P419120 | 1.17 | 0.05175 | 0.075976 | 0.510926 | 0.999497 | 0.715863 | 0.999623 | 0 |
| IRF7 | 3665 A_24_P118892 | 1.39 | 0.051675 | 0.075976 | 0.818667 | 0.999497 | 0.179341 | 0.999623 | 0 |
| NOXA1 | 10811 A_23_P254353 | 1.56 | 0.051885 | 0.076078 | 0.936563 | 0.999497 | 0.606702 | 0.999623 | 0 |
| GALNTL1 | 57452 A_23_P76749 | 1.58 | 0.05192 | 0.076078 | 0.480342 | 0.999497 | 0.736755 | 0.999623 | 0 |
| BBS4 | 585 A_24_P176284 | 1.31 | 0.051959 | 0.076078 | 0.993054 | 0.999497 | 0.954196 | 0.999623 | 0 |
| FOXO1 | 2308 A_23_P151426 | -1.21 | 0.052208 | 0.076378 | 0.227461 | 0.999497 | 0.914728 | 0.999623 | 1 |
| PPP1CA | 5499 A_23_P434710 | 1.44 | 0.052271 | 0.076404 | 0.988265 | 0.999497 | 0.198388 | 0.999623 | 1 |
| LIN7C | 55327 A_24_P107257 | 1.28 | 0.052533 | 0.076625 | 0.498493 | 0.999497 | 0.671202 | 0.999623 | 0 |
| ADRM1 | 11047 A_24_P305597 | 1.6 | 0.052555 | 0.076625 | 0.945303 | 0.999497 | 0.776911 | 0.999623 | 0 |
| SRF | 6722 A_24_P346277 | 1.3 | 0.05255 | 0.076625 | 0.527336 | 0.999497 | 0.744148 | 0.999623 | 0 |
| SSX2IP | 117178 A_23_P201376 | -1.6 | 0.052655 | 0.076657 | 0.974178 | 0.999497 | 0.789061 | 0.999623 | 0 |
| LAX1 | 54900 A_24_P291278 | -1.95 | 0.052666 | 0.076657 | 0.487883 | 0.999497 | 0.422744 | 0.999623 | 0 |
| ZNF503 | 84858 A_23_P202484 | 1.44 | 0.052814 | 0.076807 | 0.728954 | 0.999497 | 0.466738 | 0.999623 | 2 |
| PTK7 | 5754 A_24_P320545 | 1.35 | 0.052966 | 0.076963 | 0.910405 | 0.999497 | 0.232492 | 0.999623 | 0 |
| RAB5A | 5868 A_24_P208809 | -1.23 | 0.053024 | 0.076982 | 0.566482 | 0.999497 | 0.295912 | 0.999623 | 0 |
| CYBB | 1536 A_24_P365767 | -1.79 | 0.053283 | 0.077294 | 0.688119 | 0.999497 | 0.312165 | 0.999623 | 0 |
| YARS | 8565 A_23_P379550 | 1.74 | 0.054031 | 0.077326 | 0.821487 | 0.999497 | 0.494963 | 0.999623 | 0 |
| MUC5AC | 4586 A_24_P935054 | 1.94 | 0.05393 | 0.077326 | 0.232507 | 0.999497 | 0.2196 | 0.999623 | 0 |
| CNTROB | 116840 A_23_P9761 | 1.66 | 0.05389 | 0.077326 | 0.91235 | 0.999497 | 0.439556 | 0.999623 | 0 |
| PHF17 | 79960 A_23_P167264 | 1.34 | 0.053962 | 0.077326 | 0.494722 | 0.999497 | 0.250703 | 0.999623 | 0 |
| ADRM1 | 11047 A_23_P68665 | 1.59 | 0.053526 | 0.077326 | 0.70912 | 0.999497 | 0.521504 | 0.999623 | 0 |
| C2CD2L | 9854 A_23_P353056 | 1.43 | 0.053976 | 0.077326 | 0.427937 | 0.999497 | 0.522298 | 0.999623 | 0 |
| LAMP2 | 3920 A_23_P416608 | -1.41 | 0.054068 | 0.077326 | 0.759732 | 0.999497 | 0.672658 | 0.999623 | 0 |
| SPON2 | 10417 A_23_P121533 | 1.35 | 0.053374 | 0.077326 | 0.893937 | 0.999497 | 0.790237 | 0.999623 | 0 |
| ING4 | 51147 A_23_P48070 | 1.56 | 0.054062 | 0.077326 | 0.602712 | 0.999497 | 0.635273 | 0.999623 | 0 |
| CXCL16 | 58191 A_23_P38505 | -1.2 | 0.053583 | 0.077326 | 0.945917 | 0.999497 | 0.989261 | 0.999623 | 0 |
| AMICA1 | 120425 A_23_P1759 | -2.06 | 0.053736 | 0.077326 | 0.090903 | 0.999497 | 0.60496 | 0.999623 | 0 |
| NPHP1 | 4867 A_24_P88801 | 1.27 | 0.053724 | 0.077326 | 0.545708 | 0.999497 | 0.132466 | 0.999623 | 0 |
| BUB1B | 701 A_23_P163481 | 1.48 | 0.053759 | 0.077326 | 0.811355 | 0.999497 | 0.876344 | 0.999623 | 1 |
| SCARB1 | 949 A_23_P369201 | 1.26 | 0.053636 | 0.077326 | 0.781537 | 0.999497 | 0.630622 | 0.999623 | 0 |
| SMAD2 | 4087 A_24_P202527 | 1.13 | 0.054062 | 0.077326 | 0.947205 | 0.999497 | 0.917569 | 0.999623 | 0 |
| RAD52 | 5893 A_23_P64990 | 1.28 | 0.053548 | 0.077326 | 0.876668 | 0.999497 | 0.263014 | 0.999623 | 1 |
| CD151 | 977 A_23_P95470 | 1.48 | 0.053984 | 0.077326 | 0.942078 | 0.999497 | 0.176278 | 0.999623 | 0 |
| DERL1 | 79139 A_24_P175347 | -1.59 | 0.054229 | 0.077428 | 0.925115 | 0.999497 | 0.380825 | 0.999623 | 0 |
| AEN | 64782 A_32_P85230 | 1.39 | 0.054207 | 0.077428 | 0.185031 | 0.999497 | 0.447625 | 0.999623 | 0 |
| ZNF675 | 171392 A_23_P339687 | -3.09 | 0.054631 | 0.077937 | 0.755138 | 0.999497 | 0.526513 | 0.999623 | 0 |
| EZR | 7430 A_32_P127492 | -1.96 | 0.054723 | 0.078004 | 0.542415 | 0.999497 | 0.088239 | 0.999623 | 0 |
| EDN2 | 1907 A_23_P312150 | 1.38 | 0.054794 | 0.07804 | 0.31998 | 0.999497 | 0.750237 | 0.999623 | 0 |
| TRAF5 | 7188 A_23_P201731 | 1.2 | 0.054863 | 0.078075 | 0.198244 | 0.999497 | 0.688574 | 0.999623 | 0 |
| CYCS | 54205 A_24_P376556 | -1.96 | 0.054981 | 0.078125 | 0.303888 | 0.999497 | 0.309641 | 0.999623 | 0 |
| SIGIRR | 59307 A_23_P84344 | 1.36 | 0.054989 | 0.078125 | 0.905737 | 0.999497 | 0.71141 | 0.999623 | 0 |
| PICALM | 8301 A_23_P147995 | -1.64 | 0.055061 | 0.078162 | 0.981661 | 0.999497 | 0.451614 | 0.999623 | 0 |
| C8G | 733 A_23_P20713 | 1.72 | 0.055299 | 0.078435 | 0.800602 | 0.999497 | 0.265125 | 0.999623 | 0 |
| CDH3 | 1001 A_23_P49155 | 1.26 | 0.055548 | 0.078724 | 0.612362 | 0.999497 | 0.787921 | 0.999623 | 0 |
| DNAJB6 | 10049 A_23_P215283 | -2.4 | 0.055707 | 0.078884 | 0.803694 | 0.999497 | 0.195436 | 0.999623 | 0 |
| MAPT | 4137 A_23_P207699 | 1.28 | 0.05579 | 0.078937 | 0.668231 | 0.999497 | 0.577542 | 0.999623 | 1 |
| NBN | 4683 A_24_P278126 | -1.86 | 0.055899 | 0.079026 | 0.690918 | 0.999497 | 0.308075 | 0.999623 | 1 |
| CLDN10 | 9071 A_23_P48350 | 1.24 | 0.05598 | 0.079044 | 0.763734 | 0.999497 | 0.247918 | 0.999623 | 0 |
| PSMC6 | 5706 A_23_P128930 | -1.59 | 0.056003 | 0.079044 | 0.58957 | 0.999497 | 0.683695 | 0.999623 | 0 |
| C1D | 10438 A_23_P67992 | -1.7 | 0.05632 | 0.079426 | 0.541511 | 0.999497 | 0.552801 | 0.999623 | 0 |
| PKP4 | 8502 A_23_P16992 | -1.81 | 0.056369 | 0.07943 | 0.953047 | 0.999497 | 0.552642 | 0.999623 | 0 |
| CREB1 | 1385 A_23_P79231 | -1.47 | 0.056448 | 0.079477 | 0.64991 | 0.999497 | 0.370657 | 0.999623 | 1 |
| SAP30BP | 29115 A_24_P304987 | 1.43 | 0.056551 | 0.079556 | 0.611487 | 0.999497 | 0.593313 | 0.999623 | 0 |
| KCNIP3 | 30818 A_23_P356004 | -1.38 | 0.056702 | 0.079703 | 0.982035 | 0.999497 | 0.844064 | 0.999623 | 0 |

TABLE S7-continued

Significant differences between CR and CNR

| | | Fold-change CNR vs CR | Cytokine response | | Age: 60-65 yo vs 74+ yo | | Gender | | |
|---|---|---|---|---|---|---|---|---|---|
| | | | p-value | q-value | p-value | q-value | p-value | q-value | |
| FCGBP | 8857 A_23_P21495 | 1.64 | 0.056862 | 0.079864 | 0.636412 | 0.999497 | 0.219441 | 0.999623 | 0 |
| RNF144B | 255488 A_24_P406060 | −1.78 | 0.056909 | 0.079864 | 0.865156 | 0.999497 | 0.541439 | 0.999623 | 0 |
| SIX4 | 51804 A_32_P204205 | −1.99 | 0.057173 | 0.080039 | 0.561118 | 0.999497 | 0.36626 | 0.999623 | 0 |
| PACSIN1 | 29993 A_23_P258088 | 1.39 | 0.057154 | 0.080039 | 0.242498 | 0.999497 | 0.709506 | 0.999623 | 0 |
| MYEF2 | 50804 A_23_P77079 | −1.26 | 0.057136 | 0.080039 | 0.978938 | 0.999497 | 0.870922 | 0.999623 | 0 |
| RAB4A | 5867 A_23_P369919 | −1.43 | 0.057222 | 0.080043 | 0.989662 | 0.999497 | 0.391131 | 0.999623 | 0 |
| FKBP15 | 23307 A_32_P224149 | 1.33 | 0.057299 | 0.080086 | 0.687 | 0.999497 | 0.103788 | 0.999623 | 0 |
| MUC4 | 4585 A_24_P239183 | −2.6 | 0.057632 | 0.080486 | 0.383032 | 0.999497 | 0.243007 | 0.999623 | 0 |
| PAK2 | 5062 A_32_P104075 | 1.59 | 0.057814 | 0.080675 | 0.584236 | 0.999497 | 0.717854 | 0.999623 | 0 |
| NXT2 | 55916 A_24_P91916 | −1.64 | 0.058072 | 0.080969 | 0.881595 | 0.999497 | 0.390267 | 0.999623 | 2 |
| STON2 | 85439 A_23_P309837 | 1.7 | 0.058194 | 0.081008 | 0.436436 | 0.999497 | 0.02588 | 0.999623 | 0 |
| LENG8 | 114823 A_24_P40055 | −1.3 | 0.05815 | 0.081008 | 0.933947 | 0.999497 | 0.932755 | 0.999623 | 0 |
| PHLDA2 | 7262 A_23_P47614 | −1.69 | 0.058265 | 0.081042 | 0.397269 | 0.999497 | 0.248374 | 0.999623 | 0 |
| NR3C1 | 2908 A_23_P214059 | 1.3 | 0.058418 | 0.081189 | 0.093748 | 0.999497 | 0.896398 | 0.999623 | 1 |
| RYR2 | 6262 A_23_P137797 | 1.16 | 0.058594 | 0.08136 | 0.398575 | 0.999497 | 0.137126 | 0.999623 | 0 |
| LOC442421 | 442421 A_23_P43549 | 1.34 | 0.058636 | 0.08136 | 0.716192 | 0.999497 | 0.103469 | 0.999623 | 0 |
| CASP2 | 835 A_24_P269398 | 1.3 | 0.058887 | 0.081643 | 0.97231 | 0.999497 | 0.839865 | 0.999623 | 0 |
| GAPVD1 | 26130 A_23_P372660 | −2.47 | 0.059076 | 0.08184 | 0.592779 | 0.999497 | 0.281485 | 0.999623 | 0 |
| NP | 4860 A_23_P140256 | 1.38 | 0.059154 | 0.081881 | 0.590482 | 0.999497 | 0.952225 | 0.999623 | 0 |
| TPT1 | 7178 A_24_P179351 | −1.49 | 0.059233 | 0.081905 | 0.643797 | 0.999497 | 0.754788 | 0.999623 | 0 |
| PSMD1 | 5707 A_23_P209740 | −1.2 | 0.059266 | 0.081905 | 0.064632 | 0.999497 | 0.952043 | 0.999623 | 0 |
| IGF1 | 3479 A_24_P304419 | 1.5 | 0.059535 | 0.082145 | 0.508421 | 0.999497 | 0.954962 | 0.999623 | 1 |
| GPR56 | 9289 A_23_P206284 | 1.55 | 0.059494 | 0.082145 | 0.734577 | 0.999497 | 0.65396 | 0.999623 | 0 |
| TLR6 | 10333 A_23_P256561 | 1.41 | 0.059765 | 0.082396 | 0.723133 | 0.999497 | 0.717354 | 0.999623 | 0 |
| BUB3 | 9184 A_23_P320658 | −2.01 | 0.059886 | 0.082497 | 0.385659 | 0.999497 | 0.55939 | 0.999623 | 1 |
| UBB | 7314 A_23_P27215 | 1.68 | 0.060013 | 0.0825 | 0.293768 | 0.999497 | 0.480511 | 0.999623 | 1 |
| NID1 | 4811 A_23_P200928 | −1.34 | 0.060032 | 0.0825 | 0.181672 | 0.999497 | 0.654073 | 0.999623 | 0 |
| SEMA6A | 57556 A_23_P7752 | 1.38 | 0.059936 | 0.0825 | 0.558867 | 0.999497 | 0.473839 | 0.999623 | 0 |
| HIPK2 | 28996 A_23_P169756 | 2.3 | 0.060245 | 0.08259 | 0.794381 | 0.999497 | 0.739402 | 0.999623 | 0 |
| PPIL3 | 53938 A_23_P28213 | 1.27 | 0.060286 | 0.08259 | 0.262102 | 0.999497 | 0.165681 | 0.999623 | 0 |
| ROCK1 | 6093 A_24_P538403 | −1.71 | 0.060289 | 0.08259 | 0.782182 | 0.999497 | 0.481754 | 0.999623 | 0 |
| VNN1 | 8876 A_23_P255345 | 1.39 | 0.060223 | 0.08259 | 0.364005 | 0.999497 | 0.722212 | 0.999623 | 0 |
| BMP7 | 655 A_24_P91566 | 1.62 | 0.060355 | 0.082615 | 0.597849 | 0.999497 | 0.77366 | 0.999623 | 0 |
| UNC13B | 10497 A_23_P253395 | 1.45 | 0.060475 | 0.082714 | 0.152818 | 0.999497 | 0.241637 | 0.999623 | 0 |
| PATL1 | 219988 A_23_P373079 | 1.32 | 0.060673 | 0.082878 | 0.476153 | 0.999497 | 0.53564 | 0.999623 | 0 |
| NME6 | 10201 A_23_P313961 | 1.5 | 0.060756 | 0.082878 | 0.927312 | 0.999497 | 0.468945 | 0.999623 | 0 |
| HSP90B1 | 7184 A_24_P150361 | −1.94 | 0.060787 | 0.082878 | 0.81706 | 0.999497 | 0.188363 | 0.999623 | 0 |
| B3GNT5 | 84002 A_23_P18372 | −1.28 | 0.060787 | 0.082878 | 0.996076 | 0.999497 | 0.565651 | 0.999623 | 0 |
| PVRL1 | 5818 A_23_P76034 | 1.28 | 0.060875 | 0.082932 | 0.832488 | 0.999497 | 0.755851 | 0.999623 | 0 |
| SFRP1 | 6422 A_23_P10121 | 1.45 | 0.060928 | 0.082938 | 0.3416 | 0.999497 | 0.678176 | 0.999623 | 0 |
| IGDCC3 | 9543 A_23_P3274 | 1.36 | 0.061027 | 0.082952 | 0.477997 | 0.999497 | 0.145097 | 0.999623 | 0 |
| CTSZ | 1522 A_23_P40240 | −1.29 | 0.061034 | 0.082952 | 0.319291 | 0.999497 | 0.295555 | 0.999623 | 0 |
| THBS3 | 7059 A_23_P201047 | 1.32 | 0.061087 | 0.082958 | 0.976554 | 0.999497 | 0.443927 | 0.999623 | 0 |
| MYL10 | 93408 A_23_P393015 | 1.35 | 0.061208 | 0.082992 | 0.534713 | 0.999497 | 0.329238 | 0.999623 | 0 |
| ITGB8 | 3696 A_23_P123060 | 1.23 | 0.061199 | 0.082992 | 0.478355 | 0.999497 | 0.376422 | 0.999623 | 0 |
| PVR | 5817 A_32_P72110 | −1.43 | 0.061456 | 0.083215 | 0.957821 | 0.999497 | 0.265836 | 0.999623 | 0 |
| METTL1 | 4234 A_23_P47788 | 1.47 | 0.06147 | 0.083215 | 0.3862 | 0.999497 | 0.508648 | 0.999623 | 0 |
| HES1 | 3280 A_24_P938293 | −1.36 | 0.061548 | 0.083255 | 0.295761 | 0.999497 | 0.529289 | 0.999623 | 0 |
| TBRG4 | 9238 A_23_P215658 | 1.25 | 0.061633 | 0.083262 | 0.36624 | 0.999497 | 0.981103 | 0.999623 | 0 |
| FLJ23834 | 222256 A_32_P197942 | 1.3 | 0.061649 | 0.083262 | 0.313687 | 0.999497 | 0.887795 | 0.999623 | 0 |
| DGCR6L | 85359 A_23_P143569 | 1.39 | 0.061797 | 0.083397 | 0.412568 | 0.999497 | 0.314466 | 0.999623 | 0 |
| ICAM1 | 3383 A_23_P153320 | 1.31 | 0.062045 | 0.083404 | 0.680372 | 0.999497 | 0.634968 | 0.999623 | 0 |
| STAT2 | 6773 A_23_P76090 | 1.28 | 0.062019 | 0.083404 | 0.976264 | 0.999497 | 0.907148 | 0.999623 | 0 |
| SLC1A6 | 6511 A_24_P179467 | 1.47 | 0.061969 | 0.083404 | 0.598053 | 0.999497 | 0.712889 | 0.999623 | 0 |
| APOC3 | 345 A_23_P203183 | 1.44 | 0.061899 | 0.083404 | 0.929606 | 0.999497 | 0.205063 | 0.999623 | 1 |
| ERCC3 | 2071 A_23_P5325 | 1.16 | 0.061899 | 0.083404 | 0.959732 | 0.999497 | 0.917013 | 0.999623 | 1 |
| UNC13D | 201294 A_24_P53215 | 1.55 | 0.062123 | 0.083445 | 0.778546 | 0.999497 | 0.769676 | 0.999623 | 0 |
| POMP | 51371 A_23_P65254 | −1.39 | 0.062428 | 0.083789 | 0.441242 | 0.999497 | 0.372817 | 0.999623 | 0 |
| COL14A1 | 7373 A_24_P254789 | −2.11 | 0.062566 | 0.083863 | 0.33844 | 0.999497 | 0.744663 | 0.999623 | 0 |
| PSME3 | 10197 A_24_P352864 | −2.48 | 0.06258 | 0.083863 | 0.322004 | 0.999497 | 0.898924 | 0.999623 | 0 |
| LAMC1 | 3915 A_23_P201628 | −1.23 | 0.063032 | 0.084271 | 0.409845 | 0.999497 | 0.326379 | 0.999623 | 0 |
| IFI27 | 3429 A_24_P270460 | −2.16 | 0.062994 | 0.084271 | 0.774557 | 0.999497 | 0.043282 | 0.999623 | 0 |
| VCP | 7415 A_32_P144619 | 1.27 | 0.063002 | 0.084271 | 0.63139 | 0.999497 | 0.160201 | 0.999623 | 1 |
| HLA-E | 3133 A_23_P30848 | 1.61 | 0.063098 | 0.084294 | 0.998624 | 0.999497 | 0.63157 | 0.999623 | 0 |
| PTPRH | 5794 A_23_P101642 | 1.69 | 0.06328 | 0.084386 | 0.984408 | 0.999497 | 0.956971 | 0.999623 | 0 |
| ID2 | 3398 A_32_P69368 | −1.69 | 0.06346 | 0.084386 | 0.430629 | 0.999497 | 0.797506 | 0.999623 | 0 |
| THBS1 | 7057 A_32_P17182 | −1.28 | 0.063461 | 0.084386 | 0.485432 | 0.999497 | 0.565239 | 0.999623 | 0 |
| HFE | 3077 A_23_P342009 | 1.58 | 0.063337 | 0.084386 | 0.236346 | 0.999497 | 0.053636 | 0.999623 | 0 |
| ALCAM | 214 A_32_P74643 | 1.48 | 0.063406 | 0.084386 | 0.964084 | 0.999497 | 0.207685 | 0.999623 | 0 |
| RALA | 5898 A_23_P168479 | −1.86 | 0.063278 | 0.084386 | 0.10191 | 0.999497 | 0.298542 | 0.999623 | 0 |
| PPP1R13L | 10848 A_23_P119095 | 1.55 | 0.063529 | 0.084412 | 0.731581 | 0.999497 | 0.521979 | 0.999623 | 0 |
| C1QTNF3 | 114899 A_23_P122068 | −1.4 | 0.063721 | 0.084601 | 0.451521 | 0.999497 | 0.858492 | 0.999623 | 0 |

TABLE S7-continued

Significant differences between CR and CNR

| | | Fold-change CNR vs CR | Cytokine response | | Age: 60-65 yo vs 74+ yo | | Gender | | |
|---|---|---|---|---|---|---|---|---|---|
| | | | p-value | q-value | p-value | q-value | p-value | q-value | |
| ITGA1 | 3672 A_23_P256334 | -1.17 | 0.063888 | 0.084698 | 0.876454 | 0.999497 | 0.578364 | 0.999623 | 0 |
| SEMA3A | 10371 A_24_P192301 | -1.96 | 0.063916 | 0.084698 | 0.979359 | 0.999497 | 0.515413 | 0.999623 | 0 |
| HMGB1 | 3146 A_23_P99985 | -1.55 | 0.063941 | 0.084698 | 0.658136 | 0.999497 | 0.792064 | 0.999623 | 1 |
| TRIM35 | 23087 A_23_P502553 | 1.3 | 0.064022 | 0.084703 | 0.303103 | 0.999497 | 0.421854 | 0.999623 | 0 |
| MAPK13 | 5603 A_23_P145376 | 1.47 | 0.064043 | 0.084703 | 0.420345 | 0.999497 | 0.464172 | 0.999623 | 0 |
| CDKN1B | 1027 A_24_P81841 | -1.86 | 0.064135 | 0.084759 | 0.907395 | 0.999497 | 0.135679 | 0.999623 | 0 |
| CTSS | 1520 A_24_P242646 | -3.58 | 0.064236 | 0.084829 | 0.803693 | 0.999497 | 0.585641 | 0.999623 | 0 |
| BIN1 | 274 A_24_P156993 | 1.66 | 0.0643 | 0.084847 | 0.573023 | 0.999497 | 0.6276 | 0.999623 | 0 |
| TNFRSF18 | 8784 A_24_P411121 | 1.96 | 0.064504 | 0.084921 | 0.420216 | 0.999497 | 0.762135 | 0.999623 | 0 |
| RAPGEF3 | 10411 A_32_P393316 | -1.46 | 0.064454 | 0.084921 | 0.423967 | 0.999497 | 0.871848 | 0.999623 | 0 |
| GPR135 | 64582 A_23_P205575 | 1.14 | 0.064458 | 0.084921 | 0.336918 | 0.999497 | 0.45434 | 0.999623 | 0 |
| RAD51 | 5888 A_23_P88731 | 2.16 | 0.064646 | 0.085043 | 0.74582 | 0.999497 | 0.723942 | 0.999623 | 1 |
| CLN3 | 1201 A_23_P88971 | 1.65 | 0.064885 | 0.085293 | 0.377334 | 0.999497 | 0.726209 | 0.999623 | 0 |
| CASP10 | 843 A_23_P209408 | 1.27 | 0.06517 | 0.085602 | 0.274417 | 0.999497 | 0.294492 | 0.999623 | 0 |
| VCL | 7414 A_24_P47182 | -1.74 | 0.065316 | 0.085729 | 0.173592 | 0.999497 | 0.637623 | 0.999623 | 0 |
| HLA-DMA | 3108 A_24_P50245 | 1.37 | 0.065525 | 0.085741 | 0.769045 | 0.999497 | 0.176254 | 0.999623 | 0 |
| CDH9 | 1007 A_23_P92999 | 1.22 | 0.065399 | 0.085741 | 0.401308 | 0.999497 | 0.74778 | 0.999623 | 0 |
| ABCA7 | 10347 A_23_P39481 | 1.5 | 0.065482 | 0.085741 | 0.349054 | 0.999497 | 0.300378 | 0.999623 | 0 |
| CUL3 | 8452 A_24_P140030 | 1.21 | 0.06552 | 0.085741 | 0.194174 | 0.999497 | 0.186183 | 0.999623 | 0 |
| IRF2BP1 | 26145 A_23_P90211 | 1.56 | 0.065592 | 0.085764 | 0.530011 | 0.999497 | 0.171747 | 0.999623 | 0 |
| PVRL4 | 81607 A_23_P46441 | 1.31 | 0.065907 | 0.085791 | 0.898216 | 0.999497 | 0.289891 | 0.999623 | 0 |
| SEMA5A | 9037 A_24_P912799 | -1.43 | 0.065961 | 0.085791 | 0.086627 | 0.999497 | 0.657199 | 0.999623 | 0 |
| NFKBIZ | 64332 A_23_P212089 | 1.18 | 0.065715 | 0.085791 | 0.732808 | 0.999497 | 0.450879 | 0.999623 | 0 |
| PML | 5371 A_23_P334664 | 1.49 | 0.065847 | 0.085791 | 0.232513 | 0.999497 | 0.950817 | 0.999623 | 1 |
| LGALS1 | 3956 A_23_P166459 | 1.2 | 0.065827 | 0.085791 | 0.452585 | 0.999497 | 0.43499 | 0.999623 | 0 |
| XRCC3 | 7517 A_23_P48470 | 1.42 | 0.065881 | 0.085791 | 0.812737 | 0.999497 | 0.280094 | 0.999623 | 0 |
| VPS45 | 11311 A_24_P362394 | 1.26 | 0.065935 | 0.085791 | 0.760386 | 0.999497 | 0.366523 | 0.999623 | 0 |
| CD99 | 4267 A_23_P217510 | 1.37 | 0.066036 | 0.085824 | 0.415802 | 0.999497 | 0.877285 | 0.999623 | 0 |
| NFATC4 | 4776 A_23_P140394 | 1.56 | 0.066216 | 0.085933 | 0.278112 | 0.999497 | 0.880446 | 0.999623 | 0 |
| HIP1 | 3092 A_24_P55391 | -1.32 | 0.066219 | 0.085933 | 0.973124 | 0.999497 | 0.968862 | 0.999623 | 0 |
| LAT | 27040 A_23_P60977 | 1.45 | 0.066315 | 0.085992 | 0.739856 | 0.999497 | 0.527527 | 0.999623 | 0 |
| TDGF1 | 6997 A_23_P366376 | 2.44 | 0.066785 | 0.086537 | 0.286719 | 0.999497 | 0.420839 | 0.999623 | 0 |
| GDF11 | 10220 A_23_P76102 | 1.63 | 0.067033 | 0.086792 | 0.614453 | 0.999497 | 0.67061 | 0.999623 | 0 |
| IGFN1 | 91156 A_32_P425998 | 1.4 | 0.067271 | 0.08697 | 0.467572 | 0.999497 | 0.627504 | 0.999623 | 0 |
| COPG2 | 26958 A_23_P61280 | -1.54 | 0.067235 | 0.08697 | 0.842821 | 0.999497 | 0.770027 | 0.999623 | 0 |
| CD74 | 972 A_23_P70095 | 1.44 | 0.067389 | 0.087057 | 0.836028 | 0.999497 | 0.142043 | 0.999623 | 0 |
| TLR3 | 7098 A_23_P29922 | -1.44 | 0.067634 | 0.087309 | 0.005284 | 0.999497 | 0.41004 | 0.999623 | 0 |
| NFE2L2 | 4780 A_23_P5761 | -1.49 | 0.067864 | 0.087539 | 0.557611 | 0.999497 | 0.55885 | 0.999623 | 0 |
| ERCC6 | 2074 A_23_P1292 | -1.16 | 0.068412 | 0.088181 | 0.167979 | 0.999497 | 0.103066 | 0.999623 | 1 |
| XRCC6 | 2547 A_23_P120942 | 1.55 | 0.068528 | 0.088196 | 0.876559 | 0.999497 | 0.595161 | 0.999623 | 1 |
| FNBP1 | 23048 A_23_P32249 | 1.22 | 0.068502 | 0.088196 | 0.210089 | 0.999497 | 0.109915 | 0.999623 | 0 |
| RAB34 | 83871 A_23_P152876 | 1.36 | 0.068578 | 0.088196 | 0.164692 | 0.999497 | 0.609719 | 0.999623 | 0 |
| FCRLA | 84824 A_23_P46039 | 1.44 | 0.068685 | 0.088268 | 0.413456 | 0.999497 | 0.767929 | 0.999623 | 0 |
| SELPLG | 6404 A_23_P64860 | 1.7 | 0.068895 | 0.088472 | 0.978322 | 0.999497 | 0.293404 | 0.999623 | 0 |
| PCMT1 | 5110 A_24_P247608 | -1.66 | 0.069042 | 0.088595 | 0.982318 | 0.999497 | 0.32771 | 0.999623 | 1 |
| IL1R1 | 3554 A_24_P200023 | 1.34 | 0.06911 | 0.088616 | 0.32048 | 0.999497 | 0.293248 | 0.999623 | 0 |
| ALG1 | 56052 A_24_P586523 | 1.67 | 0.069308 | 0.088803 | 0.375108 | 0.999497 | 0.758572 | 0.999623 | 0 |
| ROCK2 | 9475 A_23_P209689 | -1.68 | 0.069371 | 0.088819 | 0.807761 | 0.999497 | 0.569649 | 0.999623 | 0 |
| MUC5B | 727897 A_24_P324141 | -1.42 | 0.069701 | 0.088911 | 0.844397 | 0.999497 | 0.58056 | 0.999623 | 0 |
| PTPN1 | 5770 A_23_P338890 | -1.46 | 0.069674 | 0.088911 | 0.697717 | 0.999497 | 0.372209 | 0.999623 | 1 |
| PSMD3 | 5709 A_24_P289726 | 1.85 | 0.069639 | 0.088911 | 0.721566 | 0.999497 | 0.556409 | 0.999623 | 0 |
| CDH6 | 1004 A_23_P214011 | 1.29 | 0.069576 | 0.088911 | 0.849494 | 0.999497 | 0.484046 | 0.999623 | 0 |
| COL20A1 | 57642 A_32_P867789 | -1.58 | 0.069579 | 0.088911 | 0.318531 | 0.999497 | 0.288065 | 0.999623 | 0 |
| HESX1 | 8820 A_23_P121106 | 1.2 | 0.069763 | 0.088924 | 0.119815 | 0.999497 | 0.60995 | 0.999623 | 1 |
| UBE4B | 10277 A_23_P201279 | -1.38 | 0.070071 | 0.089251 | 0.911792 | 0.999497 | 0.876165 | 0.999623 | 0 |
| PLAU | 5328 A_23_P24104 | 1.15 | 0.070349 | 0.089314 | 0.92319 | 0.999497 | 0.628993 | 0.999623 | 1 |
| IFI16 | 3428 A_23_P217866 | 1.43 | 0.070218 | 0.089314 | 0.50821 | 0.999497 | 0.640024 | 0.999623 | 0 |
| MAEA | 10296 A_23_P29885 | 1.21 | 0.07038 | 0.089314 | 0.25731 | 0.999497 | 0.481224 | 0.999623 | 0 |
| UBB | 7314 A_24_P113109 | 2.48 | 0.070303 | 0.089314 | 0.123697 | 0.999497 | 0.49261 | 0.999623 | 1 |
| HEPACAM | 220296 A_24_P213944 | 1.21 | 0.070325 | 0.089314 | 0.234704 | 0.999497 | 0.189901 | 0.999623 | 0 |
| CASP2 | 835 A_23_P387943 | -1.85 | 0.070579 | 0.089501 | 0.924106 | 0.999497 | 0.363611 | 0.999623 | 0 |
| TTYH1 | 57348 A_23_P50815 | 1.46 | 0.070699 | 0.089543 | 0.932101 | 0.999497 | 0.844342 | 0.999623 | 0 |
| MAPK3 | 5595 A_23_P37910 | 1.36 | 0.070716 | 0.089543 | 0.518378 | 0.999497 | 0.496882 | 0.999623 | 1 |
| CYBB | 1536 A_23_P217258 | 1.25 | 0.070904 | 0.089706 | 0.557522 | 0.999497 | 0.935803 | 0.999623 | 0 |
| AZGP1 | 563 A_23_P71270 | 1.23 | 0.070949 | 0.089706 | 0.341404 | 0.999497 | 0.942304 | 0.999623 | 0 |
| LRP1 | 4035 A_23_P124837 | 1.42 | 0.071153 | 0.089898 | 0.32079 | 0.999497 | 0.58229 | 0.999623 | 0 |
| NFE2 | 4778 A_23_P13753 | 1.23 | 0.071239 | 0.089941 | 0.467874 | 0.999497 | 0.800485 | 0.999623 | 0 |
| MAP3K10 | 4294 A_24_P284523 | 1.73 | 0.071317 | 0.089973 | 0.797461 | 0.999497 | 0.915787 | 0.999623 | 0 |
| TUBB | 203068 A_32_P78528 | 1.15 | 0.071646 | 0.090323 | 0.774126 | 0.999497 | 0.148739 | 0.999623 | 0 |
| ITGA5 | 3678 A_23_P36562 | 1.47 | 0.071722 | 0.090351 | 0.890551 | 0.999497 | 0.297712 | 0.999623 | 0 |
| CTSE | 1510 A_23_P10291 | -1.26 | 0.071836 | 0.09043 | 0.799191 | 0.999497 | 0.612963 | 0.999623 | 0 |
| ELN | 2006 A_24_P186943 | -1.8 | 0.071983 | 0.090482 | 0.959394 | 0.999497 | 0.495364 | 0.999623 | 1 |

TABLE S7-continued

Significant differences between CR and CNR

| | | Fold-change CNR vs CR | Cytokine response | | Age: 60-65 yo vs 74+ yo | | Gender | | |
|---|---|---|---|---|---|---|---|---|---|
| | | | p-value | q-value | p-value | q-value | p-value | q-value | |
| CLU | 1191 A_23_P215913 | 1.21 | 0.071959 | 0.090482 | 0.6467 | 0.999497 | 0.281353 | 0.999623 | 1 |
| MSX2 | 4488 A_24_P132006 | -2.12 | 0.072309 | 0.09076 | 0.356266 | 0.999497 | 0.638407 | 0.999623 | 0 |
| FBLN5 | 10516 A_23_P151805 | 1.26 | 0.072289 | 0.09076 | 0.421469 | 0.999497 | 0.434594 | 0.999623 | 0 |
| PPT1 | 5538 A_24_P276628 | 1.33 | 0.072512 | 0.090948 | 0.876872 | 0.999497 | 0.343297 | 0.999623 | 0 |
| DOCK7 | 85440 A_24_P203622 | 1.34 | 0.072634 | 0.091035 | 0.223385 | 0.999497 | 0.851233 | 0.999623 | 0 |
| PARVG | 64098 A_23_P250413 | 1.35 | 0.072897 | 0.091298 | 0.769423 | 0.999497 | 0.641898 | 0.999623 | 0 |
| DAXX | 1616 A_23_P122579 | 1.36 | 0.073115 | 0.091373 | 0.904887 | 0.999497 | 0.844909 | 0.999623 | 0 |
| CD300A | 11314 A_24_P159434 | -3.19 | 0.073035 | 0.091373 | 0.853224 | 0.999497 | 0.635397 | 0.999623 | 0 |
| CD300C | 10871 A_23_P26771 | 1.25 | 0.073077 | 0.091373 | 0.29654 | 0.999497 | 0.432398 | 0.999623 | 0 |
| HLA-DPB1 | 3115 A_24_P166443 | 1.66 | 0.073373 | 0.091561 | 0.829101 | 0.999497 | 0.406965 | 0.999623 | 0 |
| TERF1 | 7013 A_23_P216149 | -1.68 | 0.073368 | 0.091561 | 0.713932 | 0.999497 | 0.338605 | 0.999623 | 1 |
| SPP1 | 6696 A_23_P7313 | -1.53 | 0.073483 | 0.091632 | 0.656317 | 0.999497 | 0.215219 | 0.999623 | 0 |
| PCDHB16 | 57717 A_23_P30200 | -1.3 | 0.073663 | 0.091791 | 0.84965 | 0.999497 | 0.198622 | 0.999623 | 0 |
| CD244 | 51744 A_24_P105332 | -1.58 | 0.073895 | 0.091947 | 0.755374 | 0.999497 | 0.621937 | 0.999623 | 0 |
| SRPK2 | 6733 A_23_P406438 | -1.68 | 0.073858 | 0.091947 | 0.582662 | 0.999497 | 0.317296 | 0.999623 | 0 |
| HLA-DRB4 | 3126 A_24_P370472 | 1.89 | 0.074152 | 0.0922 | 0.792213 | 0.999497 | 0.240951 | 0.999623 | 0 |
| CD37 | 951 A_24_P82749 | 1.71 | 0.074286 | 0.092233 | 0.303824 | 0.999497 | 0.979279 | 0.999623 | 0 |
| RHOA | 387 A_24_P174550 | 1.28 | 0.074234 | 0.092233 | 0.067586 | 0.999497 | 0.830572 | 0.999623 | 0 |
| RB1 | 5925 A_24_P102636 | -1.28 | 0.07469 | 0.092602 | 0.616952 | 0.999497 | 0.739005 | 0.999623 | 1 |
| SOCS5 | 9655 A_24_P328492 | -1.62 | 0.074675 | 0.092602 | 0.292014 | 0.999497 | 0.228861 | 0.999623 | 0 |
| NEK6 | 10783 A_23_P216920 | 1.6 | 0.07497 | 0.092679 | 0.694387 | 0.999497 | 0.565284 | 0.999623 | 0 |
| PCDHB15 | 56121 A_23_P121851 | -1.26 | 0.074951 | 0.092679 | 0.759314 | 0.999497 | 0.36976 | 0.999623 | 0 |
| TGFBR1 | 7046 A_32_P146394 | 1.38 | 0.074864 | 0.092679 | 0.292577 | 0.999497 | 0.259074 | 0.999623 | 0 |
| DAPL1 | 92196 A_23_P165598 | 1.28 | 0.074982 | 0.092679 | 0.051096 | 0.999497 | 0.958694 | 0.999623 | 0 |
| NR2E1 | 7101 A_23_P338372 | 1.22 | 0.075021 | 0.092679 | 0.601793 | 0.999497 | 0.556365 | 0.999623 | 0 |
| HSPA9 | 3313 A_24_P77676 | -1.83 | 0.075085 | 0.092691 | 0.63554 | 0.999497 | 0.555625 | 0.999623 | 1 |
| PSMG1 | 8624 A_23_P68717 | 1.35 | 0.075234 | 0.092809 | 0.130119 | 0.999497 | 0.099576 | 0.999623 | 0 |
| CREBBP | 1387 A_23_P163850 | 1.63 | 0.076077 | 0.093586 | 0.75556 | 0.999497 | 0.596916 | 0.999623 | 1 |
| RECQL4 | 9401 A_23_P71558 | 1.31 | 0.076082 | 0.093586 | 0.751386 | 0.999497 | 0.876279 | 0.999623 | 1 |
| IFIT5 | 24138 A_24_P30194 | -1.52 | 0.075929 | 0.093586 | 0.410888 | 0.999497 | 0.220902 | 0.999623 | 0 |
| BUB3 | 9184 A_23_P202316 | -1.27 | 0.076012 | 0.093586 | 0.225825 | 0.999497 | 0.138415 | 0.999623 | 1 |
| AP2A2 | 161 A_23_P21853 | 1.11 | 0.07617 | 0.093629 | 0.524319 | 0.999497 | 0.916485 | 0.999623 | 0 |
| SCARF1 | 8578 A_23_P15414 | 1.32 | 0.076793 | 0.094193 | 0.751116 | 0.999497 | 0.821842 | 0.999623 | 0 |
| SNAP25 | 6616 A_23_P210756 | 1.25 | 0.076778 | 0.094193 | 0.840024 | 0.999497 | 0.388759 | 0.999623 | 0 |
| NLRC3 | 197358 A_23_P340019 | -1.31 | 0.076715 | 0.094193 | 0.781645 | 0.999497 | 0.681294 | 0.999623 | 0 |
| DSC2 | 1824 A_23_P4494 | -2.67 | 0.077134 | 0.094544 | 0.023971 | 0.999497 | 0.756781 | 0.999623 | 0 |
| ALDH1A2 | 8854 A_24_P73577 | -2.72 | 0.077249 | 0.094617 | 0.102973 | 0.999497 | 0.417413 | 0.999623 | 0 |
| BAD | 572 A_23_P150207 | 1.39 | 0.077703 | 0.095105 | 0.927524 | 0.999497 | 0.277576 | 0.999623 | 0 |
| HSPG2 | 3339 A_23_P23191 | 1.29 | 0.077788 | 0.095142 | 0.631973 | 0.999497 | 0.991037 | 0.999623 | 0 |
| VEGFA | 7422 A_24_P12401 | -2.86 | 0.077975 | 0.095168 | 0.693386 | 0.999497 | 0.176198 | 0.999623 | 1 |
| NPC1 | 4864 A_23_P107587 | -1.17 | 0.077911 | 0.095168 | 0.376908 | 0.999497 | 0.620903 | 0.999623 | 0 |
| GPR183 | 1880 A_23_P25566 | -1.22 | 0.077926 | 0.095168 | 0.510821 | 0.999497 | 0.71278 | 0.999623 | 2 |
| SEMA3F | 6405 A_24_P300076 | 1.36 | 0.078435 | 0.095595 | 0.765867 | 0.999497 | 0.93079 | 0.999623 | 0 |
| PDPN | 10630 A_24_P299685 | 1.39 | 0.078386 | 0.095595 | 0.704501 | 0.999497 | 0.153662 | 0.999623 | 0 |
| TRPC4AP | 26133 A_23_P154801 | 1.49 | 0.078556 | 0.095642 | 0.722258 | 0.999497 | 0.544348 | 0.999623 | 0 |
| BLNK | 29760 A_24_P64344 | -1.53 | 0.078585 | 0.095642 | 0.340908 | 0.999497 | 0.521439 | 0.999623 | 0 |
| ZAP70 | 7535 A_24_P169234 | 1.4 | 0.078715 | 0.095732 | 0.987112 | 0.999497 | 0.741617 | 0.999623 | 0 |
| HINT1 | 3094 A_32_P336445 | -1.52 | 0.078936 | 0.095866 | 0.823136 | 0.999497 | 0.201455 | 0.999623 | 0 |
| HRH1 | 3269 A_24_P277211 | -1.39 | 0.078892 | 0.095866 | 0.870706 | 0.999497 | 0.123979 | 0.999623 | 0 |
| NFKBID | 84807 A_23_P383422 | 2.26 | 0.079123 | 0.095958 | 0.503013 | 0.999497 | 0.563525 | 0.999623 | 0 |
| VTN | 7448 A_23_P78099 | 1.44 | 0.079123 | 0.095958 | 0.620538 | 0.999497 | 0.513387 | 0.999623 | 0 |
| PRKRIR | 5612 A_24_P321411 | -1.71 | 0.079207 | 0.095992 | 0.689103 | 0.999497 | 0.204232 | 0.999623 | 0 |
| CNTNAP3 | 79937 A_24_P418203 | 1.29 | 0.079318 | 0.096058 | 0.686473 | 0.999497 | 0.535152 | 0.999623 | 0 |
| ITGAE | 3682 A_23_P218375 | -1.5 | 0.079398 | 0.096088 | 0.659246 | 0.999497 | 0.580435 | 0.999623 | 0 |
| PTPRS | 5802 A_24_P290856 | 1.46 | 0.079634 | 0.096104 | 0.843672 | 0.999497 | 0.190119 | 0.999623 | 0 |
| CCL23 | 6368 A_24_P319088 | 1.3 | 0.079621 | 0.096104 | 0.459304 | 0.999497 | 0.68307 | 0.999623 | 0 |
| NCF1 | 653361 A_32_P116203 | 1.72 | 0.079532 | 0.096104 | 0.885633 | 0.999497 | 0.311725 | 0.999623 | 0 |
| SRGN | 5552 A_23_P86653 | -1.79 | 0.07953 | 0.096104 | 0.996046 | 0.999497 | 0.627648 | 0.999623 | 0 |
| THYN1 | 29087 A_23_P24633 | -1.21 | 0.079778 | 0.09621 | 0.336967 | 0.999497 | 0.528377 | 0.999623 | 0 |
| MBD4 | 8930 A_23_P92154 | -1.84 | 0.079838 | 0.096216 | 0.600026 | 0.999497 | 0.298133 | 0.999623 | 0 |
| NAMPT | 10135 A_23_P305060 | -1.66 | 0.080101 | 0.096465 | 0.339861 | 0.999497 | 0.921301 | 0.999623 | 0 |
| IL10RA | 3587 A_24_P107303 | -1.26 | 0.080304 | 0.096642 | 0.717485 | 0.999497 | 0.961952 | 0.999623 | 0 |
| NFATC3 | 4775 A_24_P373312 | 1.25 | 0.08054 | 0.096725 | 0.657845 | 0.999497 | 0.894317 | 0.999623 | 0 |
| AIFM2 | 84883 A_23_P138567 | 2.09 | 0.080542 | 0.096725 | 0.658303 | 0.999497 | 0.615127 | 0.999623 | 0 |
| PARD3 | 56288 A_24_P35478 | 1.33 | 0.080538 | 0.096725 | 0.37714 | 0.999497 | 0.802016 | 0.999623 | 0 |
| RB1CC1 | 9821 A_23_P9056 | -1.4 | 0.080638 | 0.096774 | 0.329588 | 0.999497 | 0.782272 | 0.999623 | 0 |
| SART1 | 9092 A_23_P86884 | 1.42 | 0.08084 | 0.096917 | 0.850047 | 0.999497 | 0.844076 | 0.999623 | 0 |
| SIK1 | 150094 A_23_P132121 | -1.54 | 0.08087 | 0.096917 | 0.757172 | 0.999497 | 0.29682 | 0.999623 | 0 |
| SYNJ2BP | 55333 A_23_P65357 | -1.51 | 0.081024 | 0.097034 | 0.952809 | 0.999497 | 0.552324 | 0.999623 | 0 |
| ITGB3 | 3690 A_24_P318656 | 1.52 | 0.081293 | 0.097289 | 0.672961 | 0.999497 | 0.574028 | 0.999623 | 0 |
| NFKB2 | 4791 A_23_P202156 | 1.48 | 0.081789 | 0.097353 | 0.713252 | 0.999497 | 0.415635 | 0.999623 | 1 |
| ITGAM | 3684 A_23_P124108 | -1.52 | 0.081799 | 0.097353 | 0.507717 | 0.999497 | 0.167789 | 0.999623 | 0 |

TABLE S7-continued

Significant differences between CR and CNR

| | | Fold-change CNR vs CR | Cytokine response | | Age: 60-65 yo vs 74+ yo | | Gender | | |
|---|---|---|---|---|---|---|---|---|---|
| | | | p-value | q-value | p-value | q-value | p-value | q-value | |
| ACTN1 | 87 A_24_P107695 | 1.34 | 0.081746 | 0.097353 | 0.585676 | 0.999497 | 0.911428 | 0.999623 | 0 |
| MLL | 4297 A_24_P281913 | 1.21 | 0.081631 | 0.097353 | 0.031315 | 0.999497 | 0.930933 | 0.999623 | 0 |
| ZYX | 7791 A_23_P254888 | 1.47 | 0.081758 | 0.097353 | 0.247784 | 0.999497 | 0.323588 | 0.999623 | 0 |
| MAP4K3 | 8491 A_23_P154130 | 1.38 | 0.081682 | 0.097353 | 0.840367 | 0.999497 | 0.770612 | 0.999623 | 0 |
| CADPS2 | 93664 A_24_P246710 | 1.34 | 0.081597 | 0.097353 | 0.271639 | 0.999497 | 0.373297 | 0.999623 | 0 |
| SP110 | 3431 A_23_P120002 | 1.18 | 0.081494 | 0.097353 | 0.874236 | 0.999497 | 0.958095 | 0.999623 | 0 |
| PTPRC | 5788 A_23_P125451 | -1.83 | 0.082063 | 0.097533 | 0.449752 | 0.999497 | 0.219033 | 0.999623 | 0 |
| NRG1 | 3084 A_23_P136493 | 1.38 | 0.082012 | 0.097533 | 0.820295 | 0.999497 | 0.783625 | 0.999623 | 1 |
| APC | 324 A_23_P70213 | 1.34 | 0.082223 | 0.097622 | 0.503368 | 0.999497 | 0.99069 | 0.999623 | 0 |
| PPID | 5481 A_23_P386411 | -1.29 | 0.082251 | 0.097622 | 0.112933 | 0.999497 | 0.502935 | 0.999623 | 0 |
| MUC16 | 94025 A_23_P5211 | 1.26 | 0.082332 | 0.09765 | 0.996124 | 0.999497 | 0.893653 | 0.999623 | 0 |
| PPP2CA | 5515 A_23_P122041 | -1.74 | 0.082538 | 0.097761 | 0.9949 | 0.999497 | 0.337659 | 0.999623 | 0 |
| SHISA5 | 51246 A_24_P394246 | 1.15 | 0.082493 | 0.097761 | 0.853586 | 0.999497 | 0.199523 | 0.999623 | 0 |
| CSNK1E | 1454 A_23_P40664 | 1.57 | 0.082721 | 0.09791 | 0.61832 | 0.999497 | 0.465145 | 0.999623 | 1 |
| OLFML3 | 56944 A_24_P11315 | 1.42 | 0.082811 | 0.097949 | 0.613862 | 0.999497 | 0.763098 | 0.999623 | 2 |
| TAF1 | 6872 A_23_P11237 | 1.14 | 0.082967 | 0.097999 | 0.651317 | 0.999497 | 0.540961 | 0.999623 | 1 |
| TAPBP | 6892 A_23_P315336 | 1.31 | 0.082916 | 0.097999 | 0.718623 | 0.999497 | 0.192495 | 0.999623 | 0 |
| FKBP14 | 55033 A_23_P215341 | 1.25 | 0.083196 | 0.098026 | 0.216126 | 0.999497 | 0.602589 | 0.999623 | 0 |
| SFRP1 | 6422 A_23_P10127 | -1.27 | 0.083274 | 0.098026 | 0.668156 | 0.999497 | 0.333082 | 0.999623 | 0 |
| BIRC2 | 329 A_24_P115774 | -1.3 | 0.083139 | 0.098026 | 0.591219 | 0.999497 | 0.546934 | 0.999623 | 0 |
| IRF2BP2 | 359948 A_23_P46588 | 1.23 | 0.083234 | 0.098026 | 0.394959 | 0.999497 | 0.922855 | 0.999623 | 0 |
| PBX1 | 5087 A_32_P25397 | -1.97 | 0.083121 | 0.098026 | 0.784926 | 0.999497 | 0.536081 | 0.999623 | 0 |
| TNNI2 | 7136 A_23_P24784 | 1.56 | 0.083615 | 0.098293 | 0.807774 | 0.999497 | 0.599572 | 0.999623 | 0 |
| IL15RA | 3601 A_23_P138680 | 1.19 | 0.083599 | 0.098293 | 0.696413 | 0.999497 | 0.946544 | 0.999623 | 0 |
| CDH10 | 1008 A_23_P144656 | 1.21 | 0.083968 | 0.098305 | 0.420776 | 0.999497 | 0.601302 | 0.999623 | 0 |
| CD244 | 51744 A_23_P85453 | -1.77 | 0.083696 | 0.098305 | 0.243443 | 0.999497 | 0.375803 | 0.999623 | 0 |
| ITM2B | 9445 A_24_P381604 | -1.86 | 0.083903 | 0.098305 | 0.770656 | 0.999497 | 0.339055 | 0.999623 | 0 |
| IFI30 | 10437 A_23_P153745 | 1.12 | 0.083774 | 0.098305 | 0.88359 | 0.999497 | 0.700128 | 0.999623 | 0 |
| ICA1L | 130026 A_23_P17224 | 1.29 | 0.083937 | 0.098305 | 0.722955 | 0.999497 | 0.175536 | 0.999623 | 0 |
| IGFBP3 | 3486 A_24_P320699 | 1.3 | 0.083937 | 0.098305 | 0.46092 | 0.999497 | 0.220558 | 0.999623 | 1 |
| FN1 | 2335 A_24_P334130 | 1.31 | 0.084151 | 0.098452 | 0.412248 | 0.999497 | 0.587847 | 0.999623 | 0 |
| TOP2A | 7153 A_23_P118834 | -1.73 | 0.084298 | 0.098558 | 0.926046 | 0.999497 | 0.168959 | 0.999623 | 1 |
| SON | 6651 A_23_P402733 | 1.11 | 0.084404 | 0.098614 | 0.932948 | 0.999497 | 0.632745 | 0.999623 | 0 |
| CDSN | 1041 A_23_P70520 | -1.61 | 0.084463 | 0.098617 | 0.76982 | 0.999497 | 0.191428 | 0.999623 | 0 |
| FADD | 8772 A_24_P278637 | 1.45 | 0.084708 | 0.098835 | 0.609665 | 0.999497 | 0.486097 | 0.999623 | 0 |
| CD69 | 969 A_23_P87879 | -1.78 | 0.084882 | 0.098972 | 0.821948 | 0.999497 | 0.312215 | 0.999623 | 0 |
| PRKDC | 5591 A_32_P25204 | 1.21 | 0.085014 | 0.099059 | 0.45833 | 0.999497 | 0.569214 | 0.999623 | 1 |
| SMO | 6608 A_23_P70818 | 1.29 | 0.085095 | 0.099087 | 0.831629 | 0.999497 | 0.524877 | 0.999623 | 0 |
| SLC23A2 | 9962 A_24_P254278 | -1.65 | 0.08528 | 0.099179 | 0.899964 | 0.999497 | 0.233504 | 0.999623 | 2 |
| RGN | 9104 A_23_P114423 | -1.12 | 0.085348 | 0.099179 | 0.745361 | 0.999497 | 0.499128 | 0.999623 | 1 |
| SORT1 | 6272 A_24_P325520 | -1.25 | 0.085323 | 0.099179 | 0.635433 | 0.999497 | 0.327292 | 0.999623 | 0 |
| ABCC4 | 10257 A_24_P16913 | -1.21 | 0.085631 | 0.099441 | 0.191325 | 0.999497 | 0.36813 | 0.999623 | 0 |
| IFI16 | 3428 A_23_P160025 | -2.13 | 0.085924 | 0.099647 | 0.995129 | 0.999497 | 0.586429 | 0.999623 | 0 |
| CNTNAP3 | 79937 A_23_P9135 | 1.4 | 0.085906 | 0.099647 | 0.988668 | 0.999497 | 0.86938 | 0.999623 | 0 |
| SEMA3A | 10371 A_23_P317591 | -1.44 | 0.085985 | 0.09965 | 0.802566 | 0.999497 | 0.807389 | 0.999623 | 0 |
| PVRIG | 79037 A_23_P8424 | 1.3 | 0.086042 | 0.09965 | 0.843982 | 0.999497 | 0.296462 | 0.999623 | 0 |
| CITED2 | 10370 A_32_P192389 | 1.25 | 0.086437 | 0.09991 | 0.741042 | 0.999497 | 0.879654 | 0.999623 | 0 |
| AIFM3 | 150209 A_23_P258194 | 1.35 | 0.08644 | 0.09991 | 0.488209 | 0.999497 | 0.771895 | 0.999623 | 0 |
| IFNAR2 | 3455 A_23_P211080 | 1.32 | 0.086353 | 0.09991 | 0.773614 | 0.999497 | 0.613828 | 0.999623 | 0 |
| PTGES3 | 10728 A_24_P343869 | 1.18 | 0.086501 | 0.099913 | 0.592575 | 0.999497 | 0.694156 | 0.999623 | 0 |
| RPS3A | 6189 A_32_P208178 | -1.93 | 0.086597 | 0.099957 | 0.354189 | 0.999497 | 0.642821 | 0.999623 | 0 |
| FGG | 2266 A_23_P148088 | -2.2 | 0.086676 | 0.099981 | 0.21771 | 0.999497 | 0.480389 | 0.999623 | 0 |

APPENDIX H

TABLE S8

Medication category listing for CR and CNR

| Medical Code | Category Name | Medication/Medication combination taken | Number of CR taking medication | Number of CNR taking medication |
|---|---|---|---|---|
| 1 | Analgesics/NSAIDS | Advil | | 1 |
| 1 | Analgesics/NSAIDS | Naproxen | | 1 |
| 3 | Antacids/H2 antagonists: | Zantac | | 1 |
| 5 | Anti-asthma/bronchodilators | Flovent | | 1 |
| 5 | Anti-asthma/bronchodilators | Beclate-100, Tiotropium Bromide | | 1 |

TABLE S8-continued

Medication category listing for CR and CNR

| Medical Code | Category Name | Medication/Medication combination taken | Number of CR taking medication | Number of CNR taking medication |
|---|---|---|---|---|
| 6 | Anti-cholesterol/Anti-hyperlipidemic | Mevacor, Zocor | | 1 |
| 6 | Anti-cholesterol/Anti-hyperlipidemic | Liptor | | 1 |
| 7 | Anti-coagulants | Coumadin | 1 | |
| 7 | Anti-coagulants | Aggrenox | 1 | |
| 7 | Anti-coagulants | Warfarin | 1 | |
| 7 | Anti-coagulants | Aspirin | | 3 |
| 8 | Antibiotics/anti-infectives/anti-parasitics/anti-microbials | Augmentin | | 1 |
| 9 | Antidepressants/mood-altering drugs | Prozac | 1 | |
| 10 | Antihistamines/Decongestants | Loratadine | | 1 |
| 10 | Antihistamines/Decongestants | NyQuil | | 1 |
| 11, 12 | Antihypertensives and Cardiovascular, other than hyperlipidemic/HTN | Maxzide | | 1 |
| 11, 12 | Antihypertensives and Cardiovascular, other than hyperlipidemic/HTN | Lisinopril, Hydrochorothiazide | | 1 |
| 11, 12 | Antihypertensives and Cardiovascular, other than hyperlipidemic/HTN | Lisinopril, Metoprolol | | 1 |
| 11, 12 | Antihypertensives and Cardiovascular, other than hyperlipidemic/HTN | Lisinopril; Lasix; Atenol | | 1 |
| 11, 12 | Antihypertensives and Cardiovascular, other than hyperlipidemic/HTN | Atenol; Captopril; Furosemide | 1 | |
| 11, 12 | Antihypertensives and Cardiovascular, other than hyperlipidemic/HTN | Diltiazem | 1 | |
| 15 | Endocrine/Metabolic agents | Fosamax | 1 | |
| 15 | Endocrine/Metabolic agents | Levothroid | 1 | 1 |
| 18 | Hormones/steroids | Estradiol | 1 | |
| 18 | Hormones/steroids | Premarin | | 1 |
| 21 | Vitamins, minerals, food supplements | Vitamin D; Aplpha-Lipoic Acid; Multi-vitamin, Tumeric Acid | | 1 |
| 21 | Vitamins, minerals, food supplements | Calcium with Vitamin D | 1 | |
| 21 | Vitamins, minerals, food supplements | Ferrous Sulphate | 1 | |
| 21 | Vitamins, minerals, food supplements | Multi-vitamin | 2 | |
| 99 | Other | Allopurinol | | 1 |
| 99 | Other | Doxazosin | | 1 |
| 99 | Other | Terazosin | | 1 |
| 99 | Other | Potassium Cholride | 1 | |

APPENDIX I

TABLE S9

Age associated differences common to both CR and CNR

| | Name | FC CR vs Yng | FC CNR vs Yng | QV CR vs Yng | QC CNR vs Yng |
|---|---|---|---|---|---|
| phenoD | GAMMA DELTA CELLS | −3.5 | −1.4 | 0.12 | 0.2 |
| phenoD | MONOCYTES | 1.3 | 1.1 | 0.16 | 0.17 |
| CytM | EOTAXIN | 2 | 1.4 | 0.02 | 0.17 |
| cytM | IP10 | 1.8 | 1.8 | 0.05 | 0.15 |
| pfD | cd8_IFNa_STAT1 | −1.4 | −4 | 0.11 | 0 |
| pfD | cd8_IL21_STAT1 | −1.4 | −2.1 | 0.11 | 0 |
| pfBaselineD | cd8_Unstimulated_STAT5 | 1.1 | 1.1 | 0.09 | 0.02 |
| pfBaselineD | cd8_Unstimulated_STAT3 | 1.2 | 1.2 | 0.09 | 0 |
| pfBaselineD | cd8_Unstimulated_STAT1 | 1.6 | 1.7 | 0.05 | 0 |
| geD | NUDCD2 | −2.1 | −1.9 | 0.02 | 0.07 |
| geD | CTNND2 | −2 | −1.9 | 0.02 | 0.13 |
| geD | TNFRSF11A | −1.3 | −1.8 | 0.05 | 0.07 |

TABLE S9-continued

Age associated differences common to both CR and CNR

| | Name | FC CR vs Yng | FC CNR vs Yng | QV CR vs Yng | QC CNR vs Yng |
|---|---|---|---|---|---|
| geD | HIVEP3 | −1.2 | −1.7 | 0.12 | 0.07 |
| geD | NF2 | −1.7 | −1.7 | 0.02 | 0.17 |
| geD | BAG5 | −1.4 | −1.6 | 0.03 | 0.07 |
| geD | IGF2BP2 | −1.4 | −1.6 | 0.04 | 0.07 |
| geD | CDH1 | −1.8 | −1.6 | 0.02 | 0.1 |
| geD | CEACAM6 | −1.3 | −1.6 | 0.06 | 0.11 |
| geD | PSME1 | −1.6 | −1.6 | 0.05 | 0.12 |
| geD | TNFAIP8L1 | −1.5 | −1.6 | 0.04 | 0.13 |
| geD | CARD14 | −1.3 | −1.6 | 0.06 | 0.13 |
| geD | SMAD3 | −1.3 | −1.6 | 0.11 | 0.17 |
| geD | FRK | −1.5 | −1.5 | 0.02 | 0.07 |
| geD | NLGN4X | −1.4 | −1.5 | 0.02 | 0.07 |
| geD | NF2 | −1.3 | −1.5 | 0.05 | 0.07 |
| geD | SARNP | −1.3 | −1.5 | 0.05 | 0.07 |
| geD | XRCC6 | −1.2 | −1.5 | 0.03 | 0.07 |
| geD | FLJ23834 | −1.1 | −1.5 | 0.12 | 0.07 |
| geD | CTNNAL1 | −2 | −1.5 | 0.04 | 0.1 |
| geD | ERC1 | −1.3 | −1.5 | 0.06 | 0.1 |
| geD | ICA1L | −1.2 | −1.5 | 0.12 | 0.1 |
| geD | PCDH7 | −1.2 | −1.5 | 0.15 | 0.1 |
| geD | PEA15 | −1.4 | −1.5 | 0.12 | 0.11 |
| geD | RIMS2 | −1.3 | −1.5 | 0.06 | 0.11 |
| geD | ROBO1 | −1.3 | −1.5 | 0.06 | 0.11 |
| geD | CDH13 | −1.7 | −1.5 | 0.02 | 0.12 |
| geD | RABEP1 | −3.3 | −1.5 | 0.02 | 0.14 |
| geD | REL | −1.4 | −1.5 | 0.04 | 0.14 |
| geD | C14orf153 | −1.4 | −1.5 | 0.11 | 0.14 |
| geD | FGA | −1.2 | −1.5 | 0.09 | 0.14 |
| geD | IFT52 | −1.5 | −1.5 | 0.06 | 0.15 |
| geD | LEAP2 | −1.4 | −1.5 | 0.06 | 0.15 |
| geD | FCRLA | −1.3 | −1.5 | 0.09 | 0.15 |
| geD | HM13 | −1.2 | −1.5 | 0.18 | 0.15 |
| geD | MAGI1 | −1.3 | −1.5 | 0.04 | 0.17 |
| geD | NDUFS1 | −1.2 | −1.5 | 0.12 | 0.17 |
| geD | SOCS4 | −1.6 | −1.5 | 0.05 | 0.18 |
| geD | RAC1 | −1.8 | −1.5 | 0.02 | 0.19 |
| geD | SIK2 | −1.3 | −1.5 | 0.09 | 0.19 |
| geD | AP1G1 | −2 | −1.4 | 0.02 | 0.07 |
| geD | ATP5B | −1.9 | −1.4 | 0.03 | 0.07 |
| geD | STXBP5 | −1.6 | −1.4 | 0.03 | 0.07 |
| geD | APEX1 | −1.6 | −1.4 | 0.07 | 0.07 |
| geD | DLL3 | −1.5 | −1.4 | 0.09 | 0.07 |
| geD | PUF60 | −1.4 | −1.4 | 0.08 | 0.07 |
| geD | SEMA5A | −1.3 | −1.4 | 0.03 | 0.07 |
| geD | BCAP29 | −1.3 | −1.4 | 0.04 | 0.07 |
| geD | INCENP | −1.3 | −1.4 | 0.05 | 0.07 |
| geD | EXOC6 | −1.3 | −1.4 | 0.05 | 0.07 |
| geD | IL17D | −1.3 | −1.4 | 0.07 | 0.07 |
| geD | PTPN11 | −1.2 | −1.4 | 0.06 | 0.07 |
| geD | PPARA | −1.2 | −1.4 | 0.07 | 0.07 |
| geD | DLC1 | −1.2 | −1.4 | 0.12 | 0.07 |
| geD | MIB1 | −1.1 | −1.4 | 0.15 | 0.07 |
| geD | ITGB8 | −1.1 | −1.4 | 0.16 | 0.07 |
| geD | MAP4K4 | −2.5 | −1.4 | 0.02 | 0.08 |
| geD | THRA | −1.8 | −1.4 | 0.03 | 0.08 |
| geD | CD1E | −1.6 | −1.4 | 0.18 | 0.09 |
| geD | RFFL | −1.3 | −1.4 | 0.12 | 0.09 |
| geD | CLN8 | −1.2 | −1.4 | 0.12 | 0.09 |
| geD | SOCS5 | −1.2 | −1.4 | 0.15 | 0.09 |
| geD | CDH4 | −1.1 | −1.4 | 0.18 | 0.09 |
| geD | EBF1 | −1.3 | −1.4 | 0.03 | 0.1 |
| geD | XCL2 | −1.3 | −1.4 | 0.04 | 0.1 |
| geD | DNM3 | −1.3 | −1.4 | 0.04 | 0.1 |
| geD | FXR1 | −1.3 | −1.4 | 0.06 | 0.1 |
| geD | PTGER2 | −1.5 | −1.4 | 0.02 | 0.11 |
| geD | SMAD1 | −1.3 | −1.4 | 0.03 | 0.11 |
| geD | SLTM | −1.8 | −1.4 | 0.04 | 0.12 |
| geD | SNAP29 | −1.5 | −1.4 | 0.03 | 0.12 |
| geD | TLN2 | −1.5 | −1.4 | 0.07 | 0.12 |
| geD | PPFIBP1 | −1.4 | −1.4 | 0.02 | 0.12 |
| geD | IL28RA | −1.3 | −1.4 | 0.04 | 0.12 |
| geD | EFNB1 | −1.1 | −1.4 | 0.18 | 0.12 |
| geD | STEAP2 | −2 | −1.4 | 0.02 | 0.13 |
| geD | USP33 | −1.5 | −1.4 | 0.02 | 0.13 |
| geD | IRAK4 | −1.5 | −1.4 | 0.05 | 0.13 |
| geD | TGFB2 | −1.4 | −1.4 | 0.03 | 0.13 |

TABLE S9-continued

Age associated differences common to both CR and CNR

| | Name | FC CR vs Yng | FC CNR vs Yng | QV CR vs Yng | QC CNR vs Yng |
|---|---|---|---|---|---|
| geD | PRUNE2 | −1.4 | −1.4 | 0.06 | 0.13 |
| geD | CASP9 | −1.3 | −1.4 | 0.06 | 0.13 |
| geD | PSMB1 | −1.2 | −1.4 | 0.12 | 0.13 |
| geD | PHB | −1.2 | −1.4 | 0.14 | 0.13 |
| geD | TIA1 | −1.3 | −1.4 | 0.07 | 0.14 |
| geD | SP3 | −1.2 | −1.4 | 0.18 | 0.14 |
| geD | ASB1 | −1.1 | −1.4 | 0.17 | 0.14 |
| geD | MIA3 | −1.6 | −1.4 | 0.02 | 0.15 |
| geD | PCDH9 | −1.3 | −1.4 | 0.07 | 0.15 |
| geD | NOD2 | −1.3 | −1.4 | 0.09 | 0.15 |
| geD | NEK11 | −1.3 | −1.4 | 0.1 | 0.15 |
| geD | ERMAP | −1.2 | −1.4 | 0.08 | 0.15 |
| geD | DYRK2 | −1.6 | −1.4 | 0.02 | 0.16 |
| geD | HMGB2 | −1.5 | −1.4 | 0.03 | 0.16 |
| geD | RSPH1 | −1.4 | −1.4 | 0.05 | 0.16 |
| geD | RALBP1 | −1.4 | −1.4 | 0.11 | 0.16 |
| geD | FKBP1B | −1.3 | −1.4 | 0.1 | 0.16 |
| geD | ZFYVE9 | −1.2 | −1.4 | 0.13 | 0.16 |
| geD | IL13RA1 | −1.2 | −1.4 | 0.13 | 0.16 |
| geD | SOD2 | −1.6 | −1.4 | 0.02 | 0.17 |
| geD | ERAP1 | −1.2 | −1.4 | 0.17 | 0.17 |
| geD | APAF1 | −2.8 | −1.4 | 0.02 | 0.18 |
| geD | ELMOD2 | −1.4 | −1.4 | 0.05 | 0.18 |
| geD | COL3A1 | −1.5 | −1.4 | 0.09 | 0.19 |
| geD | MCAM | −1.4 | −1.4 | 0.12 | 0.19 |
| geD | PSMB1 | −1.3 | −1.4 | 0.07 | 0.19 |
| geD | TCTN3 | −1.9 | −1.3 | 0.07 | 0.07 |
| geD | PTGR1 | −1.8 | −1.3 | 0.02 | 0.07 |
| geD | IL7 | −1.4 | −1.3 | 0.04 | 0.07 |
| geD | TPBG | −1.4 | −1.3 | 0.05 | 0.07 |
| geD | DDR2 | −1.3 | −1.3 | 0.12 | 0.07 |
| geD | C7orf16 | −1.2 | −1.3 | 0.05 | 0.07 |
| geD | MYST4 | −1.1 | −1.3 | 0.18 | 0.07 |
| geD | TSLP | −1.1 | −1.3 | 0.2 | 0.07 |
| geD | L3MBTL4 | −1.5 | −1.3 | 0.03 | 0.09 |
| geD | CMTM8 | −1.4 | −1.3 | 0.02 | 0.09 |
| geD | PTGR2 | −1.2 | −1.3 | 0.02 | 0.09 |
| geD | CDC42 | −1.5 | −1.3 | 0.03 | 0.1 |
| geD | MASP1 | −1.4 | −1.3 | 0.02 | 0.1 |
| geD | DMBT1 | −1.2 | −1.3 | 0.02 | 0.1 |
| geD | TAOK2 | −1.6 | −1.3 | 0.04 | 0.11 |
| geD | DNM1L | −1.4 | −1.3 | 0.03 | 0.11 |
| geD | FXR1 | −1.2 | −1.3 | 0.11 | 0.11 |
| geD | B3GALNT1 | −1.1 | −1.3 | 0.2 | 0.11 |
| geD | PSMA4 | −1.6 | −1.3 | 0.02 | 0.12 |
| geD | RRAGA | −1.5 | −1.3 | 0.03 | 0.12 |
| geD | IGBP1 | −1.4 | −1.3 | 0.02 | 0.12 |
| geD | ABL1 | −1.2 | −1.3 | 0.05 | 0.12 |
| geD | CRADD | −1.2 | −1.3 | 0.09 | 0.12 |
| geD | C9orf61 | −1.1 | −1.3 | 0.1 | 0.12 |
| geD | PURB | −1.5 | −1.3 | 0.02 | 0.13 |
| geD | DSTN | −1.4 | −1.3 | 0.03 | 0.13 |
| geD | CXCL12 | −1.3 | −1.3 | 0.04 | 0.13 |
| geD | PLDN | −1.6 | −1.3 | 0.03 | 0.14 |
| geD | SULF1 | −1.5 | −1.3 | 0.03 | 0.14 |
| geD | FKBP10 | −1.4 | −1.3 | 0.04 | 0.14 |
| geD | BUB3 | −1.3 | −1.3 | 0.06 | 0.14 |
| geD | BMP2 | −1.3 | −1.3 | 0.07 | 0.14 |
| geD | MIG7 | −1.2 | −1.3 | 0.09 | 0.14 |
| geD | CMTM4 | −1.2 | −1.3 | 0.19 | 0.14 |
| geD | SEMA5A | −1.9 | −1.3 | 0.02 | 0.15 |
| geD | DCBLD1 | −1.5 | −1.3 | 0.03 | 0.15 |
| geD | DRAM | −1.4 | −1.3 | 0.04 | 0.15 |
| geD | SIK1 | −1.3 | −1.3 | 0.1 | 0.15 |
| geD | PLG | −1.5 | −1.3 | 0.02 | 0.16 |
| geD | HNMT | −1.4 | −1.3 | 0.03 | 0.16 |
| geD | TNFRSF19 | −1.3 | −1.3 | 0.05 | 0.16 |
| geD | IFT140 | −1.1 | −1.3 | 0.09 | 0.16 |
| geD | CUL1 | −1.1 | −1.3 | 0.16 | 0.16 |
| geD | IL1RAP | −1.6 | −1.3 | 0.03 | 0.17 |
| geD | CYCS | −1.5 | −1.3 | 0.02 | 0.17 |
| geD | PPM1F | −1.3 | −1.3 | 0.06 | 0.17 |
| geD | RNMTL1 | −1.1 | −1.3 | 0.17 | 0.17 |
| geD | RYR2 | −1.1 | −1.3 | 0.19 | 0.17 |
| geD | SMURF2 | −1.8 | −1.3 | 0.04 | 0.18 |
| geD | NF2 | −1.7 | −1.3 | 0.02 | 0.18 |

TABLE S9-continued

Age associated differences common to both CR and CNR

| | Name | FC CR vs Yng | FC CNR vs Yng | QV CR vs Yng | QC CNR vs Yng |
|---|---|---|---|---|---|
| geD | ZNF346 | −1.5 | −1.3 | 0.18 | 0.18 |
| geD | KRT18 | −1.4 | −1.3 | 0.02 | 0.18 |
| geD | CDC42SE2 | −1.4 | −1.3 | 0.04 | 0.18 |
| geD | RND1 | −1.4 | −1.3 | 0.08 | 0.18 |
| geD | NOTCH2 | −1.4 | −1.3 | 0.09 | 0.18 |
| geD | STK38 | −1.4 | −1.3 | 0.16 | 0.18 |
| geD | SMAD2 | −1.3 | −1.3 | 0.04 | 0.18 |
| geD | FNBP1L | −1.3 | −1.3 | 0.07 | 0.18 |
| geD | SNIP | −1.3 | −1.3 | 0.1 | 0.18 |
| geD | TRIB1 | −1.2 | −1.3 | 0.14 | 0.18 |
| geD | PPIC | −1.5 | −1.3 | 0.04 | 0.19 |
| geD | TGFBI | −1.4 | −1.3 | 0.06 | 0.19 |
| geD | TXLNA | −1.3 | −1.3 | 0.05 | 0.19 |
| geD | SLFN5 | −1.3 | −1.3 | 0.08 | 0.19 |
| geD | SMAD5 | −1.2 | −1.3 | 0.14 | 0.19 |
| geD | SON | −1.6 | −1.3 | 0.02 | 0.2 |
| geD | SWAP70 | −1.5 | −1.3 | 0.04 | 0.2 |
| geD | ALK | −1.4 | −1.3 | 0.06 | 0.2 |
| geD | AGGF1 | −1.3 | −1.3 | 0.11 | 0.2 |
| geD | CASP10 | −1.5 | −1.2 | 0.09 | 0.07 |
| geD | DIAPH2 | −1.1 | −1.2 | 0.19 | 0.1 |
| geD | GREM2 | −1.3 | −1.2 | 0.04 | 0.11 |
| geD | SPN | −1.3 | −1.2 | 0.1 | 0.12 |
| geD | HBXIP | −1.2 | −1.2 | 0.18 | 0.15 |
| geD | C14orf153 | −1.7 | −1.2 | 0.1 | 0.16 |
| geD | JAKMIP1 | −1.3 | −1.2 | 0.05 | 0.16 |
| geD | COL27A1 | −1.3 | −1.2 | 0.06 | 0.16 |
| geD | TIAM2 | −1.1 | −1.2 | 0.14 | 0.16 |
| geD | IK | −1.2 | −1.2 | 0.07 | 0.17 |
| geD | CD9 | −1.1 | −1.2 | 0.18 | 0.17 |
| geD | VNN1 | −1.5 | −1.2 | 0.03 | 0.18 |
| geD | IFT88 | −1.5 | −1.2 | 0.04 | 0.18 |
| geD | PTK2 | −1.4 | −1.2 | 0.06 | 0.18 |
| geD | SRA1 | −1.2 | −1.2 | 0.11 | 0.18 |
| geD | SNX1 | −1.2 | −1.2 | 0.12 | 0.18 |
| geD | PRKDC | −1.3 | −1.2 | 0.06 | 0.19 |
| geD | POLA1 | −1.1 | −1.2 | 0.19 | 0.19 |
| geD | FGG | −2.6 | −1.2 | 0.04 | 0.2 |
| geD | SNX4 | −1.4 | −1.2 | 0.1 | 0.2 |
| geD | FAT3 | −1.2 | −1.2 | 0.06 | 0.2 |
| geD | LOC645166 | 1.4 | 1.1 | 0.02 | 0.18 |
| geD | TUBB | 1.4 | 1.2 | 0.02 | 0.1 |
| geD | FAF1 | 1.4 | 1.2 | 0.02 | 0.12 |
| geD | PSMB2 | 1.2 | 1.2 | 0.05 | 0.13 |
| geD | TH1L | 1.3 | 1.2 | 0.02 | 0.14 |
| geD | MAEA | 1.1 | 1.2 | 0.16 | 0.15 |
| geD | PVRL2 | 1.2 | 1.2 | 0.11 | 0.16 |
| geD | MPZL2 | 1.3 | 1.2 | 0.03 | 0.17 |
| geD | FKBP4 | 1.3 | 1.2 | 0.04 | 0.17 |
| geD | RBP4 | 1.3 | 1.2 | 0.02 | 0.18 |
| geD | LAMC2 | 1.6 | 1.2 | 0.02 | 0.2 |
| geD | CTSC | 1.3 | 1.3 | 0.03 | 0.07 |
| geD | CASP4 | 1.3 | 1.3 | 0.04 | 0.07 |
| geD | BECN1 | 1.3 | 1.3 | 0.06 | 0.07 |
| geD | C2 | 1.7 | 1.3 | 0.02 | 0.1 |
| geD | EXOC7 | 1.4 | 1.3 | 0.03 | 0.12 |
| geD | CEACAM1 | 1.2 | 1.3 | 0.07 | 0.13 |
| geD | CCM2 | 1.4 | 1.3 | 0.13 | 0.14 |
| geD | PURB | 1.3 | 1.3 | 0.05 | 0.15 |
| geD | CTSS | 1.3 | 1.3 | 0.07 | 0.15 |
| geD | LGALS3BP | 1.5 | 1.3 | 0.02 | 0.15 |
| geD | GPR135 | 1.2 | 1.3 | 0.12 | 0.16 |
| geD | MYLPF | 1.3 | 1.3 | 0.09 | 0.16 |
| geD | MUC5AC | 1.3 | 1.3 | 0.17 | 0.16 |
| geD | RHOA | 1.7 | 1.3 | 0.02 | 0.17 |
| geD | GP6 | 1.5 | 1.3 | 0.03 | 0.19 |
| geD | IFI30 | 1.5 | 1.3 | 0.03 | 0.19 |
| geD | TNFAIP8 | 1.7 | 1.3 | 0.03 | 0.2 |
| geD | LITAF | 1.2 | 1.4 | 0.1 | 0.07 |
| geD | EHD1 | 1.7 | 1.4 | 0.02 | 0.07 |
| geD | CNTNAP2 | 1.2 | 1.4 | 0.06 | 0.08 |
| geD | NRP1 | 1.3 | 1.4 | 0.04 | 0.11 |
| geD | WNK1 | 1.4 | 1.4 | 0.04 | 0.11 |
| geD | TNFAIP2 | 1.5 | 1.4 | 0.04 | 0.12 |
| geD | IFITM2 | 1.7 | 1.4 | 0.02 | 0.12 |
| geD | MLLT6 | 1.8 | 1.4 | 0.02 | 0.12 |

TABLE S9-continued

| | Age associated differences common to both CR and CNR | | | | |
|---|---|---|---|---|---|
| | Name | FC CR vs Yng | FC CNR vs Yng | QV CR vs Yng | QC CNR vs Yng |
| geD | FCGR2A | 1.3 | 1.4 | 0.03 | 0.14 |
| geD | SORL1 | 1.7 | 1.4 | 0.03 | 0.15 |
| geD | B3GALNT1 | 1.6 | 1.4 | 0.02 | 0.16 |
| geD | IGF2AS | 1.6 | 1.4 | 0.03 | 0.16 |
| geD | CEBPB | 2 | 1.4 | 0.02 | 0.16 |
| geD | CNTN2 | 1.3 | 1.4 | 0.03 | 0.17 |
| geD | LRRN2 | 1.8 | 1.4 | 0.02 | 0.17 |
| geD | THBS1 | 1.7 | 1.4 | 0.03 | 0.18 |
| geD | SLC13A2 | 1.2 | 1.4 | 0.17 | 0.19 |
| geD | ADRB3 | 1.2 | 1.5 | 0.15 | 0.07 |
| geD | CTF1 | 1.3 | 1.5 | 0.07 | 0.07 |
| geD | IRS2 | 1.4 | 1.5 | 0.02 | 0.07 |
| geD | SP3 | 1.2 | 1.5 | 0.13 | 0.08 |
| geD | LTBP2 | 1.4 | 1.5 | 0.04 | 0.1 |
| geD | ITFG3 | 1.2 | 1.5 | 0.14 | 0.12 |
| geD | STX1A | 1.5 | 1.5 | 0.03 | 0.12 |
| geD | PRKCD | 2.1 | 1.5 | 0.02 | 0.14 |
| geD | THRA | 1.1 | 1.5 | 0.19 | 0.16 |
| geD | TAL1 | 1.4 | 1.5 | 0.07 | 0.16 |
| geD | PLEKHF1 | 2 | 1.5 | 0.02 | 0.16 |
| geD | CR2 | 1.3 | 1.5 | 0.12 | 0.18 |
| geD | ACTC1 | 1.4 | 1.5 | 0.09 | 0.18 |
| geD | NINJ2 | 1.7 | 1.5 | 0.03 | 0.18 |
| geD | LIMS2 | 2.1 | 1.5 | 0.03 | 0.18 |
| geD | LAMA4 | 1.2 | 1.5 | 0.17 | 0.19 |
| geD | GYLTL1B | 1.8 | 1.5 | 0.04 | 0.19 |
| geD | RABEP1 | 2 | 1.5 | 0.04 | 0.19 |
| geD | G6PD | 1.2 | 1.6 | 0.12 | 0.09 |
| geD | TNR | 1.6 | 1.6 | 0.14 | 0.1 |
| geD | MASP2 | 1.4 | 1.6 | 0.06 | 0.11 |
| geD | PGM5 | 1.5 | 1.6 | 0.05 | 0.11 |
| geD | RAC2 | 2.2 | 1.6 | 0.02 | 0.12 |
| geD | ZFR2 | 1.7 | 1.6 | 0.04 | 0.13 |
| geD | UMOD | 1.8 | 1.6 | 0.02 | 0.13 |
| geD | TNXB | 1.4 | 1.6 | 0.09 | 0.14 |
| geD | EBI3 | 1.4 | 1.6 | 0.09 | 0.15 |
| geD | COL27A1 | 2 | 1.6 | 0.02 | 0.16 |
| geD | CEBPE | 1.7 | 1.6 | 0.04 | 0.17 |
| geD | MMP9 | 1.9 | 1.6 | 0.03 | 0.19 |
| geD | CFD | 2.2 | 1.6 | 0.03 | 0.19 |
| geD | DGKZ | 2.1 | 1.6 | 0.03 | 0.2 |
| geD | APOA4 | 1.2 | 1.7 | 0.07 | 0.07 |
| geD | HLA-DPB1 | 1.4 | 1.7 | 0.08 | 0.07 |
| geD | IL28A | 1.3 | 1.7 | 0.05 | 0.13 |
| geD | LILRA5 | 2 | 1.7 | 0.03 | 0.13 |
| geD | APOL2 | 1.9 | 1.7 | 0.03 | 0.14 |
| geD | GZMM | 1.9 | 1.7 | 0.04 | 0.16 |
| geD | MYADM | 1.7 | 1.7 | 0.05 | 0.17 |
| geD | SEMA4A | 1.8 | 1.7 | 0.05 | 0.19 |
| geD | LY86 | 2.1 | 1.7 | 0.03 | 0.19 |
| geD | TNFSF13B | 1.7 | 1.8 | 0.02 | 0.08 |
| geD | MAP4K2 | 1.3 | 1.8 | 0.09 | 0.1 |
| geD | IL12RB1 | 1.2 | 1.8 | 0.18 | 0.13 |
| geD | SSTR3 | 1.6 | 1.8 | 0.06 | 0.14 |
| geD | FOXH1 | 1.8 | 1.8 | 0.03 | 0.16 |
| geD | ZBP1 | 2.2 | 1.8 | 0.03 | 0.17 |
| geD | DEFB4 | 1.2 | 1.9 | 0.1 | 0.07 |
| geD | CASP5 | 1.6 | 1.9 | 0.07 | 0.08 |
| geD | RAPGEF3 | 1.3 | 1.9 | 0.18 | 0.1 |
| geD | PTGIR | 1.6 | 1.9 | 0.07 | 0.1 |
| geD | HRH2 | 1.4 | 1.9 | 0.07 | 0.14 |
| geD | LSP1 | 2.3 | 1.9 | 0.03 | 0.14 |
| geD | ADAM33 | 2 | 1.9 | 0.06 | 0.15 |
| geD | WAS | 2.1 | 1.9 | 0.03 | 0.16 |
| geD | CD244 | 1.3 | 2 | 0.09 | 0.07 |
| geD | CLDN11 | 1.6 | 2 | 0.04 | 0.07 |
| geD | MYADM | 1.7 | 2 | 0.02 | 0.07 |
| geD | COL20A1 | 1.2 | 2 | 0.15 | 0.1 |
| geD | PEAR1 | 1.4 | 2 | 0.07 | 0.1 |
| geD | MUC2 | 1.3 | 2 | 0.11 | 0.12 |

TABLE S9-continued

Age associated differences common to both CR and CNR

| | Name | FC CR vs Yng | FC CNR vs Yng | QV CR vs Yng | QC CNR vs Yng |
|---|---|---|---|---|---|
| geD | LAT2 | 2.1 | 2 | 0.03 | 0.12 |
| geD | PSTPIP1 | 2.8 | 2.1 | 0.02 | 0.11 |
| geD | MARCO | 2.1 | 2.1 | 0.07 | 0.16 |
| geD | UNC5A | 1.1 | 2.1 | 0.2 | 0.19 |
| geD | FCN2 | 2 | 2.1 | 0.1 | 0.19 |
| geD | HLA-DPB1 | 3.6 | 2.1 | 0.02 | 0.19 |
| geD | CD300LB | 1.9 | 2.2 | 0.02 | 0.07 |
| geD | HLA-F | 2.2 | 2.2 | 0.02 | 0.07 |
| geD | LILRA5 | 3.2 | 2.2 | 0.02 | 0.07 |
| geD | CASP8 | 1.7 | 2.2 | 0.09 | 0.1 |
| geD | GHRHR | 1.9 | 2.2 | 0.05 | 0.1 |
| geD | PIK3CD | 2.5 | 2.2 | 0.02 | 0.13 |
| geD | ITGB2 | 1.8 | 2.2 | 0.05 | 0.16 |
| geD | IRF1 | 2.8 | 2.2 | 0.04 | 0.2 |
| geD | FCGBP | 1.3 | 2.3 | 0.2 | 0.1 |
| geD | TREML1 | 1.7 | 2.3 | 0.06 | 0.1 |
| geD | PDGFRB | 1.7 | 2.3 | 0.1 | 0.17 |
| geD | ERCC2 | 2.2 | 2.4 | 0.02 | 0.07 |
| geD | SLC5A2 | 2.2 | 2.4 | 0.04 | 0.14 |
| geD | IL10RA | 1.9 | 2.4 | 0.1 | 0.16 |
| geD | MUC4 | 1.8 | 2.4 | 0.12 | 0.18 |
| geD | NKX2-3 | 1.6 | 2.5 | 0.08 | 0.07 |
| geD | HRH3 | 2.4 | 2.5 | 0.08 | 0.1 |
| geD | CDSN | 1.6 | 2.6 | 0.06 | 0.07 |
| geD | MINK1 | 2 | 2.6 | 0.04 | 0.1 |
| geD | ACVR1B | 2 | 2.7 | 0.03 | 0.07 |
| geD | UCP3 | 2.8 | 2.7 | 0.02 | 0.07 |
| geD | MUC4 | 1.9 | 2.7 | 0.06 | 0.1 |
| geD | PTCRA | 1.6 | 2.7 | 0.14 | 0.12 |
| geD | PROP1 | 1.7 | 2.7 | 0.12 | 0.12 |
| geD | HLA-J | 3.9 | 2.7 | 0.02 | 0.16 |
| geD | POLM | 2.1 | 2.7 | 0.1 | 0.18 |
| geD | KIR2DL4 | 1.7 | 2.8 | 0.06 | 0.07 |
| geD | GYPC | 2.1 | 2.8 | 0.03 | 0.07 |
| geD | CACNB3 | 2.4 | 2.8 | 0.07 | 0.15 |
| geD | LILRA3 | 2.8 | 2.8 | 0.06 | 0.16 |
| geD | LAX1 | 1.5 | 2.9 | 0.13 | 0.07 |
| geD | GHSR | 1.6 | 2.9 | 0.1 | 0.07 |
| geD | RARA | 1.7 | 2.9 | 0.12 | 0.1 |
| geD | RUNX1 | 2.2 | 3 | 0.04 | 0.07 |
| geD | HLA-B | 3.4 | 3 | 0.04 | 0.1 |
| geD | HLA-DOA | 3.5 | 3 | 0.03 | 0.14 |
| geD | JAK3 | 2.2 | 3.1 | 0.02 | 0.07 |
| geD | CEACAM19 | 2.8 | 3.1 | 0.04 | 0.15 |
| geD | CPLX2 | 2.6 | 3.3 | 0.06 | 0.12 |
| geD | TCL6 | 1.8 | 3.5 | 0.19 | 0.15 |
| geD | E2F2 | 2.1 | 3.6 | 0.03 | 0.14 |
| geD | PTAFR | 5.6 | 3.7 | 0.03 | 0.18 |
| geD | HLA-DRB1 | 2.5 | 3.8 | 0.11 | 0.15 |
| geD | CD14 | 4.2 | 4 | 0.03 | 0.11 |
| geD | MUC4 | 1.6 | 4.1 | 0.06 | 0.07 |
| geD | LALBA | 2.1 | 4.2 | 0.03 | 0.13 |
| geD | FCER1G | 2.4 | 4.3 | 0.14 | 0.16 |
| geD | TAOK2 | 2.7 | 4.4 | 0.04 | 0.07 |
| geD | BCAM | 2.9 | 4.4 | 0.07 | 0.13 |
| geD | MLXIPL | 3.1 | 4.5 | 0.07 | 0.13 |
| geD | CCL24 | 2.6 | 4.6 | 0.1 | 0.14 |
| geD | HLA-DRB3 | 2.6 | 4.8 | 0.14 | 0.14 |
| geD | LILRA6 | 8.8 | 4.8 | 0.03 | 0.18 |
| geD | IL8RA | 4.3 | 5 | 0.1 | 0.2 |
| geD | CD79A | 4 | 5.7 | 0.08 | 0.15 |
| geD | HLA-DRB5 | 4.2 | 5.7 | 0.09 | 0.16 |
| geD | FCN1 | 4.6 | 5.7 | 0.09 | 0.18 |
| geD | BCL2 | 3.5 | 6 | 0.06 | 0.1 |
| geD | ADAMTS7 | 3.8 | 6.9 | 0.1 | 0.16 |
| geD | CD4 | 3.1 | 8.5 | 0.07 | 0.07 |
| geD | RTN3 | 5.4 | 19.7 | 0.1 | 0.18 |
| geD | FCGR3B | 6.5 | 23.6 | 0.12 | 0.12 |

APPENDIX J

TABLE S10

| DataType | Name | Fold-change | Q-value |
|---|---|---|---|
| phenoD | CD8 CENTRAL MEMORY | 2.1 | 0.06 |
| phenoD | B CELLS | 1.5 | 0.12 |
| phenoD | CD4 EFFECTOR MEMORY | −2.7 | 0.12 |
| phenoD | NK T CELLS | −2.6 | 0.12 |
| phenoD | CD4 | −6.5 | 0.15 |
| geD | CD99L2 | 2.2 | 0 |
| geD | HSPD1 | −1.4 | 0.01 |
| geD | SRF | 1.7 | 0.02 |
| geD | BOK | 2.5 | 0.02 |
| geD | LRP10 | 2.8 | 0.02 |
| geD | UBE2I | 1.7 | 0.02 |
| geD | PANX1 | 1.7 | 0.02 |
| geD | NFKBIB | 1.4 | 0.02 |
| geD | BLK | 1.6 | 0.02 |
| geD | RAB5C | 1.8 | 0.02 |
| geD | MKL1 | 1.7 | 0.02 |
| geD | NFKB2 | 1.5 | 0.02 |
| geD | SMAD7 | 1.6 | 0.02 |
| geD | IGF1 | 1.5 | 0.02 |
| geD | NR3C1 | 1.5 | 0.02 |
| geD | ITGA2B | 1.4 | 0.02 |
| geD | C1R | 2.2 | 0.02 |
| geD | BOC | 1.4 | 0.02 |
| geD | CLSTN3 | 2 | 0.02 |
| geD | NISCH | 2.6 | 0.02 |
| geD | SP1 | 1.6 | 0.02 |
| geD | PI4KB | 2.2 | 0.02 |
| geD | PML | 1.6 | 0.02 |
| geD | LAMA5 | 1.8 | 0.02 |
| geD | TNFSF10 | 2.4 | 0.02 |
| geD | MUC5AC | 1.6 | 0.02 |
| geD | RAG1AP1 | 2.2 | 0.02 |
| geD | LILRA4 | 1.4 | 0.02 |
| geD | CLN3 | 1.7 | 0.02 |
| geD | CD40 | 2.1 | 0.02 |
| geD | AGPAT2 | 1.6 | 0.02 |
| geD | RAF1 | 1.8 | 0.02 |
| geD | EDN1 | 1.5 | 0.02 |
| geD | FEZ2 | 1.9 | 0.02 |
| geD | SART3 | 1.8 | 0.02 |
| geD | POGK | 1.8 | 0.02 |
| geD | PXN | 1.4 | 0.02 |
| geD | HIVEP2 | 2.3 | 0.02 |
| geD | NEK6 | 1.9 | 0.02 |
| geD | IGKC | 1.6 | 0.02 |
| geD | SECTM1 | 1.7 | 0.02 |
| geD | FCN1 | 1.5 | 0.02 |
| geD | GRB2 | 1.4 | 0.02 |
| geD | PPP1R15A | 2 | 0.02 |
| geD | GPX4 | 1.3 | 0.02 |
| geD | MAMDC4 | 1.6 | 0.02 |
| geD | SOCS7 | 2.3 | 0.02 |
| geD | COL9A1 | 1.7 | 0.02 |
| geD | TLR9 | 1.5 | 0.02 |
| geD | PTK2B | 1.8 | 0.02 |
| geD | CLDN7 | 1.8 | 0.02 |
| geD | RHOA | 1.6 | 0.02 |
| geD | NOXA1 | 1.5 | 0.02 |
| geD | PLAU | 2.5 | 0.02 |
| geD | MLL3 | 1.6 | 0.02 |
| geD | TNNI2 | 1.8 | 0.02 |
| geD | FKBP14 | 1.6 | 0.02 |
| geD | AKT1 | 1.4 | 0.02 |
| geD | THBS3 | 1.7 | 0.02 |
| geD | PCDHA5 | 2.1 | 0.02 |
| geD | F8 | 1.5 | 0.02 |
| geD | CDKN2A | 1.4 | 0.02 |
| geD | LIN7C | 1.5 | 0.02 |
| geD | APOA1 | 1.6 | 0.02 |
| geD | DYRK2 | 1.3 | 0.02 |
| geD | KIF13B | 1.7 | 0.02 |
| geD | CCR5 | 1.5 | 0.02 |
| geD | DAXX | 1.7 | 0.02 |
| geD | WNK2 | 1.6 | 0.02 |
| geD | CD52 | 1.5 | 0.02 |
| geD | ALCAM | 1.8 | 0.02 |
| geD | CISH | 1.4 | 0.02 |
| geD | TLX2 | 1.8 | 0.02 |
| geD | AHSG | 1.7 | 0.02 |
| geD | AGGF1 | 3.3 | 0.02 |
| geD | CREBBP | 1.8 | 0.02 |
| geD | CDKN2C | 1.7 | 0.02 |
| geD | GAPVD1 | 1.5 | 0.02 |
| geD | FGB | 1.5 | 0.02 |
| geD | TNIP2 | 1.3 | 0.02 |
| geD | TMEM8 | 1.4 | 0.02 |
| geD | F5 | 1.9 | 0.02 |
| geD | SART1 | 1.8 | 0.02 |
| geD | NOS3 | 1.5 | 0.02 |
| geD | PSMG3 | 1.3 | 0.02 |
| geD | MCL1 | 2.1 | 0.02 |
| geD | PPARG | 2.1 | 0.02 |
| geD | NEO1 | 1.9 | 0.02 |
| geD | TRPC4AP | 1.6 | 0.02 |
| geD | CRYAB | 1.5 | 0.02 |
| geD | CX3CL1 | 1.7 | 0.02 |
| geD | FOS | 1.5 | 0.02 |
| geD | FOXC1 | 1.4 | 0.02 |
| geD | ICAM1 | 1.8 | 0.02 |
| geD | SRC | 3.6 | 0.02 |
| geD | VAMP7 | 1.7 | 0.02 |
| geD | BYSL | 1.3 | 0.02 |
| geD | CNTROB | 1.4 | 0.02 |
| geD | BAK1 | 1.4 | 0.02 |
| geD | BBS9 | 1.4 | 0.02 |
| geD | PRKRIR | 1.6 | 0.02 |
| geD | POLL | 2.1 | 0.02 |
| geD | CLOCK | −2.3 | 0.02 |
| geD | HCFC1 | −2.8 | 0.02 |
| geD | CAV1 | −1.6 | 0.02 |
| geD | MALT1 | −2.2 | 0.02 |
| geD | TOX | −1.9 | 0.02 |
| geD | ITGAE | −2.2 | 0.02 |
| geD | CD1E | −2 | 0.02 |
| geD | CDKN1B | −1.3 | 0.02 |
| geD | SPP1 | −2 | 0.02 |
| geD | IL18 | −5.8 | 0.02 |
| geD | BRCA1 | −3.3 | 0.02 |
| geD | NAE1 | −3.1 | 0.02 |
| geD | PDCD6IP | −2.5 | 0.02 |
| geD | RAB4A | −1.5 | 0.02 |
| geD | GLO1 | −2.2 | 0.02 |
| geD | PDCD5 | −1.8 | 0.02 |
| geD | CD8A | −2.1 | 0.02 |
| geD | HIF1A | −1.6 | 0.02 |
| geD | ATP6V1H | −1.4 | 0.02 |
| geD | EDNRB | −1.8 | 0.02 |
| geD | IGFBP3 | −2.9 | 0.02 |
| geD | FER | −1.9 | 0.02 |
| geD | PTK2 | −2.4 | 0.02 |
| geD | MIA3 | −2.4 | 0.02 |
| geD | FNBP1 | −1.4 | 0.02 |
| geD | SBDS | −1.9 | 0.02 |
| geD | SLFN12 | −2.8 | 0.02 |
| geD | RAB3B | −3 | 0.02 |
| geD | PTPRC | −2.4 | 0.02 |
| geD | PTGIS | −1.8 | 0.02 |
| geD | STXBP5 | −1.4 | 0.02 |
| geD | HIF1A | −2.1 | 0.02 |
| geD | TOP1 | −2 | 0.02 |
| geD | TBP | −2.3 | 0.02 |
| geD | SMAD4 | −2.8 | 0.02 |
| geD | SEMA6A | −2 | 0.02 |
| geD | PPFIBP1 | −1.6 | 0.02 |
| geD | MSH3 | −1.7 | 0.02 |
| geD | PCNA | −1.5 | 0.02 |
| geD | KLRC2 | −2.1 | 0.02 |
| geD | SELS | −2.4 | 0.02 |

TABLE S10-continued

CR-specific measurements

| DataType | Name | Fold-change | Q-value |
|---|---|---|---|
| geD | LAMA4 | −2.3 | 0.02 |
| geD | ADAT1 | −2.2 | 0.02 |
| geD | MCTS1 | −2.1 | 0.02 |
| geD | CD69 | −2.4 | 0.02 |
| geD | ADAM10 | −2.6 | 0.02 |
| geD | CLEC4A | −2 | 0.02 |
| geD | ERCC4 | −4.5 | 0.02 |
| geD | CARD16 | −4.3 | 0.02 |
| geD | CLDN1 | −2 | 0.02 |
| geD | SYNJ1 | −1.9 | 0.02 |
| geD | UACA | −1.7 | 0.02 |
| geD | EGR1 | −2.1 | 0.02 |
| geD | FN1 | −3.9 | 0.02 |
| geD | PRKAR2A | −1.6 | 0.02 |
| geD | ESR1 | −1.8 | 0.02 |
| geD | PSME3 | −1.9 | 0.02 |
| geD | CEACAM6 | −1.6 | 0.02 |
| geD | DOCK11 | −1.7 | 0.02 |
| geD | PSMD1 | −2.6 | 0.02 |
| geD | CD247 | −1.3 | 0.02 |
| geD | CASK | −1.7 | 0.02 |
| geD | LIG4 | −2.1 | 0.02 |
| geD | GCNT2 | −2.5 | 0.02 |
| geD | ADARB1 | −1.7 | 0.02 |
| geD | SNX3 | −1.9 | 0.02 |
| geD | DGCR2 | −1.6 | 0.02 |
| geD | FKBP3 | −1.8 | 0.02 |
| geD | CD59 | −1.7 | 0.02 |
| geD | XRCC2 | −1.9 | 0.02 |
| geD | RND3 | −1.5 | 0.02 |
| geD | RAB5A | −1.9 | 0.02 |
| geD | PSMD12 | −2 | 0.02 |
| geD | LAMC1 | −2.3 | 0.02 |
| geD | ZEB2 | −2.2 | 0.02 |
| geD | ID2 | −1.4 | 0.02 |
| geD | SLC23A2 | −2 | 0.02 |
| geD | PTPN22 | −1.5 | 0.02 |
| geD | HINT1 | −2.2 | 0.02 |
| geD | STAT3 | −1.9 | 0.02 |
| geD | MCL1 | −1.8 | 0.02 |
| geD | FERMT2 | −1.9 | 0.02 |
| geD | PVRL3 | −2 | 0.02 |
| geD | PTGS2 | −2.5 | 0.02 |
| geD | GAPVD1 | −6.3 | 0.02 |
| geD | BFAR | −2.6 | 0.02 |
| geD | PDIA3 | −1.6 | 0.02 |
| geD | PACSIN2 | −2.5 | 0.02 |
| geD | ITCH | −1.6 | 0.02 |
| geD | SPOCK1 | −1.3 | 0.02 |
| geD | TNFRSF1A | −1.5 | 0.02 |
| geD | PTPN1 | −2.1 | 0.02 |
| geD | BUB3 | −1.9 | 0.02 |
| geD | MYC | −1.8 | 0.02 |
| geD | PRKRA | −1.5 | 0.02 |
| geD | PDCD2L | −1.9 | 0.02 |
| geD | EFEMP1 | −1.6 | 0.02 |
| geD | IRS1 | −1.4 | 0.02 |
| geD | IFT81 | −1.8 | 0.02 |
| geD | PKP3 | 1.8 | 0.03 |
| geD | IL1RN | 1.7 | 0.03 |
| geD | SUMO1 | 1.3 | 0.03 |
| geD | CASP10 | 1.6 | 0.03 |
| geD | C3AR1 | 1.6 | 0.03 |
| geD | ZFP36 | 1.5 | 0.03 |
| geD | CD5 | 1.7 | 0.03 |
| geD | PEX5 | 1.4 | 0.03 |
| geD | DGKZ | 2.3 | 0.03 |
| geD | BCL2L1 | 1.3 | 0.03 |
| geD | NUPR1 | 1.9 | 0.03 |
| geD | COL6A2 | 1.7 | 0.03 |
| geD | ACTN4 | 2 | 0.03 |
| geD | AMOTL1 | 1.5 | 0.03 |
| geD | GPR77 | 1.5 | 0.03 |
| geD | TCL1A | 1.3 | 0.03 |
| geD | PSEN1 | 1.4 | 0.03 |
| geD | ELMO2 | 1.8 | 0.03 |
| geD | LTBP2 | 1.6 | 0.03 |
| geD | SDK1 | 1.7 | 0.03 |
| geD | CYBA | 1.5 | 0.03 |
| geD | NTSR1 | 1.6 | 0.03 |
| geD | ITGB3BP | 1.6 | 0.03 |
| geD | TAPBP | 1.8 | 0.03 |
| geD | HOXB7 | 1.8 | 0.03 |
| geD | GDF5 | 1.6 | 0.03 |
| geD | NOG | 1.5 | 0.03 |
| geD | NF1 | 1.6 | 0.03 |
| geD | CD163L1 | 1.9 | 0.03 |
| geD | HLA-A | 1.3 | 0.03 |
| geD | PHF17 | 1.3 | 0.03 |
| geD | MGMT | 1.6 | 0.03 |
| geD | ROBO3 | 1.3 | 0.03 |
| geD | HLA-C | 1.7 | 0.03 |
| geD | BAX | 1.5 | 0.03 |
| geD | FOXJ1 | 1.5 | 0.03 |
| geD | IFI27 | 3 | 0.03 |
| geD | MAPK14 | 1.6 | 0.03 |
| geD | CLN3 | 1.5 | 0.03 |
| geD | EGF | 1.6 | 0.03 |
| geD | PARVB | 1.6 | 0.03 |
| geD | CAPN10 | 2 | 0.03 |
| geD | TERT | 1.6 | 0.03 |
| geD | PLAGL1 | 1.4 | 0.03 |
| geD | IGFALS | 1.6 | 0.03 |
| geD | CFLAR | 1.6 | 0.03 |
| geD | HDAC5 | 1.2 | 0.03 |
| geD | ERBB2 | 2.3 | 0.03 |
| geD | RRAD | 1.8 | 0.03 |
| geD | RPS3 | 1.8 | 0.03 |
| geD | ULBP2 | 1.8 | 0.03 |
| geD | CSF2RB | 1.3 | 0.03 |
| geD | GHRL | 1.7 | 0.03 |
| geD | CUTA | 2 | 0.03 |
| geD | SIRPA | 1.7 | 0.03 |
| geD | TP53AIP1 | 2 | 0.03 |
| geD | GMDS | 1.8 | 0.03 |
| geD | HMOX1 | 2.4 | 0.03 |
| geD | TNFRSF10B | 1.6 | 0.03 |
| geD | CLDN19 | 1.8 | 0.03 |
| geD | GP9 | 1.6 | 0.03 |
| geD | TRAF1 | 7.7 | 0.03 |
| geD | TGFB1I1 | 1.7 | 0.03 |
| geD | CHRNB2 | 2.4 | 0.03 |
| geD | CFHR1 | 1.3 | 0.03 |
| geD | ACIN1 | 1.4 | 0.03 |
| geD | AQP1 | 1.7 | 0.03 |
| geD | ADRM1 | 1.8 | 0.03 |
| geD | FANCC | 2.1 | 0.03 |
| geD | IL18BP | 1.5 | 0.03 |
| geD | INHBA | 1.5 | 0.03 |
| geD | LIF | 1.5 | 0.03 |
| geD | ARHGAP1 | 1.3 | 0.03 |
| geD | SOD1 | 1.5 | 0.03 |
| geD | TGFB1 | 1.4 | 0.03 |
| geD | NRP2 | 2 | 0.03 |
| geD | GATA2 | 1.9 | 0.03 |
| geD | NLRP1 | 1.5 | 0.03 |
| geD | FOLR1 | 1.6 | 0.03 |
| geD | WDR59 | 2.6 | 0.03 |
| geD | CD33 | 1.5 | 0.03 |
| geD | HRAS | 1.8 | 0.03 |
| geD | DAD1 | 1.6 | 0.03 |
| geD | WDR92 | 2.2 | 0.03 |
| geD | PRKAR1B | 1.9 | 0.03 |
| geD | MYC | 1.6 | 0.03 |
| geD | MKNK2 | 1.4 | 0.03 |
| geD | IGF2BP2 | 1.8 | 0.03 |
| geD | CCR10 | 1.7 | 0.03 |
| geD | SECTM1 | 1.3 | 0.03 |
| geD | SDF4 | 1.4 | 0.03 |
| geD | RAMP3 | 1.4 | 0.03 |
| geD | TIAM1 | 1.3 | 0.03 |
| geD | SMAD2 | −2.4 | 0.03 |

TABLE S10-continued

CR-specific measurements

| DataType | Name | Fold-change | Q-value |
|---|---|---|---|
| geD | DERL1 | −2.2 | 0.03 |
| geD | FASTKD1 | −1.8 | 0.03 |
| geD | UTP11L | −1.8 | 0.03 |
| geD | PTX3 | −2.3 | 0.03 |
| geD | ITGB8 | −1.5 | 0.03 |
| geD | ACVR1 | −2 | 0.03 |
| geD | MDM4 | −2 | 0.03 |
| geD | GSR | −1.6 | 0.03 |
| geD | TERF1 | −1.5 | 0.03 |
| geD | SCYE1 | −2.2 | 0.03 |
| geD | C5 | −2.1 | 0.03 |
| geD | MAP3K5 | −1.7 | 0.03 |
| geD | EXOC5 | −1.6 | 0.03 |
| geD | LRIG3 | −2.1 | 0.03 |
| geD | FLRT2 | −2.6 | 0.03 |
| geD | HIPK2 | −1.6 | 0.03 |
| geD | C2CD2 | −1.8 | 0.03 |
| geD | NFE2L3 | −2.6 | 0.03 |
| geD | HIVEP1 | −2.4 | 0.03 |
| geD | SCYE1 | −1.6 | 0.03 |
| geD | DCTN3 | −3.4 | 0.03 |
| geD | TDGF1 | −1.4 | 0.03 |
| geD | C1QTNF3 | −3.2 | 0.03 |
| geD | PDCD4 | −2.2 | 0.03 |
| geD | HRH1 | −2.4 | 0.03 |
| geD | ILK | −3.1 | 0.03 |
| geD | CXCL3 | −3.3 | 0.03 |
| geD | FLI1 | −1.6 | 0.03 |
| geD | M6PR | −1.7 | 0.03 |
| geD | JAK1 | −1.3 | 0.03 |
| geD | SLC1A2 | −2.1 | 0.03 |
| geD | BCL2 | −1.8 | 0.03 |
| geD | ADH5 | −2.7 | 0.03 |
| geD | CD46 | −2.3 | 0.03 |
| geD | AKAP11 | −1.4 | 0.03 |
| geD | APOH | −1.5 | 0.03 |
| geD | PAFAH1B1 | −1.7 | 0.03 |
| geD | ROCK2 | −1.4 | 0.03 |
| geD | SEMA3A | −1.7 | 0.03 |
| geD | CEACAM1 | −1.7 | 0.03 |
| geD | NPHP4 | −2.2 | 0.03 |
| geD | MDM2 | −1.4 | 0.03 |
| geD | SP1 | −1.5 | 0.03 |
| geD | LIMS1 | −3.1 | 0.03 |
| geD | DCBLD2 | −1.5 | 0.03 |
| geD | CSE1L | −1.2 | 0.03 |
| geD | PKP2 | −1.9 | 0.03 |
| geD | E2F2 | −1.3 | 0.03 |
| geD | SEMA3A | −1.8 | 0.03 |
| geD | PAFAH1B2 | −1.8 | 0.03 |
| geD | PLDN | −2.2 | 0.03 |
| geD | HIP1 | −1.6 | 0.03 |
| geD | GDF6 | −1.9 | 0.03 |
| geD | SH3KBP1 | −1.7 | 0.03 |
| geD | THAP2 | −2.7 | 0.03 |
| geD | RPS3A | −2 | 0.03 |
| geD | ADAL | −1.5 | 0.03 |
| geD | MTMR3 | −2.4 | 0.03 |
| geD | MBD4 | −1.5 | 0.03 |
| geD | SLC26A6 | −1.5 | 0.03 |
| geD | PRKAR1A | −1.5 | 0.03 |
| geD | PDLIM5 | −1.9 | 0.03 |
| geD | PDLIM5 | −1.7 | 0.03 |
| geD | STAT3 | −1.5 | 0.03 |
| geD | DYRK2 | −1.4 | 0.03 |
| geD | PSMC6 | −2.1 | 0.03 |
| geD | MLLT11 | −1.7 | 0.03 |
| geD | MPZL3 | −1.6 | 0.03 |
| geD | MAGED1 | −1.3 | 0.03 |
| geD | SERPINB9 | −1.6 | 0.03 |
| geD | SERPINB2 | −2.1 | 0.03 |
| geD | MLLT3 | −1.5 | 0.03 |
| geD | AQP1 | −1.4 | 0.03 |
| geD | RPS6KA3 | −1.6 | 0.03 |
| geD | MYO6 | −2.5 | 0.03 |
| geD | C2 | −1.8 | 0.03 |
| geD | EEF1A1 | −1.4 | 0.03 |
| geD | ROCK2 | −1.6 | 0.03 |
| geD | CCR9 | −2 | 0.03 |
| geD | PSMG2 | −4.4 | 0.03 |
| geD | FGB | −1.6 | 0.03 |
| geD | PML | −2 | 0.03 |
| geD | SMNDC1 | −1.4 | 0.03 |
| geD | HIVEP3 | 5.2 | 0.04 |
| geD | PARVG | 1.5 | 0.04 |
| geD | MAPK8 | 1.8 | 0.04 |
| geD | CD3D | 1.6 | 0.04 |
| geD | HDAC5 | 1.7 | 0.04 |
| geD | FXYD5 | 1.9 | 0.04 |
| geD | CDH23 | 1.7 | 0.04 |
| geD | PPT1 | 3.9 | 0.04 |
| geD | ZNF346 | 1.4 | 0.04 |
| geD | CIAPIN1 | 1.5 | 0.04 |
| geD | TRIM69 | 1.7 | 0.04 |
| geD | COL18A1 | 1.6 | 0.04 |
| geD | MLLT1 | 1.6 | 0.04 |
| geD | METTL11A | 1.4 | 0.04 |
| geD | SIRPA | 1.5 | 0.04 |
| geD | CXCL12 | 1.3 | 0.04 |
| geD | TMBIM6 | 2 | 0.04 |
| geD | MLLT1 | 1.2 | 0.04 |
| geD | IFI6 | 1.5 | 0.04 |
| geD | HSPA5 | 1.7 | 0.04 |
| geD | KCNH3 | 1.5 | 0.04 |
| geD | COL14A1 | 1.5 | 0.04 |
| geD | IMPDH1 | 1.6 | 0.04 |
| geD | TNFRSF18 | 2.1 | 0.04 |
| geD | SFRS17A | 1.4 | 0.04 |
| geD | MPL | 1.9 | 0.04 |
| geD | RRAGC | 1.7 | 0.04 |
| geD | HPS4 | 1.8 | 0.04 |
| geD | MUC2 | 1.3 | 0.04 |
| geD | CD276 | 2.1 | 0.04 |
| geD | IRAK1 | 4.5 | 0.04 |
| geD | PRKD2 | 1.5 | 0.04 |
| geD | CDH10 | 2.2 | 0.04 |
| geD | DAB2 | 1.8 | 0.04 |
| geD | CYBB | 1.4 | 0.04 |
| geD | B2M | 1.2 | 0.04 |
| geD | ACTN1 | 1.5 | 0.04 |
| geD | PPM1D | 1.9 | 0.04 |
| geD | C1orf38 | 1.5 | 0.04 |
| geD | ABL1 | 1.5 | 0.04 |
| geD | NOL3 | 1.5 | 0.04 |
| geD | C8A | 1.6 | 0.04 |
| geD | HDAC1 | 2 | 0.04 |
| geD | LEFTY2 | 1.4 | 0.04 |
| geD | NCF1 | 2.2 | 0.04 |
| geD | TTYH1 | 2.1 | 0.04 |
| geD | AMICA1 | 2.5 | 0.04 |
| geD | SLC26A6 | 1.8 | 0.04 |
| geD | FSTL1 | 1.9 | 0.04 |
| geD | AP2A2 | 1.6 | 0.04 |
| geD | BGLAP | 1.9 | 0.04 |
| geD | CD6 | 2.9 | 0.04 |
| geD | FKBP15 | 1.8 | 0.04 |
| geD | FASTK | 1.4 | 0.04 |
| geD | PTPN6 | 1.5 | 0.04 |
| geD | CMTM5 | 1.3 | 0.04 |
| geD | ELN | 1.4 | 0.04 |
| geD | NLRP12 | 1.6 | 0.04 |
| geD | CLDN10 | 1.5 | 0.04 |
| geD | DAP | 1.4 | 0.04 |
| geD | ADRM1 | 1.6 | 0.04 |
| geD | IFITM1 | 1.3 | 0.04 |
| geD | LAIR1 | 1.2 | 0.04 |
| geD | RP11-138L21.1 | 1.7 | 0.04 |
| geD | DDR1 | 1.8 | 0.04 |
| geD | RASSF5 | 1.7 | 0.04 |
| geD | DCTN3 | 2.6 | 0.04 |
| geD | FOXC1 | 1.6 | 0.04 |
| geD | LSP1 | 1.3 | 0.04 |

TABLE S10-continued

CR-specific measurements

| DataType | Name | Fold-change | Q-value |
|---|---|---|---|
| geD | CSNK1E | 1.5 | 0.04 |
| geD | CEBPB | 1.7 | 0.04 |
| geD | RAB5C | 2.2 | 0.04 |
| geD | EXOC6 | 1.9 | 0.04 |
| geD | CD68 | 1.4 | 0.04 |
| geD | TREML2 | 6.3 | 0.04 |
| geD | VAV1 | 1.7 | 0.04 |
| geD | SERPINB2 | 1.7 | 0.04 |
| geD | NME6 | 1.4 | 0.04 |
| geD | NFATC4 | 1.4 | 0.04 |
| geD | PSME3 | 1.3 | 0.04 |
| geD | HLA-DMA | 1.4 | 0.04 |
| geD | ATP2A2 | 1.7 | 0.04 |
| geD | ADRA1B | 1.9 | 0.04 |
| geD | CEBPA | 2.1 | 0.04 |
| geD | LYL1 | 2.9 | 0.04 |
| geD | ACTN1 | 1.8 | 0.04 |
| geD | FCGBP | 1.6 | 0.04 |
| geD | STXBP2 | 2.2 | 0.04 |
| geD | NLRP3 | 1.6 | 0.04 |
| geD | CFHR3 | −2.3 | 0.04 |
| geD | SLK | −2.6 | 0.04 |
| geD | AMIGO2 | −2.9 | 0.04 |
| geD | UBE2N | −1.6 | 0.04 |
| geD | ZFYVE16 | −2.6 | 0.04 |
| geD | GLMN | −2.5 | 0.04 |
| geD | PTCD2 | −2.3 | 0.04 |
| geD | ID2 | −1.9 | 0.04 |
| geD | ALG9 | −1.7 | 0.04 |
| geD | NBN | −1.5 | 0.04 |
| geD | AVEN | −2.2 | 0.04 |
| geD | TIAL1 | −1.6 | 0.04 |
| geD | ZEB2 | −2.5 | 0.04 |
| geD | CTNNA1 | −1.7 | 0.04 |
| geD | BBS7 | −1.7 | 0.04 |
| geD | PIK3R1 | −1.5 | 0.04 |
| geD | MYST4 | −1.3 | 0.04 |
| geD | LEF1 | −1.3 | 0.04 |
| geD | ARF6 | −3.3 | 0.04 |
| geD | PANX1 | −1.4 | 0.04 |
| geD | PTPN12 | −2.2 | 0.04 |
| geD | CLSTN1 | −2.8 | 0.04 |
| geD | IGF2 | −2.1 | 0.04 |
| geD | HMCN1 | −1.6 | 0.04 |
| geD | SLC1A1 | −1.3 | 0.04 |
| geD | TRAT1 | −4.3 | 0.04 |
| geD | HTATIP2 | −1.5 | 0.04 |
| geD | IGBP1 | −1.5 | 0.04 |
| geD | STK38L | −1.6 | 0.04 |
| geD | RGMB | −2.6 | 0.04 |
| geD | EXOC1 | −1.6 | 0.04 |
| geD | FCHSD2 | −1.5 | 0.04 |
| geD | 7-Sep | −1.4 | 0.04 |
| geD | RALA | −1.7 | 0.04 |
| geD | RHOT1 | −1.5 | 0.04 |
| geD | ITGB1 | −1.5 | 0.04 |
| geD | TOLLIP | −2 | 0.04 |
| geD | ARNTL | −1.4 | 0.04 |
| geD | BCAP29 | −1.7 | 0.04 |
| geD | AHSG | −1.5 | 0.04 |
| geD | EXOC8 | −2.2 | 0.04 |
| geD | ADH5 | −1.3 | 0.04 |
| geD | FAF2 | −1.9 | 0.04 |
| geD | NOD1 | −2.1 | 0.04 |
| geD | HPS4 | −1.5 | 0.04 |
| geD | RICTOR | −1.9 | 0.04 |
| geD | SGK1 | −1.6 | 0.04 |
| geD | FOXC1 | −1.5 | 0.04 |
| geD | PDCL3 | −2.4 | 0.04 |
| geD | CD28 | −1.9 | 0.04 |
| geD | FKBP5 | −2.3 | 0.04 |
| geD | PTPRF | −1.8 | 0.04 |
| geD | MSX2 | −1.6 | 0.04 |
| geD | SEMA5A | −2.1 | 0.04 |
| geD | PAG1 | −2.1 | 0.04 |
| geD | BLNK | −2.1 | 0.04 |
| geD | CCL3L3 | −2.2 | 0.04 |
| geD | SMAD3 | −2.6 | 0.04 |
| geD | IFT74 | −2.7 | 0.04 |
| geD | LRP8 | −1.4 | 0.04 |
| geD | MLLT3 | −1.4 | 0.04 |
| geD | WWTR1 | −1.7 | 0.04 |
| geD | DPP4 | −2.3 | 0.04 |
| geD | SHISA5 | −2.4 | 0.04 |
| geD | PRKAR2A | −1.7 | 0.04 |
| geD | EREG | −2.1 | 0.04 |
| geD | BLM | −5.3 | 0.04 |
| geD | ANXA4 | −2.5 | 0.04 |
| geD | GAPVD1 | −1.7 | 0.04 |
| geD | NAIP | −1.6 | 0.04 |
| geD | CORO1C | −1.2 | 0.04 |
| geD | LOC731884 | −1.8 | 0.04 |
| geD | CD2BP2 | −1.8 | 0.04 |
| geD | SEMA3C | −1.3 | 0.04 |
| geD | C11orf82 | −2.4 | 0.04 |
| geD | EIF2AK3 | −2.1 | 0.04 |
| geD | PRKCA | −1.6 | 0.04 |
| geD | ROBO2 | −1.4 | 0.04 |
| geD | TTYH1 | 1.9 | 0.05 |
| geD | CEBPA | 1.2 | 0.05 |
| geD | IGJ | 1.6 | 0.05 |
| geD | ACHE | 1.3 | 0.05 |
| geD | MKNK2 | 1.2 | 0.05 |
| geD | NLRC3 | 1.5 | 0.05 |
| geD | BTBD9 | 1.7 | 0.05 |
| geD | COL6A2 | 1.6 | 0.05 |
| geD | FBF1 | 1.2 | 0.05 |
| geD | CLDN11 | 1.6 | 0.05 |
| geD | HIPK2 | 1.5 | 0.05 |
| geD | PPAP2A | 1.5 | 0.05 |
| geD | CTNNB1 | 1.4 | 0.05 |
| geD | CECR2 | 1.5 | 0.05 |
| geD | BST1 | 1.6 | 0.05 |
| geD | PNN | 1.9 | 0.05 |
| geD | PCDH24 | 1.4 | 0.05 |
| geD | NFE2L1 | 1.5 | 0.05 |
| geD | CCL23 | 1.6 | 0.05 |
| geD | GP1BB | 1.7 | 0.05 |
| geD | N-PAC | 2.2 | 0.05 |
| geD | CORO1A | 1.4 | 0.05 |
| geD | LGALS12 | 1.6 | 0.05 |
| geD | CASP2 | 1.6 | 0.05 |
| geD | HLA-C | 1.5 | 0.05 |
| geD | CCR3 | 1.4 | 0.05 |
| geD | IL23A | 1.6 | 0.05 |
| geD | ANGPTL4 | 1.3 | 0.05 |
| geD | GATA2 | 2.9 | 0.05 |
| geD | PCDH1 | 1.7 | 0.05 |
| geD | DDIT4 | 1.4 | 0.05 |
| geD | RPH3AL | 1.5 | 0.05 |
| geD | HSPA1A | 1.3 | 0.05 |
| geD | RPS6KA1 | 1.4 | 0.05 |
| geD | TFPT | 1.5 | 0.05 |
| geD | SIRT6 | 1.5 | 0.05 |
| geD | CHRNA7 | 1.7 | 0.05 |
| geD | TROAP | 1.6 | 0.05 |
| geD | TAX1BP3 | 1.4 | 0.05 |
| geD | ADAM8 | 1.4 | 0.05 |
| geD | TNFRSF1B | 1.6 | 0.05 |
| geD | CSNK2B | 1.5 | 0.05 |
| geD | CD99 | 4.1 | 0.05 |
| geD | SERPINA1 | 1.7 | 0.05 |
| geD | RAC2 | 1.2 | 0.05 |
| geD | MAPK3 | 1.4 | 0.05 |
| geD | COL20A1 | 1.4 | 0.05 |
| geD | ASGR2 | 1.8 | 0.05 |
| geD | NFKBIL1 | 2.1 | 0.05 |
| geD | MXD1 | 1.4 | 0.05 |
| geD | NP | 1.3 | 0.05 |
| geD | C1QTNF4 | 1.5 | 0.05 |
| geD | NPTN | 1.4 | 0.05 |
| geD | IFI16 | 1.4 | 0.05 |

TABLE S10-continued

CR-specific measurements

| DataType | Name | Fold-change | Q-value |
|---|---|---|---|
| geD | DBNL | 1.6 | 0.05 |
| geD | MAMDC2 | 2.3 | 0.05 |
| geD | RHOB | 1.5 | 0.05 |
| geD | PCDHB13 | 1.6 | 0.05 |
| geD | ADAM33 | 1.8 | 0.05 |
| geD | IKBKB | 1.5 | 0.05 |
| geD | ORM2 | 1.5 | 0.05 |
| geD | MLXIPL | 1.4 | 0.05 |
| geD | PRSS2 | 2.6 | 0.05 |
| geD | DEDD2 | 1.4 | 0.05 |
| geD | GNL1 | 1.2 | 0.05 |
| geD | TGFBR1 | 1.6 | 0.05 |
| geD | VPREB1 | 1.4 | 0.05 |
| geD | CD320 | 1.5 | 0.05 |
| geD | HLA-C | 1.5 | 0.05 |
| geD | ITIH1 | 1.8 | 0.05 |
| geD | NEDD4L | 1.3 | 0.05 |
| geD | PCDHGA7 | 1.7 | 0.05 |
| geD | LY6E | 1.8 | 0.05 |
| geD | TNFSF14 | 1.8 | 0.05 |
| geD | ACSF3 | 1.2 | 0.05 |
| geD | HLA-DQB1 | 1.6 | 0.05 |
| geD | IL17RA | 1.5 | 0.05 |
| geD | FCN1 | 1.3 | 0.05 |
| geD | MLLT10 | 1.7 | 0.05 |
| geD | MFSD10 | 1.5 | 0.05 |
| geD | BAT3 | 1.6 | 0.05 |
| geD | IGHD | 1.5 | 0.05 |
| geD | RABEP2 | 1.5 | 0.05 |
| geD | NLRC3 | 1.2 | 0.05 |
| geD | DGKA | 1.6 | 0.05 |
| geD | ICAM2 | 1.4 | 0.05 |
| geD | VTN | 1.4 | 0.05 |
| geD | RELB | 1.6 | 0.05 |
| geD | PACSIN3 | 1.7 | 0.05 |
| geD | RAB3B | 1.3 | 0.05 |
| geD | SMAD9 | 1.3 | 0.05 |
| geD | SIGLEC7 | 1.5 | 0.05 |
| geD | LTB | 1.4 | 0.05 |
| geD | CD248 | 1.5 | 0.05 |
| geD | GSTA4 | 1.6 | 0.05 |
| geD | ACSF3 | 1.8 | 0.05 |
| geD | ITGA5 | 1.8 | 0.05 |
| geD | FOXO3 | 1.4 | 0.05 |
| geD | TSC22D3 | 1.3 | 0.05 |
| geD | CYTH2 | 1.9 | 0.05 |
| geD | MYST3 | 1.7 | 0.05 |
| geD | SDF2 | 1.5 | 0.05 |
| geD | F8 | -1.8 | 0.05 |
| geD | SPARCL1 | -1.6 | 0.05 |
| geD | DOCK3 | -1.6 | 0.05 |
| geD | DST | -1.5 | 0.05 |
| geD | NPM1 | -1.8 | 0.05 |
| geD | AP1GBP1 | -1.4 | 0.05 |
| geD | TNFAIP3 | -1.6 | 0.05 |
| geD | ADH5 | -1.8 | 0.05 |
| geD | GPR98 | -1.3 | 0.05 |
| geD | CDH11 | -2.3 | 0.05 |
| geD | BBS4 | -1.7 | 0.05 |
| geD | SDCBP | -2.3 | 0.05 |
| geD | C1QTNF3 | -1.4 | 0.05 |
| geD | LRP12 | -1.2 | 0.05 |
| geD | ICA1L | -1.8 | 0.05 |
| geD | HTATIP2 | -1.6 | 0.05 |
| geD | TRAF1 | -1.6 | 0.05 |
| geD | CDH19 | -1.6 | 0.05 |
| geD | RB1 | -2.8 | 0.05 |
| geD | BIRC6 | -1.5 | 0.05 |
| geD | BCL9 | -1.3 | 0.05 |
| geD | THAP3 | -1.7 | 0.05 |
| geD | CDC42 | -1.7 | 0.05 |
| geD | SOD2 | -1.6 | 0.05 |
| geD | LSM14A | -1.4 | 0.05 |
| geD | CD302 | -1.4 | 0.05 |
| geD | IL2RG | -1.5 | 0.05 |
| geD | VCL | -2.1 | 0.05 |
| geD | RIMS4 | -2.2 | 0.05 |
| geD | FOXP1 | -1.6 | 0.05 |
| geD | SNUPN | -1.7 | 0.05 |
| geD | NME2 | -2.6 | 0.05 |
| geD | SCARB2 | -1.4 | 0.05 |
| geD | MAPK1 | -1.2 | 0.05 |
| geD | PVR | -1.8 | 0.05 |
| geD | 6-Sep | -1.9 | 0.05 |
| geD | PRC1 | -2 | 0.05 |
| geD | IKBKB | -1.3 | 0.05 |
| geD | CLDN12 | -1.8 | 0.05 |
| geD | NAMPT | -1.9 | 0.05 |
| geD | ANGPTL1 | -2.3 | 0.05 |
| geD | IFRD1 | -2.8 | 0.05 |
| geD | RNF34 | -1.8 | 0.05 |
| geD | MAP4K4 | -1.5 | 0.05 |
| geD | TM2D1 | -2.1 | 0.05 |
| geD | CASP8 | -1.3 | 0.05 |
| geD | SRF | -1.4 | 0.05 |
| geD | TERF1 | -1.3 | 0.05 |
| geD | IFI16 | -1.5 | 0.05 |
| geD | NDUFS1 | -1.5 | 0.05 |
| geD | MIB1 | -2 | 0.05 |
| geD | SDCBP | -2 | 0.05 |
| geD | EP300 | -2 | 0.05 |
| geD | NID1 | -2 | 0.05 |
| geD | EYA1 | -1.7 | 0.05 |
| geD | GPR126 | -1.8 | 0.05 |
| geD | HDAC4 | -1.4 | 0.05 |
| geD | SH2D1A | -2.5 | 0.05 |
| geD | TLR3 | -2.4 | 0.05 |
| geD | HSPA8 | -1.6 | 0.05 |
| geD | CXADR | -1.3 | 0.05 |
| geD | PFDN6 | -1.4 | 0.05 |
| geD | SEMA4F | -1.6 | 0.05 |
| geD | FAM3C | -1.5 | 0.05 |
| geD | BMI1 | -1.4 | 0.05 |
| geD | CD86 | -2 | 0.05 |
| geD | GRAMD4 | -1.7 | 0.05 |
| geD | HSP90AA1 | -1.7 | 0.05 |
| geD | ANXA5 | -1.5 | 0.05 |
| geD | PTGES3 | -2.7 | 0.05 |
| geD | CAMK2D | -2 | 0.05 |
| geD | IGSF5 | -1.6 | 0.05 |
| geD | NCK2 | 1.4 | 0.06 |
| geD | KCNMA1 | 1.7 | 0.06 |
| geD | LOC442421 | 1.4 | 0.06 |
| geD | VPS45 | 1.3 | 0.06 |
| geD | CD81 | 1.3 | 0.06 |
| geD | CAMK1D | 1.3 | 0.06 |
| geD | CALM3 | 1.8 | 0.06 |
| geD | BAX | 1.3 | 0.06 |
| geD | HFE | 1.6 | 0.06 |
| geD | CD96 | 1.7 | 0.06 |
| geD | NFATC2IP | 1.4 | 0.06 |
| geD | MYH9 | 1.3 | 0.06 |
| geD | EEF1A2 | 1.6 | 0.06 |
| geD | MLF2 | 1.3 | 0.06 |
| geD | NAB2 | 1.4 | 0.06 |
| geD | BAT2 | 1.5 | 0.06 |
| geD | TNFSF12 | 1.7 | 0.06 |
| geD | PAK2 | 1.5 | 0.06 |
| geD | CES1 | 1.5 | 0.06 |
| geD | PAK1 | 1.5 | 0.06 |
| geD | KLF6 | 2.1 | 0.06 |
| geD | 5-Sep | 1.5 | 0.06 |
| geD | GNA12 | 1.4 | 0.06 |
| geD | BIN3 | 1.5 | 0.06 |
| geD | C4BPB | 1.9 | 0.06 |
| geD | ICAM3 | 1.3 | 0.06 |
| geD | SKAP2 | 1.6 | 0.06 |
| geD | HMCN2 | 1.5 | 0.06 |
| geD | PTPRU | 1.3 | 0.06 |
| geD | COTL1 | 1.4 | 0.06 |
| geD | HLA-DPA1 | 1.3 | 0.06 |
| geD | TYROBP | 1.3 | 0.06 |

TABLE S10-continued

CR-specific measurements

| DataType | Name | Fold-change | Q-value |
|---|---|---|---|
| geD | PGP | 1.7 | 0.06 |
| geD | LATS2 | 1.5 | 0.06 |
| geD | FKBP8 | 1.6 | 0.06 |
| geD | BSG | 1.5 | 0.06 |
| geD | RPS6KA2 | 1.4 | 0.06 |
| geD | SCRN1 | 1.6 | 0.06 |
| geD | MLL | 1.4 | 0.06 |
| geD | BID | 1.6 | 0.06 |
| geD | TRBV5-4 | 1.4 | 0.06 |
| geD | FGFR1 | 1.5 | 0.06 |
| geD | PML | 1.7 | 0.06 |
| geD | TRAF7 | 1.6 | 0.06 |
| geD | TLX2 | 1.4 | 0.06 |
| geD | DOCK5 | 2.4 | 0.06 |
| geD | HIST1H2AL | 1.3 | 0.06 |
| geD | PKD1 | 1.3 | 0.06 |
| geD | NCF1 | 1.3 | 0.06 |
| geD | EIF5A | 1.4 | 0.06 |
| geD | SPN | 1.5 | 0.06 |
| geD | PECAM1 | 1.6 | 0.06 |
| geD | CSNK1E | 1.3 | 0.06 |
| geD | CD19 | 1.8 | 0.06 |
| geD | FXYD5 | 1.3 | 0.06 |
| geD | 3-Mar | 1.5 | 0.06 |
| geD | TIMP3 | 1.2 | 0.06 |
| geD | ADAM22 | 1.3 | 0.06 |
| geD | PYDC1 | 1.6 | 0.06 |
| geD | JAK1 | 1.4 | 0.06 |
| geD | RIN1 | 1.4 | 0.06 |
| geD | ADORA2A | 1.5 | 0.06 |
| geD | CYFIP2 | 1.6 | 0.06 |
| geD | PURB | 1.5 | 0.06 |
| geD | IFT172 | 1.3 | 0.06 |
| geD | FEZF2 | 1.3 | 0.06 |
| geD | PXN | 1.7 | 0.06 |
| geD | CLDN5 | 1.6 | 0.06 |
| geD | HLA-B | 1.6 | 0.06 |
| geD | MAP3K1 | 1.4 | 0.06 |
| geD | STAT5B | 1.5 | 0.06 |
| geD | MR1 | 1.5 | 0.06 |
| geD | BIN1 | 1.3 | 0.06 |
| geD | PCDHGA2 | 1.2 | 0.06 |
| geD | STAT5A | 1.3 | 0.06 |
| geD | ITFG2 | 1.5 | 0.06 |
| geD | LAMA5 | 1.3 | 0.06 |
| geD | RALBP1 | 1.6 | 0.06 |
| geD | IGHV1-69 | 1.6 | 0.06 |
| geD | GRN | 1.4 | 0.06 |
| geD | PPM1F | 1.7 | 0.06 |
| geD | NKD2 | 1.6 | 0.06 |
| geD | SFN | 1.2 | 0.06 |
| geD | CLDN14 | 2.8 | 0.06 |
| geD | MARK3 | 1.6 | 0.06 |
| geD | GALNTL1 | 1.3 | 0.06 |
| geD | GADD45B | 1.4 | 0.06 |
| geD | TNFRSF21 | 1.5 | 0.06 |
| geD | NLRP1 | 1.2 | 0.06 |
| geD | DDR1 | 1.5 | 0.06 |
| geD | NEIL2 | 1.2 | 0.06 |
| geD | CEACAM19 | 1.4 | 0.06 |
| geD | FLRT2 | 1.4 | 0.06 |
| geD | F2 | 1.3 | 0.06 |
| geD | IRF7 | 1.6 | 0.06 |
| geD | CD3EAP | 1.3 | 0.06 |
| geD | FANCG | 1.5 | 0.06 |
| geD | ADAR | 1.5 | 0.06 |
| geD | RBM4 | 1.6 | 0.06 |
| geD | TCIRG1 | 1.4 | 0.06 |
| geD | NFATC3 | 1.3 | 0.06 |
| geD | CMKLR1 | 1.3 | 0.06 |
| geD | ITGB4 | 1.6 | 0.06 |
| geD | CPXM1 | 1.4 | 0.06 |
| geD | TMX1 | 1.6 | 0.06 |
| geD | ZFYVE9 | 1.3 | 0.06 |
| geD | PRKACA | 1.6 | 0.06 |
| geD | UBE2Z | 1.4 | 0.06 |
| geD | SPG7 | 1.6 | 0.06 |
| geD | RNF216 | 1.4 | 0.06 |
| geD | RIN3 | 1.4 | 0.06 |
| geD | SELPLG | 1.9 | 0.06 |
| geD | NEIL3 | -1.6 | 0.06 |
| geD | INHA | -1.5 | 0.06 |
| geD | C3orf38 | -1.4 | 0.06 |
| geD | IFNA4 | -1.3 | 0.06 |
| geD | MLL3 | -2 | 0.06 |
| geD | FAM3B | -1.9 | 0.06 |
| geD | NFE2L3 | -1.4 | 0.06 |
| geD | RALBP1 | -2.2 | 0.06 |
| geD | FNBP1L | -1.5 | 0.06 |
| geD | KLRF1 | -1.6 | 0.06 |
| geD | COL14A1 | -1.8 | 0.06 |
| geD | CKAP2 | -1.6 | 0.06 |
| geD | ZNF443 | -1.9 | 0.06 |
| geD | IGJ | -1.5 | 0.06 |
| geD | CTNND1 | -1.2 | 0.06 |
| geD | RAB18 | -2 | 0.06 |
| geD | TXN | -1.5 | 0.06 |
| geD | IRF4 | -1.4 | 0.06 |
| geD | RPS3A | -1.4 | 0.06 |
| geD | NFATC2 | -2.4 | 0.06 |
| geD | RYBP | -1.1 | 0.06 |
| geD | WNK1 | -1.4 | 0.06 |
| geD | DOCK8 | -1.6 | 0.06 |
| geD | DOCK5 | -2 | 0.06 |
| geD | LRP12 | -1.8 | 0.06 |
| geD | VEGFB | -1.6 | 0.06 |
| geD | RPS3A | -1.8 | 0.06 |
| geD | RAB27A | -1.7 | 0.06 |
| geD | IL2RB | -1.3 | 0.06 |
| geD | S100B | -1.7 | 0.06 |
| geD | SLFN11 | -1.3 | 0.06 |
| geD | FANCI | -1.6 | 0.06 |
| geD | LCP1 | -1.8 | 0.06 |
| geD | TRBV27 | -1.6 | 0.06 |
| geD | DOCK7 | -1.6 | 0.06 |
| geD | BNIP3L | -1.8 | 0.06 |
| geD | BCL10 | -1.3 | 0.06 |
| geD | VEZF1 | -1.3 | 0.06 |
| geD | PDIA3 | -1.5 | 0.06 |
| geD | FEZ1 | -2.5 | 0.06 |
| geD | NGFRAP1 | -1.4 | 0.06 |
| geD | TNFRSF17 | -1.5 | 0.06 |
| geD | AGGF1 | -2.2 | 0.06 |
| geD | PTPN22 | -1.9 | 0.06 |
| geD | PCDHB15 | -1.5 | 0.06 |
| geD | THRB | -1.3 | 0.06 |
| geD | CARD6 | -1.3 | 0.06 |
| geD | FAM82A2 | -2 | 0.06 |
| geD | YWHAZ | -1.3 | 0.06 |
| geD | GCLC | -1.3 | 0.06 |
| geD | HFE | -1.9 | 0.06 |
| geD | DNM1L | -1.2 | 0.06 |
| geD | FCHO2 | -1.8 | 0.06 |
| geD | IL20RB | -1.7 | 0.06 |
| geD | KIR3DL3 | -1.5 | 0.06 |
| geD | DLX1 | -1.6 | 0.06 |
| geD | PAWR | -1.8 | 0.06 |
| geD | FNDC3A | -1.3 | 0.06 |
| geD | GYPA | -1.3 | 0.06 |
| geD | IGLL1 | -1.4 | 0.06 |
| geD | MYST3 | -1.3 | 0.06 |
| geD | ITGA6 | -1.8 | 0.06 |
| geD | IL1R1 | -1.5 | 0.06 |
| geD | SCD5 | -2.2 | 0.06 |
| geD | SGK3 | -1.9 | 0.06 |
| geD | VEZF1 | -1.9 | 0.06 |
| geD | SIX4 | -1.2 | 0.06 |
| geD | FGFR1 | -1.7 | 0.06 |
| geD | CMAS | -1.4 | 0.06 |
| geD | FANCM | -1.6 | 0.06 |
| geD | NDN | -2.2 | 0.06 |
| geD | ABCC4 | -1.6 | 0.06 |

TABLE S10-continued

CR-specific measurements

| DataType | Name | Fold-change | Q-value |
|---|---|---|---|
| geD | PSMD3 | 5.5 | 0.07 |
| geD | BBC3 | 1.4 | 0.07 |
| geD | PARVA | 1.5 | 0.07 |
| geD | ITGAL | 1.3 | 0.07 |
| geD | XRCC6 | 2.2 | 0.07 |
| geD | BAI1 | 1.5 | 0.07 |
| geD | CBL | 1.3 | 0.07 |
| geD | ITGAX | 1.6 | 0.07 |
| geD | NPM1 | 1.4 | 0.07 |
| geD | MAP4K2 | 1.6 | 0.07 |
| geD | UNC5B | 1.6 | 0.07 |
| geD | OSM | 1.4 | 0.07 |
| geD | TNFRSF6B | 1.6 | 0.07 |
| geD | TNIP1 | 1.4 | 0.07 |
| geD | IL6ST | 1.6 | 0.07 |
| geD | XAF1 | 1.2 | 0.07 |
| geD | IL3RA | 1.3 | 0.07 |
| geD | PKD1 | 1.4 | 0.07 |
| geD | MEN1 | 1.5 | 0.07 |
| geD | C1QTNF2 | 1.7 | 0.07 |
| geD | HDAC4 | 1.5 | 0.07 |
| geD | CX3CL1 | 1.8 | 0.07 |
| geD | FIS1 | 1.4 | 0.07 |
| geD | BMF | 1.5 | 0.07 |
| geD | CDH18 | 1.6 | 0.07 |
| geD | PRDX2 | 1.2 | 0.07 |
| geD | FASTKD3 | 1.3 | 0.07 |
| geD | NFATC1 | 1.4 | 0.07 |
| geD | PCDHB11 | 1.3 | 0.07 |
| geD | CADM3 | 1.3 | 0.07 |
| geD | HCG18 | 1.4 | 0.07 |
| geD | TMBIM6 | 1.7 | 0.07 |
| geD | SDF2L1 | 1.2 | 0.07 |
| geD | ARRB2 | 1.4 | 0.07 |
| geD | OXSR1 | 1.3 | 0.07 |
| geD | AATK | 1.6 | 0.07 |
| geD | MUC5AC | 1.6 | 0.07 |
| geD | TNFRSF1A | 1.6 | 0.07 |
| geD | CTSD | 1.2 | 0.07 |
| geD | EXOC5 | 1.5 | 0.07 |
| geD | LOC644297 | 2.5 | 0.07 |
| geD | EMD | 1.3 | 0.07 |
| geD | DNASE1L3 | 1.3 | 0.07 |
| geD | SIAH2 | 1.5 | 0.07 |
| geD | MYD88 | 1.5 | 0.07 |
| geD | PTGDS | 1.2 | 0.07 |
| geD | NINJ1 | 1.6 | 0.07 |
| geD | TRIB3 | 1.4 | 0.07 |
| geD | MLL3 | 1.5 | 0.07 |
| geD | PCDH21 | 1.2 | 0.07 |
| geD | CLDN3 | 1.6 | 0.07 |
| geD | CD1A | 1.3 | 0.07 |
| geD | FGF3 | 1.5 | 0.07 |
| geD | PECR | 1.2 | 0.07 |
| geD | MSRA | 2.6 | 0.07 |
| geD | CTSK | 1.4 | 0.07 |
| geD | TAPBP | 1.4 | 0.07 |
| geD | PCLO | 1.4 | 0.07 |
| geD | LGALS1 | 1.1 | 0.07 |
| geD | GPR56 | 2.5 | 0.07 |
| geD | TRIP6 | 1.5 | 0.07 |
| geD | ASB1 | 1.4 | 0.07 |
| geD | TYK2 | 1.6 | 0.07 |
| geD | ELMO2 | 1.5 | 0.07 |
| geD | ENG | 1.3 | 0.07 |
| geD | NFKBIB | 1.6 | 0.07 |
| geD | NISCH | 1.6 | 0.07 |
| geD | CMTM3 | 1.3 | 0.07 |
| geD | FN1 | 1.2 | 0.07 |
| geD | CDC2L2 | 1.6 | 0.07 |
| geD | FCGRT | 1.3 | 0.07 |
| geD | COQ7 | 1.5 | 0.07 |
| geD | SMOC1 | 5.2 | 0.07 |
| geD | CAMP | 1.5 | 0.07 |
| geD | DOCK6 | 2.4 | 0.07 |
| geD | SYTL1 | 1.5 | 0.07 |
| geD | EMR1 | 1.3 | 0.07 |
| geD | THY1 | 2.2 | 0.07 |
| geD | IFIT1 | 1.2 | 0.07 |
| geD | JAK3 | 1.5 | 0.07 |
| geD | UBL7 | 1.2 | 0.07 |
| geD | FOXL2 | 2.8 | 0.07 |
| geD | PLAUR | 1.3 | 0.07 |
| geD | ROBO3 | 1.3 | 0.07 |
| geD | NLRP12 | 1.2 | 0.07 |
| geD | TBRG4 | 1.5 | 0.07 |
| geD | VEGFA | 1.3 | 0.07 |
| geD | CDH3 | 2.1 | 0.07 |
| geD | CTNND2 | 1.4 | 0.07 |
| geD | CALM3 | 1.2 | 0.07 |
| geD | ISG20 | 1.2 | 0.07 |
| geD | MAP2K3 | 1.5 | 0.07 |
| geD | CSRNP2 | 1.6 | 0.07 |
| geD | HAX1 | 1.3 | 0.07 |
| geD | SMO | 1.3 | 0.07 |
| geD | DAPK2 | 1.4 | 0.07 |
| geD | ALG1 | 1.5 | 0.07 |
| geD | IL11RA | 1.1 | 0.07 |
| geD | MAF | 1.6 | 0.07 |
| geD | ARHGDIA | 1.3 | 0.07 |
| geD | THOC5 | 1.6 | 0.07 |
| geD | NPM1 | 2.6 | 0.07 |
| geD | PSMG2 | −1.3 | 0.07 |
| geD | C1RL | −2.6 | 0.07 |
| geD | C3orf38 | −1.3 | 0.07 |
| geD | FANCD2 | −1.4 | 0.07 |
| geD | MAP3K7 | −1.5 | 0.07 |
| geD | RIMS3 | −1.2 | 0.07 |
| geD | NLGN1 | −1.5 | 0.07 |
| geD | ERBB4 | −1.6 | 0.07 |
| geD | LIN7C | −1.2 | 0.07 |
| geD | PHLDA2 | −1.9 | 0.07 |
| geD | DIAPH2 | −2.3 | 0.07 |
| geD | FANCD2 | −2.1 | 0.07 |
| geD | FASTKD2 | −1.9 | 0.07 |
| geD | NLGN4Y | −1.5 | 0.07 |
| geD | PAG1 | −1.9 | 0.07 |
| geD | SLC1A3 | −2.2 | 0.07 |
| geD | BIRC2 | −1.6 | 0.07 |
| geD | PSMD3 | −1.5 | 0.07 |
| geD | CAPN10 | −1.4 | 0.07 |
| geD | CXADR | −1.8 | 0.07 |
| geD | POSTN | −1.5 | 0.07 |
| geD | RNF34 | −1.3 | 0.07 |
| geD | RABEP1 | −1.3 | 0.07 |
| geD | GBP1 | −1.5 | 0.07 |
| geD | ALG9 | −2.5 | 0.07 |
| geD | PSMC5 | −1.5 | 0.07 |
| geD | GULP1 | −1.2 | 0.07 |
| geD | C9orf61 | −1.2 | 0.07 |
| geD | CASP8 | −1.6 | 0.07 |
| geD | NHEJ1 | −1.4 | 0.07 |
| geD | MLH1 | −1.4 | 0.07 |
| geD | ITPR1 | −1.2 | 0.07 |
| geD | C7 | −1.6 | 0.07 |
| geD | CROP | −1.6 | 0.07 |
| geD | SMURF2 | −1.9 | 0.07 |
| geD | LPP | −1.3 | 0.07 |
| geD | HMGB1 | −1.2 | 0.07 |
| geD | RABEP1 | −1.5 | 0.07 |
| geD | PCDHA11 | −1.3 | 0.07 |
| geD | CDC42SE2 | −1.4 | 0.07 |
| geD | HLA-C | −1.4 | 0.07 |
| geD | RAG1 | −1.2 | 0.07 |
| geD | RHOT1 | −1.3 | 0.07 |
| geD | HDAC4 | −1.4 | 0.07 |
| geD | EXOC5 | −1.8 | 0.07 |
| geD | ART4 | −2.2 | 0.07 |
| geD | FANCI | −1.4 | 0.07 |
| geD | WWTR1 | −1.4 | 0.07 |
| geD | MAPK9 | −1.6 | 0.07 |
| geD | PTK2 | −1.4 | 0.07 |

TABLE S10-continued

CR-specific measurements

| DataType | Name | Fold-change | Q-value |
|---|---|---|---|
| geD | COL14A1 | −1.2 | 0.07 |
| geD | HNMT | −1.3 | 0.07 |
| geD | LY75 | −1.4 | 0.07 |
| geD | LYST | −1.3 | 0.07 |
| geD | DOCK1 | −1.3 | 0.07 |
| geD | MAF | −2.2 | 0.07 |
| geD | PRKCB | −1.5 | 0.07 |
| geD | TNFRSF11B | −1.2 | 0.07 |
| geD | PSMD9 | −1.5 | 0.07 |
| geD | PTGES3 | −1.4 | 0.07 |
| geD | ALDH1A3 | −1.7 | 0.07 |
| geD | TBRG1 | −1.2 | 0.07 |
| geD | BAG3 | −1.2 | 0.07 |
| geD | CCR6 | −1.4 | 0.07 |
| geD | PSMD10 | −1.3 | 0.07 |
| geD | ANLN | −1.6 | 0.07 |
| geD | ALDH1A2 | −1.8 | 0.07 |
| geD | PRKCSH | 1.5 | 0.08 |
| geD | MZF1 | 1.3 | 0.08 |
| geD | AP3B2 | 1.7 | 0.08 |
| geD | SEMA6A | 1.5 | 0.08 |
| geD | IL16 | 1.6 | 0.08 |
| geD | ITGAX | 1.5 | 0.08 |
| geD | HLA-DPA1 | 8.8 | 0.08 |
| geD | CCND3 | 1.4 | 0.08 |
| geD | TGFB3 | 1.6 | 0.08 |
| geD | UCP2 | 1.4 | 0.08 |
| geD | LTBP3 | 1.4 | 0.08 |
| geD | WISP2 | 2.3 | 0.08 |
| geD | HLA-E | 1.6 | 0.08 |
| geD | AOAH | 1.4 | 0.08 |
| geD | F7 | 1.4 | 0.08 |
| geD | WFS1 | 1.3 | 0.08 |
| geD | ADAT3 | 1.3 | 0.08 |
| geD | SPON2 | 1.6 | 0.08 |
| geD | CLN3 | 1.2 | 0.08 |
| geD | PYCARD | 1.3 | 0.08 |
| geD | HLA-DMA | 1.3 | 0.08 |
| geD | LTBP4 | 1.2 | 0.08 |
| geD | DGCR8 | 1.3 | 0.08 |
| geD | ING4 | 1.4 | 0.08 |
| geD | IFI27L2 | 2.2 | 0.08 |
| geD | CFP | 1.3 | 0.08 |
| geD | HDAC3 | 1.7 | 0.08 |
| geD | IRF2 | 2.3 | 0.08 |
| geD | MLLT1 | 1.3 | 0.08 |
| geD | APOL2 | 1.4 | 0.08 |
| geD | PTPRS | 1.3 | 0.08 |
| geD | LST1 | 1.5 | 0.08 |
| geD | PCDHB2 | 1.3 | 0.08 |
| geD | BTNL2 | 1.5 | 0.08 |
| geD | TAPBPL | 1.4 | 0.08 |
| geD | VPS33B | 1.3 | 0.08 |
| geD | CDK5 | 1.5 | 0.08 |
| geD | HLA-DRB4 | 1.4 | 0.08 |
| geD | CDH7 | 1.4 | 0.08 |
| geD | AP1B1 | 1.3 | 0.08 |
| geD | PSMB9 | 1.7 | 0.08 |
| geD | HEPACAM | 1.8 | 0.08 |
| geD | CD97 | 1.6 | 0.08 |
| geD | NFX1 | 1.2 | 0.08 |
| geD | EXOC4 | 1.4 | 0.08 |
| geD | PRDX2 | 1.4 | 0.08 |
| geD | AIFM2 | 1.6 | 0.08 |
| geD | ITGB6 | 1.5 | 0.08 |
| geD | FKBP9 | 1.6 | 0.08 |
| geD | TOM1 | 1.2 | 0.08 |
| geD | CLPTM1L | 1.4 | 0.08 |
| geD | BIRC7 | 1.4 | 0.08 |
| geD | EPN2 | 1.9 | 0.08 |
| geD | PPIL2 | 1.6 | 0.08 |
| geD | TIMP2 | 6.7 | 0.08 |
| geD | RTN3 | 1.3 | 0.08 |
| geD | FKBP5 | 1.2 | 0.08 |
| geD | POU4F1 | 1.2 | 0.08 |
| geD | CMTM1 | 1.3 | 0.08 |
| geD | EBI3 | 1.4 | 0.08 |
| geD | LSM14A | 1.3 | 0.08 |
| geD | IL8RB | 1.2 | 0.08 |
| geD | MTCH1 | 1.3 | 0.08 |
| geD | BBS2 | 1.4 | 0.08 |
| geD | IFT122 | 1.4 | 0.08 |
| geD | LY6G6C | 1.4 | 0.08 |
| geD | LTBP4 | 1.1 | 0.08 |
| geD | DOCK2 | 1.3 | 0.08 |
| geD | MX1 | 1.3 | 0.08 |
| geD | INHBB | 1.2 | 0.08 |
| geD | EMILIN1 | 1.4 | 0.08 |
| geD | MLL4 | 1.1 | 0.08 |
| geD | TYMP | 1.3 | 0.08 |
| geD | ZYX | 1.3 | 0.08 |
| geD | CLDN3 | 1.4 | 0.08 |
| geD | PRKG1 | 1.7 | 0.08 |
| geD | SPACA3 | 1.3 | 0.08 |
| geD | ADAMTS1 | −1.3 | 0.08 |
| geD | DCBLD1 | −1.7 | 0.08 |
| geD | PAFAH1B1 | −1.5 | 0.08 |
| geD | CD164 | −1.7 | 0.08 |
| geD | HBP1 | −1.3 | 0.08 |
| geD | PHLPP | −1.8 | 0.08 |
| geD | XRCC6BP1 | −1.3 | 0.08 |
| geD | SNX6 | −1.5 | 0.08 |
| geD | ELMOD1 | −1.6 | 0.08 |
| geD | AP1G1 | −1.2 | 0.08 |
| geD | DNAJB6 | −1.3 | 0.08 |
| geD | SYVN1 | −1.8 | 0.08 |
| geD | IKBKAP | −1.5 | 0.08 |
| geD | RPS6KA3 | −1.3 | 0.08 |
| geD | CD63 | −1.3 | 0.08 |
| geD | USP33 | −1.5 | 0.08 |
| geD | BCLAF1 | −1.5 | 0.08 |
| geD | TNFAIP8L1 | −1.3 | 0.08 |
| geD | PVRL3 | −1.6 | 0.08 |
| geD | UBE2N | −1.5 | 0.08 |
| geD | DST | −1.4 | 0.08 |
| geD | SLK | −1.4 | 0.08 |
| geD | 4-Sep | −1.4 | 0.08 |
| geD | BMI1 | −1.9 | 0.08 |
| geD | PTGR2 | −1.4 | 0.08 |
| geD | PTEN | −1.7 | 0.08 |
| geD | KCNMA1 | −1.5 | 0.08 |
| geD | PROX1 | −1.6 | 0.08 |
| geD | GALNAC4S-6ST | −1.4 | 0.08 |
| geD | TOP2A | −1.6 | 0.08 |
| geD | RAB22A | −1.4 | 0.08 |
| geD | LAMP2 | −1.2 | 0.08 |
| geD | RNF144B | −1.2 | 0.08 |
| geD | STX1A | −1.6 | 0.08 |
| geD | PLDN | −1.2 | 0.08 |
| geD | PSME3 | −1.6 | 0.08 |
| geD | GNA13 | −1.3 | 0.08 |
| geD | NXT2 | −1.7 | 0.08 |
| geD | COL8A1 | −1.3 | 0.08 |
| geD | DOCK4 | −1.2 | 0.08 |
| geD | SYNJ2BP | −1.4 | 0.08 |
| geD | RPS3A | −2 | 0.08 |
| geD | NBN | −1.6 | 0.08 |
| geD | PIM1 | −1.3 | 0.08 |
| geD | FLT1 | −1.4 | 0.08 |
| geD | UCHL1 | −1.4 | 0.08 |
| geD | KLRG1 | −1.6 | 0.08 |
| geD | API5 | −1.8 | 0.08 |
| geD | RRAGC | −1.3 | 0.08 |
| geD | MBL2 | −1.3 | 0.08 |
| geD | MATN3 | −1.8 | 0.08 |
| geD | COL14A1 | −1.2 | 0.08 |
| geD | CADM1 | −1.7 | 0.08 |
| geD | ADAM12 | −1.7 | 0.08 |
| geD | B2M | −1.5 | 0.08 |
| geD | RBPJ | −1.3 | 0.08 |
| geD | SHISA5 | 1.3 | 0.09 |
| geD | FRAT2 | 1.2 | 0.09 |

TABLE S10-continued

CR-specific measurements

| DataType | Name | Fold-change | Q-value |
|---|---|---|---|
| geD | PCDHB8 | 1.5 | 0.09 |
| geD | ADRBK1 | 1.2 | 0.09 |
| geD | ZNF646 | 1.4 | 0.09 |
| geD | PARD3 | 1.3 | 0.09 |
| geD | DCTN3 | 1.4 | 0.09 |
| geD | EBF4 | 1.3 | 0.09 |
| geD | CERK | 1.4 | 0.09 |
| geD | POLM | 1.3 | 0.09 |
| geD | PTPN11 | 1.3 | 0.09 |
| geD | PTGIR | 1.4 | 0.09 |
| geD | FLVCR1 | 1.2 | 0.09 |
| geD | CD2BP2 | 1.3 | 0.09 |
| geD | PDCD1 | 1.6 | 0.09 |
| geD | BGLAP | 1.6 | 0.09 |
| geD | ATHL1 | 1.5 | 0.09 |
| geD | SAP30BP | 1.6 | 0.09 |
| geD | CLU | 1.5 | 0.09 |
| geD | THBS4 | 1.4 | 0.09 |
| geD | MST1R | 1.8 | 0.09 |
| geD | NFKBIL2 | 1.4 | 0.09 |
| geD | RECQL4 | 1.8 | 0.09 |
| geD | FUT4 | 1.3 | 0.09 |
| geD | AIF1 | 1.2 | 0.09 |
| geD | PTK7 | 1.3 | 0.09 |
| geD | CEACAM4 | 2.5 | 0.09 |
| geD | C1orf38 | 1.5 | 0.09 |
| geD | JUP | 1.4 | 0.09 |
| geD | OSCAR | 1.7 | 0.09 |
| geD | BCAP31 | 1.5 | 0.09 |
| geD | COL8A1 | 1.2 | 0.09 |
| geD | CAMK1G | 2.6 | 0.09 |
| geD | FGFR3 | 1.4 | 0.09 |
| geD | CSF2RA | 1.5 | 0.09 |
| geD | GAS1 | 1.4 | 0.09 |
| geD | TH1L | 1.8 | 0.09 |
| geD | ICAM5 | 1.6 | 0.09 |
| geD | SHISA5 | 1.9 | 0.09 |
| geD | FIS1 | 1.3 | 0.09 |
| geD | LAG3 | 1.4 | 0.09 |
| geD | FGFR1 | 1.2 | 0.09 |
| geD | SPHK2 | 1.3 | 0.09 |
| geD | NRXN2 | 1.5 | 0.09 |
| geD | NPHP1 | 1.4 | 0.09 |
| geD | IL1R1 | 1.4 | 0.09 |
| geD | ABL1 | 1.2 | 0.09 |
| geD | RHOA | 1.6 | 0.09 |
| geD | MLLT6 | 1.6 | 0.09 |
| geD | PLD1 | 1.4 | 0.09 |
| geD | WNK1 | 1.6 | 0.09 |
| geD | ZNF3 | 1.5 | 0.09 |
| geD | LST1 | 1.5 | 0.09 |
| geD | IL21R | 3.9 | 0.09 |
| geD | TGM2 | 3.4 | 0.09 |
| geD | DNASE2 | 1.7 | 0.09 |
| geD | FCRL2 | 1.3 | 0.09 |
| geD | LILRA1 | 1.6 | 0.09 |
| geD | RAB35 | 1.4 | 0.09 |
| geD | MYH10 | 1.1 | 0.09 |
| geD | MAPK11 | 1.3 | 0.09 |
| geD | APOE | 1.4 | 0.09 |
| geD | DOK1 | 1.5 | 0.09 |
| geD | CELSR3 | 1.3 | 0.09 |
| geD | BUB1B | 1.5 | 0.09 |
| geD | GLT25D2 | 1.4 | 0.09 |
| geD | PRAM1 | 1.6 | 0.09 |
| geD | SLC4A1 | 1.4 | 0.09 |
| geD | SMAD6 | 1.3 | 0.09 |
| geD | ERBB3 | 1.4 | 0.09 |
| geD | OLFML3 | 1.4 | 0.09 |
| geD | HLA-E | 1.3 | 0.09 |
| geD | LSM14B | 1.2 | 0.09 |
| geD | KNG1 | 1.5 | 0.09 |
| geD | FBLIM1 | 1.2 | 0.09 |
| geD | CSF3R | 1.2 | 0.09 |
| geD | AP2A1 | 1.6 | 0.09 |
| geD | SEMA3F | 1.4 | 0.09 |
| geD | ANP32D | 1.3 | 0.09 |
| geD | PBX2 | 1.4 | 0.09 |
| geD | CD74 | 1.5 | 0.09 |
| geD | CSNK2B | 1.3 | 0.09 |
| geD | SYNJ1 | 1.3 | 0.09 |
| geD | VHL | 1.3 | 0.09 |
| geD | HLA-G | 1.7 | 0.09 |
| geD | WFIKKN1 | 1.3 | 0.09 |
| geD | MED1 | -1.8 | 0.09 |
| geD | GNA13 | -1.3 | 0.09 |
| geD | PDCD2 | -1.4 | 0.09 |
| geD | STK17A | -1.3 | 0.09 |
| geD | NPM1 | -1.4 | 0.09 |
| geD | ROCK1 | -1.4 | 0.09 |
| geD | PCDH8 | -1.7 | 0.09 |
| geD | RABGEF1 | -1.4 | 0.09 |
| geD | SP3 | -1.7 | 0.09 |
| geD | AP1S3 | -1.6 | 0.09 |
| geD | PIK3CB | -1.2 | 0.09 |
| geD | C8orf4 | -1.6 | 0.09 |
| geD | UBR1 | -1.5 | 0.09 |
| geD | HES1 | -1.3 | 0.09 |
| geD | CARD8 | -1.3 | 0.09 |
| geD | RTN4 | -1.4 | 0.09 |
| geD | ALB | -1.7 | 0.09 |
| geD | TERF1 | -1.7 | 0.09 |
| geD | RHD | -1.4 | 0.09 |
| geD | MLLT10 | -1.6 | 0.09 |
| geD | ROCK1 | -1.5 | 0.09 |
| geD | CDC42 | -1.3 | 0.09 |
| geD | MAP4K5 | -1.8 | 0.09 |
| geD | HSP90B1 | -1.2 | 0.09 |
| geD | CFLAR | -1.7 | 0.09 |
| geD | PPIL4 | -1.8 | 0.09 |
| geD | MICB | -1.4 | 0.09 |
| geD | CD109 | -1.8 | 0.09 |
| geD | LYAR | -1.7 | 0.09 |
| geD | PSMC6 | -1.4 | 0.09 |
| geD | MSN | -2.2 | 0.09 |
| geD | NRAS | -1.3 | 0.09 |
| geD | CFI | -1.2 | 0.09 |
| geD | TERF1 | -1.7 | 0.09 |
| geD | DYRK2 | -1.7 | 0.09 |
| geD | RAD21 | -2 | 0.09 |
| geD | BMI1 | -1.3 | 0.09 |
| geD | LAMP2 | -1.4 | 0.09 |
| geD | CFDP1 | -1.3 | 0.09 |
| geD | PTEN | -2.2 | 0.09 |
| geD | PCDH7 | -1.5 | 0.09 |
| geD | PTGS1 | -1.8 | 0.09 |
| geD | PPARGC1A | -1.7 | 0.09 |
| geD | MARCKS | -2.1 | 0.09 |
| geD | GPNMB | -1.7 | 0.09 |
| geD | DNAJB6 | -1.6 | 0.09 |
| geD | LAMP2 | -1.5 | 0.09 |
| geD | RICTOR | -1.1 | 0.09 |
| geD | CORO1C | -1.5 | 0.09 |
| geD | DAD1 | -1.3 | 0.09 |
| geD | SDF2 | -1.4 | 0.09 |
| geD | PTGER4 | -1.6 | 0.09 |
| geD | MLLT4 | 1.1 | 0.1 |
| geD | ASGR1 | 1.2 | 0.1 |
| geD | VTCN1 | 1.6 | 0.1 |
| geD | CXCL14 | 1.3 | 0.1 |
| geD | SNX3 | 1.4 | 0.1 |
| geD | MLLT6 | 2.1 | 0.1 |
| geD | TNFSF13 | 1.2 | 0.1 |
| geD | ERCC1 | 1.3 | 0.1 |
| geD | DLL3 | 1.5 | 0.1 |
| geD | IRGC | 1.3 | 0.1 |
| geD | CD36 | 1.3 | 0.1 |
| geD | C16orf5 | 1.2 | 0.1 |
| geD | PAFAH1B3 | 1.2 | 0.1 |
| geD | CDC2L1 | 1.6 | 0.1 |
| geD | CALY | 1.3 | 0.1 |
| geD | ZNF646 | 1.3 | 0.1 |

TABLE S10-continued

CR-specific measurements

| DataType | Name | Fold-change | Q-value |
|---|---|---|---|
| geD | AZGP1 | 1.3 | 0.1 |
| geD | CUBN | 1.6 | 0.1 |
| geD | EEF1A1 | 1.2 | 0.1 |
| geD | SHB | 1.2 | 0.1 |
| geD | PSMF1 | 2.8 | 0.1 |
| geD | DDX41 | 1.2 | 0.1 |
| geD | PI4KB | 1.3 | 0.1 |
| geD | PCDHB7 | 1.3 | 0.1 |
| geD | GPR126 | 1.3 | 0.1 |
| geD | MFAP4 | 1.2 | 0.1 |
| geD | ELMOD3 | 1.4 | 0.1 |
| geD | CYP26A1 | 1.4 | 0.1 |
| geD | XRCC3 | 1.4 | 0.1 |
| geD | SERPINA3 | 1.3 | 0.1 |
| geD | TP53INP1 | 1.3 | 0.1 |
| geD | PRKCQ | 1.3 | 0.1 |
| geD | RFX2 | 1.4 | 0.1 |
| geD | NCOA6 | 1.6 | 0.1 |
| geD | DSCAM | 1.4 | 0.1 |
| geD | AZU1 | 1.4 | 0.1 |
| geD | TRAF5 | 1.3 | 0.1 |
| geD | NTN1 | 1.4 | 0.1 |
| geD | CCL27 | 1.2 | 0.1 |
| geD | CLCF1 | 1.3 | 0.1 |
| geD | IRS2 | 1.3 | 0.1 |
| geD | IER3 | 1.3 | 0.1 |
| geD | PML | 1.2 | 0.1 |
| geD | SLPI | 1.9 | 0.1 |
| geD | LMNA | 1.3 | 0.1 |
| geD | ACVRL1 | 1.2 | 0.1 |
| geD | PACS2 | 1.4 | 0.1 |
| geD | TAPBP | 1.3 | 0.1 |
| geD | LTBP2 | 1.4 | 0.1 |
| geD | MICB | 1.2 | 0.1 |
| geD | PVR | 1.5 | 0.1 |
| geD | MADCAM1 | 1.2 | 0.1 |
| geD | TRIM35 | 1.2 | 0.1 |
| geD | RAB7A | 1.2 | 0.1 |
| geD | HEPACAM | 1.3 | 0.1 |
| geD | TOLLIP | 1.2 | 0.1 |
| geD | MYO18A | 1.4 | 0.1 |
| geD | VCP | 1.5 | 0.1 |
| geD | NGFR | 1.4 | 0.1 |
| geD | BSG | 1.2 | 0.1 |
| geD | COL15A1 | 1.4 | 0.1 |
| geD | BAT4 | 1.7 | 0.1 |
| geD | MYST1 | 2.6 | 0.1 |
| geD | MAST1 | 1.3 | 0.1 |
| geD | PBX4 | 1.6 | 0.1 |
| geD | FLNA | 1.2 | 0.1 |
| geD | MALL | 1.2 | 0.1 |
| geD | IL8RB | 1.3 | 0.1 |
| geD | HCG18 | 1.6 | 0.1 |
| geD | PVRIG | 1.2 | 0.1 |
| geD | CCL15 | 1.2 | 0.1 |
| geD | AREG | 1.4 | 0.1 |
| geD | CCL16 | 1.3 | 0.1 |
| geD | CEACAM7 | 1.4 | 0.1 |
| geD | CHST10 | 1.2 | 0.1 |
| geD | VEGFB | 1.4 | 0.1 |
| geD | TNFRSF8 | 1.2 | 0.1 |
| geD | ADAT2 | 1.4 | 0.1 |
| geD | CHRD | 1.4 | 0.1 |
| geD | ROM1 | 1.1 | 0.1 |
| geD | SHFM1 | −1.3 | 0.1 |
| geD | TOR1AIP2 | −1.2 | 0.1 |
| geD | ATP1A2 | −1.4 | 0.1 |
| geD | PCMT1 | −1.4 | 0.1 |
| geD | CP110 | −2.1 | 0.1 |
| geD | RGN | −1.7 | 0.1 |
| geD | PICALM | −2.3 | 0.1 |
| geD | FANCB | −1.3 | 0.1 |
| geD | ZNF675 | −1.6 | 0.1 |
| geD | IBTK | −1.3 | 0.1 |
| geD | CCAR1 | −1.6 | 0.1 |
| geD | YWHAZ | −1.3 | 0.1 |
| geD | ATP2A2 | −1.5 | 0.1 |
| geD | HTATSF1 | −1.4 | 0.1 |
| geD | NR4A1 | −1.9 | 0.1 |
| geD | CREB1 | −1.3 | 0.1 |
| geD | KYNU | −1.3 | 0.1 |
| geD | CRKL | −1.3 | 0.1 |
| geD | STON1 | −1.3 | 0.1 |
| geD | MSN | −1.3 | 0.1 |
| geD | MLL3 | −1.6 | 0.1 |
| geD | MIA3 | −1.5 | 0.1 |
| geD | FANCF | −2.2 | 0.1 |
| geD | CXADR | −1.3 | 0.1 |
| geD | ADAR | −1.6 | 0.1 |
| geD | RP6-213H19.1 | −1.6 | 0.1 |
| geD | TOP2B | −1.3 | 0.1 |
| geD | FASTKD2 | −1.2 | 0.1 |
| geD | PRKAR2B | −1.5 | 0.1 |
| geD | CXCL1 | −1.9 | 0.1 |
| geD | PSMC1 | −1.2 | 0.1 |
| geD | LOC442421 | −1.8 | 0.1 |
| geD | COL29A1 | −1.4 | 0.1 |
| geD | NFAT5 | −1.2 | 0.1 |
| geD | DLEU2 | −1.5 | 0.1 |
| geD | SRFBP1 | −1.3 | 0.1 |
| geD | ITGAV | −1.4 | 0.1 |
| geD | ELF1 | −1.4 | 0.1 |
| geD | HBP1 | −1.6 | 0.1 |
| geD | KCNIP3 | −1.3 | 0.1 |
| geD | ICK | −1.2 | 0.1 |
| geD | EXOC6B | −1.8 | 0.1 |
| geD | PCDHB9 | −1.6 | 0.1 |
| geD | TNFRSF19 | −1.2 | 0.1 |
| geD | ZMYM2 | −1.1 | 0.1 |
| geD | COPG2 | −1.3 | 0.1 |
| geD | DLC1 | −1.2 | 0.1 |
| geD | ACVR1C | −1.2 | 0.1 |
| geD | ATR | −1.2 | 0.1 |
| geD | UBE4B | −1.5 | 0.1 |
| geD | CAMK2D | −1.3 | 0.1 |
| geD | IL16 | −1.7 | 0.1 |
| geD | BECN1 | −1.2 | 0.1 |
| geD | COL13A1 | −1.9 | 0.1 |
| geD | BIRC3 | −1.5 | 0.1 |
| geD | CD55 | −1.3 | 0.1 |
| geD | UTP14A | −1.5 | 0.1 |
| geD | PPT1 | −1.3 | 0.1 |
| geD | GNA12 | 1.3 | 0.11 |
| geD | LTBR | 1.3 | 0.11 |
| geD | NFKBIE | 1.4 | 0.11 |
| geD | IL15RA | 1.3 | 0.11 |
| geD | SCARB1 | 1.4 | 0.11 |
| geD | RAB26 | 1.3 | 0.11 |
| geD | C1QTNF6 | 1.3 | 0.11 |
| geD | EMILIN2 | 1.1 | 0.11 |
| geD | BICD2 | 1.6 | 0.11 |
| geD | ITFG2 | 1.3 | 0.11 |
| geD | CD97 | 1.6 | 0.11 |
| geD | BBC3 | 1.3 | 0.11 |
| geD | LOC91316 | 1.9 | 0.11 |
| geD | FOXO3 | 1.2 | 0.11 |
| geD | GPX1 | 3.6 | 0.11 |
| geD | OLFML3 | 1.4 | 0.11 |
| geD | CBX4 | 1.4 | 0.11 |
| geD | ERBB3 | 1.4 | 0.11 |
| geD | GPR17 | 1.3 | 0.11 |
| geD | INHBC | 2.7 | 0.11 |
| geD | ARHGEF11 | 1.2 | 0.11 |
| geD | PRDX1 | 1.9 | 0.11 |
| geD | SNX17 | 1.3 | 0.11 |
| geD | RYBP | 1.3 | 0.11 |
| geD | PNN | 2.5 | 0.11 |
| geD | CLDN9 | 1.4 | 0.11 |
| geD | IL3RA | 1.2 | 0.11 |
| geD | TNFRSF10B | 1.2 | 0.11 |
| geD | ADORA2A | 1.3 | 0.11 |
| geD | ACOX1 | 1.3 | 0.11 |

TABLE S10-continued

CR-specific measurements

| DataType | Name | Fold-change | Q-value |
|---|---|---|---|
| geD | IL10RA | 1.2 | 0.11 |
| geD | FKBP1A | 1.5 | 0.11 |
| geD | IFI27L1 | 2 | 0.11 |
| geD | PTAFR | 2.5 | 0.11 |
| geD | GDF15 | 1.1 | 0.11 |
| geD | CARD17 | 1.8 | 0.11 |
| geD | YKT6 | 1.4 | 0.11 |
| geD | ADAM12 | 1.2 | 0.11 |
| geD | MYST4 | 1.3 | 0.11 |
| geD | RPS6KA5 | 9.5 | 0.11 |
| geD | BBS7 | 1.3 | 0.11 |
| geD | CXCL5 | 1.3 | 0.11 |
| geD | COL16A1 | 1.3 | 0.11 |
| geD | CYTL1 | 1.2 | 0.11 |
| geD | FBLIM1 | 1.6 | 0.11 |
| geD | COL6A1 | 1.1 | 0.11 |
| geD | TNFRSF4 | 1.4 | 0.11 |
| geD | SYVN1 | 1.4 | 0.11 |
| geD | CD300C | 1.3 | 0.11 |
| geD | TCTA | 1.3 | 0.11 |
| geD | CCL17 | 1.3 | 0.11 |
| geD | PSMD9 | 1.6 | 0.11 |
| geD | EPOR | 1.3 | 0.11 |
| geD | ERCC3 | 1.3 | 0.11 |
| geD | IGF2BP3 | 1.5 | 0.11 |
| geD | PEX5 | 1.4 | 0.11 |
| geD | RIMS4 | 1.5 | 0.11 |
| geD | PPIH | 1.2 | 0.11 |
| geD | NAB2 | 1.3 | 0.11 |
| geD | EXOC4 | −1.3 | 0.11 |
| geD | RHCE | −1.3 | 0.11 |
| geD | SGMS1 | −1.4 | 0.11 |
| geD | PSMD12 | −1.2 | 0.11 |
| geD | SNAP29 | −1.5 | 0.11 |
| geD | DLG1 | −1.3 | 0.11 |
| geD | FEN1 | −1.5 | 0.11 |
| geD | TTRAP | −1.2 | 0.11 |
| geD | CUL5 | −1.3 | 0.11 |
| geD | TOPORS | −1.5 | 0.11 |
| geD | CDON | −1.4 | 0.11 |
| geD | PCMT1 | −1.3 | 0.11 |
| geD | RPS3A | −1.5 | 0.11 |
| geD | BMPR1A | −1.3 | 0.11 |
| geD | PSMA1 | −1.1 | 0.11 |
| geD | POGK | −1.5 | 0.11 |
| geD | SSX2IP | −1.1 | 0.11 |
| geD | SRPK1 | −1.3 | 0.11 |
| geD | EZR | −1.5 | 0.11 |
| geD | KLRC4 | −1.4 | 0.11 |
| geD | PCSK9 | −1.3 | 0.11 |
| geD | PDCD10 | −1.2 | 0.11 |
| geD | CTNND1 | −1.4 | 0.11 |
| geD | ARF6 | −1.2 | 0.11 |
| geD | PPIC | −1.2 | 0.11 |
| geD | SDCBP | −1.2 | 0.11 |
| geD | PLG | −1.2 | 0.11 |
| geD | GNA12 | −1.2 | 0.11 |
| geD | ATP2C1 | −1.4 | 0.11 |
| geD | SNRK | −1.2 | 0.11 |
| geD | PSMF1 | −1.4 | 0.11 |
| geD | EFNB2 | −1.6 | 0.11 |
| geD | THBS2 | −1.5 | 0.11 |
| geD | MRPS30 | −1.4 | 0.11 |
| geD | JUB | −1.3 | 0.11 |
| geD | PLAGL2 | −1.4 | 0.11 |
| geD | IL17RD | −1.8 | 0.11 |
| geD | CP110 | −1.2 | 0.11 |
| geD | TRIB1 | −1.4 | 0.11 |
| geD | OXSR1 | −1.3 | 0.11 |
| geD | TGFB2 | −1.7 | 0.11 |
| geD | NEDD4L | −1.7 | 0.11 |
| geD | TAX1BP1 | −1.3 | 0.11 |
| geD | STK3 | −1.3 | 0.11 |
| geD | APIP | −1.3 | 0.11 |
| geD | GCH1 | −1.3 | 0.11 |
| geD | F2R | −1.2 | 0.11 |
| geD | GNE | −1.3 | 0.11 |
| geD | HSPE1 | −1.3 | 0.11 |
| geD | PLSCR1 | −1.4 | 0.11 |
| geD | BAG3 | −1.4 | 0.11 |
| geD | MYH9 | −1.2 | 0.11 |
| geD | FAM3C | −1.4 | 0.11 |
| geD | SMOC1 | −1.8 | 0.11 |
| geD | SLAMF7 | −1.2 | 0.11 |
| geD | YWHAG | −1.5 | 0.11 |
| geD | IRAK1BP1 | −1.8 | 0.11 |
| geD | CBLB | −1.3 | 0.11 |
| geD | PSMD14 | −1.5 | 0.11 |
| geD | PDCL3 | −1.6 | 0.11 |
| geD | RAB5B | 1.3 | 0.12 |
| geD | MDM2 | 1.2 | 0.12 |
| geD | WDR92 | 1.3 | 0.12 |
| geD | BMP1 | 1.4 | 0.12 |
| geD | CHST4 | 1.2 | 0.12 |
| geD | BCL11B | 1.1 | 0.12 |
| geD | TBXAS1 | 1.4 | 0.12 |
| geD | N-PAC | 1.2 | 0.12 |
| geD | CD59 | 1.7 | 0.12 |
| geD | ITGA11 | 1.4 | 0.12 |
| geD | IGFBP3 | 1.6 | 0.12 |
| geD | CLDN23 | 1.3 | 0.12 |
| geD | TCTA | 1.2 | 0.12 |
| geD | POLG | 1.5 | 0.12 |
| geD | RAB3D | 1.1 | 0.12 |
| geD | TRAP1 | 1.2 | 0.12 |
| geD | MAF | 1.2 | 0.12 |
| geD | STX1A | 1.3 | 0.12 |
| geD | VCP | 1.2 | 0.12 |
| geD | KYNU | 1.2 | 0.12 |
| geD | CRKL | 1.3 | 0.12 |
| geD | CD63 | 1.2 | 0.12 |
| geD | PODXL2 | 1.4 | 0.12 |
| geD | BNIP3L | 1.3 | 0.12 |
| geD | VCP | 1.5 | 0.12 |
| geD | BNIP1 | 1.2 | 0.12 |
| geD | HSPB1 | 1.3 | 0.12 |
| geD | MYH9 | 1.2 | 0.12 |
| geD | CD3E | 1.2 | 0.12 |
| geD | PLG | 1.2 | 0.12 |
| geD | HTT | 1.6 | 0.12 |
| geD | DCHS1 | 1.3 | 0.12 |
| geD | AQP3 | 1.1 | 0.12 |
| geD | PDPK1 | 1.3 | 0.12 |
| geD | TAF8 | 1.3 | 0.12 |
| geD | B3GNTL1 | 1.3 | 0.12 |
| geD | C8G | 1.3 | 0.12 |
| geD | SIGLEC10 | 1.2 | 0.12 |
| geD | CNTFR | 1.3 | 0.12 |
| geD | NID2 | 2.2 | 0.12 |
| geD | NME3 | 1.2 | 0.12 |
| geD | SNX2 | 1.9 | 0.12 |
| geD | COL24A1 | 1.3 | 0.12 |
| geD | CROP | 1.3 | 0.12 |
| geD | CXCR5 | 1.5 | 0.12 |
| geD | TRIP10 | 1.4 | 0.12 |
| geD | PIN1 | 1.5 | 0.12 |
| geD | AIFM2 | 1.1 | 0.12 |
| geD | NFATC1 | 19.3 | 0.12 |
| geD | LDLRAP1 | 1.5 | 0.12 |
| geD | PSMB2 | 1.1 | 0.12 |
| geD | RIN2 | 1.1 | 0.12 |
| geD | BMPR1A | 1.5 | 0.12 |
| geD | PKP4 | −1.3 | 0.12 |
| geD | FUT8 | −1.5 | 0.12 |
| geD | MLLT10 | −1.2 | 0.12 |
| geD | CASP8AP2 | −1.2 | 0.12 |
| geD | HES1 | −1.7 | 0.12 |
| geD | CPLX1 | −1.4 | 0.12 |
| geD | RNF216 | −1.2 | 0.12 |
| geD | HDAC9 | −1.1 | 0.12 |
| geD | SGPP1 | −1.9 | 0.12 |
| geD | PSMD1 | −1.7 | 0.12 |

TABLE S10-continued

CR-specific measurements

| DataType | Name | Fold-change | Q-value |
|---|---|---|---|
| geD | HINT1 | −2.3 | 0.12 |
| geD | GRAMD4 | −1.2 | 0.12 |
| geD | JMY | −1.6 | 0.12 |
| geD | PDGFC | −1.2 | 0.12 |
| geD | LEPR | −1.3 | 0.12 |
| geD | B3GNT5 | −1.4 | 0.12 |
| geD | LDLR | −1.3 | 0.12 |
| geD | POMP | −1.3 | 0.12 |
| geD | BCL2A1 | −1.4 | 0.12 |
| geD | PDCL3 | −1.3 | 0.12 |
| geD | CXCL12 | −1.3 | 0.12 |
| geD | MLLT10 | −1.2 | 0.12 |
| geD | CUL2 | −1.2 | 0.12 |
| geD | MLL5 | −1.2 | 0.12 |
| geD | PRLR | −1.3 | 0.12 |
| geD | IFIT5 | −1.3 | 0.12 |
| geD | CLSTN2 | −1.7 | 0.12 |
| geD | SH2D1A | −1.2 | 0.12 |
| geD | HSP90AA1 | −1.6 | 0.12 |
| geD | COL15A1 | −1.4 | 0.12 |
| geD | KRAS | −1.6 | 0.12 |
| geD | THYN1 | −1.3 | 0.12 |
| geD | FASTKD5 | −1.3 | 0.12 |
| geD | BSCL2 | 1.6 | 0.13 |
| geD | RAD51 | 1.2 | 0.13 |
| geD | PCDHA1 | 1.2 | 0.13 |
| geD | FSCN1 | 1.2 | 0.13 |
| geD | DBN1 | 1.4 | 0.13 |
| geD | GDF3 | 1.3 | 0.13 |
| geD | CCL21 | 1.5 | 0.13 |
| geD | EDA | 1.1 | 0.13 |
| geD | S100A9 | 1.4 | 0.13 |
| geD | ZNF346 | 1.3 | 0.13 |
| geD | MYBPH | 1.1 | 0.13 |
| geD | PRKCDBP | 1.3 | 0.13 |
| geD | MUC5B | 1.4 | 0.13 |
| geD | CCND1 | 1.2 | 0.13 |
| geD | EPO | 1.2 | 0.13 |
| geD | FAT1 | 1.4 | 0.13 |
| geD | DBNL | 1.2 | 0.13 |
| geD | RAE1 | 1.3 | 0.13 |
| geD | NRG1 | 17.7 | 0.13 |
| geD | PDLIM7 | 1.3 | 0.13 |
| geD | ZBP1 | 1.4 | 0.13 |
| geD | TSTA3 | 1.2 | 0.13 |
| geD | SCFD2 | 1.3 | 0.13 |
| geD | SOCS1 | 6.1 | 0.13 |
| geD | PTPRF | 1.5 | 0.13 |
| geD | ESR1 | 1.2 | 0.13 |
| geD | CAT | 1.4 | 0.13 |
| geD | FOXO1 | 1.3 | 0.13 |
| geD | IGF2 | 1.3 | 0.13 |
| geD | MARK4 | 1.1 | 0.13 |
| geD | SNAPIN | 1.3 | 0.13 |
| geD | ADAMTS7 | 1.2 | 0.13 |
| geD | HLA-DMB | 1.2 | 0.13 |
| geD | ALG9 | 1.2 | 0.13 |
| geD | EXTL1 | 1.7 | 0.13 |
| geD | ATL1 | 1.5 | 0.13 |
| geD | RAC2 | 1.2 | 0.13 |
| geD | HMGB3 | 1.2 | 0.13 |
| geD | SIGIRR | 1.3 | 0.13 |
| geD | IGSF8 | 2.2 | 0.13 |
| geD | CCND3 | 1.3 | 0.13 |
| geD | ISG20L2 | 1.2 | 0.13 |
| geD | RTN3 | 1.2 | 0.13 |
| geD | CFB | 1.4 | 0.13 |
| geD | MLF1 | 1.5 | 0.13 |
| geD | CLTCL1 | 1.2 | 0.13 |
| geD | THAP3 | 1.3 | 0.13 |
| geD | PDZD2 | 1.3 | 0.13 |
| geD | DNM2 | 1.2 | 0.13 |
| geD | GDF11 | 1.4 | 0.13 |
| geD | ARFGEF1 | 1.9 | 0.13 |
| geD | CTNNA1 | 1.2 | 0.13 |
| geD | HLA-E | 1.3 | 0.13 |
| geD | MAPK13 | 1.3 | 0.13 |
| geD | EI24 | 1.4 | 0.13 |
| geD | FBLN5 | 1.3 | 0.13 |
| geD | FEZ1 | 1.4 | 0.13 |
| geD | DAP | 1.4 | 0.13 |
| geD | MYEF2 | −1.2 | 0.13 |
| geD | RAB13 | −1.5 | 0.13 |
| geD | HIP1 | −1.3 | 0.13 |
| geD | NPC1 | −1.4 | 0.13 |
| geD | PDGFRL | −1.2 | 0.13 |
| geD | MAP4K3 | −1.2 | 0.13 |
| geD | RALA | −1.1 | 0.13 |
| geD | SCARB2 | −1.5 | 0.13 |
| geD | PRKAR1A | −1.5 | 0.13 |
| geD | UBP1 | −1.3 | 0.13 |
| geD | IFT81 | −1.5 | 0.13 |
| geD | ZFYVE16 | −1.6 | 0.13 |
| geD | VPS41 | −1.5 | 0.13 |
| geD | SEMA4D | −1.5 | 0.13 |
| geD | PDCD6IP | −1.1 | 0.13 |
| geD | CD109 | −1.7 | 0.13 |
| geD | GTF2H2 | −1.2 | 0.13 |
| geD | GPR98 | −2 | 0.13 |
| geD | TXNDC5 | −1.5 | 0.13 |
| geD | ZC3H12A | −1.7 | 0.13 |
| geD | PEG10 | −1.2 | 0.13 |
| geD | GDNF | −2.3 | 0.13 |
| geD | HMGB1 | −1.5 | 0.13 |
| geD | GAB3 | −1.3 | 0.13 |
| geD | CUL4A | −1.3 | 0.13 |
| geD | CREBBP | −1.2 | 0.13 |
| geD | RFX5 | −1.2 | 0.13 |
| geD | BAG5 | −1.4 | 0.13 |
| geD | PCDHB5 | −1.6 | 0.13 |
| geD | BAG4 | −1.3 | 0.13 |
| geD | RALB | −1.6 | 0.13 |
| geD | RARG | 1.4 | 0.14 |
| geD | CTSH | 1.3 | 0.14 |
| geD | RAD52 | 1.7 | 0.14 |
| geD | MSLN | 1.2 | 0.14 |
| geD | CD38 | 1.5 | 0.14 |
| geD | NFKBIL2 | 1.3 | 0.14 |
| geD | RHOT2 | 1.3 | 0.14 |
| geD | WWP2 | 1.2 | 0.14 |
| geD | DEDD | 1.2 | 0.14 |
| geD | TRAF2 | 2.1 | 0.14 |
| geD | TNFRSF25 | 1.3 | 0.14 |
| geD | TREML2 | 1.3 | 0.14 |
| geD | MAPK13 | 1.2 | 0.14 |
| geD | SEMA4G | 1.3 | 0.14 |
| geD | MAP4K4 | 1.3 | 0.14 |
| geD | MYBPC2 | 1.2 | 0.14 |
| geD | CD151 | 1.3 | 0.14 |
| geD | NRGN | 1.4 | 0.14 |
| geD | MADD | 1.2 | 0.14 |
| geD | MGC29506 | 1.5 | 0.14 |
| geD | BCL9L | 1.2 | 0.14 |
| geD | HCP5 | 1.2 | 0.14 |
| geD | IL4I1 | 1.4 | 0.14 |
| geD | LTB4R2 | 1.3 | 0.14 |
| geD | LOC441795 | 1.2 | 0.14 |
| geD | CD200 | 1.2 | 0.14 |
| geD | LRIG1 | 1.2 | 0.14 |
| geD | CIAPIN1 | 1.4 | 0.14 |
| geD | RAB34 | 1.3 | 0.14 |
| geD | RIN2 | 1.3 | 0.14 |
| geD | TFDP1 | 2 | 0.14 |
| geD | EEF2 | 1.3 | 0.14 |
| geD | ALG1 | 1.3 | 0.14 |
| geD | COL7A1 | 1.3 | 0.14 |
| geD | CD37 | 1.2 | 0.14 |
| geD | HTRA2 | 1.3 | 0.14 |
| geD | CD8B | 1.2 | 0.14 |
| geD | NPTN | 1.1 | 0.14 |
| geD | KLF10 | −1.2 | 0.14 |
| geD | PCDHB16 | −1.3 | 0.14 |

TABLE S10-continued

CR-specific measurements

| DataType | Name | Fold-change | Q-value |
|---|---|---|---|
| geD | TRAF7 | −1.9 | 0.14 |
| geD | CLN3 | −1.3 | 0.14 |
| geD | SON | −1.3 | 0.14 |
| geD | MPZL2 | −1.7 | 0.14 |
| geD | PSMD5 | −1.2 | 0.14 |
| geD | NCKAP1 | −1.2 | 0.14 |
| geD | NLRC3 | −1.2 | 0.14 |
| geD | DLL1 | −1.2 | 0.14 |
| geD | DHCR24 | −1.4 | 0.14 |
| geD | C1D | −1.4 | 0.14 |
| geD | BAALC | −1.3 | 0.14 |
| geD | VHL | −1.3 | 0.14 |
| geD | RAB27A | −1.3 | 0.14 |
| geD | CBR1 | −1.2 | 0.14 |
| geD | JAG1 | −1.2 | 0.14 |
| geD | ADAM11 | −1.3 | 0.14 |
| geD | PRKRIR | −1.9 | 0.14 |
| geD | XCL1 | −1.5 | 0.14 |
| geD | FANCI | −1.4 | 0.14 |
| geD | FYB | −1.2 | 0.14 |
| geD | CYCS | −1.6 | 0.14 |
| geD | CETN2 | −1.1 | 0.14 |
| geD | BCL11A | −1.4 | 0.14 |
| geD | PSMC6 | −1.6 | 0.14 |
| geD | PBX1 | −1.2 | 0.14 |
| geD | SIRT1 | −1.1 | 0.14 |
| geD | TBX21 | −1.3 | 0.14 |
| geD | HOXA3 | −1.5 | 0.14 |
| geD | LSM14A | −1.3 | 0.14 |
| geD | TXNDC17 | −2.1 | 0.14 |
| geD | CROP | −1.5 | 0.14 |
| geD | HDAC5 | 1.2 | 0.15 |
| geD | MAPK7 | 1.3 | 0.15 |
| geD | ZAN | 1.7 | 0.15 |
| geD | XRCC1 | 1.8 | 0.15 |
| geD | ITGB5 | 1.2 | 0.15 |
| geD | METTL1 | 1.2 | 0.15 |
| geD | SIPA1 | 1.1 | 0.15 |
| geD | MRC2 | 1.3 | 0.15 |
| geD | HLA-DOB | 1.6 | 0.15 |
| geD | LRP10 | 1.1 | 0.15 |
| geD | CDKN1B | 1.4 | 0.15 |
| geD | ARVCF | 2.1 | 0.15 |
| geD | ITGA9 | 1.4 | 0.15 |
| geD | CD59 | 1.2 | 0.15 |
| geD | VPRBP | 1.3 | 0.15 |
| geD | RELT | 1.2 | 0.15 |
| geD | FCRLB | 1.6 | 0.15 |
| geD | HSF1 | 1.2 | 0.15 |
| geD | PSMB3 | 1.2 | 0.15 |
| geD | HLA-DMB | 2.4 | 0.15 |
| geD | FBLN7 | 1.2 | 0.15 |
| geD | KLF1 | 1.2 | 0.15 |
| geD | SH3GL3 | 1.3 | 0.15 |
| geD | PHLDA1 | 1.2 | 0.15 |
| geD | CLDN9 | 1.3 | 0.15 |
| geD | TNFRSF13C | 1.2 | 0.15 |
| geD | PRKAR1B | 1.3 | 0.15 |
| geD | SCFD1 | −1.3 | 0.15 |
| geD | PAX3 | −1.2 | 0.15 |
| geD | SWAP70 | −1.3 | 0.15 |
| geD | MAP4K5 | −1.6 | 0.15 |
| geD | MLL2 | −1.6 | 0.15 |
| geD | RFFL | −1.4 | 0.15 |
| geD | SOCS5 | −1.3 | 0.15 |
| geD | STK4 | −1.4 | 0.15 |
| geD | AMOTL1 | −1.1 | 0.15 |
| geD | MLF1 | −1.3 | 0.15 |
| geD | RACGAP1 | −1.6 | 0.15 |
| geD | PPID | −1.4 | 0.15 |
| geD | YWHAZ | −1.4 | 0.15 |
| geD | GPR183 | −1.2 | 0.15 |
| geD | SRPK2 | −1.4 | 0.15 |
| geD | FAM19A2 | −1.5 | 0.15 |
| geD | HSPA8 | −1.3 | 0.15 |
| geD | CELSR1 | −1.3 | 0.15 |
| geD | MYST4 | −1.3 | 0.15 |
| geD | HSPA5 | −1.4 | 0.15 |
| geD | RBM24 | −1.5 | 0.15 |
| geD | MYST4 | −1.5 | 0.15 |
| geD | CCL28 | −1.3 | 0.15 |

APPENDIX K

TABLE S11

CNR-specific measurements

| DataType | Name | Fold-change | Q-value |
|---|---|---|---|
| phenoD | CD4 TERM DIFF EFFECTOR MEMORY | 3.4 | 0 |
| phenoD | CD4 EFFECTOR MEMORY | 2.9 | 0 |
| phenoD | CD8 TERM DIFF EFFECTOR MEMORY | 10.9 | 0.01 |
| phenoD | CD8 EFFECTOR MEMORY | 4.9 | 0.03 |
| phenoD | NK T CELLS | 2.1 | 0.03 |
| phenoD | CD4 | 2.5 | 0.03 |
| phenoD | CD8 | 3.3 | 0.06 |
| phenoD | CD4 NAIVE | −2.3 | 0 |
| phenoD | CD8 NAIVE | −2.3 | 0.01 |
| phenoD | B CELLS | −1.4 | 0.02 |
| pfBaselineD | cd20_Unstimulated_STAT1 | 2.6 | 0 |
| pfBaselineD | cd20_Unstimulated_STAT3 | 4.3 | 0 |
| pfBaselineD | cd20_Unstimulated_STAT5 | 2.5 | 0 |
| pfBaselineD | cd4_Unstimulated_STAT1 | 1.1 | 0 |
| pfBaselineD | cd4_Unstimulated_STAT3 | 1.2 | 0 |
| pfBaselineD | cd4_Unstimulated_STAT5 | 1.1 | 0.01 |
| pfBaselineD | mono_Unstimulated_STAT1 | 1.1 | 0.02 |
| pfBaselineD | mono_Unstimulated_STAT3 | 1.1 | 0.06 |
| pfD | cd20_IFNg_STAT3 | 1.1 | 0.02 |
| pfD | cd20_IL6_STAT5 | 1 | 0.02 |
| pfD | cd20_IL7_STAT3 | 1.1 | 0.06 |
| pfD | cd20_IL7_STAT5 | 1.1 | 0.07 |
| pfD | cd20_IL10_STAT5 | 1 | 0.12 |
| pfD | mono_IL10_STAT5 | 1.1 | 0.13 |
| pfD | mono_IL21_STAT1 | 1 | 0.14 |
| pfD | mono_IL21_STAT5 | 1 | 0.15 |
| pfD | cd20_IFNa_STAT1 | −4.2 | 0 |
| pfD | cd20_IFNa_STAT3 | −6 | 0 |
| pfD | cd20_IFNa_STAT5 | −3.7 | 0 |
| pfD | cd20_IFNg_STAT1 | −4 | 0 |
| pfD | cd20_IL21_STAT1 | −3.4 | 0 |
| pfD | cd20_IL21_STAT3 | −2 | 0 |
| pfD | cd20_IL7_STAT1 | −6.6 | 0 |
| pfD | cd4_IFNa_STAT1 | −4.4 | 0 |
| pfD | cd4_IFNa_STAT3 | −1.9 | 0 |
| pfD | cd4_IFNa_STAT5 | −1.7 | 0 |
| pfD | cd4_IFNg_STAT1 | −3.4 | 0 |
| pfD | cd4_IFNg_STAT3 | −1.5 | 0 |
| pfD | cd4_IL10_STAT1 | −3.3 | 0 |
| pfD | cd4_IL10_STAT3 | −2.2 | 0 |
| pfD | cd4_IL21_STAT1 | −1.3 | 0 |
| pfD | cd4_IL21_STAT3 | −2 | 0 |
| pfD | cd4_IL21_STAT5 | −2 | 0 |
| pfD | cd4_IL6_STAT1 | −1.1 | 0 |
| pfD | cd4_IL6_STAT3 | −11.2 | 0 |
| pfD | cd4_IL6_STAT5 | −1.6 | 0 |
| pfD | cd4_IL7_STAT1 | −2.3 | 0 |
| pfD | cd4_IL7_STAT3 | −1.3 | 0 |
| pfD | cd4_IL7_STAT5 | −1.4 | 0 |
| pfD | cd8_IFNa_STAT3 | −1.8 | 0 |
| pfD | cd8_IFNa_STAT5 | −1.5 | 0 |
| pfD | cd8_IFNg_STAT1 | −2.8 | 0 |
| pfD | cd8_IFNg_STAT3 | −1.2 | 0 |
| pfD | cd8_IFNg_STAT5 | −1.9 | 0 |
| pfD | cd8_IL10_STAT1 | −1.7 | 0 |
| pfD | cd8_IL10_STAT3 | −1.4 | 0 |

TABLE S11-continued

CNR-specific measurements

| DataType | Name | Fold-change | Q-value |
|---|---|---|---|
| pfD | cd8_IL21_STAT3 | −1.7 | 0 |
| pfD | cd8_IL21_STAT5 | −1.2 | 0 |
| pfD | cd8_IL6_STAT1 | −2.4 | 0 |
| pfD | cd8_IL6_STAT3 | −1.3 | 0 |
| pfD | cd8_IL6_STAT5 | −1 | 0 |
| pfD | cd8_IL7_STAT1 | −1.2 | 0 |
| pfD | cd8_IL7_STAT3 | −1.2 | 0.01 |
| pfD | cd8_IL7_STAT5 | −1.2 | 0.01 |
| pfD | mono_IFNa_STAT1 | −1.4 | 0.01 |
| pfD | mono_IFNa_STAT3 | −1.4 | 0.01 |
| pfD | mono_IFNa_STAT5 | −1.1 | 0.01 |
| pfD | mono_IFNg_STAT1 | −1.2 | 0.02 |
| pfD | mono_IFNg_STAT3 | −1.1 | 0.04 |
| pfD | mono_IFNg_STAT5 | −1.1 | 0.05 |
| pfD | mono_IL10_STAT3 | −1 | 0.07 |
| pfD | mono_IL21_STAT3 | −1.1 | 0.07 |
| pfD | mono_IL6_STAT1 | −1.1 | 0.09 |
| pfD | mono_IL6_STAT3 | −1 | 0.11 |
| pfD | mono_IL7_STAT5 | −1.1 | 0.14 |
| cytM | RANTES | −1.3 | 0.15 |
| geD | FKBP1A | 1.8 | 0.07 |
| geD | TOLLIP | 2.1 | 0.07 |
| geD | RIMS4 | 1.5 | 0.07 |
| geD | CAV3 | 2.1 | 0.07 |
| geD | HSPA8 | 2.3 | 0.07 |
| geD | AIRE | 1.4 | 0.07 |
| geD | NEIL3 | 1.5 | 0.07 |
| geD | INHBC | 1.9 | 0.07 |
| geD | GH1 | 2.2 | 0.08 |
| geD | DUB3 | 2.3 | 0.09 |
| geD | ICOSLG | 1.6 | 0.1 |
| geD | HIP1 | 1.5 | 0.1 |
| geD | ISLR2 | 1.9 | 0.1 |
| geD | MYBPC3 | 1.5 | 0.1 |
| geD | MUC5AC | 1.5 | 0.1 |
| geD | DSC2 | 3 | 0.1 |
| geD | GREM2 | 1.4 | 0.11 |
| geD | MNT | 2 | 0.11 |
| geD | ELN | 2.1 | 0.11 |
| geD | PXN | 1.3 | 0.11 |
| geD | CTSE | 1.3 | 0.11 |
| geD | BAG3 | 1.5 | 0.12 |
| geD | SORT1 | 1.6 | 0.12 |
| geD | CTSB | 1.8 | 0.13 |
| geD | ICAM5 | 2.9 | 0.14 |
| geD | YWHAZ | 1.2 | 0.14 |
| geD | SBDS | 1.5 | 0.14 |
| geD | CLN3 | 1.5 | 0.14 |
| geD | DOCK3 | 2 | 0.15 |
| geD | SERPING1 | −1.6 | 0.03 |
| geD | ICA1 | −1.6 | 0.07 |
| geD | DNASE1 | −1.5 | 0.07 |
| geD | CASQ1 | −1.4 | 0.07 |
| geD | F5 | −1.5 | 0.07 |
| geD | LENG1 | −1.4 | 0.07 |
| geD | PGM5 | −1.4 | 0.07 |
| geD | EP300 | −1.6 | 0.07 |
| geD | DGKE | −1.5 | 0.07 |
| geD | IGFALS | −1.6 | 0.07 |
| geD | MYL10 | −1.6 | 0.07 |
| geD | CCL26 | −1.4 | 0.07 |
| geD | MYC | −1.5 | 0.07 |
| geD | MASP1 | −1.4 | 0.07 |
| geD | IGF1R | −1.6 | 0.07 |
| geD | THBS1 | −1.4 | 0.07 |
| geD | TNNC2 | −1.3 | 0.07 |
| geD | ZNF346 | −1.4 | 0.07 |
| geD | LEFTY1 | −1.4 | 0.07 |
| geD | DCBLD1 | −1.6 | 0.07 |
| geD | MARK2 | −1.4 | 0.07 |
| geD | 3-Sep | −1.4 | 0.07 |
| geD | CBLB | −1.4 | 0.07 |
| geD | SIX4 | −1.5 | 0.07 |
| geD | PIK3R2 | −1.5 | 0.07 |
| geD | CAMK1G | −1.4 | 0.08 |
| geD | ARHGDIA | −1.4 | 0.08 |
| geD | MIF | −1.4 | 0.08 |
| geD | SLIT2 | −1.3 | 0.08 |
| geD | XRCC6BP1 | −1.4 | 0.08 |
| geD | TEC | −1.3 | 0.08 |
| geD | BTG1 | −1.4 | 0.08 |
| geD | LPP | −1.5 | 0.08 |
| geD | MARK1 | −1.3 | 0.08 |
| geD | LAMB2 | −1.4 | 0.09 |
| geD | HIP1 | −1.3 | 0.09 |
| geD | AR | −1.3 | 0.09 |
| geD | BCL2L2 | −1.4 | 0.09 |
| geD | SCD5 | −1.3 | 0.09 |
| geD | CD1B | −1.4 | 0.1 |
| geD | TNFRSF13B | −1.3 | 0.1 |
| geD | EDNRA | −1.4 | 0.1 |
| geD | SKAP2 | −1.4 | 0.1 |
| geD | LMLN | −1.3 | 0.1 |
| geD | TRAF7 | −1.5 | 0.1 |
| geD | SFRS17A | −1.5 | 0.1 |
| geD | COL6A1 | −1.3 | 0.1 |
| geD | HSPB1 | −1.7 | 0.1 |
| geD | NFE2L2 | −1.5 | 0.1 |
| geD | HAPLN3 | −1.4 | 0.1 |
| geD | C1QTNF2 | −1.2 | 0.1 |
| geD | SYNJ2BP | −1.3 | 0.1 |
| geD | NPNT | −1.4 | 0.1 |
| geD | ERCC5 | −1.4 | 0.1 |
| geD | CUL4A | −1.4 | 0.1 |
| geD | KEL | −1.3 | 0.1 |
| geD | PSMA5 | −1.4 | 0.1 |
| geD | SOD2 | −1.3 | 0.1 |
| geD | ARHGDIA | −1.5 | 0.1 |
| geD | RAB22A | −1.4 | 0.11 |
| geD | MAGED1 | −1.3 | 0.11 |
| geD | LTBP2 | −1.3 | 0.11 |
| geD | PPP1R13B | −1.3 | 0.11 |
| geD | ULBP2 | −1.4 | 0.11 |
| geD | ATP2A1 | −1.4 | 0.12 |
| geD | BAT1 | −1.5 | 0.12 |
| geD | CSNK1E | −1.3 | 0.12 |
| geD | NLGN3 | −1.4 | 0.12 |
| geD | ITGA9 | −1.5 | 0.12 |
| geD | XKR3 | −1.5 | 0.12 |
| geD | FMOD | −1.4 | 0.12 |
| geD | CDC42SE2 | −1.3 | 0.12 |
| geD | ALCAM | −1.3 | 0.12 |
| geD | FN1 | −1.4 | 0.12 |
| geD | RIPK1 | −1.4 | 0.12 |
| geD | CDH16 | −1.3 | 0.12 |
| geD | STK17A | −1.2 | 0.12 |
| geD | TXLNA | −1.3 | 0.12 |
| geD | HESX1 | −1.3 | 0.12 |
| geD | COL6A1 | −1.3 | 0.13 |
| geD | SGPL1 | −1.7 | 0.13 |
| geD | PDLIM7 | −1.5 | 0.13 |
| geD | FUT3 | −1.2 | 0.13 |
| geD | MSN | −1.4 | 0.13 |
| geD | CLN8 | −1.3 | 0.13 |
| geD | PLDN | −1.4 | 0.13 |
| geD | PLD1 | −1.4 | 0.13 |
| geD | MYST4 | −1.4 | 0.13 |
| geD | BLID | −1.5 | 0.13 |
| geD | BCL6B | −1.4 | 0.13 |
| geD | CNTFR | −1.2 | 0.13 |
| geD | COL24A1 | −1.3 | 0.13 |
| geD | SH3GL2 | −1.3 | 0.14 |
| geD | GSG2 | −1.3 | 0.14 |
| geD | BAALC | −1.2 | 0.14 |
| geD | ADAL | −1.5 | 0.14 |
| geD | BDNF | −2 | 0.14 |
| geD | WISP1 | −1.4 | 0.14 |
| geD | BCL7A | −1.3 | 0.14 |
| geD | CDC2L2 | −1.2 | 0.14 |
| geD | NCAM1 | −1.3 | 0.14 |
| geD | CEACAM5 | −1.3 | 0.14 |
| geD | CD96 | −1.4 | 0.14 |

TABLE S11-continued

CNR-specific measurements

| DataType | Name | Fold-change | Q-value |
|---|---|---|---|
| geD | EMILIN1 | −1.3 | 0.14 |
| geD | HAPLN4 | −1.4 | 0.14 |
| geD | TXLNA | −1.4 | 0.14 |
| geD | VNN1 | −1.4 | 0.15 |
| geD | C1QTNF1 | −1.3 | 0.15 |
| geD | MMP12 | −1.5 | 0.15 |

APPENDIX L

TABLE S12

Fold-change - response classification results

| condition | maxFold | Unstim | FC.diff | fIDR | FdiffDR | hMFI | classify notes |
|---|---|---|---|---|---|---|---|
| *Classification of aging associated cytokine response assays (q < 0.15)* | | | | | | | |
| cd20_IFNg_STAT3 | 1.1 | 1 | 0 | 1 | 0 | 1 | BD |
| cd20_IL7_STAT3 | 1.2 | 1 | 0 | 0 | 0 | 1 | BD |
| cd4_IFNa_STAT1 | 6.3 | 1 | 1 | 0 | 0 | 0 | BD |
| cd4_IFNa_STAT3 | 3.8 | 1 | 1 | 0 | 1 | 0 | BD |
| cd4_IFNg_STAT1 | 1.6 | 1 | 0 | 0 | 1 | 1 | BD |
| cd4_IL10_STAT1 | 2.2 | 1 | 0 | 1 | 0 | 1 | BD |
| cd4_IL10_STAT3 | 6.0 | 1 | 1 | 0 | 1 | 0 | BD |
| cd4_IL21_STAT1 | 1.6 | 1 | 0 | 1 | 0 | 1 | BD |
| cd4_IL21_STAT5 | 1.5 | 1 | 0 | 1 | 1 | 0 | BD |
| cd4_IL7_STAT5 | 5.0 | 1 | 1 | 1 | 0 | 0 | BD |
| cd8_IL10_STAT1 | 1.9 | 1 | 0 | 1 | 0 | 1 | BD |
| cd8_IL21_STAT5 | 1.4 | 1 | 0 | 1 | 1 | 0 | BD |
| cd8_IL7_STAT1 | 1.2 | 1 | 0 | 1 | 0 | 1 | BD |
| cd8_IL7_STAT3 | 1.4 | 1 | 0 | 0 | 0 | 1 | BD |
| cd20_IFNa_STAT1 | 4.2 | 1 | 1 | 0 | 0 | 1 | BRD |
| cd20_IFNa_STAT3 | 2.8 | 1 | 1 | 1 | 1 | 1 | BRD |
| cd20_IFNa_STAT5 | 1.7 | 1 | 1 | 1 | 0 | 1 | BRD |
| cd4_IFNa_STAT5 | 3.4 | 1 | 1 | 1 | 0 | 1 | BRD |
| cd4_IL21_STAT3 | 5.5 | 1 | 1 | 1 | 1 | 0 | BRD |
| cd4_IL6_STAT1 | 6.0 | 1 | 1 | 0 | 1 | 1 | BRD |
| cd4_IL6_STAT3 | 5.9 | 1 | 1 | 1 | 1 | 1 | BRD |
| cd4_IL6_STAT5 | 2.1 | 1 | 1 | 1 | 1 | 1 | BRD |
| cd4_IL7_STAT3 | 1.3 | 1 | 1 | 1 | 0 | 1 | BRD |
| cd8_IFNa_STAT1 | 7.2 | 1 | 1 | 0 | 0 | 1 | BRD |
| cd8_IFNa_STAT3 | 3.7 | 1 | 1 | 1 | 1 | 1 | BRD |
| cd8_IFNa_STAT5 | 2.8 | 1 | 1 | 0 | 0 | 1 | BRD |
| cd8_IFNg_STAT1 | 1.5 | 1 | 1 | 0 | 1 | 1 | BRD |
| cd8_IL21_STAT1 | 1.7 | 1 | 1 | 1 | 1 | 1 | BRD |
| cd8_IL6_STAT1 | 4.7 | 1 | 1 | 0 | 1 | 1 | BRD |
| cd8_IL6_STAT3 | 5.8 | 1 | 1 | 0 | 1 | 1 | BRD |
| cd8_IL6_STAT5 | 1.5 | 1 | 1 | 1 | 1 | 0 | BRD |
| mono_IFNa_STAT1 | 3.1 | 0 | 1 | 0 | 0 | 1 | RD |
| mono_IFNa_STAT3 | 2.3 | 0 | 1 | 0 | 0 | 1 | RD |
| mono_IFNa_STAT5 | 1.5 | 0 | 1 | 1 | 0 | 1 | RD |
| mono_IL6_STAT3 | 2.3 | 0 | 1 | 1 | 1 | 1 | RD |
| mono_IFNg_STAT3 | 1.5 | 0 | 0 | 1 | 1 | 0 | UNK |
| mono_IFNg_STAT5 | 1.6 | 0 | 0 | 1 | 0 | 0 | UNK |
| mono_IL6_STAT1 | 1.2 | 0 | 0 | 0 | 0 | 1 | UNK |
| mono_IL7_STAT5 | 1.3 | 0 | 0 | 1 | 0 | 0 | UNK |
| *Classification of cytokine response assays not shown to be different in the aging in the general (29 individuals) population* | | | | | | | |
| cd20_IFNg_STAT5 | 1.4 | 1 | 0 | 1 | 0 | 1 | BD |
| cd20_IL10_STAT1 | 1.7 | 1 | 0 | 1 | 0 | 1 | BD |
| cd20_IL10_STAT5 | 1.3 | 1 | 0 | 1 | 0 | 1 | BD |
| cd20_IL21_STAT5 | 1.4 | 1 | 0 | 1 | 0 | 1 | BD |
| cd20_IL6_STAT1 | 1.2 | 1 | 0 | 1 | 1 | 1 | BD |
| cd20_IL6_STAT5 | 1.3 | 1 | 0 | 1 | 0 | 1 | BD |
| cd20_IL7_STAT5 | 1.3 | 1 | 0 | 1 | 0 | 1 | BD |
| cd4_IL10_STAT5 | 1.5 | 1 | 0 | 1 | 0 | 1 | BD |
| cd4_IL7_STAT1 | 1.3 | 1 | 0 | 1 | 0 | 1 | BD |
| cd8_IFNg_STAT3 | 1.2 | 1 | 0 | 0 | 0 | 1 | BD |
| cd8_IFNg_STAT5 | 1.2 | 1 | 0 | 1 | 0 | 1 | BD |
| cd8_IL10_STAT5 | 1.3 | 1 | 0 | 1 | 0 | 1 | BD |
| cd20_IFNg_STAT1 | 3.5 | 1 | 0 | 1 | 0 | 1 | BD |
| cd20_IL10_STAT3 | 5.1 | 1 | 0 | 1 | 0 | 0 | BD |
| cd20_IL21_STAT1 | 1.5 | 1 | 0 | 0 | 0 | 1 | BD |
| cd20_IL7_STAT1 | 1.2 | 1 | 0 | 1 | 0 | 1 | BD |
| cd4_IFNg_STAT3 | 1.1 | 1 | 0 | 0 | 0 | 1 | BD |
| cd4_IFNg_STAT5 | 1.2 | 1 | 0 | 1 | 0 | 1 | BD |

TABLE S12-continued

Fold-change - response classification results

| condition | maxFold | Unstim | FC.diff | fIDR | FdiffDR | hMFI | classify notes |
|---|---|---|---|---|---|---|---|
| cd8_IL10_STAT3 | 6.1 | 1 | 0 | 1 | 0 | 0 | BD |
| cd8_IL21_STAT3 | 5.8 | 1 | 1 | 1 | 0 | 0 | BD |
| cd20_IL6_STAT3 | 1.3 | 1 | 1 | 1 | 1 | 1 | BRD |
| cd20_IL21_STAT3 | 3.7 | 1 | 1 | 1 | 0 | 1 | BRD |
| cd8_IL7_STAT5 | 3.9 | 1 | 1 | 1 | 0 | 1 | BRD |
| mono_IL21_STAT3 | 1.7 | 0 | 1 | 1 | 0 | 1 | RD |
| mono_IL10_STAT1 | 1.9 | 0 | 0 | 1 | 0 | 1 | UNK |
| mono_IL10_STAT5 | 1.4 | 0 | 0 | 1 | 0 | 1 | UNK |
| mono_IL21_STAT1 | 1.4 | 0 | 0 | 0 | 0 | 1 | UNK |
| mono_IL21_STAT5 | 1.2 | 0 | 0 | 1 | 0 | 1 | UNK |
| mono_IL6_STAT5 | 1.2 | 0 | 0 | 1 | 0 | 1 | UNK |
| mono_IL7_STAT1 | 1.2 | 0 | 0 | 0 | 0 | 1 | UNK |
| mono_IL7_STAT3 | 1.2 | 0 | 0 | 0 | 0 | 1 | UNK |
| mono_IFNg_STAT1 | 3.8 | 0 | 0 | 1 | 0 | 0 | UNK |
| mono_IL10_STAT3 | 5.4 | 0 | 0 | 1 | 1 | 0 | UNK |

What is claimed is:

1. A method of assaying an individual for immune impairment based on an assessment of cytokine responses, the method comprising:
receiving an individual blood sample from an individual of a given age;
separating a baseline sample and a response sample from the individual blood sample;
permeabilizing the baseline sample and the response sample;
stimulating the response sample using at least one cytokine;
staining the baseline sample and the response sample using at least one STAT protein;
measuring the phosphorylation of the at least one STAT protein within the baseline sample and the phosphorylation of the at least one STAT protein within the response sample based on phosphoprotein abundance;
measuring the cytokine stimulation response of the individual by comparing the determined phosphorylation levels of STAT proteins of the baseline sample with the phosphorylation levels of STAT proteins of the response sample;
generating a cytokine response score for the individual based on a comparison of the cytokine stimulation response of the individual to cytokine response profiles from a database of cytokine response profiles;
phenotyping the individual for cytokine response based on the cytokine response score,
wherein an individual is defined as a cytokine responder phenotype if the cytokine response score is within two standard deviations from the average cytokine response score of the cytokine response profiles from the database of cytokine response profiles; and
wherein an individual is defined as a cytokine non-responder phenotype if the cytokine response score is more than two standard deviations from the average cytokine response score of the cytokine response profiles from the database of cytokine response profiles, and wherein the cytokine non-responder phenotype is associated with immune impairment; and
treating the individual based on the phenotype of the individual, wherein the treatment is vaccination for a recurring disease that is appropriate for the cytokine responder phenotype.

2. The method of claim 1 wherein the at least one STAT protein comprises at least one of STAT1 protein in B-cells, STAT1 protein in T-cells, STAT3 protein in B-cells, STAT3 protein in T-cells, STAT5 protein in B-cells, STAT5 protein in T-cells, and STAT1 in monocytes.

3. The method of claim 1 wherein the at least one cytokine comprises at least one of IFN-α, IFN-γ, IL6, IL7, IL10 or IL21.

4. The method of claim 1, wherein the phenotyping of the peripheral blood mononuclear cell sample is performed using flow cytometry centrifugation.

5. The method of claim 1 wherein the cytokine response score is generated using a Z-score transformation.

6. The method of claim 1 wherein the individual is over 60 years of age.

7. The method of claim 1 wherein the permeabilizing of the baseline sample and the response sample is performed using methanol.

8. The method of claim 1, wherein comparing the determined phosphorylation levels of STAT proteins of the baseline sample with the phosphorylation levels of STAT proteins of the response sample further comprises calculating a ratio of fold changes between the baseline sample and the response sample.

9. The method of claim 1, wherein the cytokine response profiles have been previously determined using a regression analysis on measurements of age-associated traits that show a statistically significant change in expression with age.

10. The method of claim 1, wherein the given age of the individual is at least 60 years old.

* * * * *